US012649935B2

(12) United States Patent
Hamberger et al.

(10) Patent No.: US 12,649,935 B2
(45) Date of Patent: Jun. 9, 2026

(54) METHODS FOR PRODUCTION OF NOVEL DITERPENE SCAFFOLDS

(71) Applicant: Board of Trustees of Michigan State University, East Lansing, MI (US)

(72) Inventors: Björn Hamberger, Okemos, MI (US); Sean Johnson, Bedford, MA (US); Wajid Waheed Bhat, Haslett, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 18/458,762

(22) Filed: Aug. 30, 2023

(65) Prior Publication Data

US 2024/0124899 A1 Apr. 18, 2024

Related U.S. Application Data

(62) Division of application No. 17/265,482, filed as application No. PCT/US2019/044887 on Aug. 2, 2019, now Pat. No. 11,827,915.

(60) Provisional application No. 62/714,216, filed on Aug. 3, 2018.

(51) Int. Cl.

| | |
|---|---|
| ***C12N 9/10*** | (2006.01) |
| ***C12N 15/82*** | (2006.01) |
| ***C12P 5/00*** | (2006.01) |
| ***C12P 17/02*** | (2006.01) |
| ***C12P 17/06*** | (2006.01) |

(52) U.S. Cl.

CPC ............ *C12P 5/002* (2013.01); *C12N 9/1022* (2013.01); *C12N 9/1085* (2013.01); *C12N 15/8243* (2013.01); *C12P 17/02* (2013.01); *C12P 17/06* (2013.01); *C12Y 202/01007* (2013.01); *C12Y 205/01029* (2013.01)

(58) Field of Classification Search

None

See application file for complete search history.

(56) References Cited

U.S. PATENT DOCUMENTS

| | | | |
|---|---|---|---|
| 2003/0175678 | A1 | 9/2003 | Bowen et al. |
| 2012/0064629 | A1 | 3/2012 | Mendez et al. |
| 2016/0318893 | A1 | 11/2016 | Hamberger et al. |
| 2018/0037912 | A1 | 2/2018 | Hamberger et al. |
| 2022/0372526 | A1 | 11/2022 | Hamberger et al. |

FOREIGN PATENT DOCUMENTS

| | | | |
|---|---|---|---|
| CN | 105456245 | | 4/2016 |
| WO | WO-2015113570 | A1 | 8/2015 |
| WO | WO-2020028795 | A1 | 2/2020 |

OTHER PUBLICATIONS

"U.S. Appl. No. 17/265,482, Non Final Office Action mailed Jan. 27, 2023", 12 pgs.
"U.S. Appl. No. 17/265,482, Notice of Allowance mailed Jul. 18, 2023", 9 pgs.
"U.S. Appl. No. 17/265,482, Preliminary Amendment Filed Feb. 2, 2021", 19 pgs.
"U.S. Appl. No. 17/265,482, Response filed May 10, 2023 to Non Final Office Action mailed Jan. 27, 2023", 21 pgs.
"U.S. Appl. No. 17/265,482, Response filed Dec. 12, 2022 to Restriction Requirement mailed Sep. 16, 2022", 18 pgs.
"U.S. Appl. No. 17/265,482, Restriction Requirement mailed Sep. 16, 2022", 9 pgs.
"U.S. Appl. No. 62/714,216, Preliminary Amendment Filed Aug. 8, 2018", 3 pgs.
"Dictionary of Natural Products 26.2", [online]. [Archived on Feb. 20, 2018]. Retrieved from the Internet: <URL: https://web.archive.org/web/20180220224845/http://dnp.chemnetbase.com/faces/chemical/ChemicalSearch.xhtml;jsessionid=7993CED448E4ED19650860B9148462FE>, (2018), 1 pg.
"European Application Serial No. 19843571.1, Communication Pursuant to Article 94(3) EPC mailed Dec. 2, 2022", 1 pg.
"European Application Serial No. 19843571.1, Extended European Search Report mailed Jan. 26, 2022", 16 pgs.
"European Application Serial No. 19843571.1, Supplementary Partial European Search Report mailed Sep. 22, 2021", 12 pgs.
"International Application Serial No. PCT/US2019/044887, International Preliminary Report on Patentability mailed Feb. 18, 2021", 7 pgs.
"International Application Serial No. PCT/US2019/044887, International Search Report mailed Dec. 11, 2019", 5 pgs.
"International Application Serial No. PCT/US2019/044887, Invitation to Pay Additional Fees mailed Oct. 18, 2019", 3 pgs.
"International Application Serial No. PCT/US2019/044887, Written Opinion mailed Dec. 11, 2019", 5 pgs.
"RecName: Full=Kolavenyl diphosphate synthase TPS5, chloroplastic {ECO : 0000303 !PubMed:29315936}; EC=5.5.1.29 {ECO : 0000269 !PubMed:29315936} ; AltName: Full=Terpene synthase 5 {ECO:0000303!PubMed:29315936}; Short=VacTPS5 {ECO:0000303!PubMed:29315936}; F", (Jun. 20, 2018), 1 pg.
"RecName: Full=Miltiradiene synthase KSL1, chloroplastic {ECO:0000303| PubMed:28445526}; EC=4.2.3.131 {ECO:0000269|PubMed:28381502, ECO:0000269 |PubMed:28445526}; AltName:Full=Kaurene synthase 1 {ECO:0000303| PubMed:28381502};Short=IrKSL1 {ECO:0000303| PubMed:2", (Jul. 5, 2017), 1 pg.
Alvarenga, S. A., et al., "A computer-assisted approach for chemotaxonomic studies—Diterpenes in Lamiaceae", Phytochemistry 56(6), (Mar. 2001), 583-595.

(Continued)

*Primary Examiner* — Richard G Hutson

(74) *Attorney, Agent, or Firm* — McKee, Voorhees & Sease, PLC

(57) ABSTRACT

Enzymes and methods are described herein for manufacturing terpenes, including terpenes.

8 Claims, 22 Drawing Sheets

Specification includes a Sequence Listing.

(56) References Cited

OTHER PUBLICATIONS

Andersen-Ranberg, J., et al., "Expanding the Landscape of Diterpene Structural Diversity through Stereochemically Controlled Combinatorial Biosynthesis", Angew Chem Int Ed 55(6), (2016), 2142-2146.
Arima, Y., et al., "Natural product synthesis from (8aR)- and (8aS)-bicyclofarnesols: synthesis of (+)-wiedendiol A, (+)-norsesterterpene diene ester and (−)-subersic acid", Tetrahedron: Asymmetry 18(14), (2007), 1701-1711.
Banerjee, A., et al., "P450s controlling metabolic bifurcations in plant terpene specialized metabolism.", Phytochem Rev 17(1), (2018), 81-111.
Barton, D. H. R., et al., "Diterpenoid bitter principles. Part III. The constitution of clerodin", J Chem Soc (Resumed), (1961), 5061-5073.
Belles, X., et al., "Insect antifeedant activity of clerodane diterpenoids against larvae of Spodoptera Littoralis (Boisd.) (Lepidoptera)", J Chem Ecol 11(10), (1985), 1439-1445.
Benson, D. A., et al., "GenBank", Nucleic Acids Res 41(D1), (2013), D36-D42.
Boachon, B., et al., "Phylogenomic Mining of the Mints Reveals Multiple Mechanisms Contributing to the Evolution of Chemical Diversity in Lamiaceae", Molecular Plant. 11, (Aug. 2018), 1084-1096.
Boalino, D. M., et al., "Labdane Diterpenes of Leonurus sibiricus", J Nat Prod 67(4), (2004), 714-717.
Bohlmann, F., et al., "Neue labdan- und pimaren-derivate aus Palafoxia rosea", Phytochemistry 18(1), (1979), 115-118.
Bremner, Paul D., et al., "Neo-clerodane diterpenoid insect antifeedants from Ajuga reptans cv Catlins Giant", Phytochemistry, 47(7), (Apr. 1, 1998), 1227-1232.
Busta, L., et al., "Moving beyond the ubiquitous: the diversity and biosynthesis of specialty compounds in plant cuticular waxes", Phytochem Rev:1-30, (2017), 1-30.
Camacho, C., et al., "BLAST+: architecture and applications", BMC Bioinformatics 10:421, (2009), 9 pgs.
Caniard, A, et al., "Discovery and functional characterization of two diterpene synthases for sclareol biosynthesis in *Salvia sclarea*(L.) and their relevance for perfume manufacture", BMC Plant Biol. 12 (1), 119, (2012), 119.
Challis, G. L., et al., "Genome Mining for Novel Natural Product Discovery", J Med Chem 51(9), (2008), 2618-2628.
Chau, M., et al., "Regioselectivity of taxoid-O-acetyltransferases: heterologous expression and characterization of a new taxadien-5a-ol-O-acetyltransferase", Archives of Biochemistry and Biophysics 430(2), (Oct. 15, 2004), 237-246.
Chen, et al., "Archives of Biochemistry and Biophysics", vol. 324, No. 2, (Dec. 20, 1995), 255-266.
Chen, F., et al., "The Family of terpene synthases in plants: a mid-size family of genes for specialized metabolism that is highly diversified throughout the kingdom", The Plant Journal 66(1), (Apr. 2011), 212-229.
Chen, X., et al., "A (−)-kolavenyl diphosphate synthase catalyzes the first step of salvinorin A biosynthesis in Salvia divinorum", J Exp Bot 68(5), (2017), 1109-1122.
Chen, Y.-L., et al., "Bioactive Cembrane Diterpenoids of Anisomeles indica", J Nat Prod 71(7), (2008), 1207-1212.
Christoph, Crocoll, et al., "Terpene synthases of oregano (*Origanum vulgare* L.) and their roles in the pathway and regulation of terpene biosynthesis", Plant Molecular Biology, vol. 73, No. 6, (Apr. 25, 2010), 587-603.
Coll, J., et al., "neo-Clerodane diterpenoids from Ajuga: structural elucidation and biological activity", Phytochem Rev 7(1), (2008), 25-49.
Cui, G., et al., "Functional divergence of diterpene syntheses in the medicinal plant *Salvia miltiorrhiza* Bunge", Plant Physiol 169(3), (2015), 1607-1618.
Dairi, T., et al., "Eubacterial Diterpene Cyclase Genes Essential for Production of the Isoprenoid Antibiotic Terpentecin", J Bacteriol 183(20), (2001), 6085-6094.
Ennajdaoui, H., et al., "Trichome specific expression of the tobacco (*Nicotiana sylvestris*) cembratrien-ol synthase genes is controlled by both activating and repressing cis-regions", Plant Mol Biol 73(6), (2010), 673-685.
Federhen, S., et al., "The NCBI Taxonomy database", Nucleic Acids Res 40(D1), (2012), D136-D143.
Fischedick, J. T., et al., "NMR spectroscopic search module for Spektraris, an online resource for plant natural product identification—Taxane diterpenoids from Taxus x media cell suspension cultures as a case study", Phytochemistry 113, (2015), 87-95.
Gao, W., et al., "A Functional Genomics Approach to Tanshinone Biosynthesis Provides Stereochemical Insights", Org Lett 11(22), (2009), 5170-5173.
Geuskens, R. B. M., et al., "Antifeedant activity of some ajugarin derivatives in three lepidopterous species", Experientia 39(4), (1983), 403-404.
Gonzalez, A. G., et al., "Diterpenes from Salvia mellifera", Phytochemistry 30(12), (1991), 4067-4070.
Gray, C. A., et al., "The absolute stereochemistry of a diterpene from Ballota aucheri", Phytochemistry 63(4), (2003), 409-413.
Gunnewich, N., et al., "A diterpene synthase from the clary sage *Salvia sclarea* catalyzes the cyclization of geranylgeranyl diphosphate to (8R)-hydroxy-copalyl diphosphate", Phytochemistry 91, (2013), 93-99.
Guo, J., et al., "CYP76AH1 catalyzes turnover of miltiradiene in tanshinones biosynthesis and enables heterologous production of ferruginol in yeasts", Proc. Natl. Acad. Sci. USA, 110(29), (2013), 12108-12113.
Hamano, Y., et al., "Functional Analysis of Eubacterial Diterpene Cyclases Responsible for Biosynthesis of a Diterpene Antibiotic, Terpentecin", J Biol Chem 277(40), (2002), 37098-37104.
Hamberger, B., et al., "Plant P450s as versatile drivers for evolution of species-specific chemical diversity", Philosophical transactions of the Royal Society of London B: Biological Sciences 368(1612), (Feb. 19, 2013).
Han, Q.-B., et al., "Maoecrystal Z, a Cytotoxic Diterpene from Isodon eriocalyx with a Unique Skeleton", Org Lett 8(21), (2006), 4727-4730.
Harris, L. J., et al., "The Maize An2 Gene is Induced by Fusarium Attack and Encodes an ent-Copalyl Diphosphate Synthase", Plant Mol Biol 59(6), (2005), 881-894.
Heller, S. R., et al., "InChl, the IUPAC International Chemical Identifier", J Cheminform 7. doi:10.1186/s13321-015-0068-4., (2015).
Helliwell, C. A., et al., "The CYP88A cytochrome P450, ent-kaurenoic acid oxidase, catalyzes three steps of the gibberellin biosynthesis pathway", Proc. Natl. Acad. Sci. USA 98(4), (2001), 2065-2070.
Heskes, A.M., et al., "Biosynthesis of bioactive diterpenoids in the medicinal plant *Vitex agnus-castus*", Plant J 93(5): 943-958, 2018., (Mar. 2018), 16 pgs.
Hillwig, M. L., et al., "Domain loss has independently occurred multiple times in plant terpene synthase evolution", The Plant Journal 68(6), (2011), 1051-1060.
Hong, L.-L., et al., "Unusual Anti-allergic Diterpenoids from the Marine Sponge *Hippospongia lachne*", Scientific Reports 7, Article No. 43138, (2017), 7 pgs.
Hong, L.-L., et al., "Unusual Anti-allergic Diterpenoids from the Marine Sponge *Hippospongia lachne*", Supplementary Information, Scientific Reports 7, Article No. 43138, (2017), 34 pgs.
Huang, A. C., et al., "Unearthing a sesterterpene biosynthetic repertoire in the Brassicaceae through genome mining reveals convergent evolution", Proc. Natl. Acad. Sci. USA 114(29), (2017), E6005-E6014.
Huerta-Cepas, J., et al., "ETE 3: Reconstruction, Analysis, and Visualization of Phylogenomic Data", Mol Biol Evol 33(6), (2016), 1635-1638.
Ikeda, H., et al., "Biosynthesis of mercapturic acid derivative of the labdane-type diterpene, cyslabdan that potentiates imipenem activity against methicillin-resistant *Staphylococcus aureus*: cyslabdan is generated by mycothiol-mediated xenobiotic detoxification", J. Ind Microbiol Biotechnol 43(2-3), (2016), 325-342.

(56) References Cited

OTHER PUBLICATIONS

Jia, M., et al., "Extreme promiscuity of a bacterial and a plant diterpene synthase enables combinatorial biosynthesis", Metabolic Engineering 37, (2016), 24-34.
Jin, B., et al., "Functional diversification of kaurene synthase-like genes", Plant Physiol 174, (2017), 955-973.
Johnson, Sean R., et al., "A Database-Driven Approach Identifies Additional Diterpene Synthase Activities in the Mint Family (*Lamiaceae*)", J. Biol. Chem, 294(4), (2019), 1349-1362.
Johnson, Sean R., et al., "Systematic diterpene synthase discovery across Lamiaceae", (Abstract), 57th Annual Meeting of the Phytochemical Society of North America, Aug. 4-8, 2018, University of San Luis Potosi, San Luis Potosi, Mexico, (2018), p. 26 (2 pgs.).
Keeling, C. I., et al., "The Primary Diterpene Synthase Products of Picea abies Levopimaradiene/Abietadiene Synthase (PaLAS) Are Epimers of a Thermally Unstable Diterpenol", J Biol Chem 286(24), (2011), 21145-21153.
King, A. J., et al., "Production of Bioactive Diterpenoids in the Euphorbiaceae Depends on Evolutionarily Conserved Gene Clusters", The Plant Cell Online 26(8), (2014), 3286-3298.
Kirby, J., et al., "Cloning of casbene and neocembrene synthases from Euphorbiaceae plants and expression in *Saccharomyces cerevisiae*", Phytochemistry 71(13), (2010), 1466-1473.
Klein Gebbinck, E. A., et al., "Insect antifeedant activity of clerodane diterpenes and related model compounds", Phytochemistry 61(7), (2002), 737-770.
Kodama, Y., et al., "The sequence read archive: explosive growth of sequencing data", Nucleic Acids Res 40(D1), (2012), D54-D56.
Kuhn, S., et al., "From chemical shift data through prediction to assignment and NMR LIMS—multiple functionalities of nmrshiftdb2", Journal of Cheminformatics 4(Suppl 1):P52, (2012), 1 pg.
Li, B., "A large-scale chloroplast phylogeny of the Lamiaceae sheds new light on its subfamilial classification", Scientific Reports 6:34343, (2016), 34343.
Li, J.-L., et al., "IeCPS2 is potentially involved in the biosynthesis of pharmacologically active Isodon diterpenoids rather than gibberellin", Phytochemistry 76, (2012), 32-39.
Li, R., et al., "Clerodane diterpenes: sources, structures, and biological activities", Nat Prod Rep 33(10), (2016), 1166-1226.
Li, X.-N., et al., "Structure and Cytotoxicity of Diterpenoids from Isodon eriocalyx", J Nat Prod 73(11), (2010), 1803-1809.
Li-Mei, L., et al., "ent-Kaurane and Cembrane Diterpenoids from Isodon sculponeatus and Their Cytotoxicity", J Nat Prod 72(10), (2009), 1851-1856.
Lopez-Perez, J. L., et al., "NAPROC-13: a database for the dereplication of natural product mixtures in bioassay-guided protocols", Bioinformatics 23(23), (2007), 3256-3257.
Lou, H., et al., "Vulgarisin A, a New Diterpenoid with a Rare 5/6/4/5 Ring Skeleton from the Chinese Medicinal Plant *Prunella vulgaris*", Org. Lett. 16(10), (2014), 2696-2699.
Lou, H., et al., "Vulgarisin A, a New Diterpenoid with a Rare 5/6/4/5 Ring Skeleton from the Chinese Medicinal Plant *Prunella vulgaris*", Supporting Information, Org. Lett. 16(10), (2014), 1-19.
Lou, H.-Y., et al., "Vulgarisins B-D, three novel diterpenoids with a rare skeleton isolated from *Prunella vulgaris* Linn", Tetrahedron Letters 58(5), (2017), 401-404.
Loub, W. D., et al., "NAPRALERT: computer handling of natural product research data", J Chem Inf Comput Sci 25(2), (1985), 99-103.
Monaco, P., et al., "Terpenes from the bled resin of Araucaria hunsteinii", Rendiconto della Academia delle scienze fisiche e matematiche 48, (1982), pp. 465-470.
Ngo, et al., "In The Protein Folding Problem and Tertiary Structure Prediction", (1994), 492-495.
Ohaski, A., et al., "The isolation and in vivo Potent Antitumor activity of clerodane diterpenoid from the oleoresin of the brazilian medicinal plant, copaifera langsdorfi desfon", Bioorganic and Medicinal Chemistry Letters 4(24), (Dec. 1994), 2889-2892.
Ondari, M.E., et al., "The Taxol Pathway 10-O-Acetyltransferase shows Regioselective Promiscuity with the Oxetane Hydroxyl of 4-deacetyltaxanes", J Am Chem Soc 130(50), (Nov. 14, 2008), 17187-17194.
Pateraki, Irini, et al., "Manoyl Oxide (13R), the Biosynthetic Precursor of Forskolin, Is Synthesized in Specialized Root Cork Cells in Coleus forskohlii", Plant Physiology, vol. 164, (Mar. 2014), 1222-1236.
Pelot, K. A., et al., "Biosynthesis of the oxygenated diterpene nezukol in the medicinal plant Isodon rubescens is catalyzed by a pair of diterpene synthases", PLOS One 12(4):e0176507, (2017), 17 pgs.
Pelot, K.A., et al., "Biosynthesis of the psychotropic plant diterpene salvinorin A: Discovery and characterization of the Salvia divinorum clerodienyl diphosphate synthase", Plant J 89(5): 885-897, 2017., (Mar. 2017), 13 pgs.
Peters, R.J., "Two Rings in them All: The labdane-related diterpenoids", Natural Product Reports 27(11): 1521-1530., (Oct. 1, 2010), 29 pgs.
Roengsumran, S., et al., "Labdane diterpenoids from Croton oblongifolius", Phytochemistry 50(3), (Feb. 10, 1999), 449-453.
Rudi, A., et al., "Chelodane, Barekoxide, and Zaatirin—Three New Diterpenoids from the Marine Sponge *Chelonaplysilla erecta*", J Nat Prod 55(10), (Oct. 1, 1992), 1408-1414.
Schalk, M., et al., "Toward a Biosynthetic Route to Sclareol and Amber Odorants", J Am Chem Soc 134(46), (2012), 18900-18903.
Scotti, M. T., et al., "SistematX, an Online Web-Based Cheminformatics Tool for Data Management of Secondary Metabolites", Molecules 23(1):103, (2018).
Sievers, et al., "Fast, Scalable Generation of High-Quality Protein Multiple Sequence Alignments Using Clustal Omega", Mol. Syst. Biol., vol. 7 (539), (2011), 1-6.
Stamatakis, A., "RAxML version 8: a tool for phylogenetic analysis and post-analysis of large phylogenies", Bioinformatics 30(9), (2014), 1312-1313.
Suzuki, H., et al., "Two labdane diterpenoids from Nicotiana setchellii", Phytochemistry 22(5), (1983), 1294-1295.
Toll, "Current Opinion in Plant Biology", vol. 9, (Apr. 2006), 297-304.
Urones, J. G., et al., "Compounds with the labdane skeleton from *Halimium viscosum*", Phytochemistry 35(3), (Feb. 1994), 713-719.
Vogel, B. S., et al., "Abietadiene synthase from grand fir (*Abies grandis*) cDNA isolation, characterization, and bacterial expression of a bifunctional diterpene cyclase involved in resin acid biosynthesis", J Biol Chem 271(38), (1996), 23262-23268.
Wu, C.L., et al., "Labdanoids and bis(bibenzyls) from *Jungermannia* species", Phytochemistry 44(1), (1997), 101-105.
Xiang, W., et al., "ent-Clerodanoids from Isodon scoparius", Helvetica Chimica Acta 87(11), (Nov. 24, 2004), 2860-2865.
Xu, H., et al., "Analysis of the Genome Sequence of the Medicinal Plant *Salvia miltiorrhiza*", Molecular Plant 9(6), (2016), 949-952.
Yamada, Y., et al., "Chemical diversity of labdane-type bicyclic diterpene biosynthesis in Actinomycetales microorganisms", The Journal of Antibiotics 69(7), (Jan. 27, 2016), 515-523.
Zerbe, P., et al., "Diterpene synthases of the biosynthetic system of medicinally active diterpenoids in Marrubium vulgare", Plant J. 79(6), (2014), 914-927.
Zerbe, P., et al., "Exploring diterpene metabolism in non-model species:transcriptome-enabled discovery and functionalcharacterization of labda-7,13E-dienyl diphosphate synthasefromGrindelia robusta", The Plant Journal, 83(5), (Jun. 28, 2015), 783-793.
Zerbe, P., et al., "Plant diterpene synthases: exploring modularity and metabolic diversity for bioengineering", Trends in Biotechnology 33(7)., (May 20, 2015), 419-428.
Zhan, X., et al., "Additional diterpenes from Physcomitrella patens synthesized by copalyl diphosphate/kaurene synthase (PpCPS/KS)", Plant Physiology and Biochemistry 96, (2015), 110-114.
U.S. Appl. No. 17/265,482, filed Feb. 2, 2021, Method for Production of Novel Diterpene Scaffolds.

0
1
2
3
4
5
6
7
8
9
10
11
12
13
14
15
16
17
18
19
20
21
22
23
24
25
26
27
28
29
30
31
32
33
34
35
36
37
38

SEQUENCE LISTING

```
Sequence total quantity: 177
SEQ ID NO: 1            moltype = AA  length = 588
FEATURE                 Location/Qualifiers
source                  1..588
                        mol_type = protein
                        organism = Ajuga reptans
SEQUENCE: 1
MSLSFTIKVT PFSGQRVHSS TESFPIQQFP TITTKSAMAV KCSSLSTATV SFQDFVGKIR  60
DTINGKVDNS PAATTIHPAD IPSNLCVVDT LQRLGVDRYF QSEIDSVLND TYRFWQQKGE  120
DIFTDVACRA MAFRLLRVKG YEVSSDELAS YAEQEHVNLQ PSDITTVIEL YRASQTRLYE  180
DEGNLEKLHT WTSNFLKQQL QSETISDEKL HKQVEYYLKN YHGILDRAGV RQSLDLYDIN  240
QYQNLKSTDR FPTLSNEDLL EFAKQDFNFC QAQHQKELQQ LQRWYADCKL DTLTYGRDVV  300
RVASFLTAAI FGEPEFSDAR LAFAKHIILV TRIDDFFDHG GSIEESYKIL DLVKEWEDKP  360
AEEYPSKEVE ILFTAVYNTV NDLAEMAYIE QGRSIKPLLI KLWVEILTSF KKELDSWTED  420
TELTLEEYLA SSWVSIGCRI CSLNSLQFLG ITLSEEMLSS EECMELCRHV SSVDRLLNDV  480
QTFEKERLEN TINSVSLQLA EAQREGRTIT EEEAMSKIKD LADYHRRQLM QMVYKDGTIF  540
PRQCKDVFLR VCRIGYYLYA SGDEFTTPQQ MMGDMKSLVY EPLNTSSS              588

SEQ ID NO: 2            moltype = DNA  length = 1767
FEATURE                 Location/Qualifiers
source                  1..1767
                        mol_type = other DNA
                        organism = Ajuga reptans
SEQUENCE: 2
atgtcactct cgttcaccat caaagtcacc cccttttcgg gccagagagt tcacagcagc  60
acagaaagct ttccaatcca acaatttcca acgatcacca ccaaatccgc catggctgtc  120
aaatgcagca gcctcagtac cgcaacagta agcttccagg atttcgtcgg aaaaatcaga  180
gatacgatca acgggaaagt tgacaattct ccagcagcga ccactattca tcctgcagat  240
ataccctcca atctctgcgt ggtggatacc ctccaaagat tgggagttga ccgttacttc  300
caatctgaaa tcgacagcgt tcttaacgac acatacaggt tctggcagca gaaaggagaa  360
gatatcttca ctgatgttgc ttgtcgtgca atggcatttc gacttttgcg agttaaagga  420
```

```
tatgaagttt catcagatga actggcttcg tatgctgaac aagagcatgt taacctgcaa  480
ccaagtgaca taactacggt tatcgagctt tacagagcat cacagacaag attatatgaa  540
gacgagggca atcttgagaa gttacatact tggactagca attttctgaa gcaacaattg  600
cagagtgaaa ctatttctga cgagaaattg cacaaacagg tggagtatta cttgaagaac  660
taccacggca tactagaccg tgctggagtt agacaaagtc tcgatttata tgacataaac  720
caataccaga atctaaaatc tacagataga ttccctactt taagtaacga agatttactt  780
gaattcgcga agcaagattt taacttttgc caagctcaac accagaaaga gcttcagcaa  840
ctgcaaaggt ggtatgcgga ttgtaaattg gatacattga cttacggaag agatgtggta  900
cgtgttgcaa gtttcctgac agctgcaatt tttggtgagc ctgaattctc tgatgctcgt  960
ctagccttcg ccaaacacat catcctcgtg acacgtattg atgatttctt cgatcatggt  1020
gggtctatag aagagtcata caagatcctg gatttagtaa aagaatggga agataagcca  1080
gctgaggaat atccttccaa ggaagttgaa atcctcttta cagcagtata taatacagta  1140
aatgacttgg cagaaatggc ttatattgag caaggccgtt ccattaaacc tcttctaatt  1200
aaactgtggg ttgaaatact gacaagtttc aagaaagaac tggattcatg gacagaagac  1260
acagaactaa ccttggagga gtacttggct tcctcctggg tgtcgatcgg ttgcagaatc  1320
tgcagtctca attcgctgca gttccttggt ataacattat ccgaagaaat gctttcaagc  1380
gaagagtgca tggagttgtg taggcatgtt tcttcagtcg acaggctact caatgacgtg  1440
caaactttcg agaaggaacg cctagaaaat acgataaaca gtgtgagcct acagctagca  1500
gaagctcaga gagaaggaag aaccattaca gaagaggagg ctatgtcaaa gattaaagac  1560
ctggctgatt atcacaggag acaactgatg cagatggttt ataaggatgg gaccatattt  1620
ccgagacaat gcaaagatgt ctttttgagg gtatgcagga ttggctacta cttatacgcg  1680
agcggcgatg aattcactac tccacaacaa atgatggggg atatgaaatc attggtttat  1740
gaacccctaa acacttcatc ctcttga                                     1767

SEQ ID NO: 3            moltype = AA  length = 567
FEATURE                 Location/Qualifiers
source                  1..567
                        mol_type = protein
                        organism = Leonotis leonurus
SEQUENCE: 3
MSVAFNLIVV RFPGHGIQSS RETFPAKIIT RTKSSMRFQS SLNTSTDFVG KIREMIRGKT  60
DNSINPLDIP STLCVIDTLH SFGIDRYFQS EINSVLHHTY RLWNDRNNII FKDVICCAIA  120
FRLLRVKGYQ VSSDELAPFA QQQVTGLQTS DIATILELYR ASQERLHEDD DTLDKLHDWS  180
SNLLKLHLLN ENIPDHKLHK RVGYFLKNYH GMLDRVAVRR NIDLHNINHY QIPEVADRFP  240
TEAFLEFSRQ DFNICQAQHQ KELQQLHRWY ADCRLDTLNH GTDVVHFANF LTSAIFGEPE  300
FSEARLAFAK QVILITRMDD FFDHDGSREE SHKILHLVQQ WKEKPAEEYG SKEVEILFTA  360
VYTTVNSLAE KACMEQGRSV KQLLIKLWVE LLTSFKKELD SWTEKMALTL DEYLSFSWVS  420
IGCRLCILNS LQFLGIKLSE EMLWSQECLD LCRHVSSVVR LLNDLQTFKK ERIENTINGV  480
DVQLAARKGE RAITEEEAMS KIKEMADHHR RKLMQIVYKE GTIFPRECKD VFLRVCRIGY  540
YLYSGDELTS PQQMKEDMKA LVHESSS                                     567

SEQ ID NO: 4            moltype = DNA  length = 1704
FEATURE                 Location/Qualifiers
source                  1..1704
                        mol_type = other DNA
                        organism = Leonotis leonurus
SEQUENCE: 4
atgtcggtgg cgttcaacct catagtcgtc cgttttccgg gccatggaat tcagagcagt  60
agagaaactt ttccagccaa aattattacc agaactaaat caagcatgag attccaaagc  120
agcctcaaca cttcaacaga tttcgtggga aaaataagag agatgatcag agggaaaact  180
gataattcta ttaatcccct ggatattccc tccactctat gcgtaatcga caccctacac  240
agcttcggaa ttgatcgcta ctttcaatcc gaaatcaact ctgttcttca ccacacatac  300
agattatgga acgacagaaa taatatcatc ttcaaagatg tcatttgctg cgcaattgcc  360
tttagacttt tgcgagtgaa aggatatcaa gtctcatcag atgaactggc gccatttgcc  420
caacaacagg tgactggact acaaacaagc gacattgcca cgattctaga gctctacaga  480
gcatcacagg agagattaca cgaagacgac gacactcttg acaaactaca tgattggagc  540
agcaaccttc tgaagctgca tctgctgaat gagaacattc ctgatcataa actgcacaaa  600
cgggtggggt atttcttgaa gaactaccat ggcatgctag atcgcgttgc ggttagacga  660
aacatcgacc ttcacaacat aaaccattac caaatcccag aagttgcaga taggttccct  720
actgaagctt ttcttgaatt ttcaaggcaa gattttaata tttgccaagc tcaacaccag  780
aaagaacttc agcaactgca taggtggtat gcagattgta gattggacac actgaatcac  840
ggaacagacg tagtacattt tgctaatttt ctaacttcag caattttcgg agagcctgaa  900
ttctccgagg ctcgtctagc ctttgctaaa caggttatcc taataacacg tatggatgat  960
ttcttcgatc acgatgggtc tagagaagaa tcacacaaga tcctccatct agttcaacaa  1020
tggaaagaga agcccgccga agaatatggt tcaaaggaag ttgagatcct ctttacagca  1080
gtgtacacta cagtaaatag cttggcagaa aaggcttgta tggagcaagg ccgtagtgtc  1140
aaacaacttc taattaagct gtgggtcgag ctgctaacaa gtttcaagaa agaattggat  1200
tcatggacgg agaagatggc gctaaccttg gatgagtact tgtctttctc ctgggtgtca  1260
attggctgca gactctgcat tctcaattcc ctgcaatttc ttgggataaa attatctgaa  1320
gaaatgctgt ggagtcaaga gtgtctggat ttatgccggc atgtttcatc agtggttcgc  1380
ctgctcaacg atttacaaac tttcaagaag gagcgcatag aaaatacgat aaacggtgtg  1440
gacgttcagc tagctgctcg taaaggcgaa agagccatta cagaagagga ggccatgtcc  1500
aagattaagg aaatggctga ccatcacagg agaaaactga tgcaaattgt gtataaagaa  1560
ggaaccattt ttccaagaga atgcaaagat gtgtttttga gagtgtgcag gattggctac  1620
tatctctact cgggcgatga gttaacttct ccacaacaaa tgaaggagga tatgaaagcg  1680
ttggtacatg aatcatcctc ttga                                        1704

SEQ ID NO: 5            moltype = AA  length = 751
FEATURE                 Location/Qualifiers
```

```
VARIANT                 1..751
                        note = Xaa = Any Amino Acid
source                  1..751
                        mol_type = protein
                        organism = Mentha spicata
SEQUENCE: 5
MSSIRNLSLH IDLPKAEKKL VEKIRERIRN GRVEMSPSAY DTAWVAMVPS RGYSGRPGFP  60
ECVDWIIENQ NPDGSWGLDS DQPLLVKDSL SSTLACLLAL RKWKTHNQLV QRGMEFIDSR  120
GWAATDDDNQ ISPIGFNIAF PAMINYAKEL NLTLPLHPPS IHSLLHIRDS EIRKRNWEYV  180
AEGVVDDTSN WKQIIGTHQR NNGSLFNSPA TTAAAVIHSH DDKCFRYLIS TLENSNGGWV  240
PTIYPYDIYA PLCMIDTLER LGIHTYFEVE LSGIFDDIYR NWQEREEEIF CNVMCRALAF  300
RLLRMRGYHV SSDELAEFVD KEEFFNSVSM QESGEGTVLE LYRASLTKIN EEERILDKIH  360
AWTKPFLKHQ LLNRSIRDKR LEKQVEYDLK NFYGALVRFQ NRRTIDSYDA KSIQISKTAY  420
RCSTVYNEDF IHLSVEDFKI SRAQYLKELE EMNKWYSDCR LDLLTKGRNA CRESYILTAA  480
IIVDPHESMA RISYAQSILL ITVFDDFFDH YGSKEEALNI IDLVKEWKPA GSYCSKEVEI  540
LFTALHDTIN EIAAKADAEQ GFSSKQQLIN MWVELLESAV REKDSLSXNK VSTLEEYLSF  600
APITIGCKLC VLTSVHFLGI KLSEEIWTSE ELSSLCRHGN VVCRLLNDLK TYEREREENT  660
LNSVSVQTVG GGVSEEEAVT KVEEVLEFHR RKVMQLACRR GGSSVPRECK ELVWKTCTIG  720
YCLYGHDGGD ELSSPKDILK DINAMMFEPL K                                751

SEQ ID NO: 6            moltype = DNA  length = 2256
FEATURE                 Location/Qualifiers
variation               1..2256
                        note = X - A, T, G or C
source                  1..2256
                        mol_type = other DNA
                        organism = Mentha spicata
SEQUENCE: 6
atgagttcca ttcgaaattt aagtttgcat attgatctgc caaaggccga gaagaagttg  60
gttgagaaaa tcagagagag gataagaaat gggagggtgg agatgtcgcc gtcggcttac  120
gacaccgcgt gggtggccat ggtgccgtct cgaggatatt ccggcaggcc gggtttcccg  180
gagtgcgtgg attggataat cgagaaccag aatccggacg ggtcgtgggg tttggattcg  240
gatcaaccac ttctggtcaa agactccctc tcgtccacct tggcatgcct acttgccctg  300
cgtaaatgga aacacacaa ccaactagtg caaaggggca tggagttcat cgactcccgt  360
ggttgggctg caactgatga tgacaatcag atttctccta ttggattcaa tattgccttt  420
cctgcaatga ttaattacgc caaagagctt aatttaactc tgcctctaca tccaccttcg  480
attcattcat tgttacacat tagagattca gaaataagaa agcgaaactg ggaatacgta  540
gctgaaggag tagtcgacga tacaagcaat tggaagcaaa taatcggcac gcatcaaaga  600
aataatggat ccttgttcaa ctcacctgct accactgcag ctgctgttat tcactctcac  660
gacgataaat gtttccgata tttgatctcc actcttgaga attctaacgg tggatgggta  720
ccaactatct atccatacga tatatacgct cctctctgca tgatcgatac gctagaaaga  780
ttaggaatac acacatattt tgaagttgaa ctcagcggca tttttgatga catatacagg  840
aattggcaag agagagaaga agagatcttt tgtaatgtta tgtgtcgagc tctggcattt  900
cggcttctac gaatgagggg atatcatgtt tcatctgatg aactagcaga atttgtggac  960
aaggaggagt tttttaatag cgtgagcatg caagagagcg gcgaaggcac agtgcttgag  1020
ctttacagag cttcactcac aaaaaatcaac gaagaagaaa ggattctcga caaaattcat  1080
gcatggacca aaccatttct caagcaccag cttctcaacc gcagcattcg cgacaaacga  1140
ttagagaagc aggtggaata cgacttgaag aacttctacg gcgcactagt ccgattccag  1200
aacagaagaa ccatcgactc atacgatgct aaatcaatcc aaatttcgaa aacagcatat  1260
aggtgctcta cagtttacaa tgaagacttc atccatttat ccgttgagga cttcaaaatc  1320
tcccgagcac aatacctaaa agaacttgaa gaaatgaaca agtggtactc tgattgtagg  1380
ttggacctct taactaaagg aagaaatgca tgtcgagaat cttacatttt aacagctgca  1440
atcattgtcg atcctcacga atccatggct cgaatctctt acgctcaatc tattcttctt  1500
ataactgttt tcgacgactt tttcgatcat tatgggtcta aagaagaggc tctcaatatt  1560
attgatctag tcaaggaatg gaagccagct ggcagttact gctccaaaga agtggagatt  1620
ttgtttactg cattacacga cacgataaat gagattgcag ccaaggctga tgcagagcaa  1680
ggcttttctt ccaaacaaca gcttatcaac atgtgggtgg agctacttga gagcgccgtg  1740
agagaaaagg actcgctgag tggnaacaaa gtgtcgactc tagaagagta cttatctttc  1800
gcaccaatca ccatcggctg caaactttgc gtcctgacgt ctgtccattt cctcggaatc  1860
aaactgtccg aggaaatctg gacttccgag gagttgagca gtctgtgcag gcacggcaat  1920
gttgtctgca gactgctcaa cgacctcaag acttacgaga gagagcgcga agagaacacg  1980
ctcaacagcg tgagcgtgca gacagtggga ggaggcgttt cggaggaaga ggcggtgacg  2040
aaggtggagg aggtgttgga atttcataga agaaaagtga tgcagctcgc gtgtcgaaga  2100
ggaggaagca gtgttccgag agaatgtaag gagctggtgt ggaagacgtg cacgataggt  2160
tactgcttgt acggtcacga cggaggcgat gagttatcgt ctccgaagga tattctaaag  2220
gacattaatg caatgatgtt tgagcctctc aagtga                           2256

SEQ ID NO: 7            moltype = AA  length = 800
FEATURE                 Location/Qualifiers
source                  1..800
                        mol_type = protein
                        organism = Nepeta mussinii
SEQUENCE: 7
MSLPLSSCVL FPPNDSRFPV SRFSRASASL EVGLQGATSA KVSSQSSCFE ETKRRITKLF  60
HKDELSVSTY DTAWVAMVPS PTSSEEPCFP GCLTWLLENQ CRDGSWARPH HHSLLKKDVL  120
SSTLACILAL KKWGVGEEQI NKGLHFIELN CASATEKCQI TPVGFDIIFP AMLDYARDFS  180
LNLRLEPTTF NDLMDKRDLE LKRCYQNYTP EREAYLAYIV EGMGRLQDWE LVMKYQRKNG  240
SLFNCPSTTA AAFIALRDSA CLNYLNLSLK KFGNAVPAVY PLDIYSQLCT VDNLERLGIN  300
QYFIAEIQSV LDETYRCWIQ GNEDIFLDTS TCALAFRILR MNGYDVTSDS LTKILEECFS  360
```

-continued

```
SSFRGNMTDI NTTLDLYRAS ELMLYPDEKD LEKHNLRLKL LLKQKLSTVL IQSFQLGRNI  420
NEEVKQTLEH PFYASLDRIA KRKNIEHYNF DNTRILKTSY CSPNFGNKDF FFLSIEDFNW  480
CQVIHRQELA ELERWLIENR LDELKFARSK SAYCYFSAAA TFFAPELSDA RMSWAKSGVL  540
TTVVDDFFDV GGSMEELKNL IQLVELWDVD ASTKCSSHNV HIIFSALRRT IYEIGNKGFK  600
LQGRNITNHI IDIWLDLLNS MMKETEWARD NFVPTIDEYM SNAYTSFALG PIVLPTLYLV  660
GPKLSEEMIN HSEYHNLFKL MSTCGRLLND IRGYERELKD GKLNALSLYI INNGGKVSKE  720
AGISEMKSWI EAQRRELLRL VLESNKSVLP KSCKELFWHM CSVVHLFYCK DDGFTSQDLI  780
QVVNAVIHEP IALKDFKVHE                                             800

SEQ ID NO: 8            moltype = DNA  length = 2403
FEATURE                 Location/Qualifiers
source                  1..2403
                        mol_type = other DNA
                        organism = Nepeta mussinii
SEQUENCE: 8
atgtctcttc cgctctcctc ttgtgtctta tttcccccca atgactcacg ttttccggtc  60
tcccgctttt ctcgcgcttc agcttctttg gaagtcgggc ttcaaggagc tacttcagca  120
aaagtctcct cacaatcatc gtgttttgag gagacaaaga gaaggataac aaagttgttt  180
cataaggacg aactttcggt ttcgacatat gacacagcat gggttgctat ggtcccttct  240
ccaacttctt cagaggaacc ttgcttccca ggttgtttga cttggttgct tgaaaaccag  300
tgtcgagatg gttcatgggc tcgtccccac catcactctt tgttaaaaaa agatgtcctt  360
tcttctacct tggcatgcat tctcgcactt aaaaaatggg gggttggtga agaacaaatc  420
aacaagggtt tgcattttat agagctaaat tgtgcttcag ctaccgagaa gtgtcaaatt  480
actcccgtgg ggtttgacat tatatttcct gccatgcttg attatgcaag agacttctct  540
ttgaacttgc gtttagagcc aactacgttt aatgatttga tggataaaag ggatttagag  600
ctcaaaaggt gttaccaaaa ttacacaccg gagagggaag catacttggc atatatagtt  660
gaaggaatgg gaagattgca agattgggaa ttggtgatga aatatcaaag aaagaatgga  720
tctcttttca attgtccatc tacaactgca gcagctttta ttgcccttcg ggattctgcg  780
tgcctcaact atctgaattt gtctttgaaa aagttcggga atgcagttcc tgcagtttat  840
cctctagata tatattctca actttgcacg gttgataatc ttgaaaggct ggggatcaac  900
caatatttta tagcagaaat tcagagtgtg ttggatgaaa cgtacagatg ttggatacag  960
ggaaacgaag acatattttt ggacacctca acttgtgctt tagcattccg aatattgaga  1020
atgaatggct atgatgtgac ttcagattca cttacaaaaa tcctagaaga gtgcttttca  1080
agttcctttc gtggaaatat gacagacatt aacacaactc ttgacttata tagggcatca  1140
gaacttatgt tatatccaga tgaaaaggat ctggagaaac ataatttaag gcttaaactc  1200
ttacttaagc aaaaactatc cactgtttta atccaatcat ttcaacttgg aagaaatatc  1260
aatgaagagg tgaaacagac tctcgagcat cccttttatg caagtttgga taggattgca  1320
aagcggaaaa atatagagca ttacaacttt gataacacaa gaattcttaa aacttcatat  1380
tgttcgccaa attttggcaa caaggatttc ttttttcttt ccatagaaga cttcaattgg  1440
tgtcaagtca tacatcgaca agaactcgca gaacttgaaa gatggttaat tgaaaataga  1500
ttggatgagc tgaagtttgc aaggagtaag tctgcatact gttattttc tgcggcagca  1560
actttttttg ctccagaatt gtcggatgcc cgcatgtcat gggctaaaag tggtgttcta  1620
accacagtgg tagatgactt ttttgatgtt ggaggttcta tggaggaatt gaagaactta  1680
attcaattgg ttgaactatg ggatgtggat gctagcacaa aatgctcttc tcataatgtc  1740
catataatat tttcagcact taggcgcacc atctatgaga tagggaacaa aggatttaag  1800
ctacaaggac gtaacattac caatcatata attgacattt ggctagattt actaaactct  1860
atgatgaaag aaaccgaatg ggccagagac aactttgtcc caacaattga tgaatacatg  1920
agcaatgcat atacatcgtt tgctctgggg ccaattgtcc ttccaactct ctatcttgtc  1980
gggcccaagc tctcagaaga gatgattaac cactccgaat accataacct attcaaattg  2040
atgagtacgt gcggacgtct tctaaatgac atccgtggtt atgagagaga actgaaagat  2100
ggtaaattga acgcgttatc attgtacata attaataatg gtggtaaagt aagtaaagaa  2160
gctggcatct cggagatgaa aagttggatc gaggcacaac gaagagagtt actgagatta  2220
gttttggaga gcaacaaaag cgtccttccg aagtcgtgca aggaattgtt ttggcatatg  2280
tgctcagtgg tgcatctatt ctactgcaaa gatgatggat tcacctcgca ggatttgatt  2340
caagttgtaa atgcagttat tcatgaacct attgctctca aggattttaa ggtgcatgaa  2400
taa                                                               2403

SEQ ID NO: 9            moltype = AA  length = 579
FEATURE                 Location/Qualifiers
source                  1..579
                        mol_type = protein
                        organism = Origanum majorana
SEQUENCE: 9
MASLAFTPGA ATFSGNVVRR RKDNFPVHGF PTTIRSSVSV TVKCYVSTTN LMVKIKEKFK  60
GKNVNSLTVE AADDDMPSNL CIIDTLQRLG IDRYFQPQVD SVLDHAYKLW QGKEKDTVYS  120
DISIHAMAFR LLRVKGYQVS SEELDPYIDV ERMKKLKTVD VPTVIELYRA AQERMYEEEG  180
SLERLHVWST NFLMHQLQAN SIPDEKLHKL VEYYLKNYHG ILDRVGVRRN LDLFDISHYP  240
TLRARVPNLC TEDFLSFAKE DFNTCQAQHQ KEHEQLQRWF EDCRFDTLKF GRETAVGAAH  300
FLSSAILGES ELCNVRLALA KHMVLVVFID DFFDHYGSRE DSFKILHLLK EWKEKPAGEY  360
GSEEVEILFT AVYNTVNELA EMAHVEQGRN IKGFLIELWV EIVSIFKIEL DTWSNDTTLT  420
LDEYLSSSWV SVGCRICILV SMQLLGVQLT DEMLLSDECI NLCKHVSMVD RLLNDVGTFE  480
KERKENTGNS VSLLLAAAVK EGRPITEEEA IIKIKKMAEN ERRKLMQIVY KRESVFPRKC  540
KDMFLKVCRI GCYLYASGDE FTSPQKMKED VKSLIYESL                         579

SEQ ID NO: 10           moltype = DNA  length = 1740
FEATURE                 Location/Qualifiers
source                  1..1740
                        mol_type = other DNA
                        organism = Origanum majorana
```

```
SEQUENCE: 10
atggcgtcgc tcgcgttcac acccggagcc gccactttct ccggcaacgt agttcggagg  60
aggaaagata actttccggt ccacggattt ccgacgacga tcaggtcatc ggtctccgtc  120
accgtcaaat gctacgtcag tacaacgaat ttgatggtga aaatcaaaga gaagttcaag  180
ggtaaaaacg tcaattcgct gacagttgaa gctgctgatg acgatatgcc ctctaatctg  240
tgcataattg acaccctcca acgattggga atcgaccgtt acttccaacc ccaagtcgac  300
tctgttctcg accacgccta caaactatgg caagggaaag agaaagatac ggtgtattcg  360
gacattagta ttcatgcgat ggcatttaga cttttacgag tcaaaggcta tcaagtctct  420
tcggaggaac tggatcccata catcgatgtg gagcgaatga agaaactgaa aacagttgat  480
gttccgacgg ttatcgaact gtacagagcg gcacaggaga gaatgtatga agaagaaggt  540
agccttgaga gactccatgt ttggagcacc aacttcctca tgcaccagct gcaggctaac  600
tcaattcctg atgaaaagct acacaaactg gtggaatact acttgaagaa ctaccatggc  660
atactggata gagttggagt tcgacgaaac ctcgacctat tcgacataag ccattatcca  720
acactcagag ctagggttcc gaacctatgt accgaagatt ttctatcgtt cgcgaaggaa  780
gatttcaata cttgccaagc ccaacaccag aaagaacatg agcaactaca aaggtggttc  840
gaagattgta ggttcgatac gttgaagttc ggaagggaga cagccgtagg cgctgctcat  900
tttctatctt cagcaatact tggtgaatct gaactatgta atgttcgtct tgcccttgct  960
aagcatatgg tgcttgtggt attcatcgat gacttcttcg accattatgg ctctagagaa  1020
gactccttca agatcctcca cctcttaaaa gaatggaaag agaagccggc cggagaatac  1080
ggttccgagg aagtcgaaat cctcttcaca gccgtataca atacagtaaa cgagttggcg  1140
gagatggctc atgtcgaaca aggacgtaat atcaaaggat ttctaattga attgtgggtt  1200
gaaatagtgt caattttcaa gatagaactg gatacatgga gcaatgacac aacactaacc  1260
ttggatgagt acttgtcctc ctcatgggtg tcggtcggtt gcagaatctg catcctcgtc  1320
tcaatgcagc tcctcggtgt acaactaacc gacgaaatgc ttctgagcga cgagtgcata  1380
aacctgtgta agcatgtctc gatggtcgat cgcctcctca acgacgtcgg aacattcgag  1440
aaggaacgga aggagaatac aggaaacagt gtgagccttc tgctagcagc agctgtgaaa  1500
gaaggaaggc ctattaccga agaggaagct attattaaaa ttaaaaaaat ggcggaaaac  1560
gagaggagga aactaatgca gattgtgtat aaaagagaga gtgttttccc cagaaaatgc  1620
aaggatatgt tcttgaaggt gtgtagaatt gggtgctatc tatacgcgag cggcgacgaa  1680
tttacgtctc ctcagaaaat gaaggaagat gtgaaatcct taatttatga atccttgtag  1740

SEQ ID NO: 11           moltype = AA  length = 563
FEATURE                 Location/Qualifiers
source                  1..563
                        mol_type = protein
                        organism = Origanum majorana
SEQUENCE: 11
MSLAFSHVST FFSGQRVVGS RREIIPVNGV PTTANKPSFA VKCNLTTKDL MVKMKEKLKG  60
QDGNLTVGVA DMPSSLCVID TLERLGVDRY FRSEIHVILH DTYRLWQQKD KDICSNVTTH  120
AMAFRLLRVN GYEVSSEELA PYANLEHFSQ QKVDTAMAIE LYRAAQERIH EDESGLDKIL  180
AWTTTFLEQQ LLTNSILDNK LHKLVEYYLN NYHGQTNRVG ARRHLDLYEM SHYQNLKPSH  240
SLCNEDLLAF AKQGFRDFQI QQQKEFEQLQ RWYEDCRLDK LSYGRDVVKI SSFMASILMD  300
DPELADVRLS IAKQMVLVTR IDDFFDHGGS REDSYKIIEL VKEWKEKAEY DSEEVKILFT  360
AVYTTVNELA EACVQQGRNS TTVKEFLVQL WIEILSAFKV ELDTWSDGTE VSLDEYLSWS  420
WISNGCRVSI VTTMHLLPTK LCSDEMLRSE ECKDLCRHVS MVGRLLNDIH SFEKEHEENT  480
GNSVSILVAG EDTEEEAIGK IKEIVEYERR KLMQIVYKRG TILPRECKDI FLKACRATFY  540
VYSSTDEFTS PRQVMEDMKT LSS                                          563

SEQ ID NO: 12           moltype = DNA  length = 1692
FEATURE                 Location/Qualifiers
source                  1..1692
                        mol_type = other DNA
                        organism = Origanum majorana
SEQUENCE: 12
atgtcactcg ccttcagcca tgttagtacc tttttctccg gccaaagagt cgtcggaagc  60
aggagagaga ttattccagt taacggagtt ccgacgacgg ccaataagcc gtcgttcgcc  120
gttaagtgca accttactac aaaggatttg atggtgaaaa tgaaggagaa gttgaagggg  180
caagacggta atttgactgt cggagtagcc gatatgccct ctagcctgtg cgtgatcgac  240
actcttgaaa ggttgggagt tgaccgatac ttccgatctg aaatccacgt tattctacac  300
gacacttacc ggttatggca acaaaaggac aaagatatat gttccaacgt tactactcat  360
gcaatggcgt ttagacttct gagagtgaat ggatacgagg tttcatcaga ggaactggct  420
ccatatgcta acctagagca ctttagccag caaaaagttg atactgcaat ggctatagag  480
ctctacagag cagcacagga gagaatacac gaagacgaga gcggtctcga caaaatactt  540
gcttggacca ccactttct cgagcaacag ctgctcacta actccattct tgacaataaa  600
ttgcataaac tggtggagta ctacttgaac aactaccacg gccaaacgaa tagggtcgga  660
gctagacgac acctcgacct atatgagatg agccattacc aaaatctaaa accttcacat  720
agtctatgca atgaagacct tctagcattt gcaaagcaag gttttcgaga ttttcaaatc  780
cagcagcaga aagaattcga gcaactgcaa aggtggtatg aagattgcag gttggacaag  840
ttgagttatg ggagagatgt agtaaaaatt tctagtttca tggcttcaat attgatggat  900
gatccagaat tagccgatgt tcgtctctcc atcgccaaac agatggtgct cgtgacacgt  960
atcgatgatt tcttcgacca cggtggctct agagaagact cctacaagat cattgaacta  1020
gtaaaagaat ggaaggagaa ggcagaatac gattccgagg aagtaaaaat cctttttaca  1080
gcagtataca cccacagtaaa tgagctagca gaggcttgtg ttcaacaagg aaggaatagt  1140
actactgtca aagaattcct agttcagttg tggattgaaa tactatcagc tttcaaggtc  1200
gagctagata cgtggagcga tggcacggaa gtaagcctgg acgagtactt gtcgtggtcg  1260
tggatttcga atggctgcag agtgtctata gtaacgacga tgcatttgct ccctacgaaa  1320
ttatgcagtg atgaaatgct taggagtgaa gagtgcaagg atttgtgtag gcatgtttct  1380
atggttggcc gcttgctcaa cgacatccac tcttttgaga aggagcatga ggagaatacg  1440
ggaaacagtg tgagcattct agtagcaggt gaggataccg aagaggaagc tattggaaag  1500
```

-continued

```
atcaaagaga tagttgagta tgagaggaga aaattgatgc aaattgtgta caagagagga  1560
accattctcc caagagaatg caaagacata ttcttgaagg cgtgtagggc tacattttac  1620
gtgtactcga gcacggatga gtttacgtct cctcgacaag tgatggaaga tatgaaaacc  1680
ctaagctcct ag                                                      1692

SEQ ID NO: 13          moltype = AA  length = 604
FEATURE                Location/Qualifiers
source                 1..604
                       mol_type = protein
                       organism = Origanum majorana
SEQUENCE: 13
MVSACLKLKN NPFLDHRFRK SSNGFSVNFP ATMLTTVKCS RDNSEDLIAK IKERMNEKFV  60
TVPAREYSVI EHRNPKPAWC GGLQSKTVIE EEVCSRLFLV EHLQDLGVDR FFQSEIQHIL  120
HHTFRLWQQK DEQVFKDVTC RAMAFRLLRL EGYHVSSGEL GEYVDEEKFF RTVRLEWRST  180
DTILELYKAS QVRLPEDDND NSNILKNLHE WTFIFLKEQL RRKTILDKGL ERKVEFYLKN  240
YHGILDAVKH RRSLDHTRFW KTTAYNPAVY DEDLFRLSAQ DFMARQAQSQ KELEMLLKWY  300
DECRLDKMEY GRNVIHVSHF LNANNFPDPR LSETRLSFAK TMTLVTRLDD FFDHHGSRED  360
SVLIIELIRQ WNEPSTITTI FPSEEVEILY SALHSTVTDI AEKAYPIQGR CIKSLIIHLW  420
VEILSSFMSE MDSCTAETQP DFHEYLGFAW ISIGCRICIL IAIHFLGEKV SQQMVMGAEC  480
TELCRHVSTI ARLLNDLQTF KKEREERKVN SVIIQLKGDK ISEEVAVSNI ERMVEYHRKE  540
LLKMVVRREG SLVPKRCKDV FWKSCNIAYY LYAFTDEFTS PQQMKEDMKL LFRDPINCVP  600
SIPS                                                               604

SEQ ID NO: 14          moltype = DNA  length = 1815
FEATURE                Location/Qualifiers
source                 1..1815
                       mol_type = other DNA
                       organism = Origanum majorana
SEQUENCE: 14
atggtatctg catgtctaaa actcaaaaat aatcctttct tggaccatcg attcaggaaa  60
agcagcaatg gattttcagt taattttccg gcgaccatgc tcaccactgt caagtgcagc  120
cgcgataatt cagaagactt gatagcaaag ataaaagaaa ggatgaatga aaaatttgtt  180
acggtgccgg cgagggaata ttccgtcatt gagcatcgga atccgaagcc ggcgtggtgc  240
ggtggtttgc aatccaaaac agtaatagaa gaagaagtgt gcagccgtct gtttctggtc  300
gaacaccttc aagatttagg agtagaccgc ttctttcaat cagaaatcca acatattcta  360
catcacacat tcagattatg gcagcaaaaa gatgaacaag tttttaaaga cgtgacatgt  420
cgcgccatgg cattcagact cctgcgtctc gaaggttatc atgtctcgtc aggagaattg  480
ggggagtatg ttgatgagga aaaattcttt agaacggtaa ggttagaatg gagaagtacg  540
gatacaattc ttgagctgta caaagcatca caggtaagac tacctgaaga cgacaacgac  600
aattccaata tcctcaaaaa cttgcacgaa tggaccttca tatttttgaa ggagcagttg  660
cggcgtaaaa ctattcttga taaaggttta gagagaaagg tagaatttta cttgaagaat  720
taccacggca tattagacgc ggttaagcat agacgaagcc tcgatcacac acgattctgg  780
aaaactactg cgtataaccc tgcagtgtat gatgaggatc ttttccgatt gtcggcccaa  840
gatttcatgg ctcgccaagc tcagagccag aaggaacttg agatgttgct caagtggtac  900
gatgaatgta gactggacaa gatggagtat gggcgaaacg tgatacacgt ttcccatttc  960
ttaaacgcaa acaacttccc cgatcctcgc ctgtccgaaa ctcgtctatc ctttgcgaaa  1020
accatgactc tcgtcacgcg tttggatgat ttcttcgatc accatggctc tagagaagat  1080
tcggtcctca tcatcgaatt aataaggcag tggaatgagc cttcaactat tacaacaata  1140
ttcccctccg aagaagtgga gattctctac tctgcactcc actccaccgt aacagatata  1200
gcagagaagg cttatcccat ccagggtcgc tgcatcaaat cgctcataat tcatctgtgg  1260
gtcgagatac tgtcgagctt catgagcgaa atggactcgt gcaccgcgga aactcagccg  1320
gactttcacg agtacttagg gtttgcatgg atctcgatcg gctgcagaat ctgcattctc  1380
atagctatac atttcttggg ggagaaggta tctcaacaaa tggttatggg tgctgagtgc  1440
accgagttat gtaggcacgt ttctacgatc gcacgccttc tcaacgatct ccaaaccttt  1500
aagaaggaga gagaagagag gaaggtaaac agcgtgataa tccagctcaa aggggataag  1560
atatcggagg aggtggccgt gtcgaatata gagagaatgg ttgaatatca caggaaagag  1620
ctgctgaaga tggtggttcg gagagaagga agcttggttc ctaagaggtg taaggacgtg  1680
ttctggaaat cctgcaacat tgcttactat ctgtacgctt ttacagatga attcacttcg  1740
cctcaacaaa tgaaggaaga tatgaaacta ctctttcgtg atccaatcaa ctgcgttcct  1800
tcaattcctt catga                                                   1815

SEQ ID NO: 15          moltype = AA  length = 584
FEATURE                Location/Qualifiers
source                 1..584
                       mol_type = protein
                       organism = Perovskia atriplicifolia
SEQUENCE: 15
MLLAFNISDV PLSQHRVILS RREHFPRHAF QEFPMIAATK SSVNAICSLA TPTDLMGKIK  60
EKFKAKDGDP LAAAAIQLAA DIPSSLCIID TLQRLGVDRY FQSEIDSILE ETHKLWKVKD  120
RDIYSEVTTH AMAFRLLRVK GYEVSSEELA PYAEQERFDL QTIDLATVIE LYRAAQERTC  180
EENDNSLEKL LAWTTTFLKH QLLTNSIPDT KLHKQVEYYL KNYHGILDRM GVRRSLDLYD  240
ISHYRPLRAR FPNLCNEDFL SFARQDFSMC QAQHQKELEQ LQRWYSDCRL DALLKFGRNV  300
VRVSSFLTSA IIGEPELSEV RLVFAKHIIL VTLIDDLFDH GGTREESYKI LELVTEWKEK  360
TAAEYGSEEV EILFTAVYNT VNELVERAHV EQGRSVKEFL IKLWVQILSI FKIELDTWSD  420
ETALTLDEYL SSSWVSIGCR ICILMSMQFI GIKLTDEMLL SEECTDLCRH VSMVDRLLND  480
VQTFEKERKE NTGNSVSLLL AANKDVTEEE AIRRAKEMAE CNRRQLMQIV YKTGTIFPRK  540
CKDMFLKVCR IGCYLYASGD EFTSPQQMME DMKSLVYEPL YLPN                   584

SEQ ID NO: 16          moltype = DNA  length = 1755
```

```
FEATURE                 Location/Qualifiers
source                  1..1755
                        mol_type = other DNA
                        organism = Perovskia atriplicifolia
SEQUENCE: 16
atgttacttg cgttcaacat aagcgatgtc cctctctcgc agcatagagt aattctgagc  60
aggagggaac attttccacg tcatgcattc caggaatttc cgatgatcgc cgctactaag  120
tcatctgtta atgccatttg cagcctcgct actccaactg atttgatggg aaaaataaaa  180
gagaagttca aggccaagga cggcgatcct cttgccgccg cggctattca actcgcggcg  240
gatataccct cgagtctgtg tataatcgac accctccaga ggttgggagt cgaccgatac  300
ttccaatccg aaatcgactc tattctagag gaaacacaca agttatggaa agtgaaagat  360
agagatatat actctgaggt tactactcat gcaatggcgt ttagacttct gcgagtgaag  420
ggatatgaag tttcatcaga ggaactagct ccgtatgctg agcaagagcg ctttgacctg  480
caaacgattg atctggcgac ggttatcgag ctttacagag cagcacagga gagaacatgc  540
gaagaaaacg acaacagtct tgagaaacta cttgcttgga ccaccacctt tctcaagcac  600
caattgctca ccaactccat acctgacacc aaattgcaca aacaggtgga atactacttg  660
aagaactacc acgggatatt agatagaatg ggagttagac gaagcctcga cctatacgac  720
ataagccatt atcgacctct gagagcaaga ttccctaatc tgtgtaatga agatttccta  780
tcatttgcga ggcaagattt cagtatgtgc caagcccaac accagaagga acttgagcaa  840
ctgcaaaggt ggtattctga ttgtaggttg gacgcgttgt tgaagtttgg aagaaatgta  900
gtgcgcgttt ctagctttct gacttcagca attattggtg aacccgaatt gtctgaagtt  960
cgactagtct ttgccaaaca tattattctc gttacactta ttgatgattt attcgatcat  1020
ggtggaacta gagaagagtc atacaagatc cttgaattag taacagaatg gaaagagaag  1080
accgcagcag aatatggttc cgaggaagtt gaaatccttt ttacagcggt ctacaacaca  1140
gtaaatgagt tggtagagag ggctcatgtc gaacaagggc gcagtgtcaa agaatttctt  1200
attaaactgt gggttcaaat actatcaatt ttcaagatag aattagatac atggagcgat  1260
gagactgcgc taaccttgga tgaatacttg tcttcgtcgt gggtgtcaat tggttgcaga  1320
atctgcattc tcatgtcgat gcaattcatc ggtataaaat taactgatga aatgcttctg  1380
agtgaagagt gcactgattt gtgtaggcat gtttcgatgg ttgaccggct gctcaacgat  1440
gtgcaaacct tcgagaagga acgcaaagaa aatacaggaa acagtgtaag ccttctgcta  1500
gcagctaaca aagatgttac tgaagaggaa gcaattagaa gagcaaaaga aatggcggaa  1560
tgcaacagga gacaactgat gcagattgtg tataaaacag gaaccatttt cccaagaaaa  1620
tgcaaagata tgtttctcaa ggtatgcagg attggctgtt atttgtatgc aagcggcgac  1680
gaattcacat ctccacaaca aatgatggaa gatatgaaat ccttggttta tgaacccctc  1740
tacctaccta attaa                                                   1755

SEQ ID NO: 17           moltype = AA  length = 593
FEATURE                 Location/Qualifiers
source                  1..593
                        mol_type = protein
                        organism = Perovskia atriplicifolia
SEQUENCE: 17
MSLTFNAGVV RFSSHRVRST KDCFTVYGFP MIANKAAFAV KCSLTPTDLM GRVEEKFKGK  60
NGNSLAASTT VESADIPSNL CIIDTLQRLG VDRYFQTEIN AILEDTYRLW ERKDKDIYSD  120
ATTHAMAFRL LRVKGYEVSS EELAPYADQE CVNVQTADVA TVIELYRAAQ VRISEEESSL  180
KKLHAWTTTF LKYQLQSNSI PEKKLHKLVE YYLKNYHGIL DRMGVRMDLD LFDISHYRTL  240
QASDRFSSLR NEDFLEFARQ DFNICQAKHQ KELQQLQRWY ADCRLDTLKF GRDVVRVANF  300
LTSAIFGEPE LSDARLIFAK HIVLVTCIDE FFDHGGSKEE SYKILELVEE WKEKPTGEYG  360
CEEVEILFTA VYSTVNELAE MAHVEQGRSV KEFLVKLWVQ ILSIFKIELD TWSDDTELTL  420
DSYLNNSWVS IGCRICILMS MQFAGVKLSD EMLLSEECVD LCRHVSMVDR LLNDVQTFEK  480
ERKENTGNSV SLLQAAAERE GRAITEEEAI TQIKELAEYH RRKLMQIVYK TDTIFPRKCK  540
DMFLKVCRIG CYLYASGDEF TTPQQMMEDM KSLVYQPLTV DDMSAKELTS VRN         593

SEQ ID NO: 18           moltype = DNA  length = 1782
FEATURE                 Location/Qualifiers
source                  1..1782
                        mol_type = other DNA
                        organism = Perovskia atriplicifolia
SEQUENCE: 18
atgtcactca ctttcaacgc tggagtcgtc cgtttctcca gccaccgcgt tcggagcacg  60
aaagattgct ttacagttta cggatttccg atgattgcaa ataaggcagc tttcgcagtt  120
aaatgcagcc ttactccaac cgatttgatg ggagagagtag aggagaagtt caagggcaaa  180
aatggtaatt cactagcagc ctcgacgacg gttgaatccg cggatatacc ctcgaacctg  240
tgtataatcg acaccctcca aagattggga gtcgaccgat actttcaaac tgaaatcaat  300
gccattctag aggacactta cagattatgg gaacgaaaag acaaagacat atattccgat  360
gccacaactc acgcgatggc gtttaggtta ctacgagtga aaggatacga agtttcatca  420
gaggaactgg ctccttacgc tgatcaagag tgcgtgaacg tgcaaacggc tgatgtggca  480
acagttatcg agctttacag agcagcgcag gtgagaataa gcgaagaaga gagcagtctt  540
aagaagcttc atgcttggac caccaccttt ctcaaatatc agttgcagag taactccata  600
cctgaaaaga aactgcacaa actggtggaa tattacttga agaactacca tggcatattg  660
gatagaatgg gagttcgaat ggacctcgac ttattcgaca tcagccatta tcgaactcta  720
caagcttccg ataggttctc tagtctgcgt aacgaagatt ttctagagtt tgcaaggcaa  780
gatttcaata tctgccaagc caagcaccag aaagaactcc aacaactgca aaggtggtat  840
gcagattgca ggctcgacac cttgaagttc gggagagacg tcgtacgcgt tgctaatttt  900
ctgacttcag caatctttgg cgaacccgag ctatccgatg ctcgtctgat ctttgccaag  960
catatcgtgc tcgtaacatg tatcgatgaa ttcttcgatc atggtgggtc taaagaagag  1020
tcctacaaga tccttgaatt agtagaagaa tggaaagaga agccaactgg agaatatggg  1080
tgtgaggagg ttgagatcct tttcacagca gtgtacagta cagtgaatga gttggcagag  1140
atggctcatg tcgaacaagg acgtagtgtg aaagagtttc tagttaaact gtgggtgcag  1200
```

-continued

```
atactgtcga ttttcaagat agaactggat acatggagtg atgacacgga actgacgttg  1260
gacagctact tgaacaactc gtgggtgtcg atcggatgca gaatctgcat tctcatgtcg  1320
atgcagttcg ccggtgtaaa actgtccgac gaaatgcttc tgagtgaaga gtgtgttgac  1380
ttgtgcaggc acgtctccat ggtcgatcgc ctcctgaacg atgtgcaaac tttcgagaag  1440
gaacgcaagg aaaatacagg aaacagtgtg agccttctgc aagcagcagc tgagagagaa  1500
ggaagagcca ttacagaaga ggaagctatt acacagatca aagaattggc tgaataccac  1560
aggagaaaac tgatgcagat tgtgtacaaa acagacacca ttttcccaag aaaatgcaaa  1620
gatatgttct tgaaggtgtg caggattggg tgctatctgt acgcaagtgg agacgaattc  1680
acaactccac aacaaatgat ggaagacatg aaatcattgg tttatcaacc cctaacagtt  1740
gatgacatga gtgccaaaga attgacttct gtgagaaact ag                    1782

SEQ ID NO: 19          moltype = AA  length = 590
FEATURE                Location/Qualifiers
source                 1..590
                       mol_type = protein
                       organism = Salvia officinalis
SEQUENCE: 19
MSLAFNAAVA TFSGHRIRSR REILPGQGFP MITNKSSFAV KCNLTTTDLM GKITEKFKGR  60
DSNFSAATAV QPAADIPSNL CIIDTLQRLG VDRYFQSEID TILEDTYRLW QRKEREIFSD  120
ITIHAMAFRL LRVKGYVVSS EELAPYADQE RINLQRIDVA TVIELYRAAQ ERISEDESSL  180
EKLHAWTATY LKQQLLTNSI PDKKLNKLVE CYLKNYHGIL DRMGVRQNLD LYDISHYQTL  240
KAADRFSNLR NEDFLAFARQ DFNICQEQHQ KELQQLQRWY ADCRLDTLKY GRDVVRVANF  300
LTSAIIGDPE LSEVRLVFAK HIVLVTRIDD FFDHGGSREE SYKILELLKE WKEKPAAEYG  360
SKEVEILFTA VYNTVNELAE MAHIEQGRSV KEFLIKLWVQ IISIFKIELD TWSDETALTL  420
DEYLSSSWVS IGCRICILMS MQFIGIKLSD EMLLSEECID LCRHVSMVDR LLNDVQTFEK  480
ERKENTGNSV SLLLAANKDD SAFTEEEAIT KAKEMAECNR RQLMKIVYKT GTIFPRKCKD  540
MFLKVCRIGC YLYASGDEFT SPQQMMEDMK SLVYEPLTVD PLEAKNVSGK            590

SEQ ID NO: 20          moltype = DNA  length = 1773
FEATURE                Location/Qualifiers
source                 1..1773
                       mol_type = other DNA
                       organism = Salvia officinalis
SEQUENCE: 20
atgtccctcg ccttcaacgc agcagttgcc actttctccg gccacagaat tcggagcagg  60
agagaaattc ttccggggca aggatttccg atgatcacca acaagtcgtc tttcgccgtg  120
aaatgtaacc ttactacaac agatttgatg ggcaagataa cagagaaatt caagggaaga  180
gacagtaatt tttcagcagc aacggctgtt caacctgcgg cggatatacc ctctaacctg  240
tgcataatcg acaccctcca aaggttggga gtcgaccgat acttccaatc tgaaatcgac  300
actattctag aggacacata caggttatgg caaaggaaag agagagagat attttcggat  360
ataactattc atgcaatggc atttagactt ttgcgagtta aaggatatgt agtttcatca  420
gaggaactgg ctccgtatgc tgaccaagag cgcattaacc tgcaaaggat tgatgtagcg  480
acagttatcg agctttacag agcagcacag gagagaataa gtgaagacga gagcagtctt  540
gagaaactac atgcttggac cgccacctat ctcaagcagc agctgctcac taactccatt  600
cctgacaaga aattgaacaa actggtggaa tgctacttga agaactatca cgggatatta  660
gatagaatgg gagttagaca aaacctcgac ctctacgaca taagccacta tcaaactcta  720
aaagctgcag ataggttctc taatctacgt aatgaagatt ttctagcatt tgcgaggcaa  780
gattttaata tttgccaaga acaacaccaa aaagaacttc agcaactgca aaggtggtat  840
gcagattgta ggttggacac attgaagtat ggaagagatg tcgtgcgggt tgctaatttt  900
ctaacatcag caattattgg tgatcctgaa ttgtctgaag tccgtctagt cttcgccaaa  960
catattgtgc ttgtaacacg tattgatgat tttttcgatc atggtggatc tagagaagag  1020
tcctacaaga tccttgaatt actaaaagaa tggaaagaga agccagctgc agaatatggt  1080
tccaaagaag ttgaaattct tttcacagca gtatacaata cagtaaacga gttggcagag  1140
atggctcaca tcgaacaagg acgtagtgtt aaagaatttc taataaagct gtgggttcaa  1200
atcatatcga ttttcaagat agaattagat acatggagcg atgagacagc gctgaccttg  1260
gatgagtact tgtcttcgtc gtgggtgtca attgggtgca gaatctgcat tctcatgtcg  1320
atgcaattca ttggtataaa attatctgat gaaatgcttc tgagtgaaga gtgtattgat  1380
ttgtgtcggc atgtctccat ggttgaccgg ctgctcaacg acgtgcagac tttcgagaag  1440
gaacgcaagg aaaatacagg aaatagcgtg agccttctgc tagcagctaa caaagacgac  1500
agcgccttta ctgaagagga agctattaca aaagcaaaag aaatggcgga atgtaacagg  1560
agacaactga tgaagattgt gtataaaaca ggaaccattt tcccaagaaa atgcaaagat  1620
atgtttctga aggtatgcag gattggctgt tacttgtatg caagcggcga tgaattcaca  1680
tctccacaac aaatgatgga agatatgaaa tccttggtct atgaacccct aacagttgat  1740
cctctcgagg ccaaaaatgt gagtggcaaa tga                              1773

SEQ ID NO: 21          moltype = AA  length = 798
FEATURE                Location/Qualifiers
source                 1..798
                       mol_type = protein
                       organism = Ajuga reptans
SEQUENCE: 21
MASLSTFHLY SSSLLHRKTL QSSPKLNLSS ECFSTRTWMN SSKNLSLNYQ VNQKIGKLTG  60
TRVATVDAPQ QLEHDDSTAK GHDIVDIETQ DPIEYIRMLL NTTGDGRISV SPYDTAWIAL  120
IKDVEGRDFP QFPSSLEWIA NHQLADGSWG DEGFFCVYDR LVNTIACVVA LRSWNVHHDK  180
SQRGIQYIKE NVHQLKDGNA EHMMCGFEVV FPALLQKAKN MGIDDLPYEA PVIQDIYHTR  240
EQKLKRIPLE MMHKVPTSLL FSLEGLENLD WDKLLKLQSA DGSFLTSPSS TAFAFMQTKD  300
EKCFQFIKNT VETFNGGAPH TYPVDVFGRL WAVDRLQRLG ISRFFEAEIA DCLSHIHRYW  360
NDKGLFSGRE SDFVDIDDTS MGFRLLRMQG YDVSPNVLRN FKNGDKFSCY GGQTIESSTP  420
IYNLYRASQF RFPGEEILEE ADKFAHEFLS EQLGNNQLLD KWVISDRLQE EISIGLGMPF  480
```

-continued

```
YATLPRVEAS YYIQHYAGAD DVWIGKTLYR MPEISNDTYL ELARNDFKRC QAQHQFEWIY  540
MQEWYESCNI EEFGISRKEL LRVYFLACSS IFEVERTKER MAWAKSQIIS RMITSFFNKQ  600
TTSSEEKETL LTEFRNINGL HKSNNTRDGD MNIVLATLHQ FFAGFDRYTS HQLKNAWGVW  660
LSKLQRGAVD GGADAELITT TINVCAGHIA LKEDILSHDE YKTLTDLTSK ICQQLSHIQN  720
EKVVEIDGGI TAKSRLKNEE LQRDMQSLVK LVLEKSVGLN RNIKQTFLTV AKTYYYRAYN  780
AEETMDAHIF KVLFEPVA                                               798

SEQ ID NO: 22          moltype = DNA  length = 2397
FEATURE                Location/Qualifiers
source                 1..2397
                       mol_type = other DNA
                       organism = Ajuga reptans
SEQUENCE: 22
atggcctctt tgtccacttt ccacctctac tcttcctcac tccttcaccg caaaacactg  60
caatcttcac caaagcttaa cctgtcttca gaatgcttct ccaccagaac ttggatgaac  120
agcagcaaaa acttgtcgtt aaattaccaa gttaatcaga aaataggaaa gctgacaggg  180
actcgagttg ccactgtgga tgcgccacaa caacttgaac acgatgattc aactgctaaa  240
ggccatgata tagtcgatat tgaaactcag gatccaattg aatatattag aatgctgttg  300
aacacaacag gcgatggcag aatcagcgtt tcgccttacg acacagcatg gattgctctt  360
attaaggacg tggaaggacg tgattttcct caatttccat ccagccttga gtggatcgcg  420
aaccatcaac tcgctgatgg ttcatgggga gacgaaggat ttttctgtgt gtatgatcgg  480
ctcgtaaata ctatagcatg tgtcgtagca ttgagatcat ggaatgtcca tcacgacaag  540
agccaaagag gaatacaata tatcaaggaa aatgtgcatc aacttaagga tggaaatgct  600
gagcacatga tgtgtggttt cgaagtagtg tttcctgcac ttcttcaaaa agccaaaaat  660
atgggcattg atgatcttcc atatgaggct cctgtcatcc aggatattta ccatacaagg  720
gagcagaaat tgaaaaggat accattggag atgatgcaca aagtgcctac ttctctgctg  780
tttagtttgg aaggactgga gaatttagat tgggataaac tccttaagtt gcagtcagct  840
gatggctctt tcctcacttc tccctcctct actgctttcg cattcatgca aacaaaagac  900
gaaaaatgct tccagttcat caagaacact gttgaaacct ttaatggagg agcaccacat  960
acttatccgg tcgatgtttt tggaagactt tgggcggttg ataggctgca gcgcctcgga  1020
atttctcgat tctttgaggc tgagattgct gattgcttaa gtcacattca tagatattgg  1080
aatgataagg ggcttttcag tggacgtgaa tcggactttg tcgatattga cgacacatcc  1140
atgggtttca gacttctaag aatgcaaggc tatgatgtta gtccaaatgt actgaggaat  1200
ttcaagaatg gtgacaagtt ttcatgttac ggaggtcaaa cgatcgagtc atcaactcca  1260
atatacaatc tgtacagagc ttctcaattc cggtttccag gagaagaaat tcttgaagaa  1320
gccgacaagt tcgcccatga gttcttgtcc gaacagcttg gcaacaacca attgcttgat  1380
aaatgggtta tatccgaccg cttgcaggaa gagataagta ttggattggg gatgccattt  1440
tatgccaccc ttcccagagt tgaagcaagc tactatatac aacattacgc tggtgccgac  1500
gacgtgtgga tcggcaagac actctacagg atgccggaaa taagtaatga tacatacctg  1560
gagctagcaa gaaatgattt caagagatgc caagcacaac atcagttcga gtggatctac  1620
atgcaagaat ggtatgagag ttgcaacatt gaagaattcg ggataagccg aaaggagctc  1680
cttcgcgttt actttttggc ttgctctagc atctttgagg tcgagaggac taaagagaga  1740
atggcatggg caaaatctca aattatttct agaatgatca cttctttctt taataaacaa  1800
actacttcat ctgaggaaaa agaaacactt ttaaccgaat tcagaaacat caacggtctg  1860
cacaaatcaa acaatacaag agatggagat atgaacattg tgcttgcaac cctccatcaa  1920
ttcttcgctg gatttgacag atatactagc catcaactga aaaatgcttg gggagtatgg  1980
ttgagcaagc tgcaacgagg agcagtagac ggtggagcag acgcagagct gataacaacc  2040
accataaacg tatgcgccgg tcatatagct cttaaggaag acatattgtc ccacgatgag  2100
tacaagactc tcaccgacct caccagcaag atttgtcagc agctttctca tattcaaaac  2160
gaaaaggttg tggaaattga cggtgggatt acagcaaaat ctaggttgaa gaatgaggaa  2220
ctgcaacgtg acatgcaatc attggtgaaa ttagtacttg agaaatcagt tgggctcaac  2280
cggaatataa agcaaacatt tctaacggtt gcaaaaacat actactacag agcctacaat  2340
gctgaggaaa ctatggatgc ccatatattc aaagttcttt tcgaaccagt tgcgtga     2397

SEQ ID NO: 23          moltype = AA  length = 798
FEATURE                Location/Qualifiers
source                 1..798
                       mol_type = protein
                       organism = Ajuga reptans
SEQUENCE: 23
MSFASQATSL LSSPNRLGHV PTPSSPARFA AGGAPFWKIL FTARSNGQYK AISRARNQGN  60
VEYIDEIQKG PQVVLEAENS LEDDTQKDTD QIRELVENVR VKLQNIGGGG ISISAYDTAW  120
VALVEDINGS GQPQFPTSLD WISNHQFPDG SWGSSKFLYY DRILCTLACI VALKTWNVHP  180
DKYHKGLDFI RENIHKLADE EEVHMPIGFE VAFPSIIETA KKVGIEIPED FPGKKEIYAK  240
RDLKLKKIPM DILHKMPTPL LFSIEGMEGL DWQKLFKFRD DGSFLTSPSS TAYALQQTKD  300
ELCLKYLTDL VKKDNGGVPN AFPVDLFDRN YTVDRLRRLG ISRYFQPEIE ECMKYVYRFW  360
DKRGISWARN TNVQDLDDTA QGFRNLRMHG YEVTLDVFKQ FEKCGEFFSF HGQSSDAVLG  420
MFNLYRASQV LFPGEHMLAD ARKYAANYLH KRRLNNRVVD KWIINKDLEG EVAYGLDVPF  480
YASLPRLEAR FYIEQYGGSD DVWIGKALYR MVNVSCDTYL ELAKLDYNKC QSVHQNEWKS  540
FQKWYKSCSL GEFGFSEGSL LQAYYIAAST IFEPEKSGER LAWAKTAALM ETIQQLSSQQ  600
KREFVDEFKH KNILKNENGE RYRSSTSLVE TLISTVNQLS SDILLEQGRD VHQELCHVWL  660
KWLSTWEERG NLVEAEAELL LRTLHLNSGL DESSFSHPKY QQLLEVSTKV CHLLRLFQKR  720
KVYDPEGCTT DIATGTTFQI EACMQELVKL VFSRSSEDLD SLTKLRFLDV ARSFYYTAHC  780
DPQVVESHID KVLFEKVV                                               798

SEQ ID NO: 24          moltype = DNA  length = 2397
FEATURE                Location/Qualifiers
source                 1..2397
                       mol_type = other DNA
```

organism = Ajuga reptans
SEQUENCE: 24
atgtcatttg cttcccaagc cacctccctc ctatcatccc ccaaccgtct cggccatgtt 60
ccgacgccaa gctcgccggc tcgtttcgct gccggtggtg ccccattttg gaagatatta 120
tttacagcta ggtctaatgg gcagtataaa gctatttcaa gagctcgtaa ccaaggaaat 180
gtagagtaca ttgatgagat tcagaaaggc ccgcaagtcg tattggaggc agaaaacagc 240
ttggaagatg acacacaaaa agatactgat cagataaggg aactagtgga aaatgtccga 300
gtaaagctgc agaatatcgg tggtggaggg ataagcatat cggcgtacga caccgcatgg 360
gtggcgctgg tggaggacat caacggcagt ggccagccac agtttccgac gagcctcgat 420
tggatatcga accatcagtt ccctgatggg tcatggggca gcagcaagtt tttgtattat 480
gatcggattc tatgcacatt agcatgtata gttgcattga aaacctggaa tgtgcatcct 540
gataagtacc acaaagggtt ggatttcatc agagagaaca ttcacaagct tgcggacgaa 600
gaagaagtgc acatgccaat tgggttcgaa gtggcattcc catcaattat tgaaacagct 660
aaaaaagtag gaatcgaaat ccctgaggat tttcctggca agaaagaaat ttatgcaaaa 720
agagatttaa agctaaaaaa aataccaatg gatatactgc ataaaatgcc cacaccattg 780
ctcttcagca tagaaggaat ggaaggcctt gactggcaaa agctattcaa attccgcgat 840
gatggctcgt ttcttacgtc tccgtcctca acagcctatg cactccagca aacaaaggat 900
gagctatgcc tcaagtatct aacagatctt gtcaagaaag acaacggagg agttccgaat 960
gcatttccag tagacctgtt tgatcgtaac tatacagtag accgcttgcg aaggctagga 1020
atttcacggt actttcaacc tgaaattgaa gaatgcatga aatatgttta cagattttgg 1080
gataaaagag gaattagctg ggcaagaaat accaatgttc aggaccttga tgacactgca 1140
cagggattca ggaatttaag gatgcatggt tatgaagtca ctctagatgt tttcaaacaa 1200
tttgagaaat gtggagagtt tttcagtttt catgggcaat ccagcgatgc tgttttagga 1260
atgttcaact tgtaccgggc ttctcaggtt ttatttccgg gagaacacat gcttgcagat 1320
gcgaggaagt atgcagccaa ctatttgcat aaacgaagac ttaataatag ggtggtcgac 1380
aaatggatta tcaacaaaga ccttgaaggc gaggtggcat atgggctaga tgttccgttc 1440
tacgccagcc tacctcgact cgaagcaagg ttctacatag aacaatatgg gggtagtgat 1500
gatgtgtgga ttggaaaagc tttatacaga atggtaaatg taagctgcga cacttacctt 1560
gagctagcaa aattagacta caacaaatgc caatccgtgc atcagaatga gtggaaaagc 1620
tttcaaaaat ggtacaaaag ttgcagtctt ggggagtttg ggttcagtga aggaagccta 1680
ctccaagctt actacatagc agcctcaact atattcgagc cagagaaatc aggagaacgc 1740
ctagcttggg ctaaaacagc agctctaatg gagacaattc aacaactttc cagccagcaa 1800
aaacgtgaat ttgttgatga attcaaacat aaaaacatac tgaagaatga aaatggagaa 1860
aggtatagat caagtaccag tttggtagag actctgataa gcactgtaaa tcagctctca 1920
tcagacatac tattggagca aggcagagac gttcatcaag aattatgtca cgtgtggcta 1980
aaatggctga gtacatggga ggaaagagga aacctggtgg aagcggaagc cgagcttctt 2040
ctgcgaacct tacatctcaa cagcggattg gatgaatcat cattttccca ccctaaatat 2100
caacagctct tggaggtgtc taccaaagtt tgccacctcc ttcgcctatt tcagaaacga 2160
aaggtgtatg atcccgaagg gtgtacaacc gacatagcaa caggaacaac gttccagata 2220
gaagcatgca tgcaagaact agtgaaatta gtgttcagca gatcctcaga agatttagat 2280
tctcttacta agttgagatt tttggatgtt gctagaagtt tctattacac tgcccattgt 2340
gatccacagg tggtcgagtc ccacatcgat aaagtattgt ttgagaaggt agtctag 2397

SEQ ID NO: 25 moltype = AA length = 800
FEATURE Location/Qualifiers
VARIANT 1..800
note = Xaa = Any Amino Acid
source 1..800
mol_type = protein
organism = Plectranthus barbatus
SEQUENCE: 25
MQASMSSLNL NNAPAVCSSR SQLSAKLHPP EYSTVGAWLN RGNKNQRLGY RIRPKQLSKL 60
TECRVASADV SQEIGKVGQS VRTPEEVNKK IEESIKYVKE LLMTSGDGRI SVAPYDTAIV 120
ALIKDLEGRD APEFPSCLEW IANNQKDDGS WGDDFFCIYD RIVNTIASVV ALKSWNVHPD 180
KIERGVSYIK ENAHKLKGGN LEHMTSGFEF VVPGCFDRAK ALGIEGLPYD DPIIKEIYAT 240
KERRLSKVPK DMIYKVPTTL LFSLEGLGME DLDWQKILKL QSGDGSFLTS PSSTAYAFMQ 300
TGDEKCYKFL QNAVRNCNGG APHTYPVDVF ARLWAVDRLQ RLGISRFFQP EIKFCLDHIK 360
NVWTKNGVFS GRDSEFVDID DTSMGIRLLK MHGYDVDPNA LKHFKQEDGR FSCYGGQMIE 420
SASPIYNLYR AAQLRFPGEE ILEEATKFAY NFLQQKLANN QIQEKWVISE HLIDEIKMGL 480
KMPWYATLPR VEASYYLQYY AASGDVWIGK TFYRMPEISN DTYKELALLD FNRCQAQHQF 540
EWIYMQEWYQ SNNIKEFGIS KKELLLAYFL AAATIFEPER SQERIVWAKT QVVSKMITSF 600
LSQENALSSX QKTALFIDFG HSINGLNQIT SVEKENGLAQ TVLATFGQLL EEFDRYTRHQ 660
LKNAWSQWFM KLQQGDDNGG ADAELLANTL NICAGHIAFN EDILSHNEYT SLSSLTNKIC 720
QRLSQIRDNK ILEIEDGSIK DKELEQEMQA LVKLVLEETG GIDRNIKQTF LSVFKMFYYR 780
AYHDAEAIDX HIFKVMFEPV 800

SEQ ID NO: 26 moltype = DNA length = 2406
FEATURE Location/Qualifiers
variation 1..2406
note = X =A, T, G, or C
source 1..2406
mol_type = other DNA
organism = Plectranthus barbatus
SEQUENCE: 26
atgcaggctt ctatgtcatc tctgaacttg aacaatgcac cggccgtctg cagcagcagg 60
tcacagctat ccgctaaact tcacccgccg gaatattcca ccgtgggtgc atggctgaat 120
cgtggcaaca aaaaccagcg gttgggctac cggattcgtc caaagcaact atcaaaacta 180
actgagtgtc gagtagcaag tgcagatgtg tcacaagaga ttggaaaagt cggccaatct 240
gttcggactc ctgaagaggt aaataaaaag atagaggaat ccatcaagta cgtgaaggag 300

-continued

```
ctgctgatga cgtcgggcga cgggcgaatc agtgtggcgc cctacgacac ggccatagtt  360
gcccttatca aggacttgga agggcgcgat gccccggagt ttccatcttg cttggagtgg  420
attgcaaaca atcaaaaaga cgatggttct tggggggatg acttcttctg catctatgat  480
cggatcgtta ataccatagc atccgtcgtc gccttaaaat catggaatgt gcacccagac  540
aagattgaga gaggagtatc ctacatcaag gaaaacgcgc ataaactaaa aggtgggaat  600
ctcgaacaca tgacatcagg gttcgagttc gtggttcccg gctgttttga cagagccaaa  660
gccttgggga tcgaaggcct tccctatgat gatcccatca tcaaggagat ttatgctaca  720
aaagaaagga gattgagcaa ggtaccgaag gacatgatct acaaagttcc gacaactcta  780
ttgtttagtt tagagggact gggcatggag gatttggact ggcaaaagat actgaaactg  840
cagtcgggcg acggctcatt cctcacctct ccgtcgtcca ccgcctacgc attcatgcag  900
accggagacg aaaaatgcta caaattcctc cagaacgccg tcagaaattg caacggcgga  960
gcgccgcaca cttatccagt cgacgtcttt gcacggctct gggcggtcga ccgacttcag  1020
cgactcggaa tttctcgctt ctttcagccc gagatcaagt tttgcctaga ccacatcaaa  1080
aatgtgtgga ctaagaacgg agttttcagt ggacgggatt cagagtttgt ggatatcgac  1140
gacacatcca tgggcatcag gcttctgaaa atgcacggat acgatgtcga cccaaatgca  1200
ctgaaacatt tcaagcagga ggatgggagg ttttcatgct acggtggtca aatgatcgag  1260
tctgcatctc cgatttacaa tctctacagg gctgctcagc ttcgttttcc aggagaagaa  1320
attcttgaag aagccactaa atttgcctac aacttcctgc aacagaagct ggccaacaat  1380
caaattcaag aaaagtgggt catatccgag cacctaattg atgagataaa aatgggattg  1440
aagatgccat ggtacgccac cctacctaga gttgaggctt catactatct ccaatattat  1500
gcagcttctg gcgacgtatg gattggcaag actttttaca ggatgccaga aataagtaat  1560
gacacgtaca aagagcttgc actattggat ttcaaccgat gccaagcaca acatcagttc  1620
gaatggattt acatgcaaga gtggtatcaa agcaacaaca ttaaagaatt tgggataagc  1680
aagaaagagc ttcttcttgc ttacttcttg gctgctgcaa ccatttttga acccgaacga  1740
tcgcaagagc ggatcgtgtg ggctaaaacc caagttgttt ctaagatgat cacatcgttt  1800
ctgtctcaag aaaacgcttt gtcatcggan caaaagactg cactttttcat cgatttttggg  1860
catagtatca atggcctcaa tcaaataact agtgttgaga aagagaatgg gcttgctcag  1920
actgtgctgg caaccttcgg acaactactc gaggaattcg acagatacac aaggcatcaa  1980
ctgaaaaatg cttggagcca atggttcatg aaactgcagc aaggagatga caatggcggg  2040
gcagacgcag agctcctagc aaacacattg aacatctgcg ctggtcatat tgcttttaac  2100
gaagacatat tatctcacaa cgaatacacc tctctctcct ccctcacaaa caaaatctgt  2160
cagcggctaa gtcaaattcg agataataag atactggaaa ttgaggatgg gagcataaaa  2220
gataaggaac tagaacagga aatgcaggcg ctggtgaagt tagtcctgga agaaaccggt  2280
ggcatcgaca ggaacatcaa gcaaacattt ttgtcagttt tcaaaatgtt ttactacaga  2340
gcctaccacg atgctgaggc tatcgatgnc catattttca aagtaatgtt tgaaccagtc  2400
gtatga                                                             2406
```

```
SEQ ID NO: 27          moltype = AA  length = 776
FEATURE                Location/Qualifiers
source                 1..776
                       mol_type = protein
                       organism = Hyptis suaveolens
SEQUENCE: 27
MAYMISISNL NCSSLLNTNL SAKIQLHQGL KGTWLKTSKR MCMDQQVHGK QIAKVIESRV  60
TDKDVSTAQD FEVLKVNRVE DLISSIKSSL KTMEDGRISV SPYSTSWIAL IPSIDGRQTP  120
QFPSSLEWIV KHQLSDGSWG DALFFCVYDR LVNTIACIIA LHTWKVHADK VKKGVSFVKE  180
NIWKLEDANE VHMTSGFEVI FPILLRRARD MGIDGLPSDD TPVVRMISAA RDHKLKKIPR  240
EVMHQVTTTL LYSLEGLEDL DWSRLFKLQS ADGSFLTSPS STAFAFMQTN NHNCLRFITS  300
VVQTFNGGAP DNYPIDIFAR LWAVDRLQRL GISRFFEQEI NDCLSYVYRF WNANGVFSAG  360
ATNFCDLDDT SMAFRLLRLH GYDVDPNVLR KFKEGDRFCC HSGEVAMSTS PTYALYRASQ  420
IQFPGEEILD EAFSFTRDYL QDWLARDQVL DKWIVSKDLP DEIKVGLEVP WYASLPRVEA  480
AYYMQRHYGG STDAWVAKTC YRMPDVSNDD YLELARLDFK RCQAQHQSEL SYMQRWYDSC  540
NVEEFGISRK ELLVAYFVAA ATIFEPERAT ERIVWAKTEI VSKMIKAFFG EDSLDQKTML  600
LKEFRNSINN GSHRFMKSEH RIVNILLQAL QELLHGSDDC RIGQLKNAWY EWLMKFEGGD  660
EASLWGEGEL LVTTLNICTA HFLQHHDLLL NHDYITLSEL TNKICLKLSQ IQVGEMNEMR  720
EDMQALTKLV IGESCIVNKN IKQTFLAVAK TFYYRAYFDA DTVDLHIFKV LFEPIV      776
```

```
SEQ ID NO: 28          moltype = DNA  length = 2331
FEATURE                Location/Qualifiers
source                 1..2331
                       mol_type = other DNA
                       organism = Hyptis suaveolens
SEQUENCE: 28
atggcgtata tgatatctat ttcaaatctc aactgttcct cgctactaaa caccaatctt  60
tcagcaaaga ttcagctgca ccaaggtctc aaaggaacat ggctaaaaac cagcaaacgc  120
atgtgcatgg atcaacaggt tcatggcaag cagatagcaa aagtgatcga gagccgagtt  180
actgataagg atgtttccac tgctcaggac tttgaagtgt taaaggtcaa tagagtggag  240
gatctgatat caagcattaa gagttcattg aagacaatgg aagatggaag aataagcgtg  300
tcgccctaca gcacatcatg gatcgcactc attccaagta ttgatgggcg ccagacgccc  360
cagtttccat cttcactgga gtggatcgtg aagcatcagc tatcagatgg ttcatggggt  420
gatgcccttt ttttctgcgt ttatgatcgt ctcgtaaata cgattgcatg catcattgcc  480
ctgcacacct ggaaggttca tgcagacaag gttaaaaaag gagtaagttt tgtgaaggaa  540
aatatatgga aacttgaaga cgccaacgag gtccacatga ctagtggttt cgaagttata  600
tttcccatcc ttcttcgaag agcacgagac atgggaattg atggtcttcc ttctgatgat  660
actccagttg ttaggatgat ttctgctgct agggatcaca aattgaaaaa gattccgagg  720
gaggtgatgc accaagtgac aacaactcta ttatatagtt tggaagggtt ggaagattta  780
gactggtcaa ggcttttcaa acttcagtca gctgatggtt cattcttaac ttctccatct  840
tcaactgcct tcgcattcat gcaaactaat aaccacaatt gcttgagatt catcactagc  900
gttgtccaaa cattcaatgg aggagctcca gataactatc caatcgacat ctttgcgaga  960
```

```
ctgtgggcag ttgacaggtt acagcggtta gggatttctc gtttcttcga gcaggagata  1020
aatgattgcc taagctatgt atatagattt tggaatgcaa atggagtttt cagtgcagga  1080
gccactaatt tttgtgatct tgacgacaca tccatggctt tccggctact acgtttgcat  1140
ggatatgatg tcgacccaaa tgttctgagg aaattcaaag agggagacag attctgttgc  1200
cacagtggtg aagtggcgat gtcgacatcg ccaacgtacg ctctctacag agcttcccaa  1260
attcagtttc caggagaaga aattctggat gaagccttca gcttcactcg cgactatcta  1320
caggactggt tagcaagaga tcaagttctt gataagtgga ttgtatccaa ggaccttcca  1380
gatgagatta aggtaggact agaggtgcca tggtatgcca gcctgccacg ggtagaggct  1440
gcttattaca tgcaacgaca ttacggcggg tctactgatg cgtgggtggc caagacttgt  1500
tacaggatgc ctgatgtgag caacgatgat tacctggagc ttgcaagatt ggatttcaag  1560
agatgtcaag cccaacatca gagtgaattg agttacatgc aacgatggta tgacagttgc  1620
aatgtcgaag aattcggaat aagcagaaaa gagttgcttg tagcttattt tgtggctgct  1680
gcaactattt ttgaacctga gagagcaact gagagaattg tgtgggcaaa aactgaaata  1740
gtttctaaga tgatcaaagc atttttggt gaagactcat tagaccaaaa aactatgttg  1800
ttaaaagaat tcagaaacag catcaataat ggctcccaca gattcatgaa gagtgagcat  1860
agaatcgtca acattctact acaagccttg caggagctat tacatggatc tgatgattgt  1920
cgtattggtc aactcaaaaa tgcttggtat gagtggctga tgaaattcga gggaggagat  1980
gaagcaagtt tgtggggaga aggagagctt cttgtcacca ccttaaacat ttgcacagct  2040
catttccttc aacaccatga tttactgttg aatcatgact acataactct ttctgagctc  2100
acaaacaaga tctgcctcaa gctttctcag attcaggtag gagaaatgaa tgaaatgaga  2160
gaagatatgc aggcgttgac gaaattagtg attggggaat catgcatcgt caacaaaaac  2220
attaagcaaa catttcttgc agttgcaaag actttctatt acagagccta cttcgatgcc  2280
gacaccgttg atctccatat atttaaagtt ctatttgagc ccattgtctg a           2331

SEQ ID NO: 29          moltype = AA  length = 787
FEATURE                Location/Qualifiers
source                 1..787
                       mol_type = protein
                       organism = Leonotis leonurus
SEQUENCE: 29
MASTASTLNL TINSTPFVST KTQAKVSLPA CLWMQDRSSS RHVSLKHKFC RNQQLKCRAS  60
LDVQQVRDEV FSTAQSPESV DKKIEERKKW VKNLLSTMDD GRINWSAYDT AWISLIKEFE  120
GRDAPQFPST LMRIAENQLA DGSWGDPDYD CSYDRIINTL ACVVALTTWN AHPEHNKKGI  180
KYIKENMYKL EETPVVLMTS AFEVVFPALL NRAKNLGIQD LPYDMPIVKE ICKIGDEKLA  240
RIPKKMMEKE PTSLMYAAEG VENLDWEKLL KQRTPENGSF LSSPAATAVA FMHTKDENCL  300
RYIMYLLDKF NGGAPNVYPI DLWSRLWATD RIQRLGISRF FKEEIKEILS YVYSYWTDIG  360
VYCTRDSKYA DIDDTSMGFR LLRMHGFKMD PNVFKYFQKD DRFVCLGGQM NDSPTATYNL  420
YRAAQYQFPG EKILEDARKF SQEFLQHCID TNNLLDKWVI SPRFPEELKF GMEMTWYSCL  480
PRIEARYYVQ HYGATEDVWL GKTFFRMEEI SNENYKELAK LDFSKCQAQH QTEWIHMQEW  540
YESSNAKEFG ISRKDLLFAY FLAAASIFET ERAKERILWA KSQIICKMVK SYLENQTASL  600
EHKIAFLTGF GDNNNGLHTI NKGSGPVNNV MRTLQQLLGE FDGYISSQLE NAWAAWLTKL  660
EQGEANDGEL LATTLNICSG RIVYNEDTLS NKEYKAFADL TNKICQNLAQ IQNKKGDEIK  720
DPNEGEKDKE VEQGMQALAK LVFEESGLER SIKETFLAVV RTYHYGAYVA DEKIDVHMFK  780
VLFEPVE                                                            787

SEQ ID NO: 30          moltype = DNA  length = 2364
FEATURE                Location/Qualifiers
source                 1..2364
                       mol_type = other DNA
                       organism = Leonotis leonurus
SEQUENCE: 30
atggcctcca ctgcatccac tctaaatttg accatcaata gtacaccatt tgtaagcacc  60
aaaacgcaag caaaggtttc cttgcccgca tgtttatgga tgcaggatag aagcagcagt  120
agacacgtgt cgttaaaaca caaattctgt cgaaatcaac aacttaagtg tcgagcaagt  180
ctggatgttc agcaagtacg tgatgaagtt ttttccactg ctcaatcccc tgaatcggtg  240
gataaaaaaa tagaggaacg taaaaaatgg gtgaagaatt tgttgagtac aatggacgat  300
ggacgaataa attggtcagc ctatgacacg gcatggattt cacttattaa agaatttgaa  360
ggacgagatg ctccccagtt tccgtcgact ctcatgcgca tcgcggagaa ccaattggcc  420
gacgggtcat ggggcgatcc agattacgac tgctcctatg atcggataat aaacacacta  480
gcgtgtgttg tagccttgac aacatggaat gctcatcctg aacacaataa aaaaggaata  540
aaatacatca aggaaaatat gtataaacta gaagagacgc ctgttgtact catgactagt  600
gcatttgaag ttgtgtttcc ggcgcttctt aacagagcta aaaacttggg cattcaagat  660
cttccctatg atatgcccat cgtgaaggag atttgtaaaa taggggatga gaagttggca  720
aggataccaa agaaaatgat ggagaaagag ccaacatcgc tgatgtatgc cgcggaagga  780
gtcgaaaact tggactggga aaagcttctg aaacagcgga cacccgagaa tggctcgttc  840
ctctcttccc cggccgcaac tgccgttgca tttatgcaca caaaagatga aaattgctta  900
agatacatca tgtacctttt ggacaaattt aatggaggag caccaaatgt ttatccgatc  960
gacctctggt caagactttg ggcaacggac aggatacaac gtctgggaat ttcccgcttc  1020
tttaaggaag agattaagga aatcttaagt tatgtctata gctattggac agacattgga  1080
gtctattgta cacgagattc caaatatgct gacattgacg acacatccat gggattcagg  1140
cttctgagga tgcacggatt taaaatggac ccaaatgtat ttaaatactt ccagaaagac  1200
gacagatttg tttgtctagg tggtcaaatg aatgattctc caactgcaac atacaatctt  1260
tacagggctg ctcaatacca atttccaggt gaaaaaattc tagaagatgc tagaaagttc  1320
tctcaagagt ttctacaaca ttgtatagac accaataacc ttctagataa atgggtgata  1380
tccccgcgct ttccggaaga gttgaaattt ggaatggaga tgacatggta ttcctgccta  1440
ccacgaattg aggctagata ctacgtacaa cattatggtg ctacagagga cgtctggctt  1500
ggaaagactt ttttcaggat ggaagaaatc agtaatgaga actataagga gcttgcaaaa  1560
cttgatttca gtaaatgcca agcacaacat cagacagagt ggattcatat gcaagagtgg  1620
tatgaaagta gcaatgctaa ggaatttggg ataagcagaa aagacctact tttgcttac   1680
```

-continued

```
tttttggctg cagcttccat atttgaaacc gaaagggcaa aagagagaat tctgtgggca  1740
aaatctcaaa ttatttgcaa gatggttaag tcatatctgg aaaaccaaac ggcgtcgttg  1800
gagcacaaaa tcgccttttt aactggattc ggagataaca acaatggcct gcacacaatt  1860
aataaggggt ctggacctgt taacaatgtc atgagaaccc tccaacagct ccttggagaa  1920
ttcgacggat atattagtag tcaattggaa aatgcttggg cagcatggtt gacgaaactc  1980
gagcaaggcg aggccaacga tggcgagctc ctcgcaacca cactaaacat ttgttctggg  2040
cgtattgtgt ataacgagga tacattatcg aacaaggagt acaaggcttt cgcagacctc  2100
acaaataaaa tttgtcaaaa tcttgctcaa atccaaaata aaaagggtga cgaaattaag  2160
gatccgaatg aaggcgaaaa ggacaaggaa gtcgagcaag gcatgcaggc attggctaag  2220
ttagtttttg aggaatctgg gcttgagagg agtatcaaag aaacattctt agcagtggtg  2280
agaacttatc actatggggc ctatgttgct gatgagaaga ttgatgtcca catgttcaag  2340
gttttgttcg aaccagttga atga                                          2364

SEQ ID NO: 31           moltype = AA  length = 799
FEATURE                 Location/Qualifiers
source                  1..799
                        mol_type = protein
                        organism = Nepeta mussinii
SEQUENCE: 31
MTSISSLNLS NAAAARRRLQ LPANVHLPEF HSVCAWLNSS SKHDPFSCRI HRKQKSKVTE  60
CRVASVDASP VSDHKMSSPV QTQEEANKNM EESIEYIKNL LMTSGDGRIS VSAYDTSIVA  120
LIKDIEGRDA PQFPSCLEWI GQNQKADGSW GDDFFCIYDR FVNTLACIVA LKSWNLHPHK  180
IQKGVTYIKK NVHKLKDGRP ELMTSGFEIC VPAILQRAKD LGIQDLPYDD PMIKQITDTK  240
ERRLKKIPKD FIYQLPTTLL FSLEGQENLD WEKILKLQSA DGSFLTSPSS TAAVFMHTKD  300
EKCLKFIENA VKNCDGGVPH TYPVDVFARL WAVDRLQRLG ISRFFQPEIK YFLDHIQSVW  360
TENGVFSGRD SQFCDIDDTS MGIRLLKMHG YKIDPNALEH FKQEDGKFSC YGGQMIESAS  420
PIYNLYRAAQ LRFPGEEILE EAIKFSYNFL QEKLAKDEIQ EKWVISEHLI DEIKIGLKMP  480
WYATLPRVEA AYYLDYYAGS GDVWIGKTFY RMPEISNDTY KEMAILDFNR CQAQHQFEWI  540
YMQEWYESSN VKEFGISKKE LLVAYFLAAS TIFEPERAQE RIMWAKTKIV SKMIASSLNK  600
QTTLSLDQKT ALFTQLEHSL NGLDSDEKDN GVAETKNLVA TFQQLLDGFD KYTRHQLKNA  660
WSQWLKQVQQ GEATGGADAE LEANTLNICA GHIAFNEQVL SHNEYTTLST LTNKICHRLT  720
QIQDKKTLEI IDGGIRYKEL EQEMQALVKL VVEENDGGGI DRNIKQTFLS VFKNYYYSAY  780
HDAHTTDVHI FKVLFGPVV                                                799

SEQ ID NO: 32           moltype = DNA  length = 2400
FEATURE                 Location/Qualifiers
source                  1..2400
                        mol_type = other DNA
                        organism = Nepeta mussinii
SEQUENCE: 32
atgacttcaa tatcctctct aaatttgagc aatgcagcag ctgctcgccg caggttacaa  60
ctaccagcaa acgttcacct gccggaattt cactccgtct gtgcatggct gaatagcagc  120
agcaaacacg atccctttag ttgccgaatt catcgaaagc aaaaatcgaa agtaaccgag  180
tgtcgagtag caagcgtgga tgcatcacca gtgagtgatc ataaaatgag ttctcctgtt  240
caaactcaag aagaggcaaa taaaaatatg gaggagtcaa tcgagtacat aaagaatttg  300
ttgatgacat ctggagacgg gcgaataagc gtgtcggcat acgacacgtc aatagtcgcc  360
ctaattaagg acatagaagg acgggacgcc ccgcaatttc catcatgcct ggagtggatc  420
gggcaaaacc aaaaggccga tggctcgtgg ggggacgact tcttctgtat ttacgaccgc  480
ttcgtaaata cactagcatg tatcgtggcc ttgaaatcat ggaaccttca ccctcacaag  540
attcaaaaag gagtgacata catcaagaaa aacgtgcata agcttaaaga tgggaggcct  600
gagctgatga cgtcagggtt cgaaatttgt gttcccgcca ttcttcaaag agccaaagac  660
ttgggcatcc aagatcttcc ctatgatgat cccatgatta aacagatcac tgatacgaaa  720
gagcgacgac tcaaaaagat accgaaggat tttatatacc aattgccgac gactttactc  780
ttcagtttgg aagggcagga gaatttggac tgggaaaaga tactcaaact gcagtcagct  840
gacggctcct tccttacttc gccgtcctcc accgccgccg tcttcatgca taccaaagat  900
gaaaaatgct tgaagttcat agagaacgcc gtcaaaaatt gcgacggcgg agtgccccat  960
acctacccag tagacgtgtt tgcaagactt tgggcagttg acagactaca acgcctaggg  1020
atttctcgct tttttcagcc tgagattaaa tatttcttag atcacataca aagcgtttgg  1080
actgagaacg gagttttcag tggacgagat tcacaatttt gcgacattga tgatacgtcc  1140
atggggataa ggcttctgaa aatgcatgga tacaaaatcg acccaaatgc acttgagcat  1200
ttcaagcagg aggatggtaa attttcgtgc tacggtggtc aaatgatcga gtctgcatca  1260
ccgatataca atctgtaccg agctgctcaa ctccgatttc caggagaaga aattcttgaa  1320
gaggccatta aattttccta taactttttg caagaaaagc tagccaagga tgaaattcaa  1380
gaaaaatggg tcatatcgga gcacttaatt gatgagatta agatcgggct aaagatgcca  1440
tggtacgcca ctctaccccg agttgaagct gcatattacc tggactatta tgcaggatcc  1500
ggcgatgtgt ggattggcaa gactttctac aggatgccag aaatcagtaa tgatacatac  1560
aaagaaatgg ccattttgga tttcaaccga tgccaagcac aacatcagtt tgaatggatt  1620
tacatgcaag agtggtatga aagtagcaac gtaaaggaat ttgggataag caaaaaagag  1680
ctacttgttg cttatttctt ggctgcatca accatatttg aaccggaaag agcacaagag  1740
aggattatgt gggcaaaaac aaaaattgtt tccaaaatga tcgcatcatc tcttaacaaa  1800
caaaccactc tatcgttaga ccaaaagact gcacttttta cccaactcga acatagtctc  1860
aatggcctcg acagtgatga gaaagataat ggagtagctg agacgaaaaa tctagtggca  1920
accttccagc agctgctaga tggattcgac aaatacactc gccatcaatt gaaaaatgct  1980
tggagccagt ggttgaagca agtgcagcaa ggagaggcga ccgggggcgc agacgcggag  2040
ctggaagcaa acacgttgaa catctgtgcc ggtcatatcg cattcaacga acaagtatta  2100
tcgcacaacg aatacacaac tctctccaca ctcacaaaca agatctgcca ccggcttacc  2160
caaattcaag acaaaaagac gcttgagata atcgacggcg gcataagata taaggagctg  2220
gagcaggaga tgcaggcgtt ggtgaaatta gttgttgaag aaaacgacgg cggcggcata  2280
gacaggaata ttaaacaaac atttttatca gttttcaaga attattacta cagtgcctac  2340
```

```
cacgatgctc acacaaccga tgttcatatt ttcaaagtat tatttggacc ggtcgtctga  2400

SEQ ID NO: 33          moltype = AA  length = 796
FEATURE                Location/Qualifiers
source                 1..796
                       mol_type = protein
                       organism = Origanum majorana
SEQUENCE: 33
MTDVSSLRLS NAPAAGGRLP LPGKVHLPEF RTVCAWLNNG CKYEPLTCRI SRRKISECRV  60
ASLNSSQLIE KVGSPAQSLE EANKKIEDSI EYIKNLLMTS GDGRISVSAY DTSLVALIKD  120
VKGRDAPQFP SCLEWIAQNQ MADGSWGDEF FCIYDRIVNT LACLVALKSW NLHPDKIEKG  180
VTYINENVHK LKDGSTEHMT SGFEIVVPAT LERAKVLGIQ GLPYDHPFIK EIINTKERRL  240
SKIPKDLIYK LPTTLLFSLE GQGELDWEKI LKLQSSDGSF LTSPSSTASV FMRTKDEKCL  300
KFIENAVKNC GGGAPHTYPV DVFARLWAVD RLQRLGISRF FQHEIKYFLD HINSVWTENG  360
VFSGRDSQFC DIDDTSMGVR LLKMHGYNVD PNALKHFKQE DGKFSCYPGQ MIESASPIYN  420
LYRAAQLRFP GEEILEEASR FAFNFLQEKI ANHEIQEKWV ISEHLIDEIK LGLKMPWYAT  480
LPRVEAAYYL EYYAGSGDVW IGKTFYRMPE ISNDTYKEVA ILDFNTCQAQ HQFEWIYMQE  540
WYESSKVKDF GISKKDLLVA YFLAASTIFE PERTQERIIW AKTLILSRMI TSFLNKQATL  600
SSQQKNAILT QLGESVDGLD KIYSGEKDSG LAETLLATFQ QLLDGFDRYT RHQLRNAWGQ  660
WLMKVQQGEA NGGADAELIA NTLNICAGLI AFNEDVLLHS EYTTLSSLTN KICQRLSQIE  720
DEKTLEVIEG GIKDKELEED IQALVKLALE ENGGCGVDRR IKQSFLSVFK TFYYRAYHDA  780
ETTDLHIFKV LFGPVM                                                  796

SEQ ID NO: 34          moltype = DNA  length = 2391
FEATURE                Location/Qualifiers
source                 1..2391
                       mol_type = other DNA
                       organism = Origanum majorana
SEQUENCE: 34
atgaccgatg tatcctctct tcgtttgagc aatgcaccag ctgccggcgg caggttgccg  60
ctgccgggaa aggttcacct gcctgaattt cgcaccgttt gtgcatggtt gaacaatggc  120
tgcaaatacg agcccttgac ttgtcgaatt agtcgacgga agatatctga atgtcgagta  180
gcaagtctga attcgtcgca actaattgaa aaggtcggtt ctcctgctca atctctagaa  240
gaggcaaaca aaaagatcga ggactccatc gagtacatta agaatctatt gatgacatct  300
ggcgacgggc ggataagtgt gtcggcttac gacacgtcgc tagtcgccct aataaaggac  360
gtgaaaggac gagatgcccc tcagttcccg tcgtgcctgg agtggatagc gcaaaaccaa  420
atggccgacg ggtcgtgggg ggatgagttc ttctgtattt acgaccggat cgtgaataca  480
ttagcatgcc tcgttgcctt gaaatcatgg aaccttcacc ccgacaagat cgaaaaagga  540
gtgacgtaca tcaacgaaaa tgtgcacaaa ctgaaagacg ggagcaccga gcacatgacg  600
tcagggttcg aaatcgtggt ccccgccact ctagaaagag ccaaagtctt gggcatccaa  660
ggcctcccct atgatcatcc cttcattaag gagattatta atactaagga gcgaagatta  720
agcaaaatac ccaaggattt gatatacaaa ctgccaacga cgctgctgtt cagtttagaa  780
gggcagggag aattagattg ggaaaagata ctgaaactgc agtcaagcga tggctccttc  840
cttacttcgc cctcgtcgac cgcctccgtc ttcatgcgga cgaaagacga gaaatgcctc  900
aagttcattg agaacgccgt taagaattgc ggcgggggag cgccgcatac ttacccagtg  960
gatgtgtttg caagactttg ggcagttgac agactacagc gattagggat ttctcgattc  1020
ttccaacacg agattaaata cttcttagat cacattaaca gtgtatggac cgagaatgga  1080
gttttcagtg gacgagattc acaattttgt gatatcgacg acacttctat gggagttagg  1140
cttctaaaaa tgcatggata caatgttgat ccaaatgcgc tcaagcattt caagcaggag  1200
gatggcaaat tctcttgcta ccctggccaa atgatcgagt ctgcatctcc gatatacaat  1260
ctctaccgag ccgctcaact ccggttcccc ggagaagaaa ttctcgaaga agcaagtcga  1320
ttcgccttca actttctgca ggaaaagata gccaaccatg aaattcaaga aaaatgggtc  1380
atatctgagc acttaattga tgagataaag ttgggactga agatgccatg gtacgcgact  1440
ctgccccgag ttgaggccgc ttattatcta gagtattatg ctggctcagg cgacgtatgg  1500
attggaaaga ctttctaccg gatgccggaa atcagtaacg atacgtataa agaggtggcc  1560
attttggatt tcaacacatg ccaagctcaa caccagtttg aatggattta catgcaagag  1620
tggtacgaaa gtagcaaggt taaagatttc gggataagca aaaaggacct acttgttgct  1680
tactttctgg cggcatcgac tatatttgaa cccgaaagaa cacaagagag gattatttgg  1740
gcaaaaaccc taattctttc taggatgatc acatcatttc tcaacaaaca agctacactt  1800
tcatcccaac aaaagaatgc catcttaaca caacttggag agagtgtcga tggcctcgat  1860
aaaatatata gtggtgagaa agattctggg ctggctgaga ctctgctggc taccttccag  1920
caactgctcg acggattcga tagatacact cgccatcaac tgagaaatgc ttgggggcaa  1980
tggttgatga aagtgcagca aggagaggcc aacggtggcg ccgacgctga gctcatagca  2040
aacacactca atatctgcgc cggccttatc gccttcaacg aagacgtatt gttgcacagc  2100
gaatacacga ctctctcctc cctcaccaac aaaatatgcc agcgccttag ccagattgaa  2160
gatgaaaaga cgcttgaagt gattgaaggg ggcataaaag ataaggaact ggaggaggat  2220
attcaggcgt tggtgaagct agccctcgaa gaaaacggcg gctgcggcgt cgacagaaga  2280
atcaagcagt cattcttatc agtattcaag actttttact acagagccta ccatgatgct  2340
gagaccaccg atcttcatat tttcaaagta ctgtttgggc cggttatgtg a          2391

SEQ ID NO: 35          moltype = AA  length = 798
FEATURE                Location/Qualifiers
source                 1..798
                       mol_type = protein
                       organism = Perovskia atriplicifolia
SEQUENCE: 35
MTSMSSLNLS RAPATTHRLQ LQAKVHVPEF YAVCAWLNSS SKQAPLSCQI RCKQLSRVTE  60
CRVASLDASQ VSEKDTSHVQ TPDEVNKKIE DYIEYVKNLL MTSGDGRISV SPYDTSIVAL  120
IKDSKGRNIP QFPSCLEWIA QHQMADGSWG DQFFCIYDRI LNTLACVVAL KSWNVHGDMI  180
```

-continued

```
EKGVTYVKEN VHKLKDGNIE HMTSGFEIVV PALVQRAKDL GIQGLPYDDP LIKEIADTKE  240
RRLKKIPKDM IYQTPTTLLF SLEGQGDLEW EKILKLQSGD GSFLTSPSST AHVFVQTKDE  300
KCLKFIENAV KNCSGGAPHT YPVDVFARLW AIDRLQRLGI SRFFQPEIKY FIDHINSVWT  360
ENGVFSGRDS EFCDIDDTSM GIRLLKMHGY KVDPNALNHF KQQDGKFSCY GGQMIESASP  420
IYNLYRAAQL RFPGEEILEE ASKFAFNFLQ EKIANDQFQE KWVISDHLID EVKLGLKMPW  480
YATLPRVEAA YYLQYYAGSG DVWIGKVFYR MPEISNDTYK ELAILDFNRC QAQHQFEWIY  540
MQEWYHRSSV SEFGISKKEL LRTYFLAAAT IFEPERTQER LVWAKTQIVS RMITSFVNNG  600
TTLSLDQMTA LATQIGHNFD GLDQIISAMK DHGLAGTLLT TFQQLLDGFD RYTRHQLKNA  660
WSQWFMKLQQ GEANGGEDAE LLANTLNICA GFIAFNEDVL SHDEYTTLST LTNKICKRLS  720
QIQDKKALEV VDGSIKDKEL EQDMQALVKL VLEENGGGVD RNIKQTFLSV FKTFYYTAYH  780
DDETTDVHIF KVLFGPVV                                                798

SEQ ID NO: 36          moltype = DNA  length = 2397
FEATURE                Location/Qualifiers
source                 1..2397
                       mol_type = other DNA
                       organism = Perovskia atriplicifolia
SEQUENCE: 36
atgacctcta tgtcctctct aaatttgagc agagcaccag ctaccaccca ccggttacag  60
ctacaggcaa aggttcacgt gccggaattt tatgccgtgt gtgcatggct gaatagcagc  120
agcaaacagg caccccttgag ttgccaaatt cgctgcaagc aactatcaag agtaactgaa  180
tgtcgggtag caagtctgga tgcgtcgcaa gtgagtgaaa aagacacttc tcatgtccaa  240
actcccgatg aggtgaacaa aaagatcgag gactatatcg agtacgtcaa gaatctgttg  300
atgacgtcgg gcgacgggcg aataagcgtg tcgccctacg acacgtcaat agtcgccctt  360
attaaggact cgaaagggcg caacatcccg cagtttccgt cgtgcctcga gtggatagcg  420
cagcaccaaa tggcggatgg ctcatggggg gatcaattct tctgcattta cgaccggatt  480
ctaaatacat tagcatgtgt cgtagctttg aaatcctgga acgttcacgg tgacatgatc  540
gaaaaaggag tgacgtacgt caaggaaaat gtgcataagc ttaaagatgg gaatattgag  600
cacatgacgt cggggttcga aattgtggtt cccgcccttg ttcaaagagc caaagacttg  660
ggcatccaag gcctgcccta tgatgatccc ctcatcaagg agattgctga tacaaaagaa  720
agaagattga aaaagatacc caaggatatg atttaccaaa cgccaacgac attactattc  780
agtttagaag ggcagggaga tttggagtgg gaaaagatac tgaaactgca gtcaggcgat  840
ggctccttcc tcacttcgcc gtcatccacc gcccacgtgt tcgtgcagac caaagatgaa  900
aaatgcttga aattcatcga gaacgccgtc aagaattgca gtggaggagc gccgcatact  960
tatccagtcg atgtcttcgc aagactttgg gcaattgaca gactacaacg cctaggaatt  1020
tctcgtttct tccagccgga aattaagtat ttcatagacc acatcaacag cgtttggaca  1080
gagaacggag ttttcagtgg gcgagattcg gaattttgcg atattgatga cacgtccatg  1140
ggcatcaggc ttctcaaaat gcacggatac aaagtcgacc caaatgcact caatcatttc  1200
aagcagcaag atggtaaatt ttcttgctac ggtggtcaaa tgatcgagtc tgcatctcca  1260
atatacaatc tctacagggc tgctcagcta cgatttccag gagaagaaat tcttgaagaa  1320
gccagtaaat ttgcctttaa ctttttgcaa gaaaaaatag ccaacgatca atttcaagaa  1380
aaatgggtga tatccgacca cttaatcgat gaggtgaagc tcgggctgaa gatgccatgg  1440
tacgccactc taccccgggt tgaggctgca tattatctac aatactatgc tggttctggc  1500
gacgtatgga ttggcaaggt tttctacagg atgccggaaa tcagcaatga tacatacaaa  1560
gagctggcca tattggattt caacagatgc caagcacagc atcagttcga atggatttat  1620
atgcaagagt ggtatcacag aagcagcgtt agtgaattcg ggataagcaa aaaagagctg  1680
cttcgtactt actttctggc tgcagcaacc atattcgaac ccgagagaac acaagagagg  1740
cttgtgtggg caaaaaccca aattgtctct aggatgatca catcatttgt taacaatgga  1800
actacactat ctttggacca aatgactgca cttgcaacac aaatcggcca taatttcgat  1860
ggcctcgatc aaataattag tgctatgaaa gatcatggac tggctgggac tctgctgaca  1920
accttccagc aacttctaga tggattcgac agatacactc gccatcaact caaaaatgct  1980
tggagccaat ggttcatgaa actccagcaa ggggaggcga acggcgggga agacgcggag  2040
ctcctagcaa acacgctcaa catctgcgcg ggtttcattg ctttcaacga agacgtattg  2100
tcgcacgatg aatacacgac tctctccacc cttacaaaca aaatctgcaa gcgccttagc  2160
caaattcaag ataaaaaggc gctggaagtt gtcgacggga gcataaagga taaggagctc  2220
gaacaggata tgcaggcgtt ggtgaagttg gtccttgaag aaaatggcgg cggcgtcgac  2280
aggaacatca aacagacatt tttgtccgtt ttcaagactt tttactacac cgcctaccac  2340
gatgatgaga ccactgatgt tcatattttc aaagtactgt ttggaccggt cgtatga     2397

SEQ ID NO: 37          moltype = AA  length = 783
FEATURE                Location/Qualifiers
source                 1..783
                       mol_type = protein
                       organism = Pogostemon cablin
SEQUENCE: 37
MSFASQSHVA FVLRRPSAVA PPPPTRIPTT AALSPLKPGD FSHGRSSFMP TSIKCNAIST  60
SRVEEYKYTD DHNQSGLLEH DGLISDKINE LVTKIQLMLQ NMDDGEISIS PYDTAWVSLV  120
EDVGGNDRPQ FPTSLEWISN NQLPDGSWGD PNAFLVHDRI LNTLACVVAL KSWKMHPHKC  180
NRGVSFVREN IYRMDDEKEE HMPNGFEVVF PALLQKAKTL NIDIPYEFPG IQKFYAKRDL  240
KFARIPMDIL HSVPTTLLFS LEGVRCGLDL DWGKLLELQA ADGSFLYSPS STAFALEQTK  300
DQNCLKYLSK LVRKFDGGVP NVYPVDLFEH NWAVDRLQRL GISRYFTPEI NQCLDYSYRY  360
WSNSKGMYSA SNSQIQDVDD TAMGFRLLRL NGYDVSTQGF RQFEAGGDFF CFAGQSSQAV  420
TGMYNLYRAS QVMFPGEKLL EDAKKFSTNF LQQKRANNQL TDKWVIAKDV PAEVGYALDI  480
PWYASLPRLE ARFFIQQYGG DDDVWIGKTL YRMGYVNNNT YLELAKLDYN TCQRLHQHEW  540
ITIQRWYEIN LKITSVGLSK RGVLLSYYLA AANLFEPQNS THRIAWAKTS ILVSAIQLSP  600
LQKRDFINQF HRSTANNGYE TSNVLVKSVI KGVHELSMDA MLTHNKDIHR QLFNAWRKWM  660
SVWEEGGDGE AELLLSTLNT CDGVDESTFS DPKYEHLLEI TVRVTHQLHL IQNAETKRVG  720
DREEIDLSMQ QLVKLVFTKS SSDLDSCIKQ RFFAIARSFY YVAHCDPEMV DSHIAKVLFE  780
RVM                                                                783
```

```
SEQ ID NO: 38          moltype = DNA  length = 2352
FEATURE                Location/Qualifiers
source                 1..2352
                       mol_type = other DNA
                       organism = Pogostemon cablin
SEQUENCE: 38
atgtcatttg cttctcaatc acatgtcgcc tttgtactcc gacggccatc tgccgttgct  60
ccgccaccac cgactagaat tccgacaaca gccgctcttt ctcctctcaa accaggtgat  120
ttttcccatg gcagatcatc atttatgccc acttccatta aatgtaatgc aatttccaca  180
tctcgcgtcg aagaatacaa gtacacggat gatcataatc agagtggttt attggagcat  240
gatggtttga tatcagacaa gataaatgaa ttggtgacca agatacaatt gatgctacaa  300
aacatggatg acggagagat aagcatctcc ccatatgaca ccgcatgggt gtcgttggtg  360
gaggatgtgg gcggcaacga ccgcccacag tttcctacga gcctggagtg gatatcgaat  420
aaccagctcc ccgacggctc gtggggcgac ccgaatgcct tttggtgca cgaccgtatc  480
ctcaacacat tggcatgcgt cgttgcactc aaatcctgga aatgcaccc ccacaaatgc  540
aatagaggag ttagtttcgt gagagaaaat atatacagaa tggatgatga aaaagaggaa  600
cacatgccaa atggattcga agtggtattt ccagcactcc ttcaaaaagc gaaaacccta  660
aacattgata tcccgtacga gtttccagga atacaaaaat tttatgccaa aagagattta  720
aaattcgcca ggattccaat ggatatattg catagcgttc cgacaacatt actgttcagc  780
ttagaaggtg taagatgtgg tcttgatctg gattgggga agcttctaga attgcaagct  840
gctgatggct catttctcta ctctccatcc tctactgcct ttgcactaga acaaaccaag  900
gatcaaaact gcctcaaata tctatctaaa cttgttcgaa aattcgatgg cggagtaccc  960
aacgtgtacc cggtggactt gttcgaacat aattgggcag ttgatcgtct ccaaaggctc  1020
ggaatttctc gttattttac gcctgaaatc aaccaatgtc ttgattattc ttacagatat  1080
tggtcaaata gtaaagggat gtactcggca agcaattccc agattcagga cgttgatgac  1140
accgccatgg gattcaggct tttgagactc aacggctacg atgtctctac acaagggttt  1200
aggcaattcg aggcaggggg ggacttcttc tgcttcgcgg ggcagtcgag ccaagctgta  1260
accggaatgt acaacctcta cagagcttcc caagtgatgt tccctggaga gaagctactg  1320
gaagatgcca agaaattctc caccaacttc ttgcaacaaa aacgagccaa taaccagctc  1380
actgacaagt gggttattgc caaagatgtt ccagctgagg tgggatatgc cttggatatt  1440
ccctggtatg ccagtctgcc ccgactggaa gcaagatttt tcatacaaca atacggtgga  1500
gacgacgacg tttggatcgg caaaaccttg tatagaatgg gatatgtgaa caacaacact  1560
tatctggaac tcgcaaagct agactacaac acctgccaaa ggttgcatca gcatgagtgg  1620
ataaccattc aacgatggta cgaaattaat ttaaaaatta ctagtgttgg gttgagcaaa  1680
agaggggtcc tgttgagtta ttacttagcc gcagccaatc tgtttgagcc tcaaaactca  1740
acacaccgca tcgcttgggc caaaacttcg attttagtaa gcgctattca actttctccc  1800
ctccaaaagc gcgactttat taaccaattc caccgctcca ccgcaaataa tgggtatgaa  1860
acaagtaatg tgttggtgaa gagtgtaatc aagggtgtgc atgagctctc catggacgct  1920
atgttgacgc acaataaaga catacatcgc caacttttta atgcttggcg aaagtggatg  1980
tcagtgtggg aagagggagg tgatggagaa gcggagctgt tattgtcgac gcttaacacg  2040
tgcgacggag tagatgaatc cacattcagc gatcccaaat acgagcacct cttagagatc  2100
accgtcagag tcacccacca gcttcatctc attcagaatg cagagacgaa gcgtgtgggt  2160
gaccgtgagg aaatagattt gagcatgcaa caacttgtta agttggtgtt cactaaatca  2220
tcatcggatc tggattcttg tatcaagcaa agattttttg cgattgccag aagtttctat  2280
tacgtggctc attgtgatcc ggagatggtg gactcccaca tagccaaagt attgtttgag  2340
agggtgatgt ag                                                     2352

SEQ ID NO: 39          moltype = AA  length = 599
FEATURE                Location/Qualifiers
source                 1..599
                       mol_type = protein
                       organism = Prunella vulgaris
SEQUENCE: 39
MSSLSIPFSS AICTSSIPKI STGHHRRTAR MPAHDTSRLV FRPSAVMVEG SPMTTSSNGK  60
EVQRLITTFK PSMWKDIFST FSFDNQVQEK YLKEIEELKK EVRSTLMSAT HRKLFDLIDN  120
LERMGIAYHF ETEIEDKLKQ AHASLEEEDD YDLFTTALRF RLLRQHRYHV SCDPFAKFVD  180
QDNKLKESLS SDVEGLLSLF EASHLRIHNE DVLDEAIVFT THHLNRMMPQ LESPLKEEVK  240
HALRYPLHKC LGILSLRFHI DRYENDKSRD EVVLRLGQVN FNYMQNIYMN ELYEITTWWN  300
KLQMTSKVPY FRDRLVECYM WGLAYHFEPE YAPVRVLITK YYMTATTVDD TYDNYATLEE  360
IELFTQAIDR WSEDEIDQLP DEYLKIVYKG LMNFTEEFRR DAEERGKGYV IPYFIEETKR  420
ATQGYANEQR WIMKREMPSF EEYMVNSRVT SLMYVTYVAV VAVIESATKE TVDWALSDSD  480
IFVYTNDIGR LIDDLATHRR ERKDGTMLTS MDYYMKEYGG TMEEGEAAFR KLMEEKWKLL  540
NAAWVDTING KESKEIVVQV LDLARICGTL YGDEEDGFTY PEKNFAPLVA ALLMNPIHI   599

SEQ ID NO: 40          moltype = DNA  length = 1800
FEATURE                Location/Qualifiers
source                 1..1800
                       mol_type = other DNA
                       organism = Prunella vulgaris
SEQUENCE: 40
atgagctctc tctcaattcc cttttcttcc gccatttgca cttcatcaat cccaaagatc  60
agtactgggc atcatcgccg caccgcgagg atgcccgcgc acgacacatc gcgtctcgtc  120
tttcgccctt cagctgtgat ggtggaagga agtccgatga ctacttcaag caacgggaag  180
gaagtccaac gacttataac cactttcaag cctagcatgt ggaaagatat tttttctacc  240
ttctctttcg ataatcaggt gcaagaaaag tatttgaaag aaattgagga attgaagaaa  300
gaagtaagaa gcacactaat gagtgctacg cataggaaat tgtttgactt gatcgacaat  360
ctcgagcgta tgggaatcgc ctatcatttc gagacagaaa tcgaagacaa gctcaaacaa  420
gctcatgctt ctctagagga ggaagatgac tacgacttgt tcactactgc acttcgcttt  480
```

```
cgtctgctca gacaacatcg ctatcatgtt tcttgcgatc cctttgcgaa atttgttgac  540
caagacaaca aattgaaaga gagtcttagt agcgacgtcg aggggctatt aagcttgttc  600
gaggcatccc atcttcggat ccacaacgag gatgttctag atgaagctat agtgttcaca  660
acccatcact tgaatcgaat gatgccacaa ttggaatcgc cccttaaaga agaagtgaag  720
catgctcttc gatacccccct tcacaagtgt cttggaatcc ttagccttcg ttttcatatc  780
gacagatatg agaatgataa gtcgagggat gaagttgttc tcagactagg ccaagttaat  840
ttcaattaca tgcagaacat ttacatgaac gagctctatg aaatcaccac gtggtggaac  900
aagttgcaga tgacttcaaa agtaccttac tttagagata gattggtaga gtgctatatg  960
tggggtttgg catatcattt cgaaccagaa tacgctcccg ttcgagtcct cattaccaag  1020
tactatatga ccgccacaac tgtcgacgat acctatgata attatgctac actcgaagaa  1080
atcgaactct tcactcaggc cattgacagg tggagcgagg atgagattga tcagctacct  1140
gatgaatacc taaaaatagt gtacaaaggt ctaatgaact tcactgaaga gtttagacgt  1200
gacgcagaag agcgagggaa aggctatgtg attccttact ttattgaaga aacgaagaga  1260
gcaacacagg gttatgcaaa cgagcagagg tggataatga agagagaaat gccgagtttt  1320
gaagagtata tggtgaactc aagggtaaca tcacttatgt atgtgaccta cgttgctgtt  1380
gtggcagtca tagaatcagc taccaaagaa accgtagatt gggcgctaag tgactccgat  1440
atctttgtct acactaacga tatcggccga cttatcgacg accttgccac tcatcgacgc  1500
gagaggaaag acgggacaat gcttacatcg atggattatt acatgaagga atatggcggt  1560
acgatggaag agggggaagc tgcatttagg aaattgatgg aggagaaatg gaaacttttg  1620
aatgcagcat gggtagatac tattaatgga aaagagtcga aggaaatagt tgtgcaagtt  1680
ctcgacctcg ccaggatatg cggaacgctc tatggggacg aagaagatgg cttcacctac  1740
ccagagaaga attttgcacc actcgttgct gctctattga tgaatcctat acatatttga  1800

SEQ ID NO: 41          moltype = AA  length = 821
FEATURE                Location/Qualifiers
source                 1..821
                       mol_type = protein
                       organism = Chiococca alba
SEQUENCE: 41
MSSSTSAAAT LLGLSPASRR FVSFPPANGP IETITGIWSP GKALHHFNFR LRCSTVSSPR  60
TQELGQVSQN GMSGIKWHDI VEEGVTEKGT LEANTSSWIK ESIEAIRWML RTMDDGDISI  120
SAYDTAWVAL VEDINGSGGP QFPSSLEWIA NNQLPDGSWG DSDIFSAHDR ILNTLGCVVA  180
LKSWNMHPEK SEKGLLYLRD NIHKLEDENV EHMPIGFEVA FPSLIEIAKK LSIDIPDDSA  240
ILQEIYARRN LKLTRIPKDI MHTVPTTLLH SLEGMPELDW KRLISLKCED GSFLFSPSST  300
AFALTQTKDA DCLRYLTKTV QKFNGGVPNV YPVDLFEHIW AVDRLQRLGI SRYFQSEIRE  360
CIDYVHRYWT DKGICWARNT HVYDIDDTAM GFRLLRLHGY DVSADVFRYY EKDGEFVCFA  420
GQSNQAVTGM YNLYRASQVM FPGENILSDA RKFSSEFLHD KRANNELLDK WIITKDLPGE  480
VAYALDVPWY ASLPRLETRL YLEQYGGEDD VWIGKTLYRM QKVNNNIYLE LGKLDYNNCQ  540
ALHQLEWRSI QKWYNECGLG EYGLSERSLL LSYYLAAASI FEPERSKERL AWAKTTMLIR  600
TIESYLSSEQ MVEDHNGAFV SEFQYYCSNL DYVNGGRHKP TQRLVRTLLG TLNQISLDAV  660
LVHGRDIHQY LRQAWEKWLI ALQEGDDSDM GQEEAELLVR TLNLCAGRYA SEELLLSHPK  720
YQQLLHITTR VCNQIRHFQH KKVQDGENGR ANMGDGITSI SSIESDMQEL TKLVVGNTQN  780
DLDADTKQTF LTVAKSFYYT AHCNPGTINC HIAKVLFERV L                     821

SEQ ID NO: 42          moltype = DNA  length = 2466
FEATURE                Location/Qualifiers
source                 1..2466
                       mol_type = other DNA
                       organism = Chiococca alba
SEQUENCE: 42
atgtcttctt ctacctcagc agcagcaacc cttctcggat tatcgccggc aagccgccgg  60
tttgtatcat ttcctccggc aaatggacct atagaaacta ttaccggtat ttggtcgccc  120
ggcaaagctc ttcatcactt taatttccgt ctgcgttgta gcacggtgtc cagtcctcgc  180
acccaagaat tgggccaggt gtcacaaaat ggcatgtctg gtataaagtg gcatgacata  240
gtggaagaag gagtcacaga aaaaggaact cttgaggcga acacatcaag ctggataaaa  300
gaaagcatag aagccattcg ttggatgctg cgtaccatgg atgacgggga tatcagcata  360
tctgcttatg atactgcatg ggttgccctt gtggaagata tcaacggaag tggcggtcct  420
caatttcctt caagcctcga gtggattgcc aacaatcagc ttcctgatgg ttcatggggc  480
gacagcgaca tcttttcagc tcacgatcgg attctcaaca ctttgggatg cgttgttgca  540
ttaaaatctt ggaacatgca ccctgaaaag agtgaaaaag gattattata tttaagggat  600
aacattcaca agcttgagga tgaaaatgtc gagcacatgc ctatcggttt tgaagtggca  660
tttccttcac taattgagat agccaaaaag ttgagcattg atattccgga tgattctgca  720
atcttgcagg agatatatgc cagaagaaat ctaaagctaa caaggatacc gaaggacatt  780
atgcacacag tgcccacaac attgctccac agcttggaag gcatgccaga actagactgg  840
aaaaggctaa tatctctaaa gtgtgaggat ggttcctttc tgttttctcc atcctccact  900
gcttttgccc tcacgcaaac taaagatgct gattgcctca gatatttaac taaaaccgta  960
caaaaattca atggaggagt tcccaatgtt taccccgtgg acttattcga acacatctgg  1020
gctgttgatc gacttcaaag actaggaatt tctcgatact tccagtcaga aatccgcgag  1080
tgcatcgatt atgttcaccg atattggacg gataaaggta tctgttgggc tagaaatacc  1140
cacgtttatg acattgatga tacagctatg ggttttagac ttctaaggtt gcatggctac  1200
gatgtttctg cagatgtttt cagatactat gagaaggatg gcgaattcgt ttgctttgcc  1260
ggacagtcaa accaggcggt gaccggaatg tataacctgt atagagcttc tcaagtgatg  1320
tttccagggg agaatatact ttcggatgct aggaaattct cgtccgaatt cttgcatgat  1380
aagcgagcca acaatgagct cctagataaa tggatcataa ccaaagattt gcctggggag  1440
gtagcatatg ctttagatgt tccatggtat gccagtttac ctcgtttaga aaccagattg  1500
tatttggaac aatatggcgg cgaagatgat gtctggattg gcaagacatt gtacaggatg  1560
caaaaagtta acaacaacat ctatcttgaa cttggcaaat tagattacaa caactgtcag  1620
gcattgcatc agcttgagtg gagaagcatc caaaaatggt acaatgaatg cggtcttgga  1680
gagtacggat taagcgagag aagcctcctt ctttcgtatt atttggccgc agccagtata  1740
```

```
tttgaaccgg agaggtcaaa ggaacggctt gcctgggcca aaactactat gctaatccgc  1800
acaattgaat cttatttgag tagtgaacaa atggttgagg atcacaatgg agcctttgtt  1860
agcgagttcc aatactattg cagtaacctt gactacgtaa atggtggaag gcataagcca  1920
acacaaaggc tagtgaggac tctactcgga actttaaatc agatttcttt ggacgcagtg  1980
ttagtccacg gcagagatat ccatcaatat ttgcgtcaag cctgggaaaa gtggttgata  2040
gctttgcaag agggagatga tagtgacatg ggtcaagagg aagcagaact tttagtgcgc  2100
acactaaacc tatgcgccgg tcgctacgca tcggaggagc tattgttgtc ccatcccaag  2160
tatcaacaac ttttgcacat cactactaga gtctgtaacc aaattcgtca tttccaacac  2220
aaaaaggtgc aagatgggga aaatggaaga gcaaacatgg gtgatggcat cacaagcatc  2280
agctcaatag agtcggacat gcaagaacta acgaaattag ttgtcggcaa tacccaaaac  2340
gatctagatg ctgatacgaa gcaaacattt ctcacggtgg caaaaagctt ctactacacc  2400
gcccactgca atcccggaac aatcaattgc catattgcta aagtattatt tgagagagta  2460
ctttga                                                             2466

SEQ ID NO: 43          moltype = AA  length = 747
FEATURE                Location/Qualifiers
source                 1..747
                       mol_type = protein
                       organism = Chiococca alba
SEQUENCE: 43
MPVIKSHEFI EEVGPEKGTL KLSRSSRINE LVESIQTMLQ SMDDGEISMS AYDTAWVALV  60
EDINGSSYPQ FPMSLEWIAN NQLPDGSWGD GSIFSVHDRI ISTLGCVLAL KSWNMHPDKS  120
EKGLLFIRDN IHKVGDESAE HMPIGFEVVF PSLIERAKNL DIDIPDISAI LQEIYARRNL  180
KLARIPKDIL YTVPTTLLHS LEGMPELDWQ KLLPLKCEDG SFLFSPSCTA FALMQTKDGD  240
CLRYLTNTIE KFNGGVPGVY PVDLFEHIWA VDRLQRLGIS RYFQTEIEEC MSYVYRYWTD  300
KGICWARNSK VEDIDDTAMG FRLLRLHGYM VSADVFAQFE KGGEFVCFAG QSNQALTGMF  360
NLYRASQVMF PGEKILADAK KFSSNFLHEK RANNELLDKW IITKDLPGEV TYALDVPWYA  420
SLPRVETRLY LEQYGGEDDV WIAKTLYRMR KVNNKIYLEL GILDYNNCQA LHQLEWRSIQ  480
KWYKDSGLEE YGLSERNLLL AYYLATACIF EPERLVERLS WAKTTALIYT TKSYFRTECN  540
SGEQRKAFLH EFQQYCNDLD YVSGARHKPT IRLIEALLGT LEQVSLDAIL DHGRYIHQDL  600
RNAWEKWLIA LQEGVDMDQE EAELTVLTLH LCAGSYTSEE LLLSHPKYQQ LLNITSRVCH  660
QIRQFQREKA QDTDNGRENL VAITSIKAIE SDMQELAKLV LTKSTGDLAA KIKQTFLIVA  720
KSFYYTAHCL PGIISTHIAK VLFEKVF                                      747

SEQ ID NO: 44          moltype = DNA  length = 2244
FEATURE                Location/Qualifiers
source                 1..2244
                       mol_type = other DNA
                       organism = Chiococca alba
SEQUENCE: 44
atgccagtaa taaagtcgca tgagtttatt gaagaggtcg gcccggaaaa aggaactctg  60
aagctgagca gatcaagtag gataaacgaa cttgtagaat caattcaaac gatgcttcaa  120
tcgatggatg atggggaaat aagcatgtct gcttatgaca ccgcgtgggt tgcccttgtg  180
gaagatatta atggaagcag ctaccctcaa ttccctatga gcctcgagtg gattgccaac  240
aatcagcttc ctgatggttc atggggtgac ggcagtatct tttcggttca tgatcggata  300
atcagcacat taggatgtgt tcttgcatta aaatcatgga acatgcaccc ggacaaaagc  360
gaaaaaggac tgttatttat aagggacaat attcacaagg ttggagatga gagcgctgag  420
cacatgccta ttggttttga ggtggtattt ccttcgctta ttgagagagc caaaaacttg  480
gacattgata ttccagatat ttctgctatc ttgcaagaga tttatgcacg aagaaatcta  540
aagctcgcaa ggattccaaa ggatatactg tataccgtgc ccacgacatt acttcatagc  600
ttagaaggaa tgccagaact ggactggcaa aagctactgc cattaaaatg tgaggatggt  660
tcatttctat ttctccatc gtgcactgct tttgccctca tgcagactaa ggatggtgat  720
tgcctcagat atctaactaa taccatagaa aaattcaatg gggagttcc cggtgtatac  780
cctgtggact tgttcgaaca catttgggct gttgatcgct tgcaaagact aggaatttcc  840
cggtattttc agacagaaat tgaagaatgt atgagttatg tttaccgata ttggacggat  900
aaaggtatct gttgggctag aaactccaaa gttgaagaca tcgatgacac agccatgggt  960
tttagacttc taaggttgca tggttacatg gtttctgcag atgtgtttgc acagtttgag  1020
aaagggggtg aattcgtttg ctttgctgga cagtcgaacc aggcgctgac tggaatgttt  1080
aacctgtata gagcttctca agtaatgttt ccaggggaga agatacttgc tgatgccaag  1140
aaattctcat cgaacttctt acatgaaaag cgtgcaaaca acgagcttct agataaatgg  1200
atcataacta aagatttgcc tggagaggtg acgtatgcgc tagatgttcc atggtacgcc  1260
agtttacctc gtgtagaaac gagattatat ctggaacaat atggaggaga ggatgatgtc  1320
tggattgcca agacattgta caggatgaga aaagttaaca acaaaattta ccttgaactt  1380
ggcatattag attacaataa ctgtcaagca ttgcatcagc tggagtggag aagcatccaa  1440
aaatggtata aggattctgg ccttgaagag tacgggttga gcgagaggaa ccttctcctg  1500
gcatattatc tggccacagc ttgtatattt gaacccgaaa ggttggtgga gcgcctttcc  1560
tgggcgaaaa caaccgcctt aatctacaca acaaaatctt atttcagaac tgaatgcaac  1620
tctggggaac agagaaaagc ttttcttcat gagttccaac agtactgcaa tgacctggac  1680
tacgttagtg gcgcaaggca caagccaaca ataagattga tcgaagctct acttggaacc  1740
ctagagcagg tctctttgga tgcaatatta gatcatggcc gatatatcca tcaagatttg  1800
cgtaatgctt gggagaaatg gttgatagct ttgcaagagg gagttgacat ggaccaagaa  1860
gaagcagaac ttacagtgct cacactacac ctgtgtgccg gcagctacac atcggaggag  1920
ttactgttat ctcatcccaa gtatcaacaa cttttaaata tcactagtag agtctgccac  1980
caaattcgtc aattccagcg cgaaaaggca caggatacgg ataatggaag agaaaacttg  2040
gttgccatca caagcatcaa ggcgatagaa tcagacatgc aagaacttgc gaaattagtt  2100
ctgaccaaat ccactggcga tttagctgct aaaatcaagc aaacatttct tatagtggca  2160
aagagcttct actacaccgc acattgcctt cctggaatta tcagtaccca cattgccaaa  2220
gtactatttg agaaagtttt ctga                                         2244
```

-continued

```
SEQ ID NO: 45          moltype = AA  length = 822
FEATURE                Location/Qualifiers
source                 1..822
                       mol_type = protein
                       organism = Chiococca alba
SEQUENCE: 45
MMMMMVVMNT APAHSYHPFP FAGPKSSATL FSNYYCSSRK KSSPPRISAS VSLLTGVEST  60
TAINSSDPEI KERIRKLFHD VDISLSSYDT AWVAMVPAPH SSQSPLFPQC INWLLDNQLP  120
DGSWSLPPPH HHPLLLKDAL SSTLACVLAL RRWGIGQEQV DKGIRFVELN FASASDQNQH  180
LPVGFDIIFP GMLEYARDLN LNLQLESATV NALLLKRDQE LTRFFKSYSD ESKAYLAYVS  240
EGIVKLQNWD TVMKFQRKNG SLFNSPSATA AAVMHVHNPG CLDYLHSVLE KHGNAVPTVY  300
PLDIYPRLCL VDNLERLGIC GHFRKEILSV LDDTYRCWMQ GDEEIFAEKS TCAIAFTLLR  360
KHGYNISADP LTPFLKEECF SNSLGGCLKD TSAVLELYRA LEMIISQNES ALVKKSLWSR  420
SFLKEHISGG CDLKGFSNQI SILVDDILNF PSHATLQRVA NRRSIEQYNL DSTKILKTSY  480
CSSNFSNKDL LILAVKDFNH CQLIHREELK ELERWVTDNR LDKLKFARQK SAYCYFSAAA  540
TIFSPELSDA RMSWAKNGVL ATLVDDFFDV GGSLEELKKL IELVEKWDIN VSDGCCSEPV  600
QILFSALHST IQEIGDKAFK WQARSVTNHI FKIWLDLLNS MLREAEWARN ATVPTVEEYM  660
TNGYVSFALG PIILPALYLV GPKLSEEVVK DSEFHSLFKL VSTCGRLLND VHSFERESKS  720
GQLNALSLRL IHGGVGITEA AAVAEMKSSI ENLRRELLRL VLRKEGSVVP RACKDLFWNM  780
SKVLHQFYNK DDGFTSEEMI QLVKSIIYEP IAVNEFLNSC HT                    822

SEQ ID NO: 46          moltype = DNA  length = 2469
FEATURE                Location/Qualifiers
source                 1..2469
                       mol_type = other DNA
                       organism = Chiococca alba
SEQUENCE: 46
atgatgatga tgatggtggt gatgaacaca gctcccgccc actcttacca tcctttcccc  60
tttgccggcc caaaatcctc agccacactt ttttccaatt attattgttc cagtaggaag  120
aaatcatcgc cacctcgcat ctctgcctca gtttctttgc taactggagt tgaaagcaca  180
actgcaatta attcttcaga cccggagatc aaagaaagaa taaggaaact atttcatgat  240
gttgatatct cgctttcttc atatgacact gcatgggtgg caatggtccc tgctccacat  300
tcttcccagt ctccccttt tccccagtgc attaattggt tattggacaa tcagcttcct  360
gatggctcat ggagtcttcc tcctcctcat catcatcctc tattacttaa agatgcatta  420
tcctctaccc ttgcatgtgt tcttgcgctc aggagatggg gaattggtca agaacaagtt  480
gacaagggta ttcgttttgt tgagttaaat tttgcttcag catctgacca gaaccagcat  540
ttgccagttg gatttgacat tatattccct ggcatgctcg aatatgctag agatttaaat  600
ttaaatcttc aactagaatc tgcaacagta aatgccttac ttcttaaaag agatcaggag  660
cttacaagat tctttaaaag ctactcagac gagagtaaag cataccttgc atatgtatca  720
gaaggtatag taaagttaca gaactgggat acagttatga agttccaaag aaagaacggg  780
tcactattca attcaccttc agctacagca gctgctgtta tgcatgtcca caatcctggt  840
tgcctcgatt accttcactc agtgttggag aagcatggaa atgctgttcc aacagtttac  900
cctttggata tatatccacg cctctgcttg gttgacaacc ttgagagact gggtatttgt  960
ggtcatttta ggaaggaaat tctgagtgta ttggatgata catacagatg ctggatgcag  1020
gggatgaag agatatttgc agaaaaatca acttgtgcca tagcatttac attattgcga  1080
aagcatgggt acaacatctc tgcagatcca ttgaccccat tcttaaagga agagtgtttt  1140
tccaattctt tgggtggatg tttgaaagat actagtgctg tacttgaatt ataccgggca  1200
ttagagatga ttattagcca gaatgaatca gctctggtga aaaaaagctt gtggtccaga  1260
agcttcctga aagagcatat ttctggtggt tgtgatttaa agggattcag caatcaaatt  1320
tccatactgg tggatgatat cctcaacttt ccatcgcatg ctactttgca acgggttgct  1380
aacaggagaa gcatagagca atacaactta gacagtacaa aaattttaaa aacttcatat  1440
tgctcgtcga attttagcaa caaagattta ttgatcctgg cagtcaaaga ttttaatcat  1500
tgccaactca tacaccgtga agaactgaaa gaactagaaa ggtgggtcac agacaataga  1560
ttggacaagt taaagtttgc taggcagaag tctgcatact gttacttttc tgctgcagca  1620
accatattct cacctgaact ttctgatgcc cgcatgtcat gggccaagaa tggtgtactt  1680
gctactttgg ttgatgactt ctttgacgtg ggaggttctc tagaggaatt aaagaaactg  1740
attgagttgg ttgaaaagtg ggatataaat gtcagtgatg gttgttgctc tgaaccagtg  1800
caaatcctct tctcagcact acatagtaca atccaggaga ttggagataa agcattcaaa  1860
tggcaagcac gcagtgtaac aaaccacata tttaagatat ggttagattt gcttaattct  1920
atgttgaggg aagctgagtg ggctagaaat gcaacagtgc ctacagttga agaatatatg  1980
acaaatggtt atgtatcatt tgctttgggg ccaattatcc tccctgctct ttatcttgtt  2040
ggacctaagc tgtcagagga agtagttaag gattctgaat tccactccct ttttaagcta  2100
gtgagtacct gtgggcggct tctgaatgat gtccacagct tcgagaggga atcaaagtcc  2160
ggccaactaa atgctctgtc tctgcgcctg attcatggtg gtgttggcat tactgaagca  2220
gctgctgttg cagagatgaa gagttcaatt gagaatctaa ggagagaact gctgagacta  2280
gtcttgcgca aagagggtag tgtagttcca agagcttgca aggatttgtt ttggaatatg  2340
agtaaagtgc tacatcaatt ttacaacaaa gatgatggat ttacttcaga ggagatgatt  2400
cagcttgtga agtcgatcat ttatgagcca attgcggtca atgaattttt gaatagttgc  2460
catacatga                                                          2469

SEQ ID NO: 47          moltype = AA  length = 817
FEATURE                Location/Qualifiers
source                 1..817
                       mol_type = protein
                       organism = Chiococca alba
SEQUENCE: 47
MMIMVMNTAP VHAYHALPIP TQKSSTTLFP NYNCSSRKKS SPPRISAASV SLQTGVERTT  60
AIHSSDLEIK ERIRKLFHDV DISLSSYDTA WVAMVPAPHS SQSPLFPQCI NWLLDNQLPD  120
GSWSLPPHHH HHHPLLLKDA LSSTLACVLA LRRWGIGQEQ VDKGIRFVEL NFASASDQNQ  180
```

```
HLPVGFDIIF PGMLEYARDL NLNLQLESAT VDALLLKRDQ ELIRFFKSYS DESKAYLAYV  240
SEGIIKLQNW DTVMKFQRKN GSLFNSPSAT AAAVMHVHNP GCLDYLHSVL EKHGNAVPTV  300
YPLDIYPRLC LVDNLERLGI CGHFRKEILS VLDDTYRCWM QGDEEIFAEK STCAIAFTLL  360
RKHGYNISAD PLTPFLKEEC FSNSLGGCLK DTSAVLELYR ALEMIISQNE SALVKKSLWS  420
RSFLKEHISG GCDLKGFSNQ ISKQVDDILN FPSHATLQRV ANRRSIEQYN LDSTKILKTS  480
YCSSNFSNKD LLILAVKDFN HCQLIHREEL KELERWVADN RLDKLKFARQ KSAYCYFSAA  540
ATIFSPELSD ARISWAKNGV LTTLVDDFFD VGGSLEELKK LIELVEKWDI NVSDGCCSEP  600
VQILFSALHS TIQEIGDKAF KWQARSVTNH IIKIWLDLLN SMLREAEWAR NATVPTVEEY  660
MTNGYVSFAL GPIILPALYL VGPKLSEELV KDSEFHSLFK LVSTCGRLLN DVHSFERESK  720
AGQLNALSLR LIHGGVGITE AAAVAEMKSS IEKQRRELLR LVLRKEGSVV PRACKDLFWN  780
MSRVLHQFYV KDDGFTSEEM IELVKSIIYE PIAVNEF                          817

SEQ ID NO: 48          moltype = DNA  length = 2454
FEATURE                Location/Qualifiers
source                 1..2454
                       mol_type = other DNA
                       organism = Chiococca alba
SEQUENCE: 48
atgatgataa tggtgatgaa cacagctccc gtccacgctt accacgcttt acccattccc  60
acccaaaaat cctcaaccac actttttccc aattataact gttccagtag gaagaaatca  120
tcgccacctc gcatctctgc cgcctcagtt tctttgcaaa ctggagttga aagaacgacg  180
gcaattcatt cttcagacct agagatcaaa gaaagaataa ggaaactatt tcatgatgtt  240
gatatctcgc tttcttcata tgacactgca tgggtggcaa tggtccctgc tccacattct  300
tcccagtctc cccttttttcc ccagtgcatt aattggttat tggacaatca gcttcctgat  360
ggctcatgga gtcttcctcc tcatcatcat catcatcatc ccctattact taaagatgca  420
ttatcctcta cgcttgcatg tgttcttgcg ctcaggagat ggggaattgg tcaagaacaa  480
gttgacaagg gtattcgttt tgttgagtta aattttgctt ctgcatctga ccagaaccag  540
catttgccag ttggatttga cattatattc cctggcatgc tcgaatatgc tagagattta  600
aatttaaatc ttcaactaga atccgcaact gtagatgcct tacttctcaa aagagatcag  660
gagcttataa gattctttaa aagctactca gacgagagta aagcatacct tgcatatgta  720
tcagaaggta tcataaagtt acagaactgg gatacagtta tgaagttcca aagaaagaac  780
gggtcactgt tcaattcacc ttcagctaca gcagctgctg ttatgcatgt ccacaatcct  840
ggctgcctcg attaccttca ctcagtgttg gagaagcatg gcaatgctgt tccaacagtt  900
taccctttgg atatatatcc acgcctctgc ttggttgaca accttgagag actgggtatt  960
tgtggtcatt ttaggaagga aattctgagt gtattggatg atacatacag atgctggatg  1020
caggggggatg aagagatatt tgcagaaaaa tcaacttgtg ccatagcatt tacattattg  1080
cgaaagcatg ggtacaacat ctctgcagat ccattgaccc cattcttaaa ggaagagtgt  1140
ttttccaatt ctttgggtgg atgtttgaaa gatactagtg ctgtacttga attataccgg  1200
gcattagaga tgattattag ccagaatgaa tcagctctgg tgaaaaaaag cttgtggtcc  1260
agaagcttcc tgaaagagca tatttctggt ggttgtgatt taaagggatt cagcaatcaa  1320
atttccaaac aggtggatga tatcctcaac tttccatcgc atgctacttt gcaacgggtt  1380
gctaacagga gaagcataga gcaatacaac ttagacagta caaaaatttt aaaaacttca  1440
tattgctcgt cgaattttag taacaaagat ttattgatcc tggcagtcaa agattttaat  1500
cattgccaac tcatacaccg tgaagaactg aaagaactag aaaggtgggt cgcagacaat  1560
agattggaca agttaaagtt tgctaggcag aagtctgcat actgttactt ttctgctgca  1620
gcaaccatat tctcacctga actttctgat gcccgcatct catgggccaa aaatggtgta  1680
cttactactt tggttgatga cttctttgac gtgggaggtt ctctagagga attaaagaaa  1740
ctgattgagt tggttgaaaa gtgggatata aatgtcagtg atggttgttg ctctgaacca  1800
gtgcaaatcc tcttctcagc actacatagt acaatccagg agattggaga taaagcattc  1860
aaatggcaag cacgcagtgt aacaaaccac ataattaaga tatggttaga tttgcttaat  1920
tctatgttga gggaagctga gtgggctaga aatgcaacag tgcctacagt tgaagaatat  1980
atgacaaatg gttatgtatc atttgccttg gggccaatta tcctccctgc tctttatctt  2040
gttggaccta agctgtcaga ggaattagtt aaggattctg aattccactc cctttttaag  2100
ctagtgagta cctgtgggcg gcttctgaat gatgtccaca gcttcgagag ggaatcaaag  2160
gccggccaac taaatgctct ttctctgcgc ctgattcatg gtggagttgg cattactgaa  2220
gcagctgctg ttgcagagat gaagagttca attgagaagc aaaggagaga actgctgaga  2280
ctagtcttgc gcaaagaggg tagtgtagtt ccaagagctt gcaaggattt gttttggaat  2340
atgagtaggg tgctacatca attttacgtc aaagatgatg gatttacttc agaggagatg  2400
attgagcttg tgaagtcgat catttatgag ccaattgcgg tcaatgaatt ttga        2454

SEQ ID NO: 49          moltype = AA  length = 796
FEATURE                Location/Qualifiers
source                 1..796
                       mol_type = protein
                       organism = Chiococca alba
SEQUENCE: 49
MIHTLPHGGQ AHFISHKTQP YYSSRPRFSS AASLDTRVRR TSPSNSSVLD FNETKERITK  60
LFHNVDYSIS SYDTAWVAMV PDPHSSQAPL FPECINWLLD NQFHDGSWSL PHHNSLLLKD  120
VLSSTLACVL ALKRWGIGGR QIDKGVRFIE MNFGSASDNC QHTPIGFDII FPGMLENARD  180
LDLNLRLEPR IVTDMQRKRD MQLTRLHESD LKGDQAYLAY VSEGMQKLQN WDLAMKFQRK  240
NGSLFNSPSA TAAAVMHVQN PASLNYLHSV VDKFGHAVPA VYPLDLYARL CLVDNLERLG  300
ICRHFTNEIE IVMEDTYRCW LQDDEDIFAE ISTCALAFRL LRKHGYVVSP DPLTKIIEEE  360
DVSNSSGNGY WNDIHAVMEV HRASEVVIHE NESDLKNQNT ISKHLLRHHL FNGSDVKPFP  420
NPIYKQVDYA LKFPTPLILQ RVENKTLIQN YDVDSTRLLK TSYRSSNFCN EDLLRLAVKD  480
FNDCQLLHRK ELKELERWSA DNRLHELKFA RQKAIYCSFS AAATIFIPEW YEARMSLAKN  540
SVLATVVDDF FDVGGSMEEL KKLIEFVEKW DIDITKESCS EPLKIIFSAL HSTISEIGEQ  600
AVKWQGRNVT SHIIEIWLDL LNSMLRESEW TTDVHMPTLD EYMEAAYVSF AMGPIIIPAL  660
YFVGPKLSDE IVRDPEIRSL HKLVSICGRL LNDMQGFERE KKAGKPNAVS IRISQNGDGI  720
TESAAFEEVK MELEDARREL LRLVVQKDGS VVPRACKDAF WSVSRMLHHF YFNNDGYTSE  780
```

```
VEMVELVNSI IHEPLK                                            796

SEQ ID NO: 50          moltype = DNA  length = 2391
FEATURE                Location/Qualifiers
source                 1..2391
                       mol_type = other DNA
                       organism = Chiococca alba
SEQUENCE: 50
atgattcata ctctccctca tggcggccag gctcacttca tttcccacaa aacacagcct  60
tattattcca gtagacctcg cttttcttca gcagcttctt tggacacacg agtccggaga  120
acatcgccct ctaattcctc tgtcctagac ttcaacgaga ccaaagaaag aatcacaaaa  180
ttatttcata atgttgatta ttcaatttct tcatatgata cagcatgggt tgctatggtc  240
ccggacccac attcttctca ggctcccctt ttcccagagt gcataaattg gttgctagat  300
aatcaatttc atgatggctc ctggagtctt cctcatcaca attctctatt gcttaaggat  360
gttttatcct ctacgcttgc gtgtgttctt gctcttaaga gatggggaat aggaggaagg  420
cagattgaca aaggtgttcg ctttattgag atgaattttg gctcagcatc tgacaattgc  480
cagcatactc caataggatt tgacataata tttccaggaa tgcttgaaaa tgccagagat  540
ttggatctaa atcttagact agaacccaga attgtaactg acatgcaacg taaaagagac  600
atgcagctta caagactcca tgaaagcgat ctaaaggggg accaagcata cttggcatat  660
gtatccgaag ggatgcaaaa gttacagaat tgggatttgg cgatgaagtt tcaaaggaag  720
aatggatcgc tcttcaactc accatcagct acagcagccg ctgttatgca tgtccaaaat  780
cctgcttccc tcaattatct tcattcagtc gtcgacaaat tcggccatgc agttccggct  840
gtttaccctt tggatctcta tgcgcgcctt tgcttggttg acaatcttga gaggctgggt  900
atctgtcgac attttactaa tgaaattgaa attgtaatgg aggacacgta caggtgctgg  960
ctgcaggatg atgaagatat atttgccgaa atatcaactt gtgccttagc ttttcggtta  1020
ttgagaaaac atggctatgt tgtctcccca gatccactga caaaaatcat agaagaagaa  1080
gatgtttcca attcttctgg taatggatat tggaatgata tacatgctgt aatggaagtg  1140
catcgggcat cagaggtggt tatacatgaa aatgaatcag atttaaagaa tcaaaatacc  1200
atatcaaaac accttctcag acaccatctt ttcaatggtt ctgatgtgaa gccctttcct  1260
aatccaatat acaagcaggt ggactatgct ctcaagtttc caacccccctt aattctacaa  1320
cgtgttgaaa acaagaccct catacagaac tacgacgtag acagtacaag acttcttaaa  1380
acttcatatc gatcatcaaa tttctgcaat gaagatttac tgaggttagc agtgaaagat  1440
tttaatgact gtcaactcct gcaccggaaa gaactaaaag aactagaaag atggtccgca  1500
gataacagac tgcacgaact aaaatttgct cggcagaaag ctatatactg ctccttttct  1560
gctgcagcaa cgattttcat acctgaatgg tacgaagccc gcatgtcatt ggccaaaaat  1620
agtgtactttg ctactgtggt tgatgacttc tttgatgtgg gtggttcgat ggaggaatta  1680
aagaagctaa ttgaatttgt tgaaaagtgg gatattgaca tcaccaagga atcctgctct  1740
gagccactca aaatcatatt ttcagcactg cacagtacaa tctctgagat tggagagcaa  1800
gcagttaaat ggcaaggacg caatgtaaca agccacataa ttgagatctg gttggatttg  1860
ctcaattcga tgttgaggga gtctgaatgg actacagatg tgcacatgcc aacattggat  1920
gaatatatgg aagctgctta tgtatcattc gccatggggc caattatcat ccctgctctg  1980
tattttgttg ggcctaagct atctgatgaa attgttcggg atcctgaaat acgatccctc  2040
cataagcttg tgagcatttg tgggcggctt ctaaatgata tgcaagggtt cgagagggaa  2100
aagaaggctg gtaaaccaaa tgccgtgtct atacgcatta gtcaaaatgg tgatggcatt  2160
accgaatcag cagctttcga agaagtgaag atggaattag aggatgcaag gagagaattg  2220
ctaagattag ttgtgcaaaa agatggtagt gtagttccaa gagcttgcaa ggatgcgttt  2280
tggagcgtaa gcagaatgtt gcatcatttc tacttcaata atgatggata cacgtcagag  2340
gtggagatgg ttgagctcgt gaattcaatt attcatgaac cactaaaata a           2391

SEQ ID NO: 51          moltype = AA  length = 792
FEATURE                Location/Qualifiers
source                 1..792
                       mol_type = protein
                       organism = Salvia hispanica
SEQUENCE: 51
MSIQANMSFA TSLHRSTTPG VGLPLKPCIS PSPSLSFSPN FGTFNNTSLR LKPEAGSKSY  60
EGIRRSHQLA ASTILEGQTP ITPEVESEKT RLIERIRSML QDMDNDGQIS VSPYDTAWVA  120
LVEDIGGSGG PQFPTSLEWI SNHQYDDGSW GDRKFVLYDR ILNTLACVVA LTNWKMHPNK  180
CEKGLRFIHE NIKKLADEDE ELMPVGFEIA LPSVIDLAKR LGIEIPENSA SIKRIYELRD  240
SKLKKIPMDL VHKRPTSLLF SLEGMEGLNW DKLMNFLAEG SFLSSPSSTA YALQHTKNEL  300
CLEYLLKAVK RFNGGVPNAY PVDMFEHLWS VDRLQRLGIS RYFQAEIEEN MAYAYRYWTN  360
KGITWARNMV VQDSDDSAQG FRLLRLYGYD IPIDVFKHFE QGGQFCSIPG QMTHAITGMY  420
NLYRASELLF PGEHILSDAR KYTGNFLHQR RITNTVVDKW IITKDLHGEV AYALDVPFYA  480
SLPRLEARFF IEQYGGDEDV WIGKTLYRMF KVNSDTYLEM AKLDYKQCQS VHQLEWNSMQ  540
RLYRDCNLGE FGLSERSLLL AYYIAASTTF EPEKSSERLA WAITTILVEI IASQKLSDEQ  600
KREFVDEFVK GSIVNNQNGG RHKPGNRLVE VLINNITLMA EGRGTYQQLS NAWKKWLKTW  660
EEGGDLGEAE ARLLLHTIHL SSGLDDSSFS HPKYQQLLEA TSKVCHQLRV FQSVKVYDDQ  720
ESTSQLVTRT TFQIEAGMQE LVKLVFTKTL EDLPSTTKQS FFSVARSFYY TACIHADTID  780
SHINKVLFEK IV                                                792

SEQ ID NO: 52          moltype = DNA  length = 2379
FEATURE                Location/Qualifiers
source                 1..2379
                       mol_type = other DNA
                       organism = Salvia hispanica
SEQUENCE: 52
atgagtattc aagcaaacat gtcatttgcc acctccctcc accgatcaac cacccccgga  60
gttggccttc cgctaaaacc atgtatctct ccctctccct ctctttcctt ttccccaaac  120
tttggcactt ttaacaacac aagtttgaga ctcaaaccag aggctgggag caaaagttat  180
```

```
gaggggattc gaagaagtca tcaattagca gcatcaacaa ttttggaggg tcaaactccg  240
attactccgg aggttgaatc ggagaaaaca cgcctgattg aaaggattcg ttcgatgtta  300
caagacatgg acaacgatgg ccagataagt gtgtcaccat acgacacagc atgggtggcg  360
ctcgtggaag atattggtgg cagcggaggg ccacagtttc caacgagcct agagtggatt  420
tctaaccacc agtacgacga tggatcgtgg ggggatcgca aatttgttct ctatgaccgg  480
atactcaata cattagcatg tgttgtcgca ctcacgaatt ggaaaatgca tcctaacaaa  540
tgcgaaaaag ggttgaggtt tattcatgag aatattaaga aactcgcgga tgaagatgaa  600
gagctcatgc ccgtaggatt cgaaatcgca ctgccatcag tcattgattt agctaaaaga  660
ctgggtatag aaatcccaga aaattctgca agcataaaaa gaatttatga attgagagat  720
tcaaaactta aaaaaatacc aatggattta gtgcacaaaa ggcccacatc actactcttc  780
agcttggaag gcatggaagg ccttaactgg gacaaactaa tgaattttct agccgagggt  840
tcgtttcttt catcgccatc gtccactgcc tacgctctcc aacacaccaa gaatgagtta  900
tgcctagagt atttactcaa ggcagtcaag agattcaatg gtggagttcc aaatgcatac  960
cctgtcgaca tgtttgagca tctgtggtcc gtggatcgct tacagagatt aggaatttct  1020
cggtattttc aagctgaaat tgaagaaaac atggcctatg cttacagata ctggacaaat  1080
aaaggaatca cctgggcaag aaatatggtt gtccaagaca gtgacgacag cgcacaggga  1140
ttcaggctct taaggttgta cggatacgat attcctatag atgttttcaa acatttcgag  1200
caaggtggac aattctgcag cataccagga cagatgacac acgctattac aggaatgtac  1260
aacttgtata gagcttctga acttctgttc cctggagaac acatactttc tgatgctaga  1320
aaatacacag gtaacttctt gcatcaaaga agaattacta acacggtagt agacaagtgg  1380
atcattacca aagaccttca cggcgaggtg gcttatgcat tggatgtgcc attctacgcc  1440
agtctgccac gactggaagc acgattcttc atagaacaat atggggtga tgaagatgtt  1500
tggattggga aaacattgta caggatgttt aaagtaaact ccgacacata ccttgagatg  1560
gcaaaattag attacaaaca atgccagtct gtgcatcagt tagagtggaa tagcatgcaa  1620
agattgtata gagattgcaa tctaggagag tttgggttga gcgaaagaag ccttctccta  1680
gcttactaca tagcagcctc aactacattt gagccggaaa aatcaagtga aagactggct  1740
tgggctataa caacaatttt agtcgaaata atcgcatccc aaaaactctc tgatgagcaa  1800
aagagagagt ttgttgatga atttgtaaaa ggaagcatcg tcaataacca aaatggagga  1860
agacataaac cgggaaacag attggttgaa gttttgatca acaatataac actgatggca  1920
gaaggcagag gcacatatca gcagttgtct aatgcgtgga aaaaatggct aaagacatgg  1980
gaagagggag gtgacctggg ggaagcagaa gcacggcttc tcctgcacac gatacatttg  2040
agctccggat tggatgattc atcattttcc catccaaaat atcagcagct cttggaggca  2100
accagcaaag tctgccacca acttcgcgta ttccagagtg taaaggtgta tgatgaccaa  2160
gagtctacaa gccaactggt aactaggaca actttccaaa tagaagcagg catgcaagaa  2220
ctagtgaaat tagttttcac aaaaaccttg gaagatttgc cttctactac caagcaaagc  2280
ttttttagtg ttgctagaag tttctattac actgcctgta ttcatgcaga cactatagac  2340
tcccacataa acaaagtatt gtttgaaaaa attgtctag                        2379
```

```
SEQ ID NO: 53           moltype = AA  length = 790
FEATURE                 Location/Qualifiers
source                  1..790
                        mol_type = protein
                        organism = Teucrium canadense
SEQUENCE: 53
MSFASQATSL LLSSHNATAL PPLSAARLPP LTAGAAPFGR ISFTTTSLRQ YKLVSRAQSQ  60
EVDEIEKVTQ VVLEAEKDID QEAKVRELVE NVRVKLQNIG EGGISISPYD TAWVALVEDV  120
GGSGRPQFPE SLDWISNHQF PDGSWGSHKF LYYDRVLCTL ACIVALKTWN LHPHKFDKGL  180
KFVRENIGKL ADEEDVHMPI GFEVAFPSLI ETAKRKGIDI PEDFPGKKEI YAKRDLKLKK  240
IPMDILHKIP TPLLFSIEGI EGLDWQKLFK FRDHGSFLTS PSSTAHALQQ TKDELCLKYL  300
TNLVKKNNGG VPNAFPVDLF DRNYTVDRLR RLGILRYFQP EIEECMKYVY RFWDKRGISW  360
ARNTHVQDLD DTVQGFRNLR MHGYDVTLDV FKQFERCGEF FSFHGQSSDA VLGMFNLYRA  420
SQVLFPGEDM LADARKYAAN YLHKRRVSNR VVDKWIINKD LPGEVAYGLD VPFYASLPRL  480
EARFYVEQYG GNDDVWIGKA LYRMLNVSCD TYLELAKLDY NICQAVHQKE WKSFQKWHRD  540
GEFGLDEKSL LLAYYIAAST VFEPEKSLER LAWAKTAVLM EAILSQQLPS TKKHELVDEF  600
KHASILNNQN GGSYKTRTPL VETLVNAISE LSTTILLEQD RDIHLQLSNA WLKWLSRWEA  660
RGNLVEAEAE LLLQTLHLSN GLEESSFSHP KYQQLLQVTS KVCHLLRLFQ KRKVHDPEGC  720
TTDIATGTTF QIEACMQQVV KLVFTKSSHD LDSVVKQRFL DVARSFYYTA HCDPQVIQSH  780
INKVLFEKVV                                                        790
```

```
SEQ ID NO: 54           moltype = DNA  length = 2373
FEATURE                 Location/Qualifiers
source                  1..2373
                        mol_type = other DNA
                        organism = Teucrium canadense
SEQUENCE: 54
atgtcatttg cttcccaagc cacctccctc ctcctttctt cccacaacgc caccgctctt  60
ccgcctctct ctgccgcccg ccttccgcct ctcactgccg gtgctgctcc attcggaaga  120
atatcattta ctactacctc tcttcggcag tataaactgg tgtcaagagc tcaaagccaa  180
gaggtggatg agattgaaaa agtgacacaa gtggtattgg aggcagaaaa agacatcgat  240
caagaggcga aggtaaggga gctggtggaa aatgtccgag tgaagctgca aaatatcggg  300
gaaggaggga taagcatatc gccgtacgac accgcatggg tggcgctggt ggaggatgtc  360
ggcggcagcg gcagaccgca gttcccggag agcctggatt ggatatcaaa ccaccagttc  420
ccggacgggt cgtggggcag ccacaaattc ttgtactatg accgggtttt gtgcacgtta  480
gcatgtatag ttgcattgaa aacttggaat ctgcatcctc acaaattcga caaagggttg  540
aaattcgtca gagagaacat tggaaagctc gcggatgaag aagacgtgca catgccgatt  600
gggttcgaag tggcattccc atcacttata gagactgcaa agagaaaagg aattgacatc  660
ccggaagatt tccctggcaa gaaagaaatc tatgcaaaaa gagacctaaa gctgaaaaag  720
atacctatgg atatactgca caaaatcccc acaccattac tgttcagcat agaagggata  780
gaaggccttg attggcagaa gctattcaaa ttccgcgatc acggctcctt cctcacgtcc  840
```

```
ccgtcctcaa cggcccacgc tctccagcaa acaaaggacg agttatgcct caaatatctg  900
accaatcttg tcaaaaagaa caatggggga gttccaaatg catttccggt ggacctattt  960
gatcgtaact atacagtaga tcgcctgagg aggctgggaa ttttgcgcta ttttcaacct  1020
gaaatcgagg aatgcatgaa atatgtatac agattctggg ataaaagagg aatcagctgg  1080
gcaagaaata cccatgttca ggaccttgat gataccgtac agggattcag gaacttaagg  1140
atgcatggtt atgatgtcac cttagatgtt ttcaaacagt tcgagagatg tggagaattc  1200
tttagcttcc acgggcaatc aagtgatgct gtcttaggaa tgttcaactt gtaccgagct  1260
tctcaggttc tgtttccagg agaagacatg cttgcagatg caaggaagta cgcggccaac  1320
tatttgcata aaagaagagt tagtaatagg gtcgtggaca aatggattat taacaaagat  1380
cttccaggcg aggtggcgta tggctagat gttccgttct acgccagtct acctcgactg  1440
gaagcaagat tctacgtcga acaatatggg ggtaacgatg atgtctggat tggaaaagct  1500
ttatatagaa tgttgaatgt gagctgtgat acttaccttg agctagcaaa attagactac  1560
aatatttgcc aggctgtgca tcagaaagag tggaaaagct ttcaaaaatg gcacagggat  1620
ggggagtttg gattggatga aaaaagctta cttttagctt actacatagc agcctcgact  1680
gttttcgagc ctgaaaaatc tctagagcga ctggcttggg ctaaaaccgc agttctaatg  1740
gaggcaattt tgtcccaaca acttcctagc acaaaaaaac atgagcttgt tgacgaattt  1800
aaacatgcaa gcatcctcaa caaccaaaat ggaggaagct ataaaacaag aactcctttg  1860
gtagagactc tagtaaacgc cataagtgag ctctcaacta ccatactatt ggagcaagac  1920
agagacattc atctgcaatt atctaatgcg tggctgaagt ggctaagtag atgggaggca  1980
agaggcaacc tagtggaagc agaagcagag cttcttctgc aaaccttaca tctgagcaat  2040
ggattagaag aatcatcatt ttctcatcca aaatatcaac aactcttaca ggttaccagc  2100
aaagtctgtc acctacttcg gctattccag aaacgaaagg tgcatgatcc ggaagggtgt  2160
acaacagaca ttgcaacagg gacaactttc caaatagaag catgcatgca acaagtagtg  2220
aaattagtgt tcaccaaatc ctcacatgat ttagattctg ttgttaagca gagatttttg  2280
gatgttgcca gaagtttcta ttacacagcc cactgtgatc cacaagtgat ccagtcccac  2340
attaataaag tgttgtttga aaaagtagtc tag                               2373

SEQ ID NO: 55          moltype = AA  length = 785
FEATURE                Location/Qualifiers
source                 1..785
                       mol_type = protein
                       organism = Salvia officinalis
SEQUENCE: 55
MSFASTTSLL RPSVTGFGVS PRVTSTSILS RSYGQILKGK TKYITDNRRN RQLAVKFEGQ  60
IALDLEDGVA KQTNQEAESE KIRQLKGKIR WILQNMEDGE MSVSPYDTAW VALVEDISGG  120
GGPQFPTSLE WISKNQLADG SWGDPNYFLL YDRILNTLAC VVALTTWNMH PHKCDQGLRF  180
IRDNIEKLED EDEELILVGF EIALPSLIDY AQNLGIQIQY DSPFIKKICA KRDLKLRKIP  240
MDLMHRKPTS LLYSLEGMEG LEWEKLMNLR SEGSFLSSPS STAYALQHTK DELCLDYLVK  300
AVNKFNGGVP NVYPVDMYEH LWCVDRLQRL GISRYFQLEI QQCLDYVYRY WTNEGISWAR  360
YTNIRDSDDT AMGFRLLRLY GYDVSIDAFK PFEESGEFYS MAGQMNHAVT GMYNLYRASQ  420
LMFPQEHILS DARNFSAKFL HQKRRTNALV DKWIITKDLP GEVGYALDVP FYASLPRLEA  480
RFFLEQYGGD DDVWIGKTLY RMPYVNSNTY LELAKVDYKN CQSVHQLEWK SMQKWYRECN  540
IGEFGLSERS LLLAYYIAAS TTFEPEKSGE RLAWATTAIL IETIASQQLS DEQKREFVDE  600
FENSIIIKNQ NGGRYKARNR LVKVLINTVT LVAEGRGINQ QLFNAWQKWL KTWEEGGDMG  660
EAEAQLLLRT LHLSSGFDQS SFSHPKYEQL LEATSKVCHQ LRLFQNRKVD DGQGCISRLV  720
IGTTSQIEAG MQEVVKLVFT KTSQDLTSAT KQSFFNIARS FYYTAYFHAD TIDSHIYKVL  780
FQTIV                                                              785

SEQ ID NO: 56          moltype = DNA  length = 2358
FEATURE                Location/Qualifiers
source                 1..2358
                       mol_type = other DNA
                       organism = Salvia officinalis
SEQUENCE: 56
atgtcatttg cttccaccac ctccctcctc cgaccaagcg tcactgggtt cggtgtttct  60
ccaagggtta cttccacctc cattcttagc cgaagttatg gtcaaatatt aaaaggaaaa  120
acaaaataca taactgataa ccgtagaaat cgacaattgg cggtaaaatt tgagggccaa  180
attgctttgg atttggagga tggcgtagca aagcagacga atcaagaggc ggaatctgag  240
aagataaggc aactgaaggg aaagatccga tggattctgc aaaacatgga ggacggcgag  300
atgagcgtgt cgccgtacga caccgcatgg gtggcgctgg tggaagatat cagcggcggc  360
ggcgggccgc agttcccgac gagcctcgag tggatttcca agaatcagtt ggcggatggg  420
tcatgggggg atcctaatta tttccttctc tacgacagaa tactcaatac tttagcatgt  480
gtagtcgcac tcacgacttg gaatatgcat cctcacaaat gcgatcaagg gttgaggttt  540
ataagagaca acattgagaa acttgaggat gaagatgagg agctaattct cgtaggattc  600
gagatcgcac tgccttcact cattgattat gctcaaaacc ttgggataca aatccaatat  660
gattctccat tcattaaaaa aatttgtgca aagagagatc taaaactcag aaaaatacca  720
atggatttaa tgcacagaaa gccaacatca ttgctctaca gcttggaagg catggaaggc  780
cttgagtggg aaaagctaat gaatttgcga tcggagggtt cgtttctgtc atcgccgtcg  840
tccacggcct acgctctcca acacaccaag gatgagttat gccttgacta tctggtcaag  900
gcggtcaaca aattcaatgg tggagttccc aacgtgtacc ctgtcgacat gtatgagcat  960
ctatggtgcg tagaccgctt gcagaggttg ggaatttctc gctattttca acttgaaatt  1020
caacaatgcc tcgactatgt ttacagatac tggacaaatg aaggaatttc gtgggcaaga  1080
tatactaata tccgggatag tgacgacacc gcaatgggat tcaggcttct aaggttgtac  1140
ggctatgatg tctctataga tgcttttaaa ccattcgagg aaagcggaga attctatagc  1200
atggcagggc agatgaacca cgctgttaca ggaatgtaca acttgtacag agcttctcaa  1260
cttatgttcc ctcaagaaca catactttcc gatgccagaa acttctctgc caaattcttg  1320
catcaaaaga ggcgtactaa tgcactagta gacaagtgga tcattaccaa agaccttccc  1380
ggcgaggttg gatatgcatt ggatgtgccg ttctacgcca gtctgcctcg actggaagca  1440
cgattcttct tagaacaata tgggggtgat gatgatgttt ggattggaaa aactttgtac  1500
```

-continued

```
aggatgccat atgtgaactc caacacatac cttgagcttg caaaagtaga ctacaaaaac  1560
tgccagtccg tgcatcagtt ggagtggaag agcatgcaaa aatggtacag agaatgcaat  1620
ataggtgagt ttgggttgag cgaaagaagc cttctcctag cttactacat agcagcctca  1680
actacattcg agccagaaaa atcaggtgag cggctcgctt gggctacaac agcaatttta  1740
atcgagacaa tcgcgtccca acaactctcc gatgaacaaa agagagagtt cgttgatgaa  1800
tttgaaaaca gcatcattat caagaatcaa aatggaggga gatataaagc aagaaacaga  1860
ttggtcaagg ttttgatcaa cactgtaaca ctggtagcag aaggcagagg cataaatcag  1920
cagttgttta atgcgtggca aaaatggcta aagacatggg aagaaggagg tgacatgggg  1980
gaagcagaag cccagcttct tctgcgcacg ctacatttga gctccggatt cgatcaatca  2040
tcattttccc atccaaaata tgagcagctc ttggaggcga ccagcaaagt ttgccaccaa  2100
cttcgcctat tccagaatcg aaaggtggat gatggccaag ggtgtataag tcgattggta  2160
attgggacaa cttcccaaat agaagcaggc atgcaagaag tagtgaaatt agttttcacc  2220
aaaacctcac aagacttgac ttctgctacc aagcaaagct tttcaatat tgctagaagt  2280
ttctattata ctgcctactt tcatgcagac actatagact cccacatata caaagtattg  2340
tttcaaacaa tagtatag                                                 2358

SEQ ID NO: 57          moltype = AA  length = 808
FEATURE                Location/Qualifiers
source                 1..808
                       mol_type = protein
                       organism = Scutellaria baicalensis
SEQUENCE: 57
MPFLLPSSAT SSPAFYTPAA PLAGHHVFPS FKPLIISRSS LQCNAISRPR TQEYIDVIQN  60
GLPVIKWHEA VEEDETDKDS LNKEATSDKI RELVNLIRSM LQSMGDGEIS SSPYDAAWVA  120
LVPDVGGSGG PQFPSSLEWI SKNQLPDGSW GDTCTFSIYD RIINTLACVV ALKSWNIHPH  180
KTYQGISFIK ANMDKLEDEN EEHMPIGFEV ALPSLIEIAK RLDIDISSDS RGLQEIYTRR  240
EVKLKRIPKE IMHQVPTTLL HSLEGMAELT WHKLLKLQCQ DGSFLFSPSS TAFALHQTKD  300
HNCLHYLTKY VHKFHGGVPN VYPVDLFEHL WAVDRIQRLG ISRHFKPQVD ECIAYVYRYW  360
TDKGICWARN SVVQDLDDTA MGFRLLRLHG YDVSADVFKH FENGGEFFCF KGQSTQAVTG  420
MYNLYRASQL MFPGESILED AKTFSSKFLQ RKRANNELLD KWIITKDLPG EVGYALDVPW  480
YASLPRVETR FYLEQYGGED DVWIGKTLYR MPYVNNNKYL ELAKLDYSNC QSLHQQEWKN  540
IQKWYESCNL GEFGLSERRV LLAYYVAAAC IYEPEKSNQR LAWAKTVILM ETITSYFEHQ  600
QLSAEQRRAF VNEFEHGSIL KYANGGRYKR RSVLGTLLKT LNQLSLDILL THGRNVHQPF  660
KNAWHKWLKT WEEGGDIEEG EAEVLVRTLN LSGEGRHDSY VLEQSLLSQP IYEQLLKATM  720
SVCKKLRLFQ HRKDENGCMT KMRGITTLEI ESEMQELVKL VFTKSSDDLD CEIKQNFFTI  780
ARSFYYVAYC NQGTINFHIA KVLFERVL                                       808

SEQ ID NO: 58          moltype = DNA  length = 2427
FEATURE                Location/Qualifiers
source                 1..2427
                       mol_type = other DNA
                       organism = Scutellaria baicalensis
SEQUENCE: 58
atgcctttcc tcctcccttc ctccgccacc agctccccccg cgttctatac tccggccgcg  60
cctctcgccg gtcatcatgt ttttccatct ttcaagccac tcattatttc ccgttcttca  120
ctccaatgca atgcaatctc tcgacctcgt acccaagaat acatagatgt gattcagaat  180
ggattgccag taataaagtg gcacgaagct gtggaagaag atgagacaga taaagattct  240
cttaataagg aggccacgtc agacaagata agagagttgg taaatctgat ccgttcgatg  300
ctccaatcaa tgggcgacgg agagataagc tcgtcgccgt acgacgccgc atgggtggcg  360
ctggtgccgg acgtcggcgg ctccggcggg ccccagttcc cctccagcct cgaatggata  420
tccaaaaacc aactccccga cggctcctgg ggcgacacgt gtaccttttc catttatgat  480
cgaatcatca acacactggc ttgcgttgtt gctttgaaat cttggaacat acatccccac  540
aaaacttatc aagggatttc attcataaag gcaaatatgg acaaacttga agacgagaac  600
gaggagcaca tgccgatcgg atttgaagtg gcactcccgt cgctaatcga gatagcgaaa  660
aggctcgata tcgatatttc cagcgattcg agagggctgc aagagatata cacgaggagg  720
gaggtaaagc tgaaaaggat accgaaagag ataatgcacc aagtgcccac aacactgctt  780
catagcttgg agggtatggc cgagctgacg tggcacaagc ttttgaaatt acagtgccaa  840
gatggctcct ttcttttctc tccatcttca actgcctttg ctcttcacca aactaaggac  900
cataattgtc tccattattt gaccaaatat gttcacaaat ttcatggtgg agtgccaaat  960
gtgtatccgg tggacttgtt cgagcatcta tgggcagttg atcggatcca acggctgggg  1020
atttcccggc atttcaagcc ccaagttgat gaatgtattg cctatgttta tagatattgg  1080
acagataaag gaatatgctg ggcaagaaat tcagtagttc aagatcttga tgacacagcc  1140
atgggattca ggcttcttag gttgcatggc tacgatgttt cagcagatgt tttcaaacat  1200
tttgaaaatg gtggagagtt cttctgcttc aaagggcaaa gcacgcaggc agtgactgga  1260
atgtacaatc tgtacagagc ttctcagttg atgtttcctg gagaaagcat actggaagat  1320
gctaagacct tctcatctaa gtttttgcaa cgaaaacgag ccaataacga gttgttagat  1380
aagtggatta ttaccaagga tcttcctgga gaggtgggat atgctctaga tgtaccatgg  1440
tatgctagct tacctagagt tgaaactaga ttctacttgg aacaatatgg tggtgaagat  1500
gatgtttgga ttggcaaaac tttatacagg atgccatatg ttaacaataa taaatatcta  1560
gaactggcaa aattagacta tagtaactgc cagtcattac atcaacaaga gtggaaaaac  1620
attcaaaaat ggtatgagag ttgcaatctg ggagaatttg gtttgagtga aagaagggtt  1680
ctactagcct actacgtagc tgctgcgtgt atatatgagc ccgaaaagtc aaaccagcgc  1740
ttggcttggg ccaaaaccgt aattttaatg gagactatta cttcctattt tgagcaccaa  1800
caactctccg cagaacagag acgcgccttt gttaatgaat ttgaacatgg gagtatcctc  1860
aaatatgcaa atggaggaag atacaaaagg aggagtgttt tggggacttt gctcaaaaca  1920
ctaaatcagc tttcattgga tatattattg acacacggtc gaaacgtcca tcagcctttc  1980
aaaaatgcgt ggcacaagtg gctaaaaacg tgggaagaag gaggtgacat tgaagaaggc  2040
gaagcagagg tattggtccg aaccctaaac ctaagcggcg aagggaggca cgactcctat  2100
gtattggagc aatcattatt gtcacaacct atatatgaac aacttttgaa agccaccatg  2160
```

-continued

```
agtgtttgca agaagcttcg attgttccaa catcgaaagg atgagaatgg atgtatgacg  2220
aagatgagag gcattacaac gttagagata gaatcggaga tgcaagaatt agtgaaatta  2280
gtatttacta aatcctcaga tgatttagat tgtgaaatta aacaaaactt ttttacaatt  2340
gctaggagtt tctattatgt ggcttattgt aaccaaggaa ctatcaactt tcacattgct  2400
aaggtgctct ttgaaagagt tctttag                                      2427

SEQ ID NO: 59          moltype = AA  length = 802
FEATURE                Location/Qualifiers
source                 1..802
                       mol_type = protein
                       organism = Scutellaria baicalensis
SEQUENCE: 59
MASLSTLSLN FSPAIHRKIQ QSSAKLQFQG HCFTISSCMN NSKRLSLNHQ SNHKRTSNVS  60
ELQVATLDAP QIREKEDYST AQGYEKVDEV EDPIEYIRML LNTTGDGRIS VSPYDTAWIA  120
LIKDVEGRDA PQFPSSLEWI ANNQLSDGSW GDEKFFCVYD RLVNTLACVV ALRSWNIDAE  180
KSEKGIRYIK ENVDKLKDGN PEHMTCGFEV VFPSLLQRAQ SMGIHDLPYD APVIQDIYNT  240
RESKLKRIPM EVMHKVPTSL LFSLEGLENL EWDKLLKLQS SDGSFLTSPS STAYAFMHTK  300
DPKCFEFIKN TVETFNGGAP HTYPVDVFGR LWAIDRLQRL GISRFFESEI ADCLDHIYKY  360
WTDKGVFSGR ESDFVDVDDT SMGVRLLRMH GYQVDPNVLR NFKQGDKFSC YGGQMIESSS  420
PIYNLYRASQ LRFPGEDILE DANKFAYEFL QEQLSNNQLL DKWVISKHLP DEIKLGLQMP  480
WYATLPRVEA KYYLQYYAGA DDVWIGKTLY RMPEISNDTY LELARMDFKR CQAQHQFEWI  540
SMQEWYESCN IEEFGISRKE LLQAYFLACS SVFELERTTE RIGWAKSQII SRMIASFFNN  600
ETTTADEKDA LLTRFRNING PNKTKSGQRE SEAVNMLVAT LQQYLAGFDR YTRHQLKDAW  660
SVWFRKVQEE EAIYGAEAEL LTTTLNICAG HIAFDENIMA NKDYTTLSSL TSKICQKLSE  720
IRNEKVEEME SGIKAKSSIK DKEVEHDMQS LVKLVLERCE GINNRKLKQT FLSVAKTYYY  780
RAYNADETMD IHMFKVLFEP VM                                           802

SEQ ID NO: 60          moltype = DNA  length = 2409
FEATURE                Location/Qualifiers
source                 1..2409
                       mol_type = other DNA
                       organism = Scutellaria baicalensis
SEQUENCE: 60
atggcctctc tatcaactct gagcctcaac ttttccccag caattcaccg caaaatacag  60
caatcatctg caaaacttca gttccaggga cattgtttca ccataagttc atgcatgaac  120
aacagtaaaa gactgtcttt gaaccaccaa tctaatcaca aaagaacgtc aaacgtatct  180
gagctgcaag ttgccacttt ggatgcgccc caaatacgtg aaaaagaaga ctactccact  240
gctcaaggct atgagaaggt ggatgaagta gaggatccta tcgaatatat tagaatgctg  300
ttgaacacaa caggtgatgg gcgaataagt gtgtcgccat acgacacagc ctggatcgct  360
cttattaaag acgtggaagg acgtgatgct ccccagttcc catctagtct cgaatggatt  420
gccaataatc aactgagtga tgggtcgtgg ggcgatgaga agtttttctg tgtgtatgat  480
cgccttgtta atacacttgc atgtgtcgtg gcattgagat catggaatat tgatgctgaa  540
aagagcgaga aaggaataag atacataaaa gaaaacgtgg ataaactgaa agatgggaat  600
ccagagcaca tgacctgtgg ttttgaggtg gtgtttcctt cccttcttca gagagcccaa  660
agtatgggaa ttcatgatct tccctatgat gctcctgtca tccaagacat ttacaatacc  720
agggagagta aattgaaaag gattccaatg gaggttatgc acaaggtgcc aacatctcta  780
ttgttcagct tggaaggatt ggagaatttg gagtgggata agctcctcaa acttcagtct  840
tctgatggtt cattcctcac ttctccatcc tcaactgcct atgctttcat gcacactaag  900
gaccctaaat gcttcgaatt catcaaaaac accgtcgaaa catttaatgg aggagcacct  960
catacttatc cggtggatgt ttttggaaga ctgtgggcca ttgacaggct gcagcgcctc  1020
ggaatctctc gcttctttga gtccgagatt gctgattgct tagatcacat ctataaatat  1080
tggacagaca aaggagtgtt cagtggaaga gaatcagatt ttgtggatgt ggatgacaca  1140
tccatgggtg ttaggcttct aaggatgcac ggatatcaag ttgatccaaa tgtattgagg  1200
aacttcaagc agggtgacaa attttcatgc tatggtggtc aaatgataga gtcatcatct  1260
ccgatataca atctctatag ggcttctcaa ctccgatttc caggagaaga cattcttgaa  1320
gatgccaaca aattcgcata cgagttcttg caagaacagc tatccaacaa tcaacttttg  1380
gacaaatggg ttatatccaa gcacttgcct gatgagataa agcttggatt gcagatgcca  1440
tggtatgcca ccctaccccg agtggaggct aaatactacc tacagtatta tgctggtgct  1500
gatgatgtct ggatcggcaa gactctctac agaatgccag aaatcagtaa tgatacatat  1560
ctggagttag caagaatgga tttcaagaga tgccaagcac agcatcaatt tgagtggatt  1620
tccatgcaag aatggtatga aagttgcaac attgaagaat ttgggataag cagaaaagag  1680
cttcttcagg cttacttttt ggcctgctca agtgtatttg aactcgagag gacaacagag  1740
agaataggat gggccaaatc ccaaattatt tcaaggatga tagcttcttt cttcaacaat  1800
gaaactacaa cagccgatga aaaagatgca cttttaacca gattcagaaa catcaatggc  1860
ccaaacaaaa caaaaagtgg tcagagagag agtgaagctg tgaacatgtt ggtagcaacg  1920
ctccaacaat acctggcagg atttgataga tataccagac atcaattgaa agatgcttgg  1980
agtgtgtggt tcagaaaagt gcaagaagaa gaggccatct acggggcaga agcggagctt  2040
ctaacaacca ccttaaacat ctgtgctggt catattgctt tcgacgaaaa cataatggcc  2100
aacaaagatt acaccactct ttccagcctt acaagcaaaa tttgccagaa gctttctgaa  2160
attcgaaatg aaaaggttga ggaaatggag agtggaatta aagcaaaatc aagcatcaaa  2220
gacaaggaag tggaacatga tatgcagtca ctggtgaaat tagtcctgga gagatgtgaa  2280
ggcataaaca acagaaaact gaagcaaaca tttctatcgg ttgcaaaaac atattactac  2340
agagcctata atgctgatga aaccatggac atccatatgt tcaaagtact tttcgaacca  2400
gtcatgtga                                                          2409

SEQ ID NO: 61          moltype = DNA  length = 24
FEATURE                Location/Qualifiers
source                 1..24
                       mol_type = other DNA
```

-continued

```
                      organism = synthetic construct
SEQUENCE: 61
atggttcttt catcgtcttg caca                                            24

SEQ ID NO: 62         moltype = DNA  length = 25
FEATURE               Location/Qualifiers
misc_feature          1..25
                      note = A synthetic oligonucleotide
source                1..25
                      mol_type = other DNA
                      organism = synthetic construct
SEQUENCE: 62
ttattttgcg gcggaaacag gttca                                           25

SEQ ID NO: 63         moltype = DNA  length = 30
FEATURE               Location/Qualifiers
misc_feature          1..30
                      note = A synthetic oligonucleotide
source                1..30
                      mol_type = other DNA
                      organism = synthetic construct
SEQUENCE: 63
agattgagga ttccattgag tacgtgaagg                                      30

SEQ ID NO: 64         moltype = DNA  length = 30
FEATURE               Location/Qualifiers
misc_feature          1..30
                      note = A synthetic oligonucleotide
source                1..30
                      mol_type = other DNA
                      organism = synthetic construct
SEQUENCE: 64
gaagtttaat atccttcatt ctttattaca                                      30

SEQ ID NO: 65         moltype = DNA  length = 27
FEATURE               Location/Qualifiers
misc_feature          1..27
                      note = A synthetic oligonucleotide
source                1..27
                      mol_type = other DNA
                      organism = synthetic construct
SEQUENCE: 65
agctccattc aactagagtc atgtcgt                                         27

SEQ ID NO: 66         moltype = DNA  length = 28
FEATURE               Location/Qualifiers
misc_feature          1..28
                      note = A synthetic oligonucleotide
source                1..28
                      mol_type = other DNA
                      organism = synthetic construct
SEQUENCE: 66
ttcatctggc ttaactagtt gctgacac                                        28

SEQ ID NO: 67         moltype = DNA  length = 29
FEATURE               Location/Qualifiers
misc_feature          1..29
                      note = A synthetic oligonucleotide
source                1..29
                      mol_type = other DNA
                      organism = synthetic construct
SEQUENCE: 67
ttaaagtact ctctcaaaga gtactttgg                                       29

SEQ ID NO: 68         moltype = DNA  length = 21
FEATURE               Location/Qualifiers
misc_feature          1..21
                      note = A synthetic oligonucleotide
source                1..21
                      mol_type = other DNA
                      organism = synthetic construct
SEQUENCE: 68
gcgaccaacc atcatacgac t                                               21

SEQ ID NO: 69         moltype = DNA  length = 25
FEATURE               Location/Qualifiers
misc_feature          1..25
                      note = A synthetic oligonucleotide
source                1..25
```

```
                        mol_type = other DNA
                        organism = synthetic construct
SEQUENCE: 69
aatggcctcc actgcatcca ctcta                                          25

SEQ ID NO: 70           moltype = DNA  length = 26
FEATURE                 Location/Qualifiers
misc_feature            1..26
                        note = A synthetic oligonucleotide
source                  1..26
                        mol_type = other DNA
                        organism = synthetic construct
SEQUENCE: 70
ccatactcat tcaactggtt cgaaca                                         26

SEQ ID NO: 71           moltype = DNA  length = 21
FEATURE                 Location/Qualifiers
misc_feature            1..21
                        note = A synthetic oligonucleotide
source                  1..21
                        mol_type = other DNA
                        organism = synthetic construct
SEQUENCE: 71
agcctgtgta ctcgaaatgt c                                              21

SEQ ID NO: 72           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 72
caagaggatg attcatgtac caac                                           24

SEQ ID NO: 73           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 73
tctctttcaa gaatatcccc tctc                                           24

SEQ ID NO: 74           moltype = DNA  length = 22
FEATURE                 Location/Qualifiers
misc_feature            1..22
                        note = A synthetic oligonucleotide
source                  1..22
                        mol_type = other DNA
                        organism = synthetic construct
SEQUENCE: 74
ggcattcaat gattttgagt cg                                             22

SEQ ID NO: 75           moltype = DNA  length = 23
FEATURE                 Location/Qualifiers
misc_feature            1..23
                        note = A synthetic oligonucleotide
source                  1..23
                        mol_type = other DNA
                        organism = synthetic construct
SEQUENCE: 75
aaatggcctc tttgtccact ctc                                            23

SEQ ID NO: 76           moltype = DNA  length = 23
FEATURE                 Location/Qualifiers
misc_feature            1..23
                        note = A synthetic oligonucleotide
source                  1..23
                        mol_type = other DNA
                        organism = synthetic construct
SEQUENCE: 76
ttacgcaact ggttcgaaaa gca                                            23

SEQ ID NO: 77           moltype = DNA  length = 24
FEATURE                 Location/Qualifiers
misc_feature            1..24
                        note = A synthetic oligonucleotide
```

-continued

```
source                  1..24
                        mol_type = other DNA
                        organism = synthetic construct
SEQUENCE: 77
taatgtcatt tgcttcccaa gcca                                          24

SEQ ID NO: 78           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 78
ggcctagact accttctcaa acaa                                          24

SEQ ID NO: 79           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 79
aatgtcactc tcgttcacca tcaa                                          24

SEQ ID NO: 80           moltype = DNA  length = 25
FEATURE                 Location/Qualifiers
misc_feature            1..25
                        note = A synthetic oligonucleotide
source                  1..25
                        mol_type = other DNA
                        organism = synthetic construct
SEQUENCE: 80
acttcaagag gatgaagtgt ttagg                                         25

SEQ ID NO: 81           moltype = DNA  length = 23
FEATURE                 Location/Qualifiers
misc_feature            1..23
                        note = A synthetic oligonucleotide
source                  1..23
                        mol_type = other DNA
                        organism = synthetic construct
SEQUENCE: 81
ctccaaaact cgggccggta aat                                           23

SEQ ID NO: 82           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 82
tacgtatttc ctcacaatcg agca                                          24

SEQ ID NO: 83           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 83
ctagaaatgt tacttgcgtt caac                                          24

SEQ ID NO: 84           moltype = DNA  length = 25
FEATURE                 Location/Qualifiers
misc_feature            1..25
                        note = A synthetic oligonucleotide
source                  1..25
                        mol_type = other DNA
                        organism = synthetic construct
SEQUENCE: 84
gggtaagagt tgaatttaga tgtct                                         25

SEQ ID NO: 85           moltype = DNA  length = 30
FEATURE                 Location/Qualifiers
misc_feature            1..30
```

```
                        note = A synthetic oligonucleotide
source                  1..30
                        mol_type = other DNA
                        organism = synthetic construct
SEQUENCE: 85
atgacttcaa tatcctctct aaatttgagc                            30

SEQ ID NO: 86           moltype = DNA  length = 27
FEATURE                 Location/Qualifiers
misc_feature            1..27
                        note = A synthetic oligonucleotide
source                  1..27
                        mol_type = other DNA
                        organism = synthetic construct
SEQUENCE: 86
gaatatagta atcagacgac cggtcca                               27

SEQ ID NO: 87           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 87
gccatatcat gtctcttccg ctct                                  24

SEQ ID NO: 88           moltype = DNA  length = 29
FEATURE                 Location/Qualifiers
misc_feature            1..29
                        note = A synthetic oligonucleotide
source                  1..29
                        mol_type = other DNA
                        organism = synthetic construct
SEQUENCE: 88
ttattcatgc accttaaaat ccttgagag                             29

SEQ ID NO: 89           moltype = DNA  length = 24
FEATURE                 Location/Qualifiers
misc_feature            1..24
                        note = A synthetic oligonucleotide
source                  1..24
                        mol_type = other DNA
                        organism = synthetic construct
SEQUENCE: 89
atgaccgatg tatcctctct tcgt                                  24

SEQ ID NO: 90           moltype = DNA  length = 23
FEATURE                 Location/Qualifiers
misc_feature            1..23
                        note = A synthetic oligonucleotide
source                  1..23
                        mol_type = other DNA
                        organism = synthetic construct
SEQUENCE: 90
aaacactcac ataaccggcc caa                                   23

SEQ ID NO: 91           moltype = DNA  length = 20
FEATURE                 Location/Qualifiers
misc_feature            1..20
                        note = A synthetic oligonucleotide
source                  1..20
                        mol_type = other DNA
                        organism = synthetic construct
SEQUENCE: 91
gtccttgctt tcggaatact                                       20

SEQ ID NO: 92           moltype = DNA  length = 25
FEATURE                 Location/Qualifiers
misc_feature            1..25
                        note = A synthetic oligonucleotide
source                  1..25
                        mol_type = other DNA
                        organism = synthetic construct
SEQUENCE: 92
gaagtgatct acaaggattc ataaa                                 25

SEQ ID NO: 93           moltype = DNA  length = 23
FEATURE                 Location/Qualifiers
```

```
misc_feature           1..23
                       note = A synthetic oligonucleotide
source                 1..23
                       mol_type = other DNA
                       organism = synthetic construct
SEQUENCE: 93
tcattgattt gccctgcatc cac                                          23

SEQ ID NO: 94          moltype = DNA  length = 23
FEATURE                Location/Qualifiers
misc_feature           1..23
                       note = A synthetic oligonucleotide
source                 1..23
                       mol_type = other DNA
                       organism = synthetic construct
SEQUENCE: 94
caaagctagt gctgcttctg att                                          23

SEQ ID NO: 95          moltype = DNA  length = 26
FEATURE                Location/Qualifiers
misc_feature           1..26
                       note = A synthetic oligonucleotide
source                 1..26
                       mol_type = other DNA
                       organism = synthetic construct
SEQUENCE: 95
atggtatctg catgtctaaa actcaa                                       26

SEQ ID NO: 96          moltype = DNA  length = 25
FEATURE                Location/Qualifiers
misc_feature           1..25
                       note = A synthetic oligonucleotide
source                 1..25
                       mol_type = other DNA
                       organism = synthetic construct
SEQUENCE: 96
ctttctctct cttgtgcatc ttagt                                        25

SEQ ID NO: 97          moltype = DNA  length = 23
FEATURE                Location/Qualifiers
misc_feature           1..23
                       note = A synthetic oligonucleotide
source                 1..23
                       mol_type = other DNA
                       organism = synthetic construct
SEQUENCE: 97
acgttcatct tcaatgagtt cca                                          23

SEQ ID NO: 98          moltype = DNA  length = 25
FEATURE                Location/Qualifiers
misc_feature           1..25
                       note = A synthetic oligonucleotide
source                 1..25
                       mol_type = other DNA
                       organism = synthetic construct
SEQUENCE: 98
tacgtgtatg tcgatctgtt ccaat                                        25

SEQ ID NO: 99          moltype = DNA  length = 23
FEATURE                Location/Qualifiers
misc_feature           1..23
                       note = A synthetic oligonucleotide
source                 1..23
                       mol_type = other DNA
                       organism = synthetic construct
SEQUENCE: 99
catgtcattt gcttctcaat cac                                          23

SEQ ID NO: 100         moltype = DNA  length = 26
FEATURE                Location/Qualifiers
misc_feature           1..26
                       note = A synthetic oligonucleotide
source                 1..26
                       mol_type = other DNA
                       organism = synthetic construct
SEQUENCE: 100
cccattatct aaaagtctac atcacc                                       26

SEQ ID NO: 101         moltype = DNA  length = 23
```

```
FEATURE                Location/Qualifiers
misc_feature           1..23
                       note = A synthetic oligonucleotide
source                 1..23
                       mol_type = other DNA
                       organism = synthetic construct
SEQUENCE: 101
tcctcataaa gcaatggcgt ata                                          23

SEQ ID NO: 102         moltype = DNA  length = 23
FEATURE                Location/Qualifiers
misc_feature           1..23
                       note = A synthetic oligonucleotide
source                 1..23
                       mol_type = other DNA
                       organism = synthetic construct
SEQUENCE: 102
ctaagattca gacaatgggc tca                                          23

SEQ ID NO: 103         moltype = DNA  length = 22
FEATURE                Location/Qualifiers
misc_feature           1..22
                       note = A synthetic oligonucleotide
source                 1..22
                       mol_type = other DNA
                       organism = synthetic construct
SEQUENCE: 103
gcagacgcca atctttcttg gt                                           22

SEQ ID NO: 104         moltype = DNA  length = 30
FEATURE                Location/Qualifiers
misc_feature           1..30
                       note = A synthetic oligonucleotide
source                 1..30
                       mol_type = other DNA
                       organism = synthetic construct
SEQUENCE: 104
ttatgaagtt aaaaggagtg gttcgttgac                                   30

SEQ ID NO: 105         moltype = DNA  length = 21
FEATURE                Location/Qualifiers
misc_feature           1..21
                       note = A synthetic oligonucleotide
source                 1..21
                       mol_type = other DNA
                       organism = synthetic construct
SEQUENCE: 105
ggaacgagaa atgtcactca c                                            21

SEQ ID NO: 106         moltype = DNA  length = 23
FEATURE                Location/Qualifiers
misc_feature           1..23
                       note = A synthetic oligonucleotide
source                 1..23
                       mol_type = other DNA
                       organism = synthetic construct
SEQUENCE: 106
ttctagtttc tcacagaagt caa                                          23

SEQ ID NO: 107         moltype = DNA  length = 87
FEATURE                Location/Qualifiers
misc_feature           1..87
                       note = A synthetic oligonucleotide
source                 1..87
                       mol_type = other DNA
                       organism = synthetic construct
SEQUENCE: 107
tcaaatgcag cagacgaagt tgctactcaa cttttgaatt ttgacttgct gaagttggct  60
ggtgatgttg agtcaaaccc tggacct                                      87

SEQ ID NO: 108         moltype = DNA  length = 37
FEATURE                Location/Qualifiers
misc_feature           1..37
                       note = A synthetic oligonucleotide
source                 1..37
                       mol_type = other DNA
                       organism = synthetic construct
SEQUENCE: 108
ttctgcccaa attcgatggg gtctctatcc actatga                           37
```

```
SEQ ID NO: 109          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 109
agttaaaggc ctcgatcagg cgactggttc gaaaagta                      38

SEQ ID NO: 110          moltype = DNA  length = 33
FEATURE                 Location/Qualifiers
misc_feature            1..33
                        note = A synthetic oligonucleotide
source                  1..33
                        mol_type = other DNA
                        organism = synthetic construct
SEQUENCE: 110
ttctgcccaa attcgatgtc gctcgccttc aac                           33

SEQ ID NO: 111          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 111
agttaaaggc ctcgatcaaa agacaaagga tttcata                       37

SEQ ID NO: 112          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 112
ttctgcccaa attcgatggt tctttcatcg tcttgcac                      38

SEQ ID NO: 113          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 113
agttaaaggc ctcgattatt ttgcggcgga aacaggt                       37

SEQ ID NO: 114          moltype = DNA  length = 39
FEATURE                 Location/Qualifiers
misc_feature            1..39
                        note = A synthetic oligonucleotide
source                  1..39
                        mol_type = other DNA
                        organism = synthetic construct
SEQUENCE: 114
ttctgcccaa attcgatgaa aatgttgatg atcaaaagt                     39

SEQ ID NO: 115          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 115
agttaaaggc ctcgatcaga ccactggttc aaatagta                      38

SEQ ID NO: 116          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 116
```

```
ttctgcccaa attcgatgtc gtccctcgcc ggcaacct                       38

SEQ ID NO: 117          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 117
agttaaaggc ctcgactagt tgctgacaca actcatt                        37

SEQ ID NO: 118          moltype = DNA  length = 36
FEATURE                 Location/Qualifiers
misc_feature            1..36
                        note = A synthetic oligonucleotide
source                  1..36
                        mol_type = other DNA
                        organism = synthetic construct
SEQUENCE: 118
ttctgcccaa attcgatgca ggcttctatg tcatct                         36

SEQ ID NO: 119          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 119
agttaaaggc ctcgatcata cgactggttc aaacatt                        37

SEQ ID NO: 120          moltype = DNA  length = 33
FEATURE                 Location/Qualifiers
misc_feature            1..33
                        note = A synthetic oligonucleotide
source                  1..33
                        mol_type = other DNA
                        organism = synthetic construct
SEQUENCE: 120
ttctgcccaa attcgatggc ctccactgca tcc                            33

SEQ ID NO: 121          moltype = DNA  length = 36
FEATURE                 Location/Qualifiers
misc_feature            1..36
                        note = A synthetic oligonucleotide
source                  1..36
                        mol_type = other DNA
                        organism = synthetic construct
SEQUENCE: 121
agttaaaggc ctcgatcatt caactggttc gaacaa                         36

SEQ ID NO: 122          moltype = DNA  length = 34
FEATURE                 Location/Qualifiers
misc_feature            1..34
                        note = A synthetic oligonucleotide
source                  1..34
                        mol_type = other DNA
                        organism = synthetic construct
SEQUENCE: 122
ttctgcccaa attcgatgat tcctaatccc gaaa                           34

SEQ ID NO: 123          moltype = DNA  length = 36
FEATURE                 Location/Qualifiers
misc_feature            1..36
                        note = A synthetic oligonucleotide
source                  1..36
                        mol_type = other DNA
                        organism = synthetic construct
SEQUENCE: 123
agttaaaggc ctcgattaca ttggcaatcc gatgaa                         36

SEQ ID NO: 124          moltype = DNA  length = 35
FEATURE                 Location/Qualifiers
misc_feature            1..35
                        note = A synthetic oligonucleotide
source                  1..35
                        mol_type = other DNA
                        organism = synthetic construct
```

-continued

```
SEQUENCE: 124
ttctgcccaa attcgatgtc ggtggcgttc aacct                        35

SEQ ID NO: 125          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 125
agttaaaggc ctcgatcaag aggatgattc atgtacc                      37

SEQ ID NO: 126          moltype = DNA  length = 34
FEATURE                 Location/Qualifiers
misc_feature            1..34
                        note = A synthetic oligonucleotide
source                  1..34
                        mol_type = other DNA
                        organism = synthetic construct
SEQUENCE: 126
ttctgcccaa attcgatgtc cctcgccttc aacg                         34

SEQ ID NO: 127          moltype = DNA  length = 34
FEATURE                 Location/Qualifiers
misc_feature            1..34
                        note = A synthetic oligonucleotide
source                  1..34
                        mol_type = other DNA
                        organism = synthetic construct
SEQUENCE: 127
agttaaaggc ctcgatcatt tgccactcac attt                         34

SEQ ID NO: 128          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 128
ttctgcccaa attcgatggc ctctttgtcc actttcc                      37

SEQ ID NO: 129          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 129
agttaaaggc ctcgatcacg caactggttc gaaaaga                      37

SEQ ID NO: 130          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 130
ttctgcccaa attcgatgtc atttgcttcc caagccac                     38

SEQ ID NO: 131          moltype = DNA  length = 39
FEATURE                 Location/Qualifiers
misc_feature            1..39
                        note = A synthetic oligonucleotide
source                  1..39
                        mol_type = other DNA
                        organism = synthetic construct
SEQUENCE: 131
agttaaaggc ctcgactaga ctaccttctc aaacaatac                    39

SEQ ID NO: 132          moltype = DNA  length = 37
FEATURE                 Location/Qualifiers
misc_feature            1..37
                        note = A synthetic oligonucleotide
source                  1..37
                        mol_type = other DNA
```

```
                        organism = synthetic construct
SEQUENCE: 132
ttctgcccaa attcgatgtc actctcgttc accatca                        37

SEQ ID NO: 133          moltype = DNA  length = 36
FEATURE                 Location/Qualifiers
misc_feature            1..36
                        note = A synthetic oligonucleotide
source                  1..36
                        mol_type = other DNA
                        organism = synthetic construct
SEQUENCE: 133
agttaaaggc ctcgatcaag aggatgaagt gtttag                         36

SEQ ID NO: 134          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 134
ttctgcccaa attcgatgac ctctatgtcc tctctaa                        37

SEQ ID NO: 135          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 135
agttaaaggc ctcgatcata cgaccggtcc aaacagt                        37

SEQ ID NO: 136          moltype = DNA  length = 39
FEATURE                 Location/Qualifiers
misc_feature            1..39
                        note = A synthetic oligonucleotide
source                  1..39
                        mol_type = other DNA
                        organism = synthetic construct
SEQUENCE: 136
ttctgcccaa attcgatgtt acttgcgttc aacataagc                      39

SEQ ID NO: 137          moltype = DNA  length = 38
FEATURE                 Location/Qualifiers
misc_feature            1..38
                        note = A synthetic oligonucleotide
source                  1..38
                        mol_type = other DNA
                        organism = synthetic construct
SEQUENCE: 137
agttaaaggc ctcgattaat taggtaggta gaggggtt                       38

SEQ ID NO: 138          moltype = DNA  length = 52
FEATURE                 Location/Qualifiers
misc_feature            1..52
                        note = A synthetic oligonucleotide
source                  1..52
                        mol_type = other DNA
                        organism = synthetic construct
SEQUENCE: 138
atattctgcc caaattcgat gacttcaata tcctctctaa atttgagcaa tg       52

SEQ ID NO: 139          moltype = DNA  length = 35
FEATURE                 Location/Qualifiers
misc_feature            1..35
                        note = A synthetic oligonucleotide
source                  1..35
                        mol_type = other DNA
                        organism = synthetic construct
SEQUENCE: 139
cagagttaaa ggcctcgatc agacgaccgg tccaa                          35

SEQ ID NO: 140          moltype = DNA  length = 36
FEATURE                 Location/Qualifiers
misc_feature            1..36
                        note = A synthetic oligonucleotide
source                  1..36
```

```
                        mol_type = other DNA
                        organism = synthetic construct
SEQUENCE: 140
ttctgcccaa attcgatgtc tcttccgctc tcctct                              36

SEQ ID NO: 141          moltype = DNA  length = 49
FEATURE                 Location/Qualifiers
misc_feature            1..49
                        note = A synthetic oligonucleotide
source                  1..49
                        mol_type = other DNA
                        organism = synthetic construct
SEQUENCE: 141
gataagttaa aggcctcgat tattcatgca ccttaaaatc cttgagagc               49

SEQ ID NO: 142          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 142
ttctgcccaa attcgatgac cgatgtatcc tctcttc                             37

SEQ ID NO: 143          moltype = DNA  length = 35
FEATURE                 Location/Qualifiers
misc_feature            1..35
                        note = A synthetic oligonucleotide
source                  1..35
                        mol_type = other DNA
                        organism = synthetic construct
SEQUENCE: 143
agttaaaggc ctcgatcaca taaccggccc aaaca                               35

SEQ ID NO: 144          moltype = DNA  length = 35
FEATURE                 Location/Qualifiers
misc_feature            1..35
                        note = A synthetic oligonucleotide
source                  1..35
                        mol_type = other DNA
                        organism = synthetic construct
SEQUENCE: 144
ttctgcccaa attcgatggc gtcgctcgcg ttcac                               35

SEQ ID NO: 145          moltype = DNA  length = 39
FEATURE                 Location/Qualifiers
misc_feature            1..39
                        note = A synthetic oligonucleotide
source                  1..39
                        mol_type = other DNA
                        organism = synthetic construct
SEQUENCE: 145
agttaaaggc ctcgactaca aggattcata aattaagga                           39

SEQ ID NO: 146          moltype = DNA  length = 36
FEATURE                 Location/Qualifiers
misc_feature            1..36
                        note = A synthetic oligonucleotide
source                  1..36
                        mol_type = other DNA
                        organism = synthetic construct
SEQUENCE: 146
ttctgcccaa attcgcgaat gtcactcgcc ttcagc                              36

SEQ ID NO: 147          moltype = DNA  length = 37
FEATURE                 Location/Qualifiers
misc_feature            1..37
                        note = A synthetic oligonucleotide
source                  1..37
                        mol_type = other DNA
                        organism = synthetic construct
SEQUENCE: 147
agttaaaggc ctcgagctag gagcttaggg ttttcat                             37

SEQ ID NO: 148          moltype = DNA  length = 35
FEATURE                 Location/Qualifiers
misc_feature            1..35
                        note = A synthetic oligonucleotide
```

```
source                1..35
                      mol_type = other DNA
                      organism = synthetic construct
SEQUENCE: 148
ttctgcccaa attcgatggt atctgcatgt ctaaa                            35

SEQ ID NO: 149        moltype = DNA  length = 35
FEATURE               Location/Qualifiers
misc_feature          1..35
                      note = A synthetic oligonucleotide
source                1..35
                      mol_type = other DNA
                      organism = synthetic construct
SEQUENCE: 149
agttaaaggc ctcgatcatg aaggaattga aggaa                            35

SEQ ID NO: 150        moltype = DNA  length = 39
FEATURE               Location/Qualifiers
misc_feature          1..39
                      note = A synthetic oligonucleotide
source                1..39
                      mol_type = other DNA
                      organism = synthetic construct
SEQUENCE: 150
ttctgcccaa attcgatgag ttccattcga aatttaagt                        39

SEQ ID NO: 151        moltype = DNA  length = 39
FEATURE               Location/Qualifiers
misc_feature          1..39
                      note = A synthetic oligonucleotide
source                1..39
                      mol_type = other DNA
                      organism = synthetic construct
SEQUENCE: 151
agttaaaggc ctcgatcact tgagaggctc aaacatcat                        39

SEQ ID NO: 152        moltype = DNA  length = 37
FEATURE               Location/Qualifiers
misc_feature          1..37
                      note = A synthetic oligonucleotide
source                1..37
                      mol_type = other DNA
                      organism = synthetic construct
SEQUENCE: 152
ttctgcccaa attcgatgtc atttgcttct caatcac                          37

SEQ ID NO: 153        moltype = DNA  length = 39
FEATURE               Location/Qualifiers
misc_feature          1..39
                      note = A synthetic oligonucleotide
source                1..39
                      mol_type = other DNA
                      organism = synthetic construct
SEQUENCE: 153
agttaaaggc ctcgactaca tcaccctctc aaacaatac                        39

SEQ ID NO: 154        moltype = DNA  length = 45
FEATURE               Location/Qualifiers
misc_feature          1..45
                      note = A synthetic oligonucleotide
source                1..45
                      mol_type = other DNA
                      organism = synthetic construct
SEQUENCE: 154
ttctgcccaa attcgatggc gtatatgata tctatttcaa atctc                 45

SEQ ID NO: 155        moltype = DNA  length = 39
FEATURE               Location/Qualifiers
misc_feature          1..39
                      note = A synthetic oligonucleotide
source                1..39
                      mol_type = other DNA
                      organism = synthetic construct
SEQUENCE: 155
agttaaaggc ctcgatcaga caatgggctc aaatagaac                        39

SEQ ID NO: 156        moltype = DNA  length = 37
FEATURE               Location/Qualifiers
misc_feature          1..37
```

```
                         note = A synthetic oligonucleotide
source                   1..37
                         mol_type = other DNA
                         organism = synthetic construct
SEQUENCE: 156
ttctgcccaa attcgatgca agtctctctc tccctca                        37

SEQ ID NO: 157           moltype = DNA  length = 38
FEATURE                  Location/Qualifiers
misc_feature             1..38
                         note = A synthetic oligonucleotide
source                   1..38
                         mol_type = other DNA
                         organism = synthetic construct
SEQUENCE: 157
agttaaaggc ctcgattatg aagttaaaag gagtggtt                       38

SEQ ID NO: 158           moltype = DNA  length = 37
FEATURE                  Location/Qualifiers
misc_feature             1..37
                         note = A synthetic oligonucleotide
source                   1..37
                         mol_type = other DNA
                         organism = synthetic construct
SEQUENCE: 158
ttctgcccaa attcgcgaat gtcactcact ttcaacg                        37

SEQ ID NO: 159           moltype = DNA  length = 37
FEATURE                  Location/Qualifiers
misc_feature             1..37
                         note = A synthetic oligonucleotide
source                   1..37
                         mol_type = other DNA
                         organism = synthetic construct
SEQUENCE: 159
agttaaaggc ctcgagctag tttctcacag aagtcaa                        37

SEQ ID NO: 160           moltype = DNA  length = 35
FEATURE                  Location/Qualifiers
misc_feature             1..35
                         note = A synthetic oligonucleotide
source                   1..35
                         mol_type = other DNA
                         organism = synthetic construct
SEQUENCE: 160
aggagatata ccatggccga gattcgagtt gccac                          35

SEQ ID NO: 161           moltype = DNA  length = 37
FEATURE                  Location/Qualifiers
misc_feature             1..37
                         note = A synthetic oligonucleotide
source                   1..37
                         mol_type = other DNA
                         organism = synthetic construct
SEQUENCE: 161
ggtggtggtg ctcgaaggcg actggttcga aaagtac                        37

SEQ ID NO: 162           moltype = DNA  length = 40
FEATURE                  Location/Qualifiers
misc_feature             1..40
                         note = A synthetic oligonucleotide
source                   1..40
                         mol_type = other DNA
                         organism = synthetic construct
SEQUENCE: 162
aggagatata ccatggattt catggcgaaa atgaaagaga                     40

SEQ ID NO: 163           moltype = DNA  length = 36
FEATURE                  Location/Qualifiers
misc_feature             1..36
                         note = A synthetic oligonucleotide
source                   1..36
                         mol_type = other DNA
                         organism = synthetic construct
SEQUENCE: 163
ggtggtggtg ctcgaaaaag acaaaggatt tcatat                         36

SEQ ID NO: 164           moltype = DNA  length = 40
FEATURE                  Location/Qualifiers
```

```
misc_feature           1..40
                       note = A synthetic oligonucleotide
source                 1..40
                       mol_type = other DNA
                       organism = synthetic construct
SEQUENCE: 164
aggagatata ccatgcaaat tcgtggaaag caaagatcac                              40

SEQ ID NO: 165         moltype = DNA  length = 38
FEATURE                Location/Qualifiers
misc_feature           1..38
                       note = A synthetic oligonucleotide
source                 1..38
                       mol_type = other DNA
                       organism = synthetic construct
SEQUENCE: 165
ggtggtggtg ctcgaagacc actggttcaa atagaact                                38

SEQ ID NO: 166         moltype = DNA  length = 35
FEATURE                Location/Qualifiers
misc_feature           1..35
                       note = A synthetic oligonucleotide
source                 1..35
                       mol_type = other DNA
                       organism = synthetic construct
SEQUENCE: 166
aggagatata ccatgtctaa atcatctgca gctgt                                   35

SEQ ID NO: 167         moltype = DNA  length = 35
FEATURE                Location/Qualifiers
misc_feature           1..35
                       note = A synthetic oligonucleotide
source                 1..35
                       mol_type = other DNA
                       organism = synthetic construct
SEQUENCE: 167
ggtggtggtg ctcgaagttg ctgacacaac tcatt                                   35

SEQ ID NO: 168         moltype = DNA  length = 30
FEATURE                Location/Qualifiers
misc_feature           1..30
                       note = A synthetic oligonucleotide
source                 1..30
                       mol_type = other DNA
                       organism = synthetic construct
SEQUENCE: 168
aggagatata ccatgaccgt caaatgctac                                         30

SEQ ID NO: 169         moltype = DNA  length = 35
FEATURE                Location/Qualifiers
misc_feature           1..35
                       note = A synthetic oligonucleotide
source                 1..35
                       mol_type = other DNA
                       organism = synthetic construct
SEQUENCE: 169
ggtggtggtg ctcgaacaag gattcataaa ttaag                                   35

SEQ ID NO: 170         moltype = DNA  length = 30
FEATURE                Location/Qualifiers
misc_feature           1..30
                       note = A synthetic oligonucleotide
source                 1..30
                       mol_type = other DNA
                       organism = synthetic construct
SEQUENCE: 170
aggagatata ccatgactgt caagtgcagc                                         30

SEQ ID NO: 171         moltype = DNA  length = 30
FEATURE                Location/Qualifiers
misc_feature           1..30
                       note = A synthetic oligonucleotide
source                 1..30
                       mol_type = other DNA
                       organism = synthetic construct
SEQUENCE: 171
ggtggtggtg ctcgaatgaa ggaattgaag                                         30

SEQ ID NO: 172         moltype = DNA  length = 40
```

```
FEATURE                 Location/Qualifiers
misc_feature            1..40
                        note = A synthetic oligonucleotide
source                  1..40
                        mol_type = other DNA
                        organism = synthetic construct
SEQUENCE: 172
aggagatata ccatgtttat gcccacttcc attaaatgta                          40

SEQ ID NO: 173          moltype = DNA  length = 42
FEATURE                 Location/Qualifiers
misc_feature            1..42
                        note = A synthetic oligonucleotide
source                  1..42
                        mol_type = other DNA
                        organism = synthetic construct
SEQUENCE: 173
ggtggtggtg ctcgaacatc accctctcaa acaatacttt gg                       42

SEQ ID NO: 174          moltype = DNA  length = 43
FEATURE                 Location/Qualifiers
misc_feature            1..43
                        note = A synthetic oligonucleotide
source                  1..43
                        mol_type = other DNA
                        organism = synthetic construct
SEQUENCE: 174
aggagatata ccatggtagc aaaagtgatc gagagccgag tta                      43

SEQ ID NO: 175          moltype = DNA  length = 44
FEATURE                 Location/Qualifiers
misc_feature            1..44
                        note = A synthetic oligonucleotide
source                  1..44
                        mol_type = other DNA
                        organism = synthetic construct
SEQUENCE: 175
ggtggtggtg ctcgaagaca atgggctcaa atagaacttt aaat                     44

SEQ ID NO: 176          moltype = AA  length = 575
FEATURE                 Location/Qualifiers
source                  1..575
                        mol_type = protein
                        organism = Salvia sclarea
SEQUENCE: 176
MSLAFNVGVT PFSGQRVGSR KEKFPVQGFP VTTPNRSRLI VNCSLTTIDF MAKMKENFKR  60
EDDKFPTTTT LRSEDIPSNL CIIDTLQRLG VDQFFQYEIN TILDNTFRLW QEKHKVIYGN  120
VTTHAMAFRL LRVKGYEVSS EELAPYGNQE AVSQQTNDLP MIIELYRAAN ERIYEEERSL  180
EKILAWTTIF LNKQVQDNSI PDKKLHKLVE FYLRNYKGIT IRLGARRNLE LYDMTYYQAL  240
KSTNRFSNLC NEDFLVFAKQ DFDIHEAQNQ KGLQQLQRWY ADCRLDTLNF GRDVVIIANY  300
LASLIIGDHA FDYVRLAFAK TSVLVTIMDD FFDCHGSSQE CDKIIELVKE WKENPDAEYG  360
SEELEILFMA LYNTVNELAE RARVEQGRSV KEFLVKLWVE ILSAFKIELD TWSNGTQQSF  420
DEYISSSWLS NGSRLTGLLT MQFVGVKLSD EMLMSEECTD LARHVCMVGR LLNDVCSSER  480
EREENIAGKS YSILLATEKD GRKVSEDEAI AEINEMVEYH WRKVLQIVYK KESILPRRCK  540
DVFLEMAKGT FYAYGINDEL TSPQQSKEDM KSFVF                               575

SEQ ID NO: 177          moltype = DNA  length = 1728
FEATURE                 Location/Qualifiers
source                  1..1728
                        mol_type = other DNA
                        organism = Salvia sclarea
SEQUENCE: 177
atgtcgctcg ccttcaacgt cggagttacg cctttctccg gccaaagagt tgggagcagg  60
aaagaaaaat ttccagtcca aggatttcct gtgaccaccc ccaataggtc acgtctcatc  120
gttaactgca gccttactac aatagatttc atggcgaaaa tgaaagagaa tttcaagagg  180
gaagacgata aatttccaac gacaacgact cttcgatccg aagatatacc ctctaatttg  240
tgtataatcg acaccottca aaggttgggg gtcgatcaat tcttccaata tgaaatcaac  300
actattctag ataacacatt caggttgtgg caagaaaaac acaaagttat atatggcaat  360
gttactactc atgcaatggc atttaggctt ttgcgagtga aaggatacga agtttcatca  420
gaggagttgg ctccatatgg taaccaagag gctgttagcc agcaaacaaa tgacctgccg  480
atgattattg agctttatag agcagcaaat gagagaatat atgaagaaga gaggagtctt  540
gaaaaaattc ttgcttggac taccatcttt ctcaataagc aagtgcaaga taactcaatt  600
cccgacaaaa aactgcacaa actggtggaa ttctacttga ggaattacaa aggcataacc  660
ataagattgg gagctagacg aaacctcgag ctatatgaca tgacctacta tcaagctctg  720
aaatctacaa acaggttctc taatttatgc aacgaagatt ttctagtttt cgcaaagcaa  780
gatttcgata tacatgaagc ccagaaccag aaaggacttc aacaactgca aaggtggtat  840
gcagattgta ggttggacac cttaaacttt ggaagagatg tagttattat tgctaattat  900
ttggcttcat taattattgg tgatcatgcg tttgactatg ttcgtctcgc atttgccaaa  960
acatctgtgc ttgtaacaat tatggatgat tttttcgact gtcatggctc tagtcaagag  1020
```

-continued

```
tgtgacaaga tcattgaatt agtaaaagaa tggaaggaga atccggatgc agagtacgga  1080
tctgaggagc ttgagatcct ttttatggcg ttgtacaata cagtaaatga gttggcggag  1140
agggctcgtg ttgaacaggg gcgtagtgtc aaagagtttc tagtcaaact gtgggttgaa  1200
atactctcag ctttcaagat agaattagat acatggagca atggcacgca gcaaagcttc  1260
gatgaataca tttcttcgtc gtggttgtcg aacggttccc ggctgacagg tctcctgacg  1320
atgcaattcg tcggagtaaa attgtccgat gaaatgctta tgagtgaaga gtgcactgat  1380
ttggctaggc atgtctgtat ggtcggccgg ctgctcaacg acgtgtgcag ttctgagagg  1440
gagcgcgagg aaaatattgc aggaaaaagt tatagcattc tactagcaac tgagaaagat  1500
ggaagaaaag ttagtgaaga tgaagccatt gcagagatca atgaaatggt tgaatatcac  1560
tggagaaaag tgttgcagat tgtgtataaa aaagaaagca ttttgccaag aagatgcaaa  1620
gatgtatttt tggagatggc taagggtacg ttttatgctt atgggatcaa cgatgaattg  1680
acttctcctc agcaatccaa ggaagatatg aaatcctttg tcttttga              1728
```

METHODS FOR PRODUCTION OF NOVEL DITERPENE SCAFFOLDS

This application is a divisional of U.S. application Ser. No. 17/265,482, filed Feb. 2, 2021, which is a U.S. national stage filing under 35 U.S.C. 371 from International Application No. PCT/US2019/044887, filed on 2 Aug. 2019, and published as WO 2020/028795 A1 on 6 Feb. 2020, which claims the benefit of U.S. Provisional Application Ser. No. 62/714,216, filed Aug. 3, 2018, which applications are incorporated by reference herein their entirety.

GOVERNMENT FUNDING

This invention was made with government support under 1737898 awarded by the National Science Foundation, and under DE-FC02-07ER64494 and DE-SC0018409 awarded by the U.S. Department of Energy. The government has certain rights in the invention.

INCORPORATION BY REFERENCE OF SEQUENCE LISTING

This application contains a Sequence Listing which has been submitted electronically in ST26 format and is hereby incorporated by reference in its entirety. Said ST26 file, created on Dec. 4, 2023, is named "2390069.xml" and is 293,571 bytes in size.

BACKGROUND

Plant-derived terpenoids have a wide range of commercial and industrial uses. Examples of uses for terpenoids include specialty fuels, agrochemicals, fragrances, nutraceuticals and pharmaceuticals. However, currently available methods for petrochemical synthesis, extraction, and purification of terpenoids from the native plant sources have limited economic sustainability.

SUMMARY

Described herein are enzymes useful for production of a variety of terpenes, diterpenes and terpenoids. In some cases, the enzymes synthesize diterpenes. The enzymes were isolated from the mint family (Lamiaceae). Members of the mint family accumulate a wide variety of industrially and medicinally relevant diterpenes. While there are more than 7000 plant species in Lamiaceae, diterpene synthase (diTPS) genes have been characterized from just eleven. The Mint Evolutionary Genomics Consortium (see website at mints-.plantbiology.msu.edu) has now sequenced leaf transcriptomes from at least 48 phylogenetically diverse Lamiaceae species, more than doubling the number of mint species for which transcriptomes are available. The available chemotaxonomic and enzyme activity data are described herein for diterpene synthases (diTPSs) in Lamiaceae. The diTPS sequences and terpenes produced are also described herein. One of the new enzymes produces neo-cleroda-4(18),13E-dienyl diphosphate, a molecule with promising applications in agricultural biotechnology as a precursor to potent insect anti-feedants.

Described herein are expression systems that include at least one expression cassette having at least one heterologous promoter operably linked to at least one nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. In some cases, the expression systems can have more than one expression cassettes or expression vectors, each expression cassette or expression vector can have at least one nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. Host cells that include such expression systems are also described herein.

Methods are also described herein that include incubating a host cell comprising a heterologous expression system that includes at least one expression cassette having a heterologous promoter operably linked to a nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. The expression system within host cell can include more than one expression cassettes or expression vectors.

In addition, methods are described herein for synthesizing a diterpene comprising incubating a terpene precursor with at least one enzyme having at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176. Such methods can include incubating more than one terpene precursor and/or incubating more than one enzyme in a mixture to produce one or more terpenes or terpenoid compounds.

A variety of diterpenes are also described herein.

DESCRIPTION OF THE FIGURES

FIG. 1A illustrates diterpene skeletons per genus according to both the Dictionary of Natural Products (DNP) and SISTEMAT. FIG. 1B illustrates the distribution of skeletons among Lamiaceae clades and genera, based on the DNP. Structures are shown for selected skeletons, where black structures are those where a biosynthetic route is known from Lamiaceae, and gray structures are those for which the pathway remains unknown. FIG. 1C illustrates the distribution of compounds among skeletons, based on the DNP. FIG. 1D illustrates diterpene structures per genus according to both the DNP and the NAPRALERT database. Darker spots indicate overlapping data points, some labels omitted due to space constraints.

FIG. 2A shows a maximum likelihood tree of newly characterized (blue) class II diTPS enzymes. FIG. 2B shows a maximum likelihood tree of newly characterized (blue) class I diTPS enzymes. The maximum likelihood tree of newly characterized (blue) class II and class I diTPS enzymes are shown in the context of previously reported (black) diTPSs from Lamiaceae. The bifunctional ent-kaurene synthase from *Physcomitrella patens* was used as an outgroup. After each enzyme type are listed the experimentally verified substrates (green) and their products, where the numbers correspond to compound numbers in FIG. 3. Units for scale bars are substitutions per site. Abbreviations for species are listed in Table 5 and those not listed in Table 5 are as follows: Ie, *Isodon eriocalyx*, Ir, *Isodon rubescens*; Mv, *Marrubium vulgare*, Sd, *Salvia divinorum*; Sm, *Salvia miltiorriza*, Sp, *Salvia pomifera*, Ss, *Salvia sclarea*, Vac, *Vitex agnus-castus.*

FIG. 3A shows products of diterpene synthases from Lamiaceae. Blue numbers indicate compounds experimentally verified to be products of new enzymes identified using the methods described herein. At the center is geranylgeranyl diphosphate (GGPP), a precursor to all of these diterpenes. The inner ring are class II products, the product show in the outer ring are class I products derived from the compound in the connected segment of the inner ring. FIG. 3B(A) to 3B(H) show overlapping portions of a phylogenetic tree generated from the peptide sequences from the reference set, alongside those from the new transcriptome data, including established substrates and products for each enzyme.

FIG. 4A shows products detected by gas chromatography from activity assays of *Ajuga reptans* cleroda-4(18),13E-dienyl diphosphate synthase (ArTPS2) and *Salvia sclarea* sclareol synthase (SsSS) in-vitro with purified protein contacted with GGPP, and in-vivo of *N. benthamiana* cells that transiently expressed the gene combinations. FIG. 4B shows products detected by gas chromatography from activity assays of PcTPS1+SsSS, In-vitro with purified protein contacted with GGPP, and in-vivo of *N. benthamiana* cells that transiently expressed the gene combinations. FIG. 4C shows mass spectra for the products of ArTPS2 and PcTPS1, and their combinations with SsSS.

FIG. 5A shows structures that can be generated by the activities of new class I diTPSs. Filled in blue boxes indicate which enzymes are capable of each conversion. FIG. 5B illustrates structures that can be produced by the newly characterized enzyme activities including some of the new class II enzymes. Blue genes are newly characterized. Blue square: TPS-e from that position on the key catalyzes the shown transformation. White square: corresponding TPS-e does not catalyze the shown activity. Grey square: corresponding TPS-e was not tested on the substrate.

FIG. 6A shows GC total ion chromatograms of extracts from *N. benthamiana* expressing OmTPS1 and OmTPS5, compared to extracts of various tissues of *O. majorana*. FIG. 6B shows a mass spectrum of peak B, from *O. majorana* leaf (where peak B is shown in FIG. 6A). FIG. 6C shows a mass spectrum of peak C from a *O. majorana* leaf compared to reference spectrum for palustrinol from the NIST17 library (where peak C is shown in FIG. 6A).

FIG. 7A shows GC-MS-total ion and extracted ion chromatograms illustrating production of ent-kaurene (identified from peak 1) from in vivo assays in *N. benthamiana* transiently expressing the gene combinations shown. The mass spectrum of peak 1 is shown below the chromatograms, demonstrating that peak 1 is ent-kaurene as identified through direct comparison with biosynthesized authentic standards with reference enzymes. FIG. 7B shows GC-MS-total ion and extracted ion chromatograms illustrating production of ent-dolabradiene (identified from peak 2) from in vivo assays in *N. benthamiana* transiently expressing the gene combinations shown. The mass spectrum of peak 2 is shown below the chromatograms, demonstrating that peak 2 is ent-dolabradiene as identified through direct comparison with biosynthesized authentic standards with reference enzymes. FIG. 7C shows GC-MS-total ion and extracted ion chromatograms illustrating production of (13R)-ent-manoyl oxide (identified from peak 3) from in vivo assays in *N. benthamiana* transiently expressing the gene combinations shown. The mass spectrum of peak 3 is shown below the chromatograms, demonstrating that peak 3 is (13R)-ent-manoyl oxide as identified through direct comparison with biosynthesized authentic standards with reference enzymes.

DETAILED DESCRIPTION

Figure 1A:
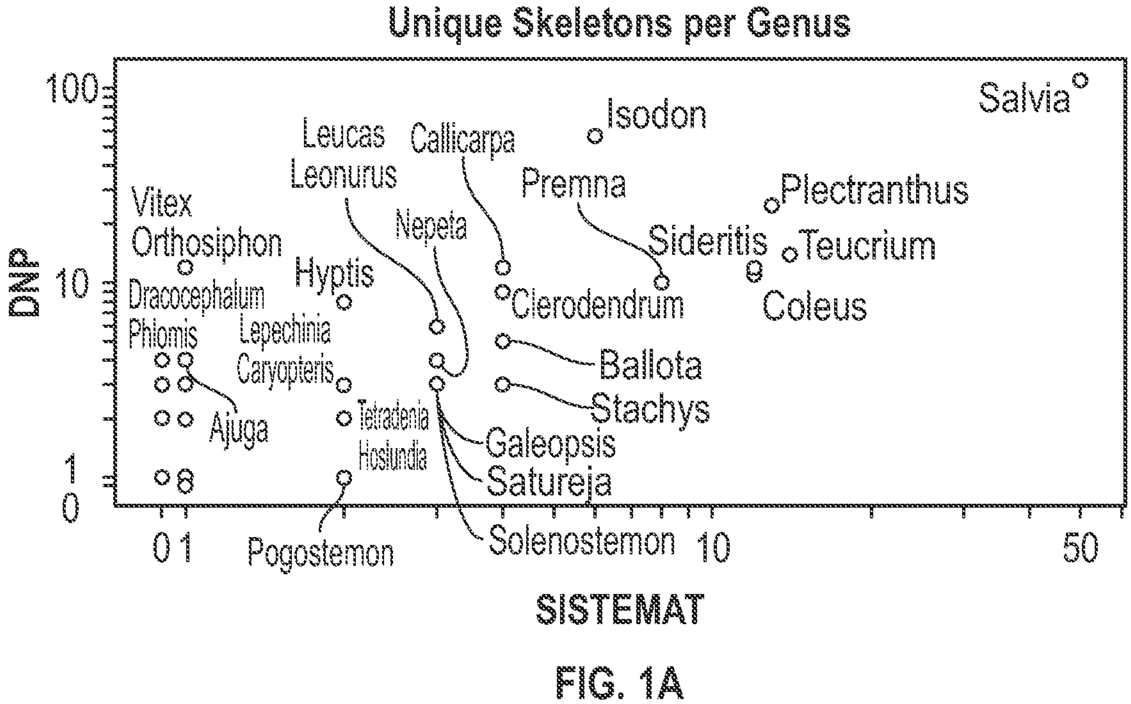
FIG. 1A-1D illustrate the distribution of diterpenes in Lamiaceae. Note that Table 4 provides a comparison of different sources for data about Lamiaceae diterpene chemotaxonomy.

Described herein are new enzymes and compounds, as well as methods that are useful for manufacturing such compounds. The compounds that can be made by the enzymes and methods are new compounds and compounds that were previously difficult to make.

The enzymes described herein are from a variety of mint plant species and can synthesize a variety of terpene skeletons and terpenes.

Terpenes

The enzymes described herein can facilitate synthesis of a variety of terpenes, diterpenes, and terpenoids. For example, the enzymes described herein can facilitate synthesis of terpenes, diterpenes, and terpenoids can generally have the structure of Formula I:

I

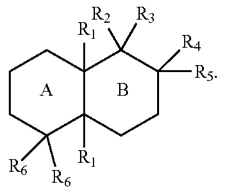

In some cases, the terpenes, diterpenes, and terpenoids can generally have the structure of Formula II:

II

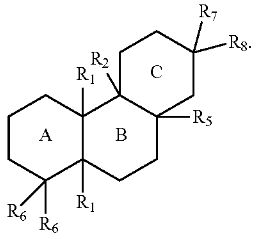

In some cases, the terpenes, diterpenes, and terpenoids can generally have the structure of Formula III:

III

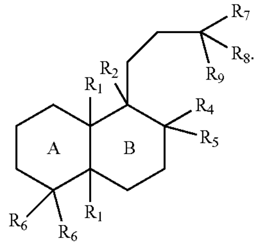

The substituents of Formulae I, II, and III can be as follows:

each $R_1$ can separately be hydrogen or lower alkyl;

$R_2$ can be hydrogen, lower alkyl, hydroxy, a bond to an adjacent ring carbon, or form a $C_4$-$C_6$ cycloheteroalkyl with $R_3$;

$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;

$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;

$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;

each $R_6$ can separately be hydrogen, lower alkyl, lower alkene, or form a bond with an adjacent carbon;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; or $R_9$ can be hydrogen, lower alkyl, lower alkene, $=CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

The alkyl group(s) can have one to ten carbon atoms. In some cases, the alkyl groups can be lower alkyl group(s) (e.g., C1-C6 alkyl groups). In some cases, where substituents such as $R_1$, $R_2$, $R_5$, and $R_6$ are lower alkyl groups, they can be a C1-C3 lower alkyl. In some cases, where substituents such as $R_1$, $R_2$, $R_5$, and $R_b$ are lower alkyl groups, they are an ethyl or methyl group.

Cycloalkyl groups are cyclic alkyl groups such as, but not limited to, cyclopropyl, cyclobutyl, cyclopentyl, cyclohexyl, cycloheptyl, and cyclooctyl groups. In some cases, the cycloalkyl group can have 3 to about 8-12 ring members, whereas in other cases the number of ring carbon atoms range from 4, 5, 6, or 7. Cycloalkyl groups can include cycloalkyl rings having at least one double bond between 2 carbons (i.e., cycloalkenyl rings). Thus, for example, the A, B and/or C rings can also be a cycloalkenyl group such as a cyclohexenyl, cyclopentenyl, or cyclohexadienyl group. Cycloalkenyl groups can have from 4 to about 8-12 ring members.

Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups. The term "cycloalkenyl" alone or in combination denotes a cyclic alkenyl group.

Heterocycloalkyl groups include ring groups containing 3 or more ring members, of which, one or more is a heteroatom such as, but not limited to, N, O, and S. The compounds described herein that have heteroatoms typically have an oxygen heteroatom. In some embodiments, heterocyclyl groups include 3 to about 15 ring members, whereas other such groups have 3 to about 10 ring members. A heterocyclyl group designated as a $C_2$-heterocyclyl can be a 5-ring with two carbon atoms and three heteroatoms, 6-ring with two carbon atoms and four heteroatoms and so forth. A $C_3$-heterocyclyl can be a 5-ring with three carbons and two heteroatoms, a 6-ring with three carbons and three heteroatoms, and so forth. A $C_4$-heterocyclyl can be a 5-ring four carbons and one heteroatom, a 6-ring with four carbons and two heteroatoms, and so forth. The number of carbon atoms plus the number of heteroatoms sums up to equal the total number of ring atoms. A heterocyclyl ring can also include one or more double bonds. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or they can be substituted. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups In some cases, only one of the $R_1$ groups is a lower alkyl, while the other is hydrogen.

In some cases, $R_2$ is hydrogen when $R_3$ forms a ring with $R_4$.

Although in many diterpenes, each $R_6$ is a lower alkyl, in some cases one $R_6$ is a lower alkene white the other is bond that contributes to lower alkene. For example, in some cases the two $R_6$ groups form a lower alkene together, for example, a $=CH_2$ group.

The compounds produced by the enzymes described herein are typically terpenes or diterpenes. Diterpenes are a class of chemical compounds composed of two terpene units, often with the molecular formula $C_{20}H_{32}$, though some can include 1-2 heteroatoms or other substituents. Diterpenes generally consist of four isoprene subunits. The positions of various atoms in a diterpene can, for example, be numbered as shown below.

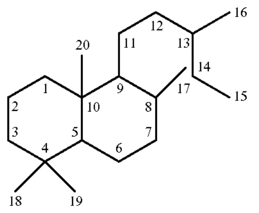

The enzymes described herein can produce compounds with the following skeletons (Sk1-Sk14), where 1-2 of the ring atoms can in some cases be heteroatoms (e.g., oxygen or nitrogen). If a heteroatom is present in it is usually an oxygen atom.
Sk1
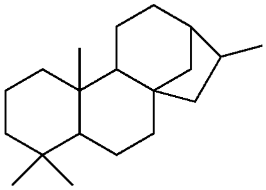
Sk2
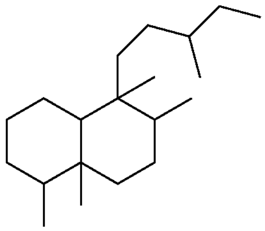
Sk3
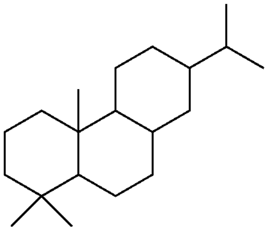
Sk4
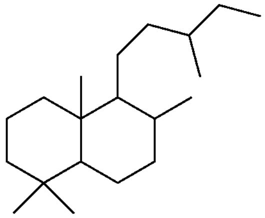
Sk5
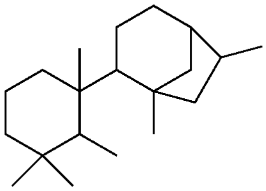
Sk6
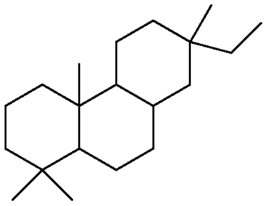
-continued
Sk7
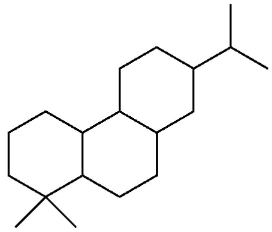
Sk8
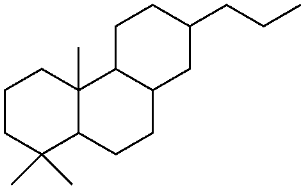
Sk9
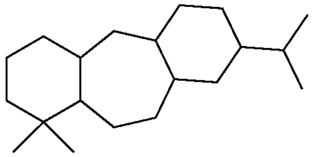
Sk10
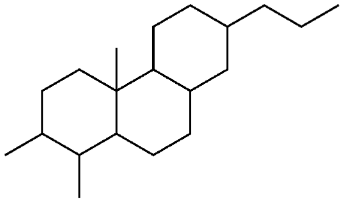
Sk11
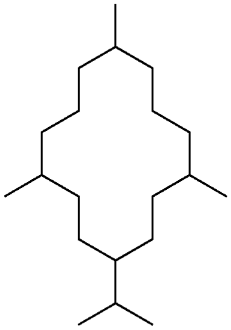
Sk12
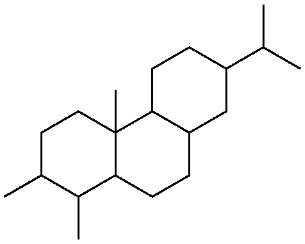
Sk13
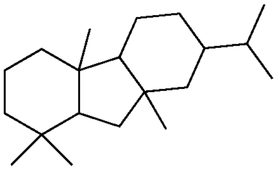

-continued

Sk14

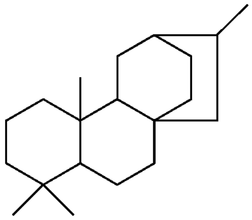

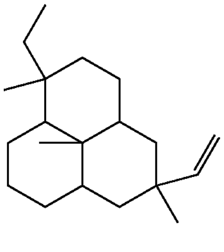

,

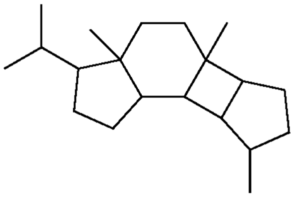

, or a combination thereof.

Enzymes

The enzymes described herein are from a variety of mint plant species and can synthesize a variety of terpenes, diterpene skeletons, and terpenoid compounds.

For example, an *Ajuga reptans* miltiradiene synthase (ArTPS3), a *Leonotis leonurus* sandaracopimaradiene synthase (LlTPS4), a *Mentha spicata* class I diterpene synthase (MsTPS1), an *Origanum majorana* trans-abienol synthase (OmTPS3), an *Origanum majorana* manool synthase (OmTPS4), an *Origanum majorana* palustradiene synthase (OmTPS5), *Perovskia atriplicifolia* miltiradiene synthase (PaTPS3), *Prunella vulgaris* miltiradiene synthase (PvTPS1), *Salvia officinalis* miltiradiene synthase (SoTPS1) were identified and isolated as described herein.

Eight of these enzymes, ArTPS3, LlTPS4, MsTPS1, OmTPS4, OmTPS5, PaTPS3, PvTPS1, and SoTPS1 can convert a labda-13-en-8-ol diphosphate ((+)-8-LPP) [compound 10]) to 13R-(+)-manoyl oxide [8].

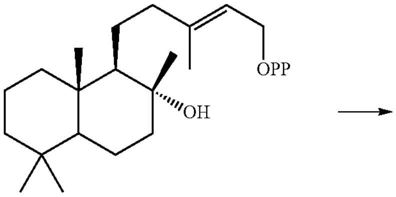

10

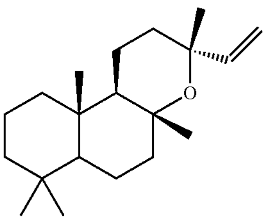

8

The ArTPS3, LlTPS4, OmTPS4, OmTPS5, PaTPS3, PvTPS1, and SoYPS1 enzymes can also convert peregrinol diphosphate (PgPP) [5] to a combination of compounds 1, 2, and 3, as illustrated below.

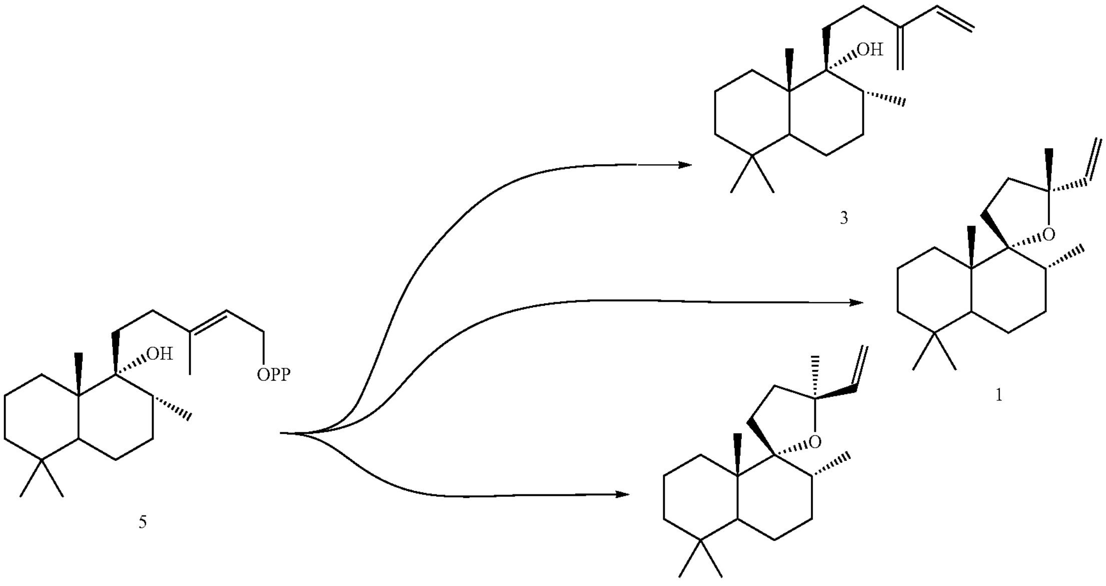

5

3

1

2

However, MsTPS1 produced only compound 3 from compound 5, while the OmTPS3 enzyme produced only 1, and 2. The OmTPS4 enzyme produced compound 4 (shown below) in addition to compounds 1, 2, and 3.

4

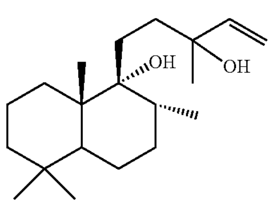

The ArTPS3, PaTPS3, PvTPS1, and SoTPS1 enzymes can also convert (+)-copalyl diphosphate ((+)-CPP) [31]) to miltiradiene [32].

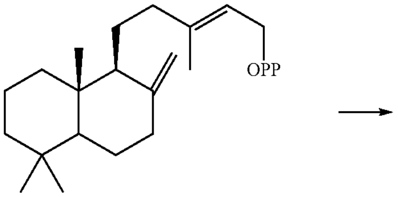

31

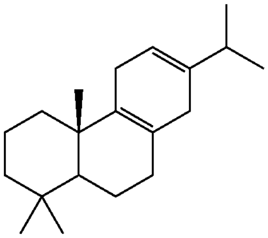

32

However, LITPS4 and MsTPS1 converted (+)-copalyl diphosphate ((+)-CPP) [31]) to sadaracopimaradiene [27], while OmTPS3 converted (+)-copalyl diphosphate ((+)-CPP) [31]) to trans-biformene [34].

27

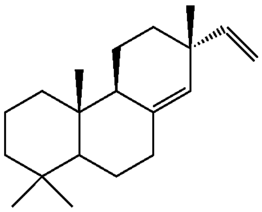

34

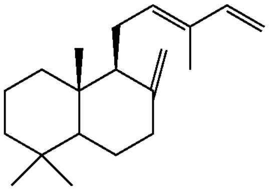

The *Ajuga reptans* miltiradiene synthase (ArTPS3) has the amino acid sequence shown below (SEQ ID NO:1).

```
  1 MSLSFTIKVT PFSGQRVHSS TESFPIQQFP TITTKSAMAV
 41 KCSSLSTATV SFQDFVGKIR DTINGKVDNS PAATTIHPAD
 81 IPSNLCVVDT LQRLGVDRYF QSEIDSVLND TYRFWQQKGE
121 DIFTDVACRA MAFRLLRVKG YEVSSDELAS YAEQEHVNLQ
161 PSDITTVIEL YRASQTRLYE DEGNLEKLHT WTSNFLKQQL
201 QSETISDEKL HKQVEYYLKN YHGILDRAGV RQSLDLYDIN
241 QYQNLKSTDR FPTLSNEDLL EFAKQDFNFC QAQHQKELQQ
281 LQRWYADCKL DTLTYGRDVV RVASFLTAAI FGEPEFSDAR
321 LAFAKHIILV TRIDDFFDHG GSIEESYKIL DLVKEWEDKP
361 AEEYPSKEVE ILFTAVYNTV NDLAEMAYIE QGRSIKPLLI
401 KLWVEILTSF KKELDSWTED TELTLEEYLA SSWVSIGCRI
441 CSLNSLQFLG ITLSEEMLSS EECMELCRHV SSVDRLLNDV
481 QTFEKERLEN TINSVSLQLA EAQREGRTIT EEEAMSKIKD
521 LADYHRRQLM QMVYKDGTIF PRQCKDVFLR VCRIGYYLYA
561 SGDEFTTPQQ MMGDMKSLVY EPLNTSSS
```

A nucleic acid encoding the *Ajuga reptans* miltiradiene synthase (ArTPS3) with SEQ ID NO:1 is shown below as SEQ ID NO:2.

```
  1 ATGTCACTCT CGTTCACCAT CAAAGTCACC CCCTTTTCGG
 41 GCCAGAGAGT TCACAGCAGC ACAGAAAGCT TTCCAATCCA
 81 ACAATTTCCA ACGATCACCA CCAAATCCGC CATGGCTGTC
121 AAATGCAGCA GCCTCAGTAC CGCAACAGTA AGCTTCCAGG
161 ATTTCGTCGG AAAAATCAGA GATACGATCA ACGGGAAAGT
201 TGACAATTCT CCAGCAGCGA CCACTATTCA TCCTGCAGAT
241 ATACCCTCCA ATCTCTGCGT GGTGGATACC CTCCAAAGAT
281 TGGGAGTTGA CCGTTACTTC CAATCTGAAA TCGACAGCGT
321 TCTTAACGAC ACATACAGGT TCTGGCAGCA GAAAGGAGAA
361 GATATCTTCA CTGATGTTGC TTGTCGTGCA ATGGCATTTC
401 GACTTTTGCG AGTTAAAGGA TATGAAGTTT CATCAGATGA
521 ACTCGCTTCG TATGCTGAAC AAGAGCATGT TAACCTGCAA
561 CCAAGTGACA TAACTACGGT TATCGAGCTT TACAGAGCAT
601 CACAGACAAG ATTATATGAA GACGAGGGCA ATCTTGAGAA
641 GTTACATACT TGGACTAGCA ATTTTCTGAA GCAACAATTG
681 CAGAGTGAAA CTATTTCTGA CGAGAAATTG CACAAACAGG
721 TGGAGTATTA CTTGAAGAAC TACCACGGCA TACTAGACCG
761 TGCTGGAGTT AGACAAAGTC TCGATTTATA TGACATAAAC
801 CAATACCAGA ATCTAAAATC TACAGATAGA TTCCCTACTT
841 TAAGTAACGA AGATTTACTT GAATTCGCGA AGCAAGATTT
881 TAACTTTTGC CAAGCTCAAC ACCAGAAAGA GCTTCAGCAA
921 CTGCAAAGGT GGTATGCGGA TTGTAAATTG GATACATTGA
961 CTTACGGAAG AGATGTGGTA CGTGTTGCAA GTTTCCTGAC
```

-continued

```
1001 AGCTGCAATT TTTGGTGAGC CTGAATTCTC TGATGCTCGT
1041 CTAGCCTTCG CCAAACACAT CATCCTCGTG ACACGTATTG
1081 ATGATTTCTT CGATCATGGT GGGTCTATAG AAGAGTCATA
1121 CAAGATCCTG GATTTAGTAA AAGAATGGGA AGATAAGCCA
1161 GCTGAGGAAT ATCCTTCCAA GGAAGTTGAA ATCCTCTTTA
1201 CAGCAGTATA TAATACAGTA AATGACTTGG CAGAAATGGC
1241 TTATATTGAG CAAGGCCGTT CCATTAAACC TCTTCTAATT
1281 AAACTGTGGG TTGAAATACT GACAAGTTTC AAGAAAGAAC
1321 TGGATTCATG GACAGAAGAC ACAGAACTAA CCTTGGAGGA
1361 GTACTTGGCT TCCTCCTGGG TGTCGATCGG TTGCAGAATC
1401 TGCAGTCTCA ATTCGCTGCA GTTCCTTGGT ATAACATTAT
1441 CCGAAGAAAT GCTTTCAAGC GAAGAGTGCA TGGAGTTGTG
1481 TAGGCATGTT TCTTCAGTCG ACAGGCTACT CAATGACGTG
1521 CAAACTTTCG AGAAGGAACG CCTAGAAAAT ACGATAAACA
1561 GTGTGAGCCT ACAGCTAGCA GAAGCTCAGA GAGAAGGAAG
1601 AACCATTACA GAAGAGGAGG CTATGTCAAA GATTAAAGAC
1641 CTGGCTGATT ATCACAGGAG ACAACTGATG CAGATGGTTT
1681 ATAAGGATGG GACCATATTT CCGAGACAAT GCAAAGATGT
1721 CTTTTTGAGG GTATGCAGGA TTGGCTACTA CTTATACGCG
1761 AGCGGCGATG AATTCACTAC TCCACAACAA ATGATGGGGG
1801 ATATGAAATC ATTGGTTTAT GAACCCCTAA ACACTTCATC
1841 CTCTTGA
```

The *Leonotis leonarus* sandaracopimaradiene synthase (LITPS4) has the amino acid sequence shown below (SEQ ID NO:3).

```
  1 MSVAFNLIVV RFPGHGIQSS RETFPAKIIT RTKSSMRFQS
 41 SLNTSTDFVG KIREMIRGKT DNSINPLDIP STLCVIDTLH
 81 SFGIDRYFQS EINSVLHHTY RLWNDRNNII FKDVICCAIA
121 FRLLRVKGYQ VSSDELAPFA QQQVTGLQTS DIATILELYR
161 ASQERLHEDD DTLDKLHDWS SNLLKLHLLN ENIPDHKLHK
201 RVGYFLKNYH GMLDRVAVRR NIDLHNINHY QIPEVADRFP
241 TEAFLEFSRQ DFNICQAQHQ KELQQLHRWY ADCRLDTLNH
281 GTDVVHFANF LTSAIFGEPE FSEARLAFAK QVILITRMDD
321 FFDHDGSREE SHKILHLVQQ WKEKPAEEYG SKEVEILFTA
361 VYTTVNSLAE KACMEQGRSV KQLLIKLWVE LLTSFKKELD
401 SWTEKMALTL DEYLSFSWVS IGCRLCILNS LQFLGIKLSE
441 EMLWSQECLD LCRHVSSVVR LLNDLQTFKK ERIENTINGV
481 DVQLAARKGE RAITEEEAMS KIKEMADHHR RKLMQIVYKE
521 GTIFPRECKD VFLRVCRIGY YLYSGDELTS PQQMKEDMKA
561 LVHESSS
```

A nucleic acid encoding *the Leonotis leonurus* sandaracopimaradiene synthase (LITPS4) with SEQ ID NO:3 is shown below as SEQ ID NO:4.

```
   1 ATGTCGGTGG CGTTCAACCT CATAGTCGTC CGTTTTCCGG
  41 GCCATGGAAT TCAGAGCAGT AGAGAAACTT TTCCAGCCAA
  81 AATTATTACC AGAACTAAAT CAAGCATGAG ATTCCAAAGC
 121 AGCCTCAACA CTTCAACAGA TTTCGTGGGA AAAATAAGAG
 161 AGATGATCAG AGGGAAAACT GATAATTCTA TTAATCCCCT
 201 GGATATTCCC TCCACTCTAT GCGTAATCGA CACCCTACAC
 241 AGCTTCGGAA TTGATCGCTA CTTTCAATCC GAAATCAACT
 281 CTGTTCTTCA CCACACATAC AGATTATGGA ACGACAGAAA
 321 TAATATCATC TTCAAAGATG TCATTTGCTG CGCAATTGCC
 361 TTTAGACTTT TGCGAGTGAA AGGATATCAA GTCTCATCAG
 401 ATGAACTGGC GCCATTTGCC CAACAACAGG TGACTGGACT
 441 ACAAACAAGC GACATTGCCA CGATTCTAGA GCTCTACAGA
 481 GCATCACAGG AGAGATTACA CGAAGACGAC GACACTCTTG
 521 ACAAACTACA TGATTGGAGC AGCAACCTTC TGAAGCTGCA
 561 TCTGCTGAAT GAGAACATTC CTGATCATAA ACTGCACAAA
 601 CGGGTGGGGT ATTTCTTGAA GAACTACCAT GGCATGCTAG
 641 ATCGCGTTGC GGTTAGACGA AACATCGACC TTCACAACAT
 681 AAACCATTAC CAAATCCCAG AAGTTGCAGA TAGGTTCCCT
 721 ACTGAAGCTT TTCTTGAATT TTCAAGGCAA GATTTTAATA
 761 TTTGCCAAGC TCAACACCAG AAAGAACTTC AGCAACTGCA
 801 TAGGTGGTAT GCAGATTGTA GATTGGACAC ACTGAATCAC
 841 GGAACAGACG TAGTACATTT TGCTAATTTT CTAACTTCAG
 881 CAATTTTCGG AGAGCCTGAA TTCTCCGAGG CTCGTCTAGC
 921 CTTTGCTAAA CAGGTTATCC TAATAACACG TATGGATGAT
 961 TTCTTCGATC ACGATGGGTC TAGAGAAGAA TCACACAAGA
1001 TCCTCCATCT AGTTCAACAA TGGAAAGAGA AGCCCGCCGA
1041 AGAATATGGT TCAAAGGAAG TTGAGATCCT CTTTACAGCA
1081 GTGTACACTA CAGTAAATAG CTTGGCAGAA AAGGCTTGTA
1121 TGGAGCAAGG CCGTAGTGTC AAACAACTTC TAATTAAGCT
1161 GTGGGTCGAG CTGCTAACAA GTTTCAAGAA AGAATTGGAT
1201 TCATGGACGG AGAAGATGGC GCTAACCTTG GATGAGTACT
1241 TGTCTTTCTC CTGGGTGTCA ATTGGCTGCA GACTCTGCAT
1281 TCTCAATTCC CTGCAATTTC TTGGGATAAA ATTATCTGAA
1321 GAAATGCTGT GGAGTCAAGA GTGTCTGGAT TTATGCCGGC
1361 ATGTTTCATC AGTGGTTCGC CTGCTCAACG ATTTACAAAC
1401 TTTCAAGAAG GAGCGCATAG AAAATACGAT AAACGGTGTG
1441 GACGTTCAGC TAGCTGCTCG TAAAGGCGAA AGAGCCATTA
1481 CAGAAGAGGA GGCCATGTCC AAGATTAAGG AAATGGCTGA
```

-continued

```
1521 CCATCACAGG AGAAAACTGA TGCAAATTGT GTATAAAGAA

1561 GGAACCATTT TTCCAAGAGA ATGCAAAGAT GTGTTTTTGA

1601 GAGTGTGCAG GATTGGCTAC TATCTCTACT CGGGCGATGA

1641 GTTAACTTCT CCACAACAAA TGAAGGAGGA TATGAAAGCG

1681 TTGGTACATG AATCATCCTC TTGA
```

The *Mentha spicata* class I diterpene synthase (MsTPS1) has the amino acid sequence shown below (SEQ ID NO:5).

```
  1 MSSIRNLSLH IDLPKAEKKL VEKIRERIRN GRVEMSPSAY

 41 DTAWVAMVPS RGYSGRPGFP ECVDWIIENQ NPDGSWGLDS

 81 DQPLLVKDSL SSTLACLLAL RKWKTHNQLV QRGMEFIDSR

121 GWAATDDDNQ ISPIGFNIAF PAMINYAKEL NLTLPLHPPS

161 IHSLLHIRDS EIRKRNWEYV AEGVVDDTSN WKQIIGTHQR

201 NNGSLFNSPA TTAAAVIHSH DDKCFRYLIS TLENSNGGWV

241 PTIYPYDIYA PLCMIDTLER LGIHTYFEVE LSGIFDDIYR

281 NWQEREEEIF CNVMCRALAF RLLRMRGYHV SSDELAEFVD

321 KEEFFNSVSM QESGEGTVLE LYRASLTKIN EEERILDKIH

361 AWTKPFLKHQ LLNRSIRDKR LEKQVEYDLK NFYGALVRFQ

401 NRRTIDSYDA KSIQISKTAY RCSTVYNEDF IHLSVEDFKI

441 SRAQYLKELE EMNKWYSDCR LDLLTKGRNA CRESYILTAA

481 IIVDPHESMA RISYAQSILL ITVFDDFFDH YGSKEEALNI

521 IDLVKEWKPA GSYCSKEVEI LFTALHDTIN EIAAKADAEQ

561 GFSSKQQLIN MWVELLESAV REKDSLSXNK VSTLEEYLSF

601 APITIGCKLC VLTSVHFLGI KLSEEIWTSE ELSSLCRHGN

641 VVCRLLNDLK TYEREREENT LNSVSVQTVG GGVSEEEAVT

681 KVEEVLEFHR RKVMQLACRR GGSSVPRECK ELVWKTCTIG

721 YCLYGHDGGD ELSSPKDILK DINAMMFEPL K
```

A nucleic acid encoding the *Mentha spicata* class I diterpene synthase (MsTPS1) with SEQ ID NO:5 is shown below as SEQ ID NO:6

```
   1 ATGAGTTCCA TTCGAAATTT AAGTTTGCAT ATTGATCTGC

  41 CAAAGGCCGA GAAGAAGTTG GTTGAGAAAA TCAGAGAGAG

  81 GATAAGAAAT GGGAGGGTGG AGATGTCGCC GTCGGCTTAC

 121 GACACCGCGT GGGTGGCCAT GGTGCCGTCT CGAGGATATT

 161 CCGGCAGGCC GGGTTTCCCG GAGTGCGTGG ATTGGATAAT

 201 CGAGAACCAG AATCCCGACG CGTCGTGGGG TTTGGATTCG

 241 GATCAACCAC TTCTGGTCAA AGACTCCCTC TCGTCCACCT

 281 TGGCATGCCT ACTTGCCCTG CGTAAATGGA AAACACACAA

 321 CCAACTAGTG CAAAGGGGCA TGGAGTTCAT CGACTCCCGT

 361 GGTTGGGCTG CAACTGATGA TGACAATCAG ATTTCTCCTA

 401 TTGGATTCAA TATTGCCTTT CCTGCAATGA TTAATTACGC
```

-continued

```
 441 CAAAGAGCTT AATTTAACTC TGCCTCTACA TCCACCTTCG

 481 ATTCATTCAT TGTTACACAT TAGAGATTCA GAAATAAGAA

 521 AGCGAAACTG GGAATACGTA GCTGAAGGAG TAGTCGACGA

 561 TACAAGCAAT TGGAAGCAAA TAATCGGCAC GCATCAAAGA

 601 AATAATGGAT CCTTGTTCAA CTCACCTGCT ACCACTGCAG

 641 CTGCTGTTAT TCACTCTCAC GACGATAAAT GTTTCCGATA

 681 TTTGATCTCC ACTCTTGAGA ATTCTAACGG TGGATGGGTA

 721 CCAACTATCT ATCCATACGA TATATACGCT CCTCTCTGCA

 761 TGATCGATAC GCTAGAAAGA TTAGGAATAC ACACATATTT

 801 TGAAGTTGAA CTCACCGGCA TTTTTGATGA CATATACAGG

 841 AATTGGCAAG AGAGAGAAGA AGAGATCTTT TGTAATGTTA

 881 TGTGTCGACC TCTGGCATTT CGGCTTCTAC GAATGAGGGG

 921 ATATCATGTT TCATCTGATG AACTAGCAGA ATTTGTGGAC

 961 AAGGAGGAGT TTTTTAATAG CGTGAGCATG CAAGAGAGCG

1001 GCGAAGGCAC AGTGCTTGAG CTTTACAGAG CTTCACTCAC

1041 AAAAATCAAC GAAGAAGAAA GGATTCTCGA CAAAATTCAT

1081 GCATGGACCA AACCATTTCT CAAGCACCAG CTTCTCAACC

1121 GCAGCATTCG CGACAAACGA TTAGAGAAGC AGGTGGAATA

1161 CGACTTGAAG AACTTCTACG GCGCACTAGT CCGATTCCAG

1201 AACAGAAGAA CCATCGACTC ATACGATGCT AAATCAATCC

1241 AAATTTCGAA AACAGCATAT AGGTGCTCTA CAGTTTACAA

1281 TGAAGACTTC ATCCATTTAT CCGTTGAGGA CTTCAAAATC

1321 TCCCGAGCAC AATACCTAAA AGAACTTGAA GAAATGAACA

1361 AGTGGTACTC TGATTGTAGG TTGGACCTCT TAACTAAAGG

1401 AAGAAATGCA TGTCGAGAAT CTTACATTTT AACAGCTGCA

1441 ATCATTGTCG ATCCTCACGA ATCCATGGCT CGAATCTCTT

1481 ACGCTCAATC TATTCTTCTT ATAACTGTTT TCGACGACTT

1521 TTTCGATCAT TATGGGTCTA AAGAAGAGGC TCTCAATATT

1561 ATTGATCTAG TCAAGGAATG GAAGCCAGCT GGCAGTTACT

1601 GCTCCAAAGA AGTGGAGATT TTGTTTACTG CATTACACGA

1641 CACGATAAAT GAGATTGCAG CCAAGGCTGA TGCAGAGCAA

1681 GGCTTTTCTT CCAAACAACA GCTTATCAAC ATGTGGGTGG

1721 AGCTACTTGA GAGCGCCGTG AGAGAAAAGG ACTCGCTGAG

1761 TGGNAACAAA GTGTCGACTC TAGAAGAGTA CTTATCTTTC

1801 GCACCAATCA CCATCGGCTG CAAACTTTGC GTCCTGACGT

1841 CTGTCCATTT CCTCGGAATC AAACTGTCCG AGGAAATCTG

1881 GACTTCCGAG GAGTTGAGCA GTCTGTGCAG GCACGGCAAT

1921 GTTGTCTGCA GACTGCTCAA CGACCTCAAG ACTTACGAGA

1961 GAGAGCGCGA AGAGAACACG CTCAACAGCG TGAGCGTGCA

2001 GACAGTGGGA GGAGGCGTTT CGGAGGAAGA GGCGGTGACG

2041 AAGGTGGAGG AGGTGTTGGA ATTTCATAGA AGAAAAGTGA
```

-continued

```
2081 TGCAGCTCGC GTGTCGAAGA GGAGGAAGCA GTGTTCCGAG

2121 AGAATGTAAG GAGCTGGTGT GGAAGACGTG CACGATAGGT

2161 TACTGCTTGT ACGGTCACGA CGGAGGCGAT GAGTTATCGT

2201 CTCCGAAGGA TATTCTAAAG GACATTAATG CAATGATGTT

2241 TGAGCCTCTC AAGTGA
```

A *Nepeta mussinii* ent-kaurene synthase (NmTPS2) was identified and isolated as described herein. This NmTPS2 enzyme was identified as an ent-kaurene synthase, which converts ent-CPP [16] into ent-kaurene [19].

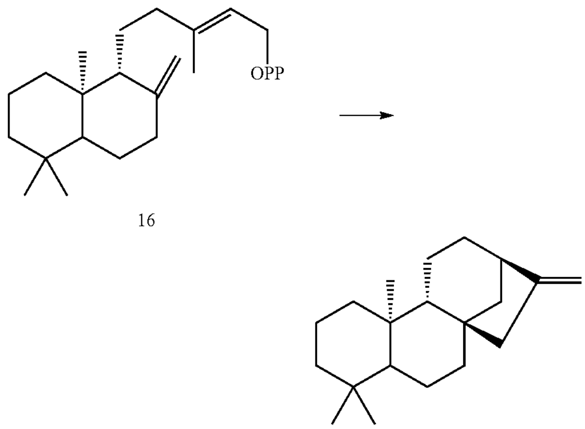

16

19

The *Nepeta mussinii* ent-kaurene synthase (NmTPS2) has the amino acid sequence shown below (SEQ ID NO:7).

```
  1 MSLPLSSCVL FPPNDSRFPV SRFSRASASL EVGLQGATSA

 41 KVSSQSSCFE ETKRRITKLF HKDELSVSTY DTAWVAMVPS

 81 PTSSEEPCFP GCLTWLLENQ CRDGSWARPH HHSLLKKDVL

121 SSTLACILAL KKWGVCEEQI NKGLHFIELN CASATEKCQI

161 TPVGFDIIFP AMLDYARDFS LNLRLEPTTF NDLMDKRDLE

201 LKRCYQNYTP EREAYLAYIV EGMGRLQDWE LVMKYQRKNG

241 SLFNCPSTTA AAFIALRDSA CLNYLNLSLK KFGNAVPAVY

281 PLDIYSQLCT VDNLERLGIN QYFIAEIQSV LDETYRCWIQ

321 GNEDIFLDTS TCALAFRILR MNGYDVTSDS TTKILEECFS

361 SSFRGNMTDI NTTLDLYRAS ELMLYPDEKD LEKHNLRLKL

401 LLKQKLSTVL IQSFQLGRNI NEEVKQTLEH PFYASLDRIA

441 KRKNIEHYNF DNTRILKTSY CSPNFGNKDF FFLSIEDFNW

481 CQVIHRQELA ELERWLIENR LDELKFARSK SAYCYFSAAA

521 TFFAPELSDA RMSWAKSGVL TTVVDDFFDV GGSMEELKNL

561 IQLVELWDVD ASTKCSSHNV HIIFSALRRT IYEIGNKGFK

601 LQGRNITNHI IDIWLDLLNS MMKETEWARD NFVPTIDEYM

641 SNAYTSFALG PIVLPTLYLV GPKLSEEMIN HSEYHNLFKL
```

-continued

```
681 MSTCGRLLND IRGYERELKD GKLNALSLYI INNGGKVSKE

721 AGISEMKSWI EAQRRELLRL VLESNKSVLP KSCKELFWHM

761 CSVVHLFYCK DDGFTSQDLI QVVNAVIHEP IALKDFKVHE
```

A nucleic acid encoding the *Nepeta mussinii* ent-kaurene synthase (NmTPS2) with SEQ ID NO:7 is shown below as SEQ ID NO:8.

```
   1 ATGTCTCTTC CGCTCTCCTC TTGTGTCTTA TTTCCCCCCA

  41 ATGACTCACG TTTTCCGCTC TCCCGCTTTT CTCGCGCTTC

  81 AGCTTCTTTG GAAGTCGGGC TTCAAGGAGC TACTTCAGCA

 121 AAAGTCTCCT CACAATCATC GTGTTTTGAG GAGACAAAGA

 161 GAAGGATAAC AAAGTTGTTT CATAAGGACG AACTTTCGGT

 201 TTCGACATAT GACACAGCAT GGGTTGCTAT GGTCCCTTCT

 241 CCAACTTCTT CAGAGGAACC TTGCTTCCCA GGTTGTTTGA

 281 CTTGGTTGCT TGAAAACCAG TGTCGAGATG GTTCATGGGC

 321 TCGTCCCCAC CATCACTCTT TGTTAAAAAA AGATGTCCTT

 361 TCTTCTACCT TGGCATGCAT TCTCGCACTT AAAAAATGGG

 401 GGGTTGGTGA AGAACAAATC AACAAGGGTT TGCATTTTAT

 441 AGAGCTAAAT TGTGCTTCAG CTACCGAGAA GTGTCAAATT

 481 ACTCCCGTGG GGTTTGACAT TATATTTCCT GCCATGCTTG

 521 ATTATGCAAG AGACTTCTCT TTGAACTTGC GTTTAGAGCC

 561 AACTACGTTT AATGATTTGA TGGATAAAAG GGATTTAGAG

 601 CTCAAAAGGT GTTACCAAAA TTACACACCG GAGAGGGAAG

 641 CATACTTGGC ATATATAGTT GAAGGAATGG GAAGATTGCA

 681 AGATTGGGAA TTGGTGATGA AATATCAAAG AAAGAATGGA

 721 TCTCTTTTCA ATTGTCCATC TACAACTGCA GCAGCTTTTA

 761 TTGCCCTTCG GGATTCTGCG TGCCTCAACT ATCTGAATTT

 801 GTCTTTGAAA AAGTTCGGGA ATGCAGTTCC TGCAGTTTAT

 841 CCTCTAGATA TATATTCTCA ACTTTGCACG GTTGATAATC

 881 TTGAAAGGCT GGGGATCAAC CAATATTTTA TAGCAGAAAT

 921 TCAGAGTGTG TTGGATGAAA CGTACAGATG TTGGATACAG

 961 CGAAACGAAG ACATATTTTT GGACACCTCA ACTTGTCCTT

1001 TAGCATTCCG AATATTGAGA ATGAATGGCT ATGATGTGAC

1041 TTCAGATTCA CTTACAAAAA TCCTAGAAGA GTGCTTTTCA

1081 AGTTCCTTTC GTGGAAATAT GACAGACATT AACACAACTC

1121 TTGACTTATA TAGGGCATCA GAACTTATGT TATATCCAGA

1161 TGAAAAGGAT CTGGAGAAAC ATAATTTAAG GCTTAAACTC

1201 TTACTTAAGC AAAAACTATC CACTGTTTTA ATCCAATCAT

1241 TTCAACTTGG AAGAAATATC AATGAAGAGG TGAAACAGAC

1281 TCTCGAGCAT CCCTTTTATG CAAGTTTGGA TAGGATTGCA

1321 AAGCGGAAAA ATATAGAGCA TTACAACTTT GATAACACAA

1361 GAATTCTTAA AACTTCATAT TGTTCGCCAA ATTTTGGCAA
```

-continued

```
1401 CAAGGATTTC TTTTTTCTTT CCATAGAAGA CTTCAATTGG
1441 TGTCAAGTCA TACATCGACA AGAACTCGGA GAACTTGAAA
1481 GATGGTTAAT TGAAAATAGA TTGGATGAGC TGAAGTTTGC
1521 AAGGAGTAAG TCTGCATACT GTTATTTTTC TGCGGCAGCA
1561 ACTTTTTTTG CTCCAGAATT GTCGGATGCC CGCATGTCAT
1601 GGGCTAAAAG TGGTGTTCTA ACCACAGTGG TAGATGACTT
1641 TTTTGATGTT GGAGGTTCTA TGGAGGAATT GAAGAACTTA
1681 ATTCAATTGG TTGAACTATG GGATGTGGAT GCTAGCACAA
1721 AATGCTCTTC TCATAATGTC CATATAATAT TTTCAGCACT
1761 TAGGCGCACC ATCTATGAGA TAGGGAACAA AGGATTTAAG
1801 CTACAAGGAC GTAACATTAC CAATCATATA ATTGACATTT
1841 GGCTAGATTT ACTAAACTCT ATGATGAAAG AAACCGAATG
1881 GGCCAGAGAC AACTTTGTCC CAACAATTGA TGAATACATG
1921 AGCAATGCAT ATACATCGTT TGCTCTGGGG CCAATTGTCC
1961 TTCCAACTCT CTATCTTGTC GGGCCCAAGC TCTCAGAAGA
2001 GATGATTAAC CACTCCGAAT ACCATAACCT ATTCAAATTG
2041 ATGAGTACGT GCGGACGTCT TCTAAATGAC ATCCGTGGTT
2081 ATGAGAGAGA ACTGAAAGAT GGTAAATTGA ACGCGTTATC
2121 ATTGTACATA ATTAATAATG GTGGTAAAGT AAGTAAAGAA
2161 GCTGGCATCT CGGAGATGAA AAGTTGGATC GAGGCACAAC
2201 GAAGAGAGTT ACTGAGATTA GTTTTGGAGA GCAACAAAAG
2241 CGTCCTTCCG AAGTCGTGCA AGGAATTGTT TTGGCATATG
2281 TGCTCAGTGG TGCATCTATT CTACTGCAAA GATGATGGAT
2321 TCACCTCGCA GGATTTGATT CAAGTTGTAA ATGCAGTTAT
2361 TCATGAACCT ATTGCTCTCA AGGATTTTAA GGTGCATGAA
2401 TAA
```

An *Origanum majorana* trans-abienol synthase (OmTPS3) was identified and isolated. When this OmTPS3 enzyme was expressed in *N. benthamiana* with *Hyptis suaveolens* labda-7,13E-dienyl diphosphate synthase (HsTPS1) a new compound, labda-7,12E,14-triene [24], was produced. The HsTPS1 enzyme produced labda-7,13(16), 14-triene [22] when HsTPS1 was expressed in *N. benthamiana*.

24

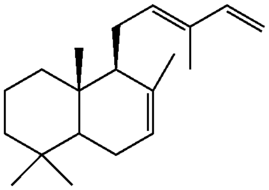

-continued

22

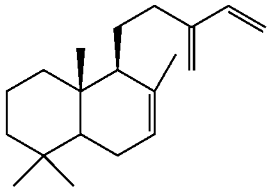

OmTPS3 also produced trans-abienol [11] from labda-13-en-8-ol diphosphate ((+)-8-LPP) [10]).

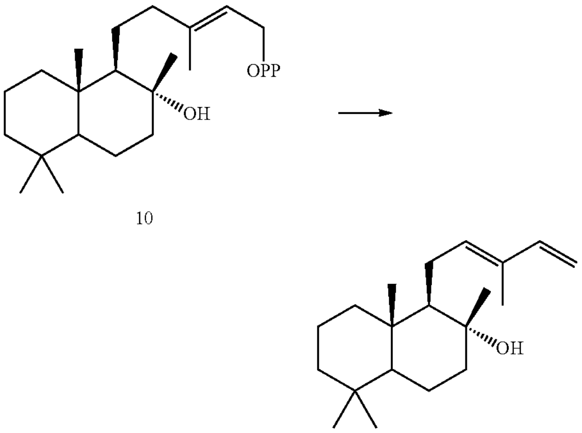

10

11

The *Origanum majorana* trans-abienol synthase (OmTPS3) has the amino acid sequence shown below (SEQ ID NO:9.

```
MASLAFTPGA ATFSGNVVRR RKDNFPVHGF PTTIRSSVSV
TVKCYVSTTN LMVKIKEKFK GKNVNSLTVE AADDDMPSNL
CIIDTLQRLG IDRYFQPQVD SVLDHAYKLW QGKEKDTVYS
DISIHAMAFR LLRVKGYQVS SEELDPYIDV ERMKKLKTVD
VPTVIELYRA AQERMYEEEG SLERLHVWST NFLMHQLQAN
SIPDEKLHKL VEYYLKNYHG ILDRVGVRRN LDLFDISHYP
TLRARVPNLC TEDFLSFAKE DFNTCQAQHQ KEHEQLQRWF
EDCRFDTLKF GRETAVGAAH FLSSAILGES ELCNVRLALA
KHMVLVVFID DFFDHYGSRE DSFKILHLLK EWKEKPAGEY
GSEEVEILFT AVYNTVNELA EMAHVEQGRN IKGFLIELWV
EIVSIFKIEL DTWSNDTTLT LDEYLSSSWV SVGCRICILV
SMQLLGVQLT DEMLLSDECI NLCKHVSMVD RLLNDVGTFE
KERKENTGNS VSLLLAAAVK EGRPITEEEA IIKIKKMAEN
ERRKLMQIVY KRESVFPRKC KDMFLKVCRI GCYLYASGDR
FTSPQKMKED VKSLIYESL
```

A nucleic acid encoding the *Origanum majorana* trans-abienol synthase (OmTPS3) with SEQ ID NO:9 is shown below as SEQ ID NO:10.

ATGGCGTCGC TCGCGTTCAC ACCCGGAGCC GCCACTTTCT
CCGGCAACGT AGTTCGGAGG AGGAAAGATA ACTTTCCGGT
CCACGGATTT CCGACGACGA TCAGGTCATC GGTCTCCGTC
ACCGTCAAAT GCTACGTCAG TACAACGAAT TTGATGGTGA
AAATCAAAGA GAAGTTCAAG GGTAAAAACG TCAATTCGCT
GACAGTTGAA GCTGCTGATG ACGATATGCC CTCTAATCTG
TGCATAATTG ACACCCTCCA ACGATTGGGA ATCGACCGTT
ACTTCCAACC CCAAGTCGAC TCTGTTCTCG ACCACGCCTA
CAAACTATGG CAAGGGAAAG AGAAAGATAC GGTGTATTCG
GACATTAGTA TTCATGCGAT GGCATTTAGA CTTTTACGAG
TCAAAGGCTA TCAAGTCTCT TCGGAGGAAC TGGATCCATA
CATCGATGTG GAGCGAATGA AGAAACTGAA AACAGTTGAT
GTTCCGACGG TTATCGAACT GTACAGAGCG GCACAGGAGA
GAATGTATGA AGAAGAAGGT AGCCTTGAGA GACTCCATGT
TTGGAGCACC AACTTCCTCA TGCACCAGCT GCAGGCTAAC
TCAATTCCTG ATGAAAAGCT ACACAAACTG GTGGAATACT
ACTTGAAGAA CTACCATGGC ATACTGGATA GAGTTGGAGT
TCGACGAAAC CTCGACCTAT TCGACATAAG CCATTATCCA
ACACTCAGAG CTAGGGTTCC GAACCTATGT ACCGAAGATT
TTCTATCGTT CGCGAAGGAA GATTTCAATA CTTGCCAAGC
CCAACACCAG AAAGAACATG AGCAACTACA AAGGTGGTTC
GAAGATTGTA GGTTCGATAC GTTGAAGTTC GGAAGGGAGA
CAGCCGTAGG CGCTGCTCAT TTTCTATCTT CAGCAATACT
TGGTGAATCT GAACTATGTA ATGTTCGTCT TGCCCTTGCT
AAGCATATGG TGCTTGTGGT ATTCATCGAT GACTTCTTCG
ACCATTATGG CTCTAGAGAA GACTCCTTCA AGATCCTCCA
CCTCTTAAAA GAATGGAAAG AGAAGCCGGC CGGAGAATAC
GGTTCCGAGG AAGTCGAAAT CCTCTTCACA GCCGTATACA
ATACAGTAAA CGAGTTGGCG GAGATGGCTC ATGTCGAACA
AGGACGTAAT ATCAAAGGAT TTCTAATTGA ATTGTGGGTT
GAAATAGTGT CAATTTTCAA GATAGAACTG GATACATGGA
GCAATGACAC AACACTAACC TTGGATGAGT ACTTGTCCTC
CTCATGGGTG TCGGTCGGTT GCAGAATCTG CATCCTCGTC
TCAATGCAGC TCCTCGGTGT ACAACTAACC GACGAAATGC
TTCTGAGCGA CGAGTGCATA AACCTGTGTA AGCATGTCTC
GATGGTCGAT CGCCTCCTCA ACGACGTCGG AACATTCGAG
AAGGAACGGA AGGAGAATAC AGGAAACAGT GTGAGCCTTC
TGCTAGCAGC AGCTGTGAAA GAAGGAAGGC CTATTACCGA
AGAGGAAGCT ATTATTAAAA TTAAAAAAAT GGCGGAAAAC
GAGAGGAGGA AACTAATGCA GATTGTGTAT AAAAGAGAGA
GTGTTTTCCC CAGAAAATGC AAGGATATGT TCTTGAAGGT

-continued

GTGTAGAATT GGGTGCTATC TATACGCGAG CGGCGACGAA
TTTACGTCTC CTCAGAAAAT GAAGGAAGAT GTGAAATCCT
TAATTTATGA ATCCTTGTAG

The *Origanum majorana* manool synthase (OmTPS4) can also convert ent-copalyl diphosphate (ent-CPP) [16] to ent-manool [20].

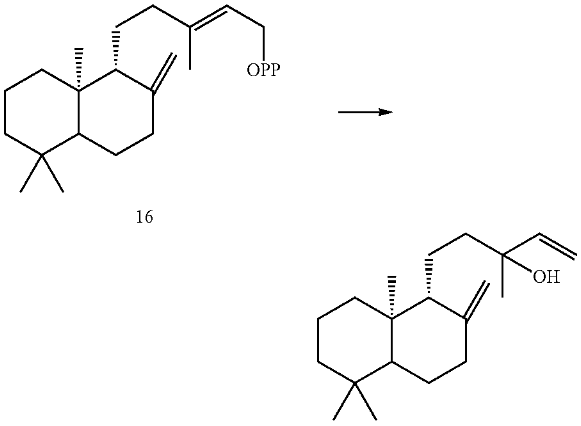

16

20

In addition, *Origanum majorana* manool synthase (OmTPS4) can also convert (+)-copalyl diphosphate ((+)-CPP) [31]) to manool [33].

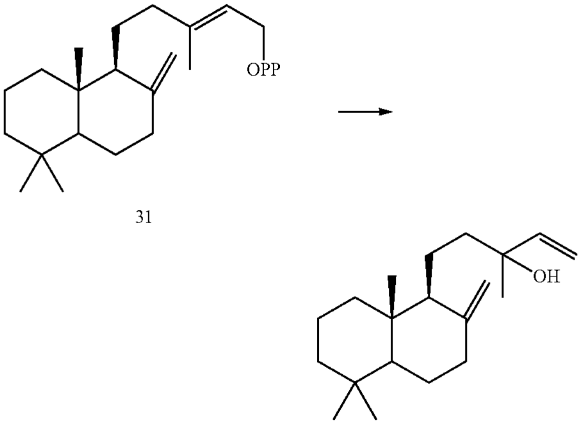

31

33

The *Origanum majorana* manool synthase (OmTPS4) can have the amino acid sequence shown below (SEQ ID NO:11).

MSLAFSHVST FFSGQRVVGS RREIIPVNGV PTTANKPSFA
VKCNLTTKDL MVKMKEKLKG QDGNLTVGVA DMPSSLCVID
TLERLGVDRY FRSEIHVILH DTYRLWQQKD KDICSNVTTH
AMAFRLLRVN GYEVSSEELA PYANLEHFSQ QKVDTAMAIE
LYRAAQERIH EDESGLDKIL AWTTTFLEQQ LLTNSILDNK

-continued

LHKLVEYYLN NYHGQTNRVG ARRHLDLYEM SHYQNLKPSH

SLCNEDLLAF AKQGFRDFQI QQQKEFEQLQ RWYEDCRLDK

LSYGRDVVKI SSFMASILMD DPELADVRLS IAKQMVLVTR

IDDFFDHGGS REDSYKIIEL VKEWKEKAEY DSEEVKILFT

AVYTTVNELA EACVQQGRNS TTVKEFLVQL WIEILSAFKV

ELDTWSDGTE VSLDEYLSWS WISNGCRVSI VTTMHLLPTK

LCSDEMLRSE ECKDLCRHVS MVCRLLNDIH SFEKEHEENT

GNSVSILVAG EDTEEEAIGK IKEIVEYERR KLMQIVYKRG

TILPRECKDI FLKACRATFY VYSSTDEFTS PRQVMEDMKT

LSS

A nucleic acid encoding *Origanum majorana* manool synthase (OmTPS4) with SEQ ID NO:11 is shown below as SEQ ID NO:12.

ATGTCACTCG CCTTCAGCCA TGTTAGTACC TTTTTCTCCG

GCCAAAGAGT CGTCGGAAGC AGGAGAGAGA TTATTCCAGT

TAACCGAGTT CCGACGACGG CCAATAAGCC GTCGTTCGCC

GTTAAGTGCA ACCTTACTAC AAAGGATTTG ATGGTGAAAA

TGAAGGAGAA GTTGAAGGGG CAAGACGGTA ATTTGACTGT

CGGAGTAGCC GATATGCCCT CTAGCCTGTG CGTGATCGAC

ACTCTTGAAA GGTTGGGAGT TGACCGATAC TTCCGATCTG

AAATCCACGT TATTCTACAC GACACTTACC GGTTATGGCA

ACAAAAGGAC AAAGATATAT GTTCCAACGT TACTACTCAT

GCAATGGCGT TTAGACTTCT GAGAGTGAAT GGATACGAGG

TTTCATCAGA GGAACTGGCT CCATATGCTA ACCTAGAGCA

CTTTAGCCAG CAAAAAGTTG ATACTGCAAT GGCTATAGAG

CTCTACAGAG CAGCACAGGA GAGAATACAC GAAGACGAGA

GCGGTCTCGA CAAAATACTT GCTTGGACCA CCACTTTTCT

CGAGCAACAG CTGCTCACTA ACTCCATTCT TGACAATAAA

TTGCATAAAC TGGTGGAGTA CTACTTGAAC AACTACCACG

GCCAAACGAA TAGGGTCGGA GCTAGACGAC ACCTCGACCT

ATGAGATG AGCCATTACC AAAATCTAAA ACCTTCACAT

AGTCTATGCA ATGAAGACCT TCTAGCATTT GCAAAGCAAG

GTTTTCGAGA TTTTCAAATC CAGCAGCAGA AAGAATTCGA

GCAACTGCAA AGGTGGTATG AAGATTGCAG GTTGGACAAG

TTGAGTTATG GGAGAGATGT AGTAAAAATT TCTAGTTTCA

TGGCTTCAAT ATTGATGGAT GATCCAGAAT TAGCCGATGT

TCGTCTCTCC ATCGCCAAAC AGATGGTGCT CGTGACACGT

ATCGATGATT tCTTCGACCA CGGTGGCTCT AGAgAaGACT

CCTACAAGAT CATTGAACTA GTAAAAGAAT GGAAGGAGAA

GGCaGAATAC GATTCCGAGG AAGTAAAAAT CCTTTTTACA

-continued

GCAGTATACA CCACAGTAAA TGAGCTAGCA GAGGCTTGTG

TTCAACAAGG AAGGAATAGT ACTACTGTCA AAGAATTCCT

AGTTCAGTTG TGGATTGAAA TACTATCAGC TTTCAAGGTC

GAGCTAGATA CGTGGAGCGA TGGCACGGAA GTAAGCCTGG

ACGAGTACTT GTCGTGGTCG TGGATTTCGA ATGGCTGCAG

AGTGTCTATA GTAACGACGA TGCATTTGCT CCCTACGAAA

TTATGCAGTG ATGAAATGCT TAGGAGTGAA GAGTGCAAGG

ATTTGTGTAG GCATGTTTCT ATGGTTGGCC GCTTGCTCAA

CGACATCCAC TCTTTTGAGA AGGAGCATGA GGAGAATACG

GGAAACAGTG TGAGCATTCT AGTAGCAGGT GAGGATACCG

AAGAGGAAGC TATTGGAAAG ATCAAAGAGA TAGTTGAGTA

TGAGAGGAGA AAATTGATGC AAATTGTGTA CAAGAGAGGA

ACCATTCTCC CAAGAGAATG CAAAGACATA TTCTTGAAGG

CGTGTAGGGC TACATTTTAC GTGTACTCGA GCACGGATGA

GTTTACGTCT CCTCGACAAG TGATGGAAGA TATGAAAACC

CTAAGCTCCT AG

*Origanum majorana* palustradiene synthase (OmTPS5) can also convert (+)-copalyl diphosphate ((+)-CPP) [31]) to palustradiene [29].

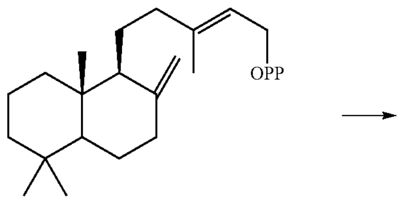

31

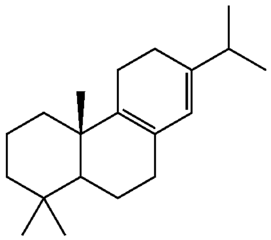

29

The *Origanum majorana* palustradiene synthase (OmTPS5) can have the amino acid sequence shown below (SEQ ID NO:13).

MVSACLKLKN NPFLDHRFRK SSNGFSVNFP ATMLTTVKCS

RDNSEDLIAK IKERMNEKFV TVPAREYSVI EHRNPKPAWC

GGLQSKTVIE EEVCSRLFLV EHLQDLGVDR FFQSEIQHIL

HHTFRLWQQK DEQVFKDVTC RAMAFRLLRL EGYHVSSGEL

GEYVDEEKFF RTVRLEWRST DTILELYKAS QVRLPEDDND

NSNILKNLHE WTFIFLKEQL RRKTILDKGL ERKVEFYLKN

-continued

```
YHGILDAVKH RRSLDHTRFW KTTAYNPAVY DEDLFRLSAQ
DFMARQAQSQ KELEMLLKWY DECRLDKMEY GRNVIHVSHF
LNANNFPDPR LSETRLSFAK TMTLVTRLDD FFDHHGSRED
SVLIIELIRQ WNEPSTITTI FPSEEVEILY SALHSTVTDI
AEKAYPIQGR CIKSLIIHLW VEILSSFMSE MDSCTAETQP
DFHEYLGFAW ISIGCRICIL IAIHFLGEKV SQQMVMGAEC
TELCRHVSTI ARLLNDLQTF KKEREERKVN SVIIQLKGDK
ISEEVAVSNI ERMVEYHRKE LLKMVVRREG SLVPKRCKDV
FWKSCNIAYY LYAFTDEFTS PQQMKEDMKL LFRDPINCVP
SIPS
```

A nucleic acid encoding the *Origanum majorana* palustradiene synthase (OmTPS5) with SEQ ID NO:13 is shown below as SEQ ID NO:14.

```
ATGGTATCTG CATGTCTAAA ACTCAAAAAT AATCCTTTCT
TGGACCATCG ATTCAGGAAA AGCAGCAATG GATTTTCAGT
TAATTTTCCG GCGACCATGC TCACCACTGT CAAGTGCAGC
CGCGATAATT CAGAAGACTT GATAGCAAAG ATAAAAGAAA
GGATGAATGA AAAATTTGTT ACGGTGCCGG CGAGGGAATA
TTCCGTCATT GAGCATCGGA ATCCGAAGCC GGCGTGGTGC
GGTCGTTTGC AATCCAAAAC AGTAATAGAA GAAGAAGTGT
GCAGCCGTCT GTTTCTGGTC GAACACCTTC AAGATTTAGG
AGTAGACCGC TTCTTTCAAT CAGAAATCCA ACATATTCTA
CATCACACAT TCAGATTATG GCAGCAAAAA GATGAACAAG
TTTTTAAAGA CGTGACATGT CGCGCCATGG CATTCAGACT
CCTGCGTCTC GAAGGTTATC ATGTCTCGTC AGGAGAATTG
GGGGAGTATG TTGATGAGGA AAAATTCTTT AGAACGGTAA
GGTTAGAATG GAGAAGTACG GATACAATTC TTGAGCTGTA
CAAAGCATCA CAGGTAAGAC TACCTGAAGA CGACAACGAC
AATTCCAATA TCCTCAAAAA CTTGCACGAA TGGACCTTCA
TATTTTTGAA GGAGCAGTTG CGGCGTAAAA CTATTCTTGA
TAAAGGTTTA GAGAGAAAGG TAGAATTTTA CTTGAAGAAT
TACCACGGCA TATTAGACGC GGTTAAGCAT AGACGAAGCC
TCGATCACAC ACGATTCTGG AAAACTACTG CGTATAACCC
TGCAGTGTAT GATGAGGATC TTTTCCGATT GTCGGCCCAA
GATTTCATGG CTCGCCAAGC TCAGAGCCAG AAGGAACTTG
AGATGTTGCT CAAGTGGTAC GATGAATGTA GACTGGACAA
GATGGAGTAT GGGCGAAACG TGATACACGT TTCCCATTTC
TTAAACGCAA ACAACTTCCC CGATCCTCGC CTGTCCGAAA
CTCGTCTATC CTTTGCGAAA ACCATGACTC TCGTCACGCG
TTTGGATGAT TTCTTCGATC ACCATGGCTC TAGAGAAGAT
```

-continued

```
TCGGTCCTCA TCATCGAATT AATAAGGCAG TGGAATGAGC
CTTCAACTAT TACAACAATA TTCCCCTCCG AAGAAGTGGA
GATTCTCTAC TCTGCACTCC ACTCCACCGT AACAGATATA
GCAGAGAAGG CTTATCCCAT CCAGGGTCGC TGCATCAAAT
CGCTCATAAT TCATCTGTGG GTCGAGATAC TGTCGAGCTT
CATGAGCGAA ATGGACTCGT GCACCGCGGA AACTCAGCCG
GACTTTCACG AGTACTTAGG GTTTGCATGG ATCTCGATCG
GCTGCAGAAT CTGCATTCTC ATAGCTATAC ATTTCTTGGG
GGAGAAGGTA TCTCAACAAA TGGTTATGGG TGCTGAGTGC
ACCGAGTTAT GTAGGCACGT TTCTACGATC GCACGCCTTC
TCAACGATCT CCAAACCTTT AAGAAGGAGA GAGAAGAGAG
GAAGGTAAAC AGCGTGATAA TCCAGCTCAA AGGGGATAAG
ATATCGGAGG AGGTGGCCGT GTCGAATATA GAGAGAATGG
TTGAATATCA CAGGAAAGAG CTGCTGAAGA TGGTGGTTCG
GAGAGAAGGA AGCTTGGTTC CTAAGAGGTG TAAGGACGTG
TTCTGGAAAT CCTGCAACAT TGCTTACTAT CTGTACGCTT
TTACAGATGA ATTCACTTCG CCTCAACAAA TGAAGGAAGA
TATGAAACTA CTCTTTCGTG ATCCAATCAA CTGCGTTCCT
TCAATTCCTT CATGA
```

The *Perovskia atriplicifolia* miltiradiene synthase (PaTPS3) can have the amino acid sequence shown below (SEQ ID NO:15).

```
MLLAFNISDV PLSQHRVILS RREHFPRHAF QEFPMIAATK
SSVNAICSLA TPTDLMGKIK EKFKAKDGDP LAAAAIQLAA
DIPSSLCIID TLQRLGVDRY FQSEIDSILE ETHKLWKVKD
RDIYSEVTTH AMAFRLLRVK GYEVSSEELA PYAEQERFDL
QTIDLATVIE LYRAAQERTC EENDNSLEKL LAWTTTFLKH
QLLTNSIPDT KLHKQVEYYL KNYHGILDRM GVRRSLDLYD
ISHYRPLRAR FPNLCNEDFL SFARQDFSMC QAQHQKELEQ
LQRWYSDCRL DALLKFGRNV VRVSSFLTSA IIGEPELSEV
RLVFAKHIIL VTLIDDLFDH GGTREESYKI LELVTEWKEK
TAAEYGSEEV EILETAVYNT VNELVERAHV EQGRSVKEFL
IKLWVQILSI FKIELDTWSD ETALTLDEYL SSSWVSIGCR
ICILMSMQFI GIKLTDEMLL SEECTDLCRH VSMVDRLLND
VQTFEKERKE NTGNSVSLLL AANKDVTEEE AIRRAKEMAE
CNRRQLMQIV YKTGTIFPRK CKDMFLKVCR IGCYLYASGD
EFTSPQQMME DMKSLVYEPL YLPN
```

A nucleic acid encoding the *Perovskia atriplicifolia* miltiradiene synthase (PaTPS3) with SEQ ID NO:13 is shown below as SEQ ID NO:16.

ATGTTACTTG CGTTCAACAT AAGCGATGTC CCTCTCTCGC
AGGATAGAGT AATTCTGAGC AGGAGGGAAC ATTTTCCACG
TCATGCATTC CAGGAATTTC CGATGATCGC CGCTACTAAG
TCATCTGTTA ATGCCATTTG CAGCCTCGCT ACTCCAACTG
ATTTGATGGG AAAAATAAAA GAGAAGTTCA AGGCCAAGGA
CGGCGATCCT CTTGCCGCCG CGGCTATTCA ACTCGCGGCG
GATATACCCT CGAGTCTGTG TATAATCGAC ACCCTCCAGA
GGTTGGGAGT CGACCGATAC TTCCAATCCG AAATCGACTC
TATTCTAGAG GAAACACACA AGTTATGGAA AGTGAAAGAT
AGAGATATAT ACTCTGAGGT TACTACTCAT GCAATGGCGT
TTAGACTTCT GCGAGTGAAG GGATATGAAG TTTCATCAGA
GGAACTAGCT CCGTATGCTC AGCAAGAGCG CTTTGACCTG
CAAACGATTG ATCTGGCGAC GGTTATCGAG CTTTACAGAG
CAGCACAGGA GAGAACATGC GAAGAAAACG ACAACAGTCT
TGAGAAACTA CTTGCTTGGA CCACCACCTT TCTCAAGCAC
CAATTGCTCA CCAACTCCAT ACCTGACACC AAATTGCACA
AACAGGTGGA ATACTACTTG AAGAACTACC ACGGGATATT
AGATAGAATG GGAGTTAGAC GAAGCCTCGA CCTATACGAC
ATAAGCCATT ATCGACCTCT GAGAGCAAGA TTCCCTAATC
TGTGTAATGA AGATTTCCTA TCATTTGCGA GGCAAGATTT
CAGTATGTGC CAACCCCAAC ACCAGAAGGA ACTTGAGCAA
CTGCAAAGGT GGTATTCTGA TTGTAGGTTG GACGCGTTGT
TGAAGTTTGG AAGAAATGTA GTGCGCGTTT CTAGCTTTCT
GACTTCAGCA ATTATTGGTG AACCCGAATT GTCTGAAGTT
CGACTAGTCT TTGCCAAACA TATTATTCTC GTTACACTTA
TTCATGATTT ATTCGATCAT GGTGGAACTA GAGAAGAGTC
ATACAAGATC CTTGAATTAG TAACAGAATG GAAAGAGAAG
ACCGCAGCAG AATATGGTTC CGAGGAAGTT GAAATCCTTT
TTACAGCGGT CTACAACACA GTAAATGAGT TGGTAGAGAG
GGCTCATGTC GAACAAGGGC GCAGTGTCAA AGAATTTCTT
ATTAAACTGT GGGTTCAAAT ACTATCAATT TTCAAGATAG
AATTAGATAC ATGGAGCGAT GAGACTGCGC TAACCTTGGA
TGAATACTTG TCTTCGTCGT GGGTGTCAAT TGGTTGCAGA
ATCTGCATTC TCATGTCGAT GCAATTCATC GGTATAAAAT
TAACTGATGA AATGCTTCTG AGTGAAGAGT GCACTGATTT
GTGTAGGCAT GTTTCGATGG TTGACCGGCT GCTCAACGAT
GTGCAAACCT TCGAGAAGGA ACGCAAAGAA AATACAGGAA
ACAGTGTAAG CCTTCTGCTA GCAGCTAACA AAGATGTTAC
TGAAGAGGAA GCAATTAGAA GAGCAAAAGA AATGGCGGAA
TGCAACAGGA GACAACTGAT GCAGATTGTG TATAAAACAG
GAACCATTTT CCCAAGAAAA TGCAAAGATA TGTTTCTCAA

-continued

GGTATGCAGG ATTGGCTGTT ATTTGTATGC AAGCGGCGAC
GAATTCACAT CTCCACAACA AATGATGGAA GATATGAAAT
CCTTGGTTTA TGAACCCCTC TACCTACCTA ATTAA

A *Perovskia atriplicifolia* miltiradiene synthase (PaTPS1) can have the amino acid sequence shown below (SEQ ID NO:17).

MSLTFNAGVV RFSSHRVRST KDCFTVYGFP MIANKAAFAV
KCSLTPTDLM GRVEEKFKGK NGNSLAASTT VESADIPSNL
CIIDTLQRLG VDRYFQTEIN AILEDTYRLW ERKDKDIYSD
ATTHAMAFRL LRVKGYEVSS EELAPYADQE CVNVQTADVA
TVIELYRAAQ VRISEEESSL KKLHAWTTTF LKYQLQSNSI
PEKKLHKLVE YYLKNYHGIL DRMGVRMDLD LFDISHYRTL
QASDRFSSLR NEDFLEFARQ DFNICQAKHQ KELQQLQRWY
ADCRLDTLKF GRDVVRVANF LTSAIFGEPE LSDARLIFAK
HIVLVTCIDE FFDHGGSKEE SYKILELVEE WKEKPTGEYG
CEEVEILFTA VYSTVNELAE MAHVEQGRSV KEFLVKLWVQ
ILSIFKIELD TWSDDTELTL DSYLNNSWVS IGCRICILMS
MQFAGVKLSD EMLLSEECVD LCRHVSMVDR LLNDVQTFEK
ERKENTGNSV SLLQAAAERE GRAITEEEAI TQIKELAEYH
RRKLMQIVYK TDTIFPRKCK DMFLKVCRIG CYLYASGDEF
TTPQQMMEDM KSLVYQPLTV DDMSAKELTS VRN

A nucleic acid encoding the *Perovskia atriplicifolia* miltiradiene synthase (PaTPS1) with SEQ ID NO:13 is shown below as SEQ ID NO:18.

ATGTCACTCA CTTTCAACGC TGGAGTCGTC CGTTTCTCCA
GCCACCGCGT TCGGAGCACG AAAGATTGCT TTACAGTTTA
CGGATTTCCG ATGATTGCAA ATAAGGCAGC TTTCGCAGTT
AAATGCAGCC TTACTCCAAC CGATTTGATG GGGAGAGTAG
AGGAGAAGTT CAAGGGCAAA AATGGTAATT CACTAGCAGC
CTCGACGACG GTTGAATCCG CGGATATACC CTCGAACCTG
TGTATAATCG ACACCCTCCA AAGATTGGGA GTCGACCGAT
ACTTTCAAAC TGAAATCAAT GCCATTCTAG AGGACACTTA
CAGATTATGG GAACGAAAAG ACAAAGACAT ATATTCCGAT
GCCACAACTC ACGCGATGGC GTTTAGGTTA CTACGAGTGA
AAGGATACGA AGTTTCATCA GAGGAACTGG CTCCTTACGC
TGATCAAGAG TGCGTGAACG TGCAAACGGC TGATGTGGCA
ACAGTTATCG AGCTTTACAG AGCAGCGCAG GTGAGAATAA
GCGAAGAAGA GAGCAGTCTT AAGAAGCTTC ATGCTTGGAC
CACCACCTTT CTCAAATATC AGTTGCAGAG TAACTCCATA
CCTGAAAAGA AACTGCACAA ACTGGTGGAA TATTACTTGA

-continued

AGAACTACCA TGGCATATTG GATAGAATGG GAGTTCGAAT
GGACCTCGAC TTATTCGACA TCAGCCATTA TCGAACTCTA
CAAGCTTCCG ATAGGTTCTC TAGTCTGCGT AACGAAGATT
TTCTAGAGTT TGCAAGGCAA GATTTCAATA TCTGCCAAGC
CAAGCACCAG AAAGAACTCC AACAACTGCA AAGGTGGTAT
GCAGATTGCA GGCTCGACAC CTTGAAGTTC GGGAGAGACG
TCGTACGCGT TGCTAATTTT CTGACTTCAG CAATCTTTGG
CGAACCCGAG CTATCCGATG CTCGTCTGAT CTTTGCCAAG
CATATCGTGC TCGTAACATG TATCGATGAA TTCTTCGATC
ATGGTGGGTC TAAAGAAGAG TCCTACAAGA TCCTTGAATT
AGTAGAAGAA TGGAAAGAGA AGCCAACTGG AGAATATGGG
TGTGAGGAGG TTGAGATCCT TTTCACAGCA GTGTACAGTA
CAGTGAATGA GTTGGCAGAG ATGGCTCATG TCGAACAAGG
ACGTAGTGTG AAAGAGTTTC TAGTTAAACT GTGGGTGCAG
ATACTGTCGA TTTTCAAGAT AGAACTGGAT ACATGGAGTG
ATGACACGGA ACTGACGTTG GACAGCTACT TGAACAACTC
GTGGGTGTCG ATCGCATGCA GAATCTGCAT TCTCATGTCG
ATGCAGTTCG CCGGTGTAAA ACTGTCCGAC GAAATGCTTC
TGAGTGAAGA GTGTGTTGAC TTGTGCAGGC ACGTCTCCAT
GGTCGATCGC CTCCTGAACG ATGTGCAAAC TTTCGAGAAG
GAACGCAAGG AAAATACAGG AAACAGTGTG AGCCTTCTGC
AAGCAGCAGC TGAGAGAGAA GGAAGACCCA TTACAGAAGA
GGAAGCTATT ACACAGATCA AAGAATTGGC TGAATACCAC
AGGAGAAAAC TGATGCAGAT TGTGTACAAA ACAGACACCA
TTTTCCCAAG AAAATGCAAA GATATGTTCT TGAAGGTGTG
CAGGATTGGG TGCTATCTGT ACGCAAGTGG AGACGAATTC
ACAACTCCAC AACAAATGAT GGAAGACATG AAATCATTGG
TTTATCAACC CCTAACAGTT GATGACATGA GTGCCAAAGA
ATTGACTTCT GTGAGAAACT AG

The *Salvia officinalis* miltiradiene synthase (SoTPS1) can have the amino acid sequence shown below (SEQ ID NO:19).

MSLAFNAAVA TFSGHRIRSR REILPGQGFP MITNKSSFAV
KCNLTTTDLM GKITEKFKGR DSNFSAATAV QPAADIPSNL
CIIDTLQRLG VDRYFQSEID TILEDTYRLW QRKEREIFSD
ITIHAMAFRL LRVKGYVVSS EELAPYADQE RINLQRIDVA
TVIELYRAAQ ERISEDESSL EKLHAWTATY LKQQLLTNSI
PDKKLNKLVE CYLKNYHGIL DRMGVRQNLD LYDISHYQTL
KAADRFSNLR NEDFLAFARQ DFNICQEQHQ KELQQLQRWY
ADCRLDTLKY GRDVVRVANF LTSAIIGDPE LSEVRLVFAK
HIVLVTRIDD FFDHGGSREE SYKILELLKE WKEKPAAEYG

-continued

SKEVEILFIA VYNTVNELAE MAHIEQGRSV KEFLIKLWVQ
IISIFKIELD TWSDETALTL DEYLSSSWVS IGCRICILMS
MQFIGIKLSD EMLLSEECID LCRHVSMVDR LLNDVQTFEK
ERKENTGNSV SLLLAANKDD SAFTEEEAIT KAKEMAECNR
RQLMKIVYKT GTIFPRKCKD MFLKVCRIGC YLYASGDEFT
SPQQMMEDMK SLVYEPLTVD PLEAKNVSGK

A nucleic acid encoding the *Salvia officinalis* miltiradiene synthase (SoTPS1) with SEQ ID NO:19 is shown below as SEQ ID NO:20.

ATGTCCCTCG CCTTCAACGC AGCAGTTGCC ACTTTCTCCG
GCCACAGAAT TCGGAGCAGG AGAGAAATTC TTCCGGGGCA
AGGATTTCCG ATGATCACCA ACAAGTCGTC TTTCGCCGTG
AAATGTAACC TTACTACAAC AGATTTGATG GGCAAGATAA
CAGAGAAATT CAAGGGAAGA GACAGTAATT TTTCAGCAGC
AACGGCTGTT CAACCTGCGG CGGATATACC CTCTAACCTG
TGCATAATCG ACACCCTCCA AAGGTTGGGA GTCGACCGAT
ACTTCCAATC TGAAATCGAC ACTATTCTAG AGGACACATA
CAGGTTATGG CAAAGGAAAG AGAGAGAGAT ATTTTCGGAT
ATAACTATTC ATGCAATGGC ATTTAGACTT TTGCGAGTTA
AAGGATATGT AGTTTCATCA GAGGAACTGG CTCCGTATGC
TGACCAAGAG CGCATTAACC TGCAAAGGAT TGATGTAGCG
ACAGTTATCG AGCTTTACAG AGCAGCACAG GAGAGAATAA
GTGAAGACGA GAGCAGTCTT GAGAAACTAC ATGCTTGGAC
CGCCACCTAT CTCAAGCAGC AGCTGCTCAC TAACTCCATT
CCTGAGAAGA AATTGAACAA ACTGGTGGAA TGCTACTTGA
AGAACTATCA CGGGATATTA GATAGAATGG GAGTTAGACA
AAACCTCGAC CTCTACGACA TAAGCCACTA TCAAACTCTA
AAAGCTGCAG ATAGGTTCTC TAATCTACGT AATGAAGATT
TTCTAGCATT TGCGAGGCAA GATTTTAATA TTTGCCAAGA
ACAACACCAA AAAGAACTTC AGCAACTGCA AAGGTGGTAT
GCAGATTGTA GGTTGGACAC ATTGAAGTAT GGAAGAGATG
TCGTGCGGGT TGCTAATTTT CTAACATCAG CAATTATTGG
TGATCCTGAA TTGTCTGAAG TCCGTCTAGT CTTCGCCAAA
CATATTGTGC TTGTAACACG TATTGATGAT TTTTTCGATC
ATGGTGGATC TAGAGAAGAG TCCTACAAGA TCCTTGAATT
ACTAAAAGAA TGGAAAGAGA AGCCAGCTGC AGAATATGGT
TCCAAAGAAG TTGAAATTCT TTTCACAGCA GTATACAATA
CAGTAAACGA GTTGGCAGAG ATGGCTCACA TCGAACAAGG
ACGTAGTGTT AAAGAATTTC TAATAAAGCT GTGGGTTCAA
ATCATATCGA TTTTCAAGAT AGAATTAGAT ACATGGAGCG

-continued

ATGAGACAGC GCTGACCTTG GATGAGTACT TGTCTTCGTC

GTGGGTGTCA ATTGGGTGCA GAATCTGCAT TCTCATGTCG

ATGCAATTCA TTGGTATAAA ATTATCTGAT GAAATGCTTC

TGAGTGAAGA GTGTATTGAT TTGTGTCGGC ATGTCTCCAT

GGTTGACCGG CTGCTCAACG ACGTGCAGAC TTTCGAGAAG

GAACGCAAGG AAAATACAGG AAATAGCGTG AGCCTTCTGC

TAGCAGCTAA CAAAGACGAC AGCGCCTTTA CTGAAGAGGA

AGCTATTACA AAAGCAAAAG AAATGGCGGA ATGTAACAGG

AGACAACTGA TGAAGATTGT GTATAAAACA GGAACCATTT

TCCCAAGAAA ATGCAAAGAT ATGTTTCTGA AGGTATGCAG

GATTGGCTGT TACTTGTATG CAAGCGGCGA TGAATTCACA

TCTCCACAAC AAATGATGGA AGATATGAAA TCCTTGGTCT

ATGAACCCCT AACAGTTGAT CCTCTCGAGG CCAAAAATGT

GAGTGGCAAA TGA

*Ajuga reptans* (+)-copalyl diphosphate synthase (ArTPS1) is a (+)-copalyl diphosphate ((+)-CPP) [31] synthase, and compound 31 is shown below.

31

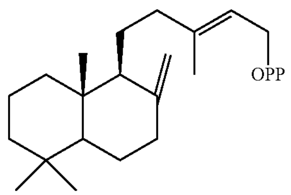

The *Ajuga reptans*(+)-copalyl diphosphate synthase (ArTPS1) can have the amino acid sequence shown below (SEQ ID NO:21).

MASLSTFHLY SSSLLHRKTL QSSPKLNLSS ECFSTRTWMN

SSKNLSLNYQ VNQKIGKLTG TRVATVDAPQ QLEHDDSTAK

GHDIVDIETQ DPIEYIRMLL NTTGDGRISV SPYDTAWIAL

IKDVEGRDFP QFPSSLEWIA NHQLADGSWG DEGFFCVYDR

LVNTIACVVA LRSWNVHHDK SQRGIQYIKE NVHQLKDGNA

EHMMCGFEVV FPALLQKAKN MGIDDLPYEA PVIQDIYHTR

EQKLKRIPLE MMHKVPTSLL FSLEGLENLD WDKLLKLQSA

DGSFLTSPSS TAFAFMQTKD EKCFQFIKNT VETFNGGAPH

TYPVDVFGRL WAVDRLQRLG ISRFFEAEIA DCLSHIHRYW

NDKGLFSGRE SDFVDIDDTS MGFRLLRMQG YDVSPNVLRN

FKNGDKFSCY GGQTIESSTP IYNLYRASQF RFPGEEILEE

ADKFAHEFLS EQLGNNQLLD KWVISDRLQE EISIGLGMPF

YATLPRVEAS YYIQHYAGAD DVWIGKTLYR MPEISNDTYL

ELARNDFKRC QAQHQFEWIY MQEWYESCNI EEFGISRKEL

LRVYFLACSS IFEVERTKER MAWAKSQIIS RMITSFFNKQ

-continued

TTSSEEKETL LTEFRNINGL HKSNNTRDGD MNIVLATLHQ

FFAGFDRYTS HQLKNAWGVW LSKLQRGAVD GGADAELITT

TINVCAGHIA LKEDILSHDE YKTLTDLTSK ICQQLSHIQN

EKVVEIDGGI TAKSRLKNEE LQRDMQSLVK LVLEKSVGLN

RNIKQTFLTV AKTYYYRAYN AEETMDAHIF KVLFEPVA

A nucleic acid encoding the *Ajuga reptans* (+)-copalyl diphosphate synthase (ArTPS1) with SEQ ID NO:21 is shown below as SEQ ID NO:22.

ATCGCCTCTT TGTCCACTTT CCACCTCTAC TCTTCCTCAC

TCCTTCACCG CAAAACACTG CAATCTTCAC CAAAGCTTAA

CCTGTCTTCA GAATGCTTCT CCACCAGAAC TTGGATGAAC

AGCAGCAAAA ACTTGTCGTT AAATTACCAA GTTAATCAGA

AAATAGGAAA GCTGACAGGG ACTCGAGTTG CCACTGTGGA

TGCGCCACAA CAACTTGAAC ACGATGATTC AACTGCTAAA

GGCCATGATA TAGTCGATAT TGAAACTCAG GATCCAATTG

AATATATTAG AATGCTGTTG AACACAACAG GCGATGGCAG

AATCAGCGTT TCGCCTTACG ACACAGCATG GATTGCTCTT

ATTAAGGACG TGGAAGGACG TGATTTTCCT CAATTTCCAT

CCAGCCTTGA GTGGATCGCG AACCATCAAC TCGCTGATGG

TTCATGGGGA GACGAAGGAT TTTTCTGTGT GTATGATCGG

CTCGTAAATA CTATAGCATG TGTCGTAGCA TTGAGATCAT

CGAATGTCCA TCACGACAAG AGCCAAAGAG GAATACAATA

TATCAAGGAA AATGTGCATC AACTTAAGGA TGGAAATGCT

GAGCACATGA TGTGTGGTTT CGAAGTAGTG TTTCCTGCAC

TTCTTCAAAA AGCCAAAAAT ATGGGCATTG ATGATCTTCC

ATATGAGGCT CCTGTCATCC AGGATATTTA CCATACAAGG

GAGCAGAAAT TGAAAAGGAT ACCATTGGAG ATGATGCACA

AAGTGCCTAC TTCTCTGCTG TTTAGTTTGG AAGGACTGGA

GAATTTAGAT TGGGATAAAC TCCTTAAGTT GCAGTCAGCT

GATGGCTCTT TCCTCACTTC TCCCTCCTCT ACTGCTTTCG

CATTCATGCA AACAAAAGAC GAAAAATGCT TCCAGTTCAT

CAAGAACACT GTTGAAACCT TTAATGGAGG AGCACCACAT

ACTTATCCGG TCGATGTTTT TGGAAGACTT TGGGCGGTTG

ATAGGCTGCA GCGCCTCGGA ATTTCTCGAT TCTTTGAGGC

TGAGATTGCT GATTGCTTAA GTCACATTCA TAGATATTGG

AATGATAAGG GGCTTTTCAG TGGACGTGAA TCGGACTTTG

TCGATATTGA CGACACATCC ATGGGTTTCA GACTTCTAAG

AATGCAAGGC TATGATGTTA GTCCAAATGT ACTGAGGAAT

TTCAAGAATG GTGACAAGTT TTCATGTTAC GGAGGTCAAA

CGATCGAGTC ATCAACTCCA ATATACAATC TGTACAGACC

-continued

TTCTCAATTC CGGTTTCCAG GAGAAGAAAT TCTTGAAGAA
GCCGACAAGT TCGCCCATGA GTTCTTGTCC GAACAGCTTG
GCAACAACCA ATTGCTTGAT AAATGGGTTA TATCCGACCG
CTTGCAGGAA GAGATAAGTA TTGGATTGGG GATGCCATTT
TATGCCACCC TTCCCAGAGT TGAAGCAAGC TACTATATAC
AACATTACGC TGGTGCCGAC GACGTGTGGA TCGGCAAGAC
ACTCTACAGG ATGCCGGAAA TAAGTAATGA TACATACCTG
GAGCTAGCAA GAAATGATTT CAAGAGATGC CAAGCACAAC
ATCAGTTCGA GTGGATCTAC ATGCAAGAAT GGTATGAGAG
TTGCAACATT GAAGAATTCG GGATAAGCCG AAAGGAGCTC
CTTCGCGTTT ACTTTTTGGC TTGCTCTAGC ATCTTTGAGG
TCGAGAGGAC TAAAGAGAGA ATGGCATGGG CAAAATCTCA
AATTATTTCT AGAATGATCA CTTCTTTCTT TAATAAACAA
ACTACTTCAT CTGAGGAAAA AGAAACACTT TTAACCGAAT
TCAGAAACAT CAACGGTCTG CACAAATCAA ACAATACAAG
AGATGGAGAT ATGAACATTG TGCTTGCAAC CCTCCATCAA
TTCTTCGCTG GATTTGACAG ATATACTAGC CATCAACTGA
AAAATGCTTG GGGAGTATGG TTGACCAAGC TGCAACGAGG
AGCAGTAGAC GGTGGAGCAG ACGCAGAGCT GATAACAACC
ACCATAAACG TATGCGCCGG TCATATAGCT CTTAAGGAAG
ACATATTGTC CCACGATGAG TACAAGACTC TCACCGACCT
CACCAGCAAG ATTTGTCAGC AGCTTTCTCA TATTCAAAAC
GAAAAGGTTG TGGAAATTGA CGGTGGGATT ACAGCAAAAT
CTAGGTTGAA GAATGAGGAA CTGCAACGTG ACATGCAATC
ATTGGTGAAA TTAGTACTTG AGAAATCAGT TGGGCTCAAC
CGGAATATAA AGCAAACATT TCTAACGGTT GCAAAAACAT
ACTACTACAG AGCCTACAAT GCTGAGGAAA CTATGGATGC
CCATATATTC AAAGTTCTTT TCGAACCAGT TGCGTGA

*Ajuga reptans* cleroda-4(18),13E-dienyl diphosphate synthase (ArTPS2) was identified and isolated as described herein. ArTPS2 was identified as a (5R,8R,9S,10R) neo-cleroda-4(18),13E-dienyl diphosphate [38] synthase. In addition, the combination of ArTPS2 and SsSS enzymes generated neo-cleroda-4(18),14-dien-13-ol [37]. These compounds are shown below.

37

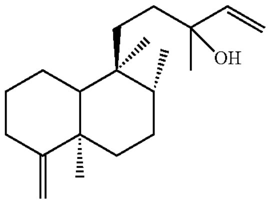

-continued

38

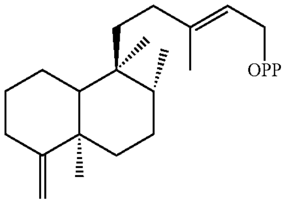

ArTPS2 is of particular interest for applications in agricultural biotechnology, for example, because it is useful for production of neo-clerodane diterpenoids. Neo-clerodane diterpenoids, particularly those with an epoxide moiety at the 4(18) position, have garnered significant attention for their ability to deter insect herbivores (Coll et al., Phytochem Rev 7(1):25 (2008); Klein Gebbinck et al. Phytochemistry 61(7):737-770 (2002); Li et al. Nat Prod Rep 33(10):1166-1226 (2016)). The 4(18)-desaturated products produced by ArTPS2 (e.g., compounds 37 and 38 with the $=CH_2$ 4(18) desaturation projecting from the A ring) the can be used in biosynthetic or semisynthetic routes to yield potent insect antifeedants.

The *Ajuga reptans* cleroda-4(18),13E-dienyl diphosphate synthase (ArTPS2) can have the amino acid sequence shown below (SEQ ID NO:23).

MSFASQATSL LSSPNRLGHV PTPSSPARFA AGGAPFWKIL
FTARSNGQYK AISRARNQGN VEYIDEIQKG PQVVLEAENS
LEDDTQKDTD QIRELVENVR VKLQNIGGGG ISISAYDTAW
VALVEDINGS GQPQFPTSLD WISNHQFPDG SWGSSKFLYY
DRILCTLACI VALKTWNVHP DKYHKGLDFI RENIHKLADE
EEVHMPIGFE VAFPSIIETA KKVGIEIPED FPGKKEIYAK
RDLKLKKIPM DILHKMPTPL LFSIEGMEGL DWQKLFKFRD
DGSFLTSPSS TAYALQQTKD ELCLKYLTDL VKKDNGGVPN
AFPVDLFDRN YTVDRLRRLG ISRYFQPEIE ECMKYVYRFW
DKRGISWARN TNVQDLDDTA QGFRNLRMHG YEVTLDVFKQ
FEKCGEFFSF HGQSSDAVLG MFNLYRASQV LFPGEHMLAD
ARKYAANYLH KRRLNNRVVD KWIINKDLEG EVAYGLDVPF
YASLPRLEAR FYIEQYGGSD DVWIGKALYR MVNVSCDTYL
ELAKLDYNKC QSVHQNEWKS FQKWYKSCSL GEFGFSEGSL
LQAYYIAAST IFEPEKSGER LAWAKTAALM ETIQQLSSQQ
KREFVDEFKH KNILKNENGE RYRSSTSLVE TLISTVNQLS
SDILLEQGRD VHQELCHVWL KWLSTWEERG NLVEAEAELL
LRTLHLNSGL DESSFSHPKY QQLLEVSTKV CHLLRLFQKR
KVYDPEGCTT DIATGTTFQI EACMQELVKL VFSRSSEDLD
SLTKLRFLDV ARSFYYTABC DPQVVESHID KVLFEKVV

A nucleic acid encoding the *Ajuga reptans* cleroda-4(18),13E-dienyl diphosphate synthase (ArTPS2) with SEQ ID NO:23 is shown below as SEQ ID NO:24.

ATGTCATTTG CTTCCCAAGC CACCTCCCTC CTATCATCCC
CCAACCGTCT CGGCCATGTT CCGACGCCAA GCTCGCCGGC
TCGTTTCGCT GCCGGTGGTG CCCCATTTTG GAAGATATTA
TTTACAGCTA GGTCTAATGG GCAGTATAAA GCTATTTCAA
GAGCTCGTAA CCAAGGAAAT GTAGAGTACA TTGATGAGAT
TCAGAAAGGC CCGCAAGTCG TATTGGAGGC AGAAAACAGC
TTGGAAGATG ACACACAAAA AGATACTGAT CAGATAAGGG
AACTAGTGGA AAATGTCCGA GTAAAGCTGC AGAATATCGG
TGGTGGAGGG ATAAGCATAT CGGCGTACGA CACCGCATGG
GTGGCGCTGG TGGAGGACAT CAACGGCAGT GGCCAGCCAC
AGTTTCCGAC GAGCCTCGAT TGGATATCGA ACCATCAGTT
CCCTGATGGG TCATGGGGCA GCAGCAAGTT TTTGTATTAT
GATCGGATTC TATGCACATT AGCATGTATA GTTGCATTGA
AAACCTGGAA TGTGCATCCT GATAAGTACC ACAAAGGGTT
GGATTTCATC AGAGAGAACA TTCACAAGCT TGCGGACGAA
GAAGAAGTGC ACATGCCAAT TGGGTTCGAA GTGGCATTCC
CATCAATTAT TGAAACAGCT AAAAAAGTAG GAATCGAAAT
CCCTGAGGAT TTTCCTGGCA AGAAAGAAAT TTATGCAAAA
AGAGATTTAA AGCTAAAAAA AATACCAATG GATATACTGC
ATAAAATGCC CACACCATTG CTCTTCAGCA TAGAAGGAAT
GGAAGGCCTT GACTGGCAAA AGCTATTCAA ATTCCGCGAT
GATGGCTCGT TTCTTACGTC TCCGTCCTCA ACAGCCTATG
CACTCCAGCA AACAAAGGAT GAGCTATGCC TCAAGTATCT
AACAGATCTT GTCAAGAAAG ACAACGGAGG AGTTCCGAAT
GCATTTCCAG TAGACCTGTT TGATCGTAAC TATACAGTAG
ACCGCTTGCG AAGGCTAGGA ATTTCACGGT ACTTTCAACC
TGAAATTGAA GAATGCATGA AATATGTTTA CAGATTTTGG
GATAAAAGAG GAATTAGCTG GGCAAGAAAT ACCAATGTTC
AGGACCTTGA TGACACTGCA CAGGGATTCA GGAATTTAAG
GATGCATGGT TATGAAGTCA CTCTAGATGT TTTCAAACAA
TTTGAGAAAT GTGGAGAGTT TTTCAGTTTT CATGGGCAAT
CCAGCGATGC TGTTTTAGGA ATGTTCAACT TGTACCGGGC
TTCTCAGGTT TTATTTCCGG GAGAACACAT GCTTGCAGAT
GCGAGGAAGT ATGCAGCCAA CTATTTGCAT AAACGAAGAC
TTAATAATAG GGTGGTCGAC AAATGGATTA TCAACAAAGA
CCTTGAAGGC GAGGTGGCAT ATGGGCTAGA TGTTCCGTTC
TACGGCAGCC TACCTCGACT CGAAGCAAGG TTCTACATAG
AACAATATGG GGGTAGTGAT GATGTGTGGA TTGGAAAAGC
TTTATACAGA ATGGTAAATG TAAGCTGCGA CACTTACCTT
GAGCTAGCAA AATTAGACTA CAACAAATGC CAATCCGTGC
ATCAGAATGA GTGGAAAAGC TTTCAAAAAT GGTACAAAAG

-continued

TTGCAGTCTT GGGGAGTTTG GGTTCAGTGA AGGAAGCCTA
CTCCAAGCTT ACTACATAGC AGCCTCAACT ATATTCGAGC
CAGAGAAATC AGGAGAACGC CTAGCTTGGG CTAAAACAGC
AGCTCTAATG GAGACAATTC AACAACTTTC CAGCCAGCAA
AAACGTGAAT TTGTTGATGA ATTCAAACAT AAAAACATAC
TGAAGAATGA AAATGGAGAA AGGTATAGAT CAAGTACCAG
TTTGGTAGAG ACTCTGATAA GCACTGTAAA TCAGCTCTCA
TCAGACATAC TATTGGAGCA AGGCAGAGAC GTTCATCAAG
AATTATGTCA CGTGTGGCTA AAATGGCTGA GTACATGGGA
GGAAAGAGGA AACCTGGTGG AAGCGGAAGC CGAGCTTCTT
CTGCGAACCT TACATCTCAA CAGCGGATTG GATGAATCAT
CATTTTCCCA CCCTAAATAT CAACAGCTCT TGGAGGTGTC
TACCAAAGTT TGCCACCTCC TTCGCCTATT TCAGAAACGA
AAGGTGTATG ATCCCGAAGG GTGTACAACC GACATAGCAA
CAGGAACAAC GTTCCAGATA GAAGCATGCA TGCAAGAACT
AGTGAAATTA GTGTTCAGCA GATCCTCAGA AGATTTAGAT
TCTCTTACTA AGTTGAGATT TTTGGATGTT GCTAGAAGTT
TCTATTACAC TGCCCATTGT GATCCACAGG TGGTCGAGTC
CCACATCGAT AAAGTATTGT TTGAGAAGGT AGTCTAG

The *Plectranthus barbatus* (+)-Copalyl diphosphate synthase (CfTPS16) was identified and isolated using the methods described herein, and this CfTPS116 protein can have the amino acid sequence shown below (SEQ ID NO:25).

MQASMSSLNL NNAPAVCSSR SQLSAKLHPP EYSTVGAWLN
RGNKNQRLGY RIRPKQLSKL TECRVASADV SQEIGKVGQS
VRTPEEVNKK IEESIKYVKE LLMTSGDGRI SVAPYDTAIV
ALIKDLEGRD APEFPSCLEW IANNQKDDGS WGDDFFCIYD
RIVNTIASVV ALKSWNVHPD KIERGVSYIK ENAHKLKGGN
LEHMTSGFEF VVPGCFDRAK ALGIEGLPYD DPIIKEIYAT
KERRLSKVPK DMIYKVPTTL LFSLEGLGME DLDWQKILKL
QSGDGSFLTS PSSTAYAFMQ TGDEKCYKFL QNAVRNCNGG
APHTYPVDVF ARLWAVDRLQ RLGISRFFQP EIKFCLDHIK
NVWTKNGVFS GRDSEFVDID DTSMGIRLLK MHGYDVDPNA
LKHFKQEDGR FSCYGGQMIE SASPIYNLYR AAQLRFPGEE
ILEEATKFAY NFLQQKLANN QIQEKWVISE HLIDEIKMGL
KMPWYATLPR VEASYYLQYY AASGDVWIGK TFYRMPEISN
DTYKELALLD FNRCQAQHQF EWIYMQEWYQ SNNIKEFGIS
KKELLLAYFL AAATIFEPER SQERIVWAKT QVVSKMITSF
LSQENALSSX QKTALFIDFG HSINGLNQIT SVEKENGLAQ
TVLATFGQLL EEYDRYTRHQ LKNAWSQWFM KLQQGDDNGG
ADAELLANTL NICAGHIAFN EDILSHNEYT SLSSLTNKIC

-continued

```
QRLSQIRDNK ILEIEDGSIK DKELEQEMQA LVKLVLEETG

GIDRNIKQTF LSVFKMFYYR AYHDAEAIDX HIFKVMFEPV

V
```

A nucleic acid encoding the *Plectranthus barbatus* (+)-Copalyl diphosphate synthase (CfTPS16) with SEQ ID NO:25 is shown below as SEQ ID NO:26.

```
ATGCAGGCTT CTATCTCATC TCTGAACTTG AACAATGCAC

CGGCCGTCTG CAGCAGCAGG TCACAGCTAT CCGCTAAACT

TCACCCGCCG GAATATTCCA CCGTGGGTGC ATGGCTGAAT

CGTGGCAACA AAAACCAGCG GTTGGGCTAC CGGATTCGTC

CAAAGCAACT ATCAAAACTA ACTGAGTGTC GAGTAGCAAG

TGCAGATGTG TCACAAGAGA TTGGAAAAGT CGGCCAATCT

GTTCGGACTC CTGAAGAGGT AAATAAAAAG ATAGAGGAAT

CCATCAAGTA CGTGAAGGAG CTGCTGATGA CGTCGGGCGA

CGGGCGAATC AGTGTGGCGC CCTACGACAC GGCCATAGTT

GCCCTTATCA AGGACTTGGA AGGGCGCGAT GCCCCGGAGT

TTCCATCTTG CTTGGAGTGG ATTGCAAACA ATCAAAAAGA

CGATGGTTCT TGGGGGGATG ACTTCTTCTG CATCTATGAT

CGGATCGTTA ATACCATAGC ATCCGTCGTC GCCTTAAAAT

CATGGAATGT GCACCCAGAC AAGATTGAGA GAGGAGTATC

CTACATCAAG GAAAACGCGC ATAAACTAAA AGGTGGGAAT

CTCGAACACA TGACATCAGG GTTCGAGTTC GTGGTTCCCG

CGTGTTTTGA CAGAGCCAAA GCCTTGGGCA TCGAAGGCCT

TCCCTATGAT GATCCCATCA TCAAGGAGAT TTATGCTACA

AAAGAAAGGA CATTGAGCAA GGTACCGAAG GACATGATCT

ACAAAGTTCC GACAACTCTA TTGTTTAGTT TAGAGGGACT

GGGCATGGAG GATTTGGACT GGCAAAAGAT ACTGAAACTG

CAGTCGGGCG ACGGCTCATT CCTCACCTCT CCGTCGTCCA

CCGCCTACGC ATTCATGCAG ACCGGAGACG AAAAATGCTA

CAAATTCCTC CAGAACGCCG TCAGAAATTG CAACGGCGGA

GCGCCGCACA CTTATCCAGT CGACGTCTTT GCACGGCTCT

GGGCGGTCGA CCGACTTCAG CGACTCGGAA TTTCTCGCTT

CTTTCAGCCC GAGATCAAGT TTTGCCTAGA CCACATCAAA

AATGTGTGGA CTAAGAACGG AGTTTTCAGT GGACGGGATT

CAGAGTTTGT GGATATCGAC GACACATCCA TGGGCATCAG

GCTTCTGAAA ATGCACGGAT ACGATGTCGA CCCAAATGCA

CTGAAACATT TCAAGCAGGA GGATGGGAGG TTTTCATGCT

ACGGTGGTCA AATGATCGAG TCTGCATCTC CGATTTACAA

TCTCTACAGG GCTGCTCAGC TTCGTTTTCC AGGAGAAGAA

ATTCTTGAAG AAGCCACTAA ATTTGCCTAC AACTTCCTGC
```

-continued

```
AACAGAAGCT GGCCAACAAT CAAATTCAAG AAAAGTGGGT

CATATCCGAG CACCTAATTG ATGAGATAAA AATGGGATTG

AAGATGCCAT GGTACGCCAC CCTACCTAGA GTTGAGGCTT

CATACTATCT CCAATATTAT GCAGCTTCTG GCGACGTATG

GATTGGCAAG ACTTTTTACA GGATGCCAGA AATAAGTAAT

GACACGTACA AAGAGCTTGC ACTATTGGAT TTCAACCGAT

GCCAAGCACA ACATCAGTTC GAATGGATTT ACATGCAAGA

GTGGTATCAA AGCAACAACA TTAAAGAATT TGGGATAAGC

AAGAAAGAGC TTCTTCTTGC TTACTTCTTG GCTGCTGCAA

CCATTTTTGA ACCCGAACGA TCGCAAGAGC GGATCGTGTG

GGCTAAAACC CAAGTTGTTT CTAAGATGAT CACATCGTTT

CTGTCTCAAG AAAACGCTTT GTCATCGGAN CAAAAGACTG

CACTTTTCAT CGATTTTGGG CATAGTATCA ATGGCCTCAA

TCAAATAACT AGTGTTGAGA AAGAGAATGG GCTTGCTCAG

ACTGTCCTGG CAACCTTCGG ACAACTACTC GAGGAATTCG

ACAGATACAC AAGGCATCAA CTGAAAAATG CTTGGAGCCA

ATGGTTCATG AAACTGCAGC AAGGAGATGA CAATGGCGGG

GCAGACGCAG AGCTCCTAGC AAACACATTG AACATCTGCG

CTGGTCATAT TGCTTTTAAC GAAGACATAT TATCTCACAA

CGAATACACC TCTCTCTCCT CCCTCACAAA CAAAATCTGT

CAGCGGCTAA GTCAAATTCG AGATAATAAG ATACTGGAAA

TTGAGGATGG GAGCATAAAA GATAAGGAAC TAGAACAGGA

AATGCAGGCG CTGGTGAAGT TAGTCCTGGA AGAAACCGGT

GGCATCGACA GGAACATCAA GCAAACATTT TTGTCAGTTT

TCAAAATGTT TTACTACAGA GCCTACCACG ATGCTGAGGC

TATCGATGNC CATATTTTCA AAGTAATGTT TGAACCAGTC

GTATGA
```

*Hyptis suaveolens* labda-7,13E-dienyl diphosphate synthase (HsTPS1) was identified and isolated as described herein, and is a (5S, 9S, 10S) labda-7,13E-dienyl diphosphate [21] synthase. When HsTPS1 was expressed in *N. benthamiana*, labda-7,13(16),14-triene [22] was formed. The combination of HsTPS1 with OmTPS3 produced labda-7,12E,14-triene [24].

21

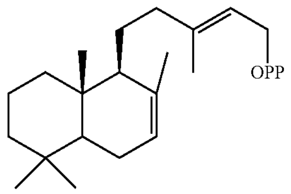

-continued

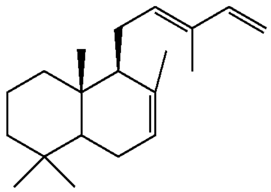

24

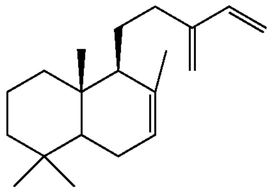

22

The *Hyptis suaveolens* labda-7,13E-dienyl diphosphate synthase (HsTPS1) can have the amino acid sequence shown below (SEQ ID NO:27).

```
MAYMISISNL NCSSLINTNL SAKIQLHQGL KGTWLKTSKR
MCMDQQVHGK QIAKVIESRV TDKDVSTAQD FEVLKVNRVE
DLISSIKSSL KTMEDGRISV SPYSTSWIAL IPSIDGRQTP
QFPSSLEWIV KHQLSDGSWG DALFFCVYDR LVNTIACIIA
LHTWKVHADK VKKGVSFVKE NIWKLEDANE VHMTSGFEVI
FPILLRRARD MGIDGLPSDD TPVVRMISAA RDHKLKKIPR
EVMHQVTTIL LYSLEGLEDL DWSRLFKLQS ADGSFLTSPS
STAFAFMQTN NHNCLRFITS VVQTFNGGAP DNYPIDIFAR
LWAVDRLQRL GISRFFEQEI NDCLSYVYRF WNANGVFSAG
ATNFCDLDDT SMAFRLLRLH GYDVDPNVLR KFKEGDRFCC
HSGEVAMSTS PTYALYRASQ IQFPGEEILD EAFSFTRDYL
QDWLARDQVL DKWIVSKDLP DEIKVGLEVP WYASLPRVEA
AYYMQRHYGG STDAWVAKTC YRMPDVSNDD YLELARLDFK
RCQAQHQSEL SYMQRWYDSC NVEEFGISRK ELLVAYFVAA
ATIFEPERAT ERIVWAKTEI VSKMIKAFFG EDSLDQKTML
LKEFRNSINN GSHRFMKSEH RIVNILLQAL QELLHGSDDC
RIGQLKNAWY EWLMKFEGGD EASLWGEGEL LVTTLNICTA
HFLQHHDLLL NHDYITLSEL TNRICLKLSQ IQVGEMNEMR
EDMQALTKLV IGESCIVNKN IKQTFLAVAK TFYYRAYFDA
DTVDLHIFKV LFEPIV
```

A nucleic acid encoding the *Hyptis suaveolens* labda-7,13E-dienyl diphosphate synthase (HsTPS1) with SEQ ID NO:27 is shown below as SEQ ID NO:28.

```
ATGGCGTATA TGATATCTAT TTCAAATCTC AACTGTTCCT
CGCTACTAAA CACCAATCTT TCAGCAAAGA TTCAGCTGCA
CCAAGGTCTC AAAGGAACAT GGCTAAAAAC CAGCAAACGC
ATGTGCATGG ATCAACAGGT TCATGGCAAG CAGATAGCAA
```

-continued

```
AAGTGATCGA GAGCCGAGTT ACTGATAAGG ATGTTTCCAC
TGCTCAGGAC TTTGAAGTGT TAAAGGTCAA TAGAGTGGAG
GATCTGATAT CAAGCATTAA GAGTTCATTG AAGACAATGG
AAGATGGAAG AATAAGCGTG TCGCCCTACA GCACATCATG
GATCGCACTC ATTCCAAGTA TTGATGGGCG CCAGACGCCC
CAGTTTCCAT CTTCACTGGA GTCGATCGTG AAGCATCAGC
TATCAGATGG TTCATGGGGT GATGCCCTTT TTTTCTGCGT
TTATGATCGT CTCGTAAATA CGATTGCATG CATCATTGCC
CTGCACACCT GGAAGGTTCA TGCAGACAAG GTTAAAAAAG
GAGTAAGTTT TGTGAAGGAA AATATATGGA AACTTGAAGA
CGCCAACGAG GTCCACATGA CTAGTGGTTT CGAAGTTATA
TTTCCCATCC TTCTTCGAAG AGCACGAGAC ATGGGAATTG
ATGGTCTTCC TTCTGATGAT ACTCCAGTTG TTAGGATGAT
TTCTGCTGCT AGGGATCACA AATTGAAAAA GATTCCGAGG
GAGGTGATGC ACCAAGTGAC AACAACTCTA TTATATAGTT
TGGAAGGGTT GGAAGATTTA GACTGGTCAA GGCTTTTCAA
ACTTCAGTCA GCTGATGGTT CATTCTTAAC TTCTCCATCT
TCAACTGCCT TCGCATTCAT GCAAACTAAT AACCACAATT
GCTTGAGATT CATCACTAGC GTTGTCCAAA CATTCAATGG
AGGAGCTCCA GATAACTATC CAATCGACAT CTTTGCGAGA
CTGTGGGCAG TTGACAGGTT ACAGCGGTTA GGGATTTCTC
GTTTCTTCGA GCAGGAGATA AATGATTGCC TAAGCTATGT
ATATAGATTT TGGAATGCAA ATGGAGTTTT CAGTGCAGGA
GCCACTAATT TTTGTGATCT TGACGACACA TCCATGGCTT
TCCGGCTACT ACGTTTGCAT GGATATGATG TCGACCCAAA
TGTTCTGAGG AAATTCAAAG AGGGAGACAG ATTCTGTTGC
CACAGTGGTG AAGTGGCGAT GTCGACATCG CCAACGTACG
CTCTCTACAG AGCTTCCCAA ATTCAGTTTC CAGGAGAAGA
AATTCTGGAT GAAGCCTTCA GCTTCACTCG CGACTATCTA
CAGGACTGGT TAGCAAGAGA TCAAGTTCTT GATAAGTGGA
TTGTATCCAA GGACCTTCCA GATGAGATTA AGGTAGGACT
AGAGGTGCCA TGGTATGCCA GCCTGCCACG GGTAGAGGCT
GCTTATTACA TGCAACGACA TTACGGCGGG TCTACTGATG
CGTGGGTGGC CAAGACTTGT TACAGGATGC CTGATGTGAG
CAACGATGAT TACCTGGAGC TTGCAAGATT GGATTTCAAG
AGATGTCAAG CCCAACATCA GACTGAATTG AGTTACATGC
AACGATGGTA TGACAGTTGC AATGTCGAAG AATTCGGAAT
AAGCAGAAAA GAGTTGCTTG TAGCTTATTT TGTGGCTGCT
GCAACTATTT TTGAACCTGA GAGAGCAACT GAGAGAATTG
TGTGGGCAAA AACTGAAATA GTTTCTAAGA TGATCAAAGC
```

-continued

ATTTTTTGGT GAAGACTCAT TAGACCAAAA AACTATGTTG

TTAAAAGAAT TCAGAAACAG CATCAATAAT GGCTCCCACA

GATTCATGAA GAGTGAGCAT AGAATCGTCA ACATTCTACT

ACAAGCCTTG CAGGAGCTAT TACATGGATC TGATGATTGT

CGTATTGGTC AACTCAAAAA TGCTTGGTAT GAGTGGCTGA

TGAAATTCGA GGGAGGAGAT GAAGCAAGTT TGTGGGGAGA

AGGAGAGCTT CTTGTCACCA CCTTAAACAT TTGCACAGCT

CATTTCCTTC AACACCATGA TTTACTGTTG AATCATGACT

ACATAACTCT TTCTGAGCTC ACAAACAAGA TCTGCCTCAA

GCTTTCTCAG ATTCAGGTAG GAGAAATGAA TGAAATGAGA

GAAGATATGC AGGCGTTGAC GAAATTAGTG ATTGGGGAAT

CATGCATCGT CAACAAAAAC ATTAAGCAAA CATTTCTTGC

AGTTGCAAAG ACTTTCTATT ACAGAGCCTA CTTCGATGCC

GACACCGTTG ATCTCCATAT ATTTAAAGTT CTATTTGAGC

CCATTGTCTG A

*Leonotis leonurus* peregrinol diphosphate synthase (LlTPS1) was identified and isolated using the methods described herein. The LlTPS1 enzyme was identified as a peregrinol diphosphate (PgPP) [5] synthase, where the peregrinol diphosphate (PgPP) [5] compound is shown below.

5

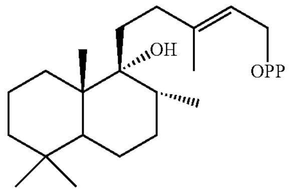

The *Leonotis leonurus* peregrinol diphosphate synthase (LlTPS1) can have the amino acid sequence shown below (SEQ ID NO:29).

MASTASTLNL TINSTPFVST KTQAKVSLTA CLWMQDRSSS

RHVSLKHKFC RNQQLKCRAS LDVQQVRDEV FSTAQSPESV

DKKIEERKKW VKNLLSTMDD GRINWSAYDT AWISLIKEFE

GRDATQFPST LMRIAENQLA DGSWGDPDYD CSYDRIINTL

ACVVALTTWN AHPEHNKKGI KYIKENMYKL EETPVVLMTS

AFEVVFPALL NRAKNLGIQD LPYDMPIVKE ICKIGDEKLA

RIPKKMMEKE PTSLMYAAEG VENLDWEKLL KQRTPENGSF

LSSPAATAVA FMHTKDENCL RYIMYLLDKF NGGAPNVYPI

DLWSRLWATD RIQRLGISRF FKEEIKEILS YVYSYWTDIG

VYCTRDSKYA DIDDTSMGFR LLRMHGFKMD PNVFKYFQKD

DRFVCLGGQM NDSPTATYNL YRAAQYQFPG EKILEDARKF

SQEFLQHCID TNNLLDKWVI SPRFPEELKF GMEMTWYSCL

PRIEARYYVQ HYGATEDVWL GKTFFRMEEI SNENYKELAK

-continued

LDFSKCQAQH QTEWIHMQEW YESSNAKEFG ISRKDLLFAY

FLAAASIFET ERAKERILWA KSQIICKMVK SYLENQTASL

EHKIAFLTGF GDNNNGLHTI NKGSGPVNNV MRTLQQLLGE

FDGYISSQLE NAWAAWLTKL EQGEANDGEL LATTLNICSG

RIVYNEDTLS NKEYKAFADL TNKICQNLAQ IQNKKGDEIK

DPNEGEKDKE VEQGMQALAK LVFEESGLER SIKETFLAVV

RTYHYGAYVA DEKIDVHMFK VLFEPVE

A nucleic acid encoding the *Leonotis leonurus* peregrinol diphosphate synthase (LlTPS1) with SEQ ID NO:29 is shown below as SEQ ID NO:30.

ATGGCCTCCA CTGCATCCAC TCTAAATTTG ACCATCAATA

GTACACCATT TGTAAGCACC AAAACGCAAG CAAAGGTTTC

CTTGCCCGCA TGTTTATGGA TGCAGGATAG AAGCAGCAGT

AGACACGTGT CGTTAAAACA CAAATTCTGT CGAAATCAAC

AACTTAAGTG TCGAGCAAGT CTGGATGTTC AGCAAGTACG

TGATGAAGTT TTTTCCACTG CTCAATCCCC TGAATCGGTG

GATAAAAAAA TAGAGGAACG TAAAAAATGG GTGAAGAATT

TGTTGAGTAC AATGGACGAT GGACGAATAA ATTGGTCAGC

CTATGACACG GCATGGATTT CACTTATTAA AGAATTTGAA

GGACGAGATG CTCCCCAGTT TCCGTCGACT CTCATGCGCA

TCGCGGAGAA CCAATTGGCC GACGGGTCAT GGGGCGATCC

AGATTACGAC TGCTCCTATG ATCGGATAAT AAACACACTA

GCGTGTGTTG TAGCCTTGAC AACATGGAAT GCTCATCCTG

AACACAATAA AAAAGGAATA AAATACATCA AGGAAAATAT

GTATAAACTA GAAGAGACGC CTGTTGTACT CATGACTAGT

GCATTTGAAG TTGTGTTTCC GGCGCTTCTT AACAGAGCTA

AAAACTTGGG CATTCAAGAT CTTCCCTATG ATATGCCCAT

CGTGAAGGAG ATTTGTAAAA TAGGGGATGA GAAGTTGGCA

AGGATACCAA AGAAAATGAT GGAGAAAGAG CCAACATCGC

TGATGTATGC CGCGGAAGGA GTCGAAAACT TGGACTGGGA

AAAGCTTCTG AAACAGCGGA CACCCGAGAA TGGCTCGTTC

CTCTCTTCCC CGGCCGCAAC TGCCGTTCCA TTTATGCACA

CAAAAGATGA AAATTGCTTA AGATACATCA TGTACCTTTT

GGACAAATTT AATGGAGGAG CACCAAATGT TTATCCGATC

GACCTCTGGT CAAGACTTTG GGCAACGGAC AGGATACAAC

GTCTGGGAAT TTCCCGCTTC TTTAAGGAAG AGATTAAGGA

AATCTTAAGT TATGTCTATA GCTATTGGAC AGACATTGGA

GTCTATTGTA CACGAGATTC CAAATATGCT GACATTGACG

ACACATCCAT GGGATTCAGG CTTCTGAGGA TGCACGGATT

TAAAATGGAC CCAAATGTAT TTAAATACTT CCAGAAAGAC

-continued

```
GACAGATTTG TTTGTCTAGG TGGTCAAATG AATGATTCTC
CAACTGCAAC ATACAATCTT TACAGGGCTG CTCAATACCA
ATTTCCAGGT GAAAAAATTC TAGAAGATGC TAGAAAGTTC
TCTCAAGAGT TTCTACAACA TTGTATAGAC ACCAATAACC
TTCTAGATAA ATGGGTGATA TCCCCGCGCT TTCCGGAAGA
GTTGAAATTT GGAATGGAGA TGACATGGTA TTCCTGCCTA
CCACGAATTG AGGCTAGATA CTACGTACAA CATTATGGTG
CTACAGAGGA CGTCTGGCTT GGAAAGACTT TTTTCAGGAT
GGAAGAAATC AGTAATGAGA ACTATAAGGA GCTTGCAAAA
CTTGATTTCA GTAAATGCCA AGCACAACAT CAGACAGAGT
GGATTCATAT GCAAGAGTGG TATGAAAGTA GCAATGCTAA
GGAATTTGGG ATAAGCAGAA AAGACCTACT TTTTGCTTAC
TTTTTGGCTG CAGCTTCCAT ATTTGAAACC GAAAGGGCAA
AAGAGAGAAT TCTGTGGGCA AAATCTCAAA TTATTTGCAA
GATGGTTAAG TCATATCTGG AAAACCAAAC GGCGTCGTTG
GAGCACAAAA TCGCCTTTTT AACTGGATTC GGAGATAACA
ACAATGGCCT GCACACAATT AATAAGGGGT CTGGACCTGT
TAACAATGTC ATGAGAACCC TCCAACAGCT CCTTGGAGAA
TTCGACGGAT ATATTAGTAG TCAATTGGAA AATGCTTGGG
CAGCATGGTT GACGAAACTC GAGCAAGGCG AGGCCAACGA
TGGCGAGCTC CTCGCAACCA CACTAAACAT TTGTTCTGGG
CGTATTGTGT ATAACGAGGA TACATTATCG AACAAGGAGT
ACAAGGCTTT CGCAGACCTC ACAAATAAAA TTTGTCAAAA
TCTTGCTCAA ATCCAAAATA AAAAGGGTGA CGAAATTAAG
GATCCGAATG AAGGCGAAAA GGACAAGGAA GTCGAGCAAG
GCATGCAGGC ATTGGCTAAG TTAGTTTTTG AGGAATCTGG
GCTTGAGAGG AGTATCAAAG AAACATTCTT AGCAGTGGTG
AGAACTTATC ACTATGGGGC CTATGTTGCT GATGAGAAGA
TTGATGTCCA CATGTTCAAG GTTTTGTTCG AACCAGTTGA
ATGA
```

*Nepeta mussinii* (+)-copalyl diphosphate synthase (NmTPS1) was identified and isolated. The NmTPS1 enzyme can synthesize compound 31, shown below.

31

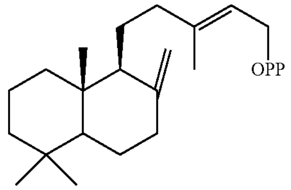

The *Nepeta mussinii* (+)-copalyl diphosphate synthase (NmTPS1) can have the amino acid sequence shown below SEQ ID NO:31).

```
MTSISSLNLS NAAAARRRLQ LPANVHLPEF HSVCAWLNSS
SKHDPFSCRI HRKQKSKVTE CRVASVDASP VSDHKMSSPV
QTQEEANKNM EESIEYIKNL LMTSGDGRIS VSAYDTSIVA
LIKDIEGRDA PQFPSCLEWI GQNQKADGSW GDDFFCIYDR
FVNTLACIVA LKSWNLHPHK IQKGVTYIKK NVHKLKDGRP
ELMTSGFEIC VPAILQRAKD LGIQDLPYDD PMIKQITDTK
ERRLKKIPKD FIYQLPTTLL FSLEGQENLD WEKILKLQSA
DGSFLTSPSS TAAVFMHTKD EKCLKFIENA VKNCDGGVPH
TYPVDVFARL WAVDRLQRLG ISRFFQPEIK YFLDHIQSVW
TENGVFSGRD SQFCDIDDTS MGIRLLKMHG YKIDPNALEH
FKQEDGKFSC YGGQMIESAS PIYNLYRAAQ LRFPGEEILE
EAIKFSYNFL QEKLAKDEIQ EKWVISEHLI DEIKTGLKMP
WYATLPRVEA AYYLDYYAGS GDVWIGKTFY RMPEISNDTY
KEMAILDFNR CQAQHQFEWI YMQEWYESSN VKEFGISKKE
LLVAYFLAAS TIFEPERAQE RIMWAKTKIV SKMIASSLNK
QTTLSLDQKT ALFTQLEHSL NGLDSDEKDN GVAETKNLVA
TFQQLLDGFD KYTRHQLKNA WSQWLKQVQQ GEATGGADAE
LEANTLNICA GHIAFNEQVL SHNEYTTLST LTNKICHRLT
QIQDKKTLEI IDGGIRYKEL EQEMQALVKL VVEENDGGGI
DRNIKQTFLS VFKNYYYSAY HDAHTTDVHI FKVLFGPVV
```

A nucleic acid encoding the *Nepeta* mussinii (+)-copalyl diphosphate synthase (NmTPS1) with SEQ ID NO:31 is shown below as SEQ ID NO:32.

```
ATGACTTCAA TATCCTCTCT AAATTTGAGC AATGCAGCAG
CTGCTCGCCG CAGGTTACAA CTACCAGCAA ACGTTCACCT
GCCGGAATTT CACTCCGTCT GTGCATGGCT GAATAGCAGC
AGCAAACACG ATCCCTTTAG TTGCCGAATT CATCGAAAGC
AAAAATCGAA AGTAACCGAG TGTCGAGTAG CAAGCGTGGA
TGCATCACCA GTGAGTGATC ATAAAATGAG TTCTCCTGTT
CAAACTCAAG AAGAGGCAAA TAAAAATATG GAGGAGTCAA
TCGAGTACAT AAAGAATTTG TTGATGACAT CTGGAGACGG
GCGAATAAGC GTGTCGGCAT ACGACACGTC AATAGTCGCC
CTAATTAAGG ACATAGAAGG ACGCCACGCC CCGCAATTTC
CATCATGCCT GGAGTGGATC GGGCAAAACC AAAAGGCCGA
TGGCTCGTGG GGGGACGACT TCTTCTGTAT TTACGACCGC
TTCGTAAATA CACTAGCATG TATCGTGGCC TTGAAATCAT
GGAACCTTCA CCCTCACAAG ATTCAAAAAG GAGTGACATA
CATCAAGAAA AACGTGCATA AGCTTAAAGA TGGGAGGCCT
GAGCTGATGA CGTCAGGGTT CGAAATTTGT GTTCCCGCCA
TTCTTCAAAG AGCCAAAGAC TTGGGCATCC AAGATCTTCC
CTATGATGAT CCCATGATTA AACAGATCAC TGATACGAAA
```

-continued

```
GAGCGACGAC TCAAAAAGAT ACCGAAGGAT TTTATATACC
AATTGCCGAC GACTTTACTC TTCAGTTTGG AAGGGCAGGA
GAATTTGGAC TGGGAAAAGA TACTCAAACT GCAGTCAGCT
CACGGCTCCT TCCTTACTTC GCCGTCCTCC ACCGCCGCCG
TCTTCATGCA TACCAAAGAT GAAAAATGCT TGAAGTTCAT
AGAGAACGCC GTCAAAAATT GCGACGGCGG AGTGCCCCAT
ACCTACCCAG TAGACGTGTT TGCAAGACTT TGGGCAGTTG
ACAGACTACA ACGCCTAGGG ATTTCTCGCT TTTTTCAGCC
TGAGATTAAA TATTTCTTAG ATCACATACA AAGCGTTTGG
ACTGAGAACG GAGTTTTCAG TGGACGAGAT TCACAATTTT
GCGACATTGA TGATACGTCC ATGGGGATAA GGCTTCTGAA
AATGCATGGA TACAAAATCG ACCCAAATGC ACTTGAGCAT
TTCAAGCAGG AGGATGGTAA ATTTTCGTGC TACGGTGGTC
AAATGATCGA GTCTGCATCA CCGATATACA ATCTGTACCG
AGCTGCTCAA CTCCGATTTC CAGGAGAAGA AATTCTTGAA
GAGGCCATTA AATTTTCCTA TAACTTTTTG CAAGAAAAGC
TAGCCAAGGA TGAAATTCAA GAAAAATGGG TCATATCGGA
GCACTTAATT GATGAGATTA AGATCGGGCT AAAGATGCCA
TGGTACGCCA CTCTACCCCG AGTTGAAGCT GCATATTACC
TGGACTATTA TGCAGGATCC GGCGATGTGT GGATTGGCAA
GACTTTCTAC AGGATGCCAG AAATCAGTAA TGATACATAC
AAAGAAATGG CCATTTTGGA TTTCAACCGA TGCCAAGCAC
AACATCAGTT TGAATGGATT TACATGCAAG AGTGGTATGA
AAGTAGCAAC GTAAAGGAAT TTGGGATAAG CAAAAAAGAG
CTACTTGTTG CTTATTTCTT GGCTGCATCA ACCATATTTG
AACCGGAAAG AGCACAAGAG AGGATTATGT GGGCAAAAAC
AAAAATTGTT TCCAAAATGA TCGCATCATC TCTTAACAAA
CAAACCACTC TATCGTTAGA CCAAAAGACT GCACTTTTTA
CCCAACTCGA ACATAGTCTC AATGGCCTCG ACAGTGATGA
GAAAGATAAT GGAGTAGCTG AGACGAAAAA TCTAGTGGCA
ACCTTCCAGC AGCTGCTAGA TGGATTCGAC AAATACACTC
GCCATCAATT GAAAAATGCT TGGAGCCAGT GGTTGAAGCA
AGTGCAGCAA GGAGAGGCGA CCGGGGGCGC AGACGCGGAG
CTGGAAGCAA ACACGTTGAA CATCTGTGCC GGTCATATCG
CATTCAACGA ACAAGTATTA TCGCACAACG AATACACAAC
TCTCTCCACA CTCACAAACA AGATCTGCCA CCGGCTTACC
CAAATTCAAG ACAAAAAGAC GCTTGAGATA ATCGACGGCG
GCATAAGATA TAAGGAGCTG GAGCAGGAGA TGCAGGCGTT
GGTGAAATTA GTTGTTGAAG AAAACGACGG CGGCGGCATA
GACAGGAATA TTAAACAAAC ATTTTTATCA GTTTTCAAGA
```

-continued

```
ATTATTACTA CAGTGCCTAC CACGATGCTC ACACAACCGA
TGTTCATATT TTCAAAGTAT TATTTGGACC GGTCGTCTGA
```

*Origanum majorana* (+)-copalyl diphosphate synthase (OmTPS1) was identified and isolated as describe herein. The OmTPS1 enzyme can synthesize compound 31. OmTPS1 can also synthesize palustradiene [29] (shown below), when combined with OmTPS5.

29

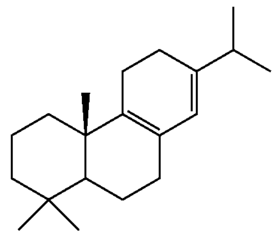

31

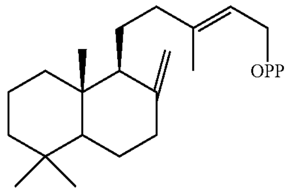

The *Origanum majorana* (+)-copalyl diphosphate synthase (OmTPS1) can have the amino acid sequence shown below (SEQ ID NO:33).

```
MTDVSSLRLS NAPAAGGRLP LPGKVHLPEF RTVCAWLNNG
CKYEPLTCRI SRRKISECRV ASLNSSQLIE KVGSPAQSLE
EANKKIEDSI EYIKNLLMTS GDGRISVSAY DTSLVALIKD
VKGRDAPQFP SCLEWIAQNQ MADGSWGDEF FCIYDRIVNT
LACLVALKSW NLHPDKIEKG VTYINENVHK LKDGSTEHMT
SGFEIVVPAT LERAKVLGIQ GLPYDHPFIK EIINTKERRL
SKIPKDLIYK LPTTLLFSLE GQGELDWEKI LKLQSSDGSF
LTSPSSTASV FMRTKDEKCL KFIENAVKNC GGGAPHTYPV
DVFARLWAVD RLQRLGISRF FQHEIKYFLD HINSVWTENG
VFSGRDSQFC DIDDTSMGVR LLKMHGYNVD PNALKHFKQE
DGKFSCYPGQ MIESASPIYN LYRAAQLRFP GEEILEEASR
FAFNFLQEKI ANHEIQEKWV ISEHLIDEIK LGLKMPWYAT
LPRVEAAYYL EYYAGSGDVW IGKTFYRMPE ISNDTYKEVA
ILDFNTCQAQ HQFEWIYMQE WYESSKVKDF GISKKDLLVA
YFLAASTIFE PERTQERIIW AKTLILSRMI TSFLNKQATL
SSQQKNAILT QLGESVDGLD KIYSGEKDSG LAETLLATFQ
QLLDGFDRYT RHQLKNAWGQ WLMKVQQGEA NGGADAELIA
NTLNICAGLI AFNEDVLLHS EYTTLSSLTN KICQRLSQIE
DEKTLEVIEG GIKDKELEED IQALVKLALE ENGGCGVDRR
IKQSFLSVFK TFYYRAYHDA ETTDLHIFKV LFGPVM
```

A nucleic acid encoding the *Origanum majorana* (+)-copalyl diphosphate synthase (OmTPS1) with SEQ ID NO:33 is shown below as SEQ ID NO:34.

```
ATGACCGATG TATCCTCTCT TCGTTTGAGC AATGCACCAG
CTGCCGGCGG CAGGTTGCCG CTGCCGGGAA AGGTTCACCT
GCCTGAATTT CGCACCGTTT GTGCATGGTT GAACAATGGC
TGCAAATACG AGCCCTTGAC TTGTCGAATT AGTCGACGGA
AGATATCTGA ATGTCGAGTA GCAAGTCTGA ATTCGTCGCA
AGTAATTGAA AAGGTCGGTT CTCCTGCTCA ATCTCTAGAA
GAGGCAAACA AAAAGATCGA GGACTCCATC GAGTACATTA
AGAATCTATT GATGACATCT GGCGACGGGC GGATAAGTGT
GTCGGCTTAC GACACGTCGC TAGTCGCCCT AATAAAGGAC
GTGAAAGGAC GAGATGCCCC TCAGTTCCCG TCGTGCCTGG
AGTGGATAGC GCAAAACCAA ATGGCCGACG GGTCGTGGGG
GGATGAGTTC TTCTGTATTT ACGACCGGAT CGTGAATACA
TTAGCATGCC TCGTTGCCTT GAAATCATGG AACCTTCACC
CCGACAAGAT CGAAAAAGGA GTGACGTACA TCAACGAAAA
TGTGCACAAA CTGAAAGACG GGAGCACCGA GCACATGACG
TCAGGGTTCG AAATCGTGGT CCCCGCCACT CTAGAAAGAG
CCAAAGTCTT GGGCATCCAA GGCCTCCCTT ATGATCATCC
CTTCATTAAG GAGATTATTA ATACTAAGGA GCGAAGATTA
AGCAAAATAC CCAAGGATTT GATATACAAA CTGCCAACGA
CGCTGCTGTT CAGTTTAGAA GGGCAGGGAG AATTAGATTG
GGAAAAGATA CTGAAACTGC AGTCAAGCGA TGGCTCCTTC
CTTACTTCGC CCTCGTCGAC CGCCTCCGTC TTCATGCGGA
CGAAAGACGA GAAATGCCTC AAGTTCATTG AGAACGCCGT
TAAGAATTGC GGCGGGGGAG CGCCGCATAC TTACCCAGTG
GATGTGTTTG CAAGACTTTG GGCAGTTGAC AGACTACAGC
GATTAGGGAT TTCTCGATTC TTCCAACACG AGATTAAATA
CTTCTTAGAT CACATTAAGA GTGTATGGAC CGAGAATGGA
GTTTTCAGTG GACGAGATTC ACAATTTTGT GATATCGACG
ACACTTCTAT GGGAGTTAGG CTTCTAAAAA TGCATGGATA
CAATGTTGAT CCAAATGCGC TCAAGCATTT CAAGCAGGAG
GATGGCAAAT TCTCTTGCTA CCCTGGCCAA ATGATCGAGT
CTGCATCTCC GATATACAAT CTCTACCGAG CCGCTCAACT
CCGGTTCCCC GGAGAAGAAA TTCTCGAAGA AGCAAGTCGA
TTCGCCTTCA ACTTTCTGCA GGAAAAGATA GCCAACCATG
AAATTCAAGA AAAATGGGTC ATATCTGAGC ACTTAATTGA
TGAGATAAAG TTGGGACTGA AGATGCCATG GTACGCGACT
CTGCCCCGAG TTGAGGCCGC TTATTATCTA GAGTATTATG
CTGGCTCAGG CGACGTATGG ATTGGAAAGA CTTTCTACCG
```

-continued

```
GATGCCGGAA ATCAGTAACG ATACGTATAA AGAGGTGGCC
ATTTTGGATT TCAACACATG CCAAGCTCAA CACCAGTTTG
AATGGATTTA CATGCAAGAG TGGTACGAAA GTAGCAAGGT
TAAAGATTTC GGGATAAGCA AAAAGGACCT ACTTGTTGCT
TACTTTCTGG CGGCATCGAC TATATTTGAA CCCGAAAGAA
CACAAGAGAG GATTATTTGG GCAAAAACCC TAATTCTTTC
TAGGATGATC ACATCATTTC TCAACAAACA AGCTACACTT
TCATCCCAAC AAAAGAATGC CATCTTAACA CAACTTGGAG
AGAGTGTCGA TGGCCTCGAT AAAATATATA GTGGTGAGAA
AGATTCTGGG CTGGCTGAGA CTCTGCTGGC TACCTTCCAG
CAACTGCTCG ACGGATTCGA TAGATACACT CGCCATCAAC
TGAGAAATGC TTGGGGGCAA TGGTTGATGA AAGTGCAGCA
AGGAGAGGCC AACGGTGGCG CCGACGCTGA GCTCATAGCA
AACACACTCA ATATCTGCGC CGGCCTTATC GCCTTCAACG
AAGACGTATT GTTGCACAGC GAATACACGA CTCTCTCCTC
CCTCACCAAC AAAATATGCC ACCGCCTTAG CCAGATTGAA
GATGAAAAGA CGCTTGAAGT GATTGAAGGG GGCATAAAAG
ATAAGGAACT GGAGGAGGAT ATTCAGGCGT TGGTGAAGCT
AGCCCTCGAA GAAAACGGCG GCTGCGGCGT CGACAGAAGA
ATCAAGCAGT CATTCTTATC AGTATTCAAG ACTTTTTACT
ACAGAGCCTA CCATGATGCT GAGACCACCG ATCTTCATAT
TTTCAAAGTA CTGTTGGGGC CGGGTATGTG A
```

A *Perovskia atriplicifolia* (+)-Copalyl diphosphate synthase (PaTPS1) enzyme was identified and isolated as described herein. This *Perovskia atriplicifolia* (+)-Copalyl diphosphate synthase (PaTPS1) enzyme was identified to be a (+)-copalyl diphosphate ((+)-CPP) synthase that can synthesize compound 31. The *Perovskia atriplicifolia* (+)-Copalyl diphosphate synthase (PaTPS1) can have the amino acid sequence shown below (SEQ ID NO:35).

```
MTSMSSLNLS RAPATTHRLQ LQAKVHVPEF YAVCAWLNSS
SKQAPLSCQI RCKQLSRVTE CRVASLDASQ VSEKDTSHVQ
TPDEVNKKIE DYIEYVKNLL MTSGDGRISV SPYDTSIVAL
IKDSKGRNIP QFPSCLEWIA QHQMADGSWG DQFFCIYDRI
LNTLACVVAL KSWNVHGDMI EKGVTYVKEN VHKLKDGNIE
HMTSGFEIVV PALVQRAKDL GIQGLPYDDP LIKEIADTKE
RRLKKIPKDM IYQTPTTLLF SLEGQGDLEW EKILKLQSGD
GSFLTSPSST AHVFVQTKDE KCLKFIENAV KNCSGGAPHT
YPVDVFARLW AIDRLQRLGI SRFFQPEIKY FIDHINSVWT
ENGVFSGRDS EFCDIDDTSM GIRLLKMHGY KVDPNALNHF
KQQDGKFSCY GGQMIESASP IYNLYRAAQL RFPGEEILEE
ASKFAFNFLQ EKIANDQFQE KWVISDHLID EVKLGLKMPW
YATLPRVEAA YYLQYYAGSG DVWIGKVFYR MPEISNDTYK
```

-continued

ELAILDFNRC QAQHQFEWIY MQEWYHRSSV SEFGISKKEL

LRTYFLAAAT IFEPERTQER LVWAKTQIVS RMITSFVNNG

TTLSLDQMTA LATQIGHNFD GLDQIISAMK DHGLAGTLLT

TFQQLLDGFD RYTRHQLKNA WSQWFMKLQQ GEANGGEDAE

LLANTLNICA GFIAFNEDVL SHDEYTTLST LTNKICKRLS

QIQDKKALEV VDGSIKDKEL EQDMQALVKL VLEENGGGVD

RNIKQTFLSV FKTFYYTAYH DDETTDVHIF KVLFGPVV

A nucleic acid encoding the *Perovskia atriplicifolia* (+)-Copalyl diphosphate synthase (PaTPS1) enzyme with SEQ ID NO:35 is shown below as SEQ ID NO:36.

ATGACCTCTA TGTCCTCTCT AAATTTGAGC AGAGCACCAG

CTACCACCCA CCGGTTACAG CTACAGGCAA AGGTTCACGT

GCCGGAATTT TATGCCGTGT GTGCATGGCT GAATAGCAGC

AGCAAACAGG CACCCTTGAG TTGCCAAATT CGCTGCAAGC

AACTATCAAG AGTAACTGAA TGTCGGGTAG CAAGTCTGGA

TGCGTCGCAA GTGAGTGAAA AAGACACTTC TCATGTCCAA

ACTCCCGATG AGGTGAACAA AAAGATCGAG GACTATATCG

AGTACGTCAA GAATCTGTTG ATGACGTCGG GCGACGGGCG

AATAAGCGTG TCGCCCTACG ACACGTCAAT AGTCGCCCTT

ATTAAGGACT CGAAAGGGCG CAACATCCCG CAGTTTCCGT

CGTGCCTCGA GTGGATAGCG CAGCACCAAA TGGCGGATGG

CTCATGGGGG GATCAATTCT TCTGCATTTA CGACCGGATT

CTAAATACAT TAGCATGTGT CGTAGCTTTG AAATCCTGGA

ACGTTCACGG TGACATGATC GAAAAAGGAG TGACGTACGT

CAAGGAAAAT GTGCATAAGC TTAAAGATGG GAATATTGAG

CACATGACGT CGGGGTTCGA AATTGTGGTT CCCGCCCTTG

TTCAAAGAGC CAAAGACTTG GGCATCCAAG GCCTGCCCTA

TGATGATCCC CTCATCAAGG AGATTGCTGA TACAAAAGAA

AGAAGATTGA AAAAGATACC CAAGGATATG ATTTACCAAA

CGCCAACGAC ATTACTATTC AGTTTAGAAG GGCAGGGAGA

TTTGGAGTGG GAAAAGATAC TGAAACTGCA GTCAGGCGAT

GGCTCCTTCC TCACTTCGCC GTCATCCACC GCCCACGTGT

TCGTGCAGAC CAAAGATGAA AAATGCTTGA AATTCATCGA

GAACGCCGTC AAGAATTGCA GTGGAGGAGC GCCGCATACT

TATCCAGTCG ATGTCTTCGC AAGACTTTGG GCAATTGACA

GACTACAACG CCTAGGAATT TCTCGTTTCT TCCAGCCGGA

AATTAAGTAT TTCATAGACC ACATCAACAG CGTTTGGACA

GAGAACGGAG TTTTCAGTGG GCGAGATTCG GAATTTTGCG

ATATTGATGA CACGTCCATG GGCATCAGGC TTCTCAAAAT

GCACGGATAC AAAGTCGACC CAAATGCACT CAATCATTTC

-continued

AAGCAGCAAG ATGGTAAATT TTCTTGCTAC GGTGGTCAAA

TGATCGAGTC TGCATCTCCA ATATACAATC TCTACAGGGC

TGCTCAGCTA CGATTTCCAG GAGAAGAAAT TCTTGAAGAA

GCCAGTAAAT TTGCCTTTAA CTTTTTGCAA GAAAAAATAG

CCAACGATCA ATTTCAAGAA AAATGGGTGA TATCCGACCA

CTTAATCGAT GAGGTGAAGC TCGGGCTGAA GATGCCATGG

TACGCCACTC TACCCCGGGT TGAGGCTGCA TATTATCTAC

AATACTATGC TGGTTCTGGC GACGTATGGA TTGGCAAGGT

TTTCTACAGG ATGCCGGAAA TCAGCAATGA TACATACAAA

GAGCTGGCCA TATTGCATTT CAACAGATGC CAAGCACAGC

ATCAGTTCGA ATGGATTTAT ATGCAAGAGT GGTATCACAG

AAGCAGCGTT AGTGAATTCG GGATAAGCAA AAAAGAGCTG

CTTCGTACTT ACTTTCTGGC TGCAGCAACC ATATTCGAAC

CCGAGAGAAC ACAAGAGAGG CTTGTGTGGG CAAAAACCCA

AATTGTCTCT AGGATGATCA CATCATTTGT TAACAATGGA

ACTACACTAT CTTTGGACCA AATGACTGCA CTTGCAACAC

AAATCGGCCA TAATTTCGAT GGCCTCGATC AAATAATTAG

TGGTATGAAA GATCATGGAC TGGCTGGGAC TCTGCTGACA

ACCTTCCAGC AACTTCTAGA TGGATTCGAC AGATACACTC

GCCATCAACT CAAAAATGCT TGGAGCCAAT GGTTCATGAA

ACTCCACCAA GGGGAGGCGA ACGGCGGGGA AGACGCGGAG

CTCCTAGCAA ACACGCTCAA CATCTGCGCG GGTTTCATTG

CTTTCAACGA AGACGTATTG TCGCACGATG AATACACGAC

TCTCTCCACC CTTACAAACA AAATCTGCAA GCGCCTTAGC

CAAATTCAAG ATAAAAAGGC GCTGGAAGTT GTCGACGGGA

GCATAAAGGA TAAGGAGCTC GAACAGGATA TGCAGGCGTT

GGTGAAGTTG GTCCTTGAAG AAAATGGCGG CGGCGTCGAC

AGGAACATCA AACAGACATT TTTGTCCGTT TTCAAGACTT

TTTACTACAC CGCCTACCAC GATGATGAGA CCACTGATGT

TCATATTTTC AAAGTACTGT TTGGACCGGT CGTATGA

*Pogostemon cablin* (10R)-labda-8,13E-dienyl diphosphate synthase (PcTPS1) was identified and isolated as described herein. This *Pogostemon cablin* (10R)-labda-8,13E-dienyl diphosphate synthase (PcTPS1) enzyme was identified to be a (10R)-labda-8,13E-dienyl diphosphate synthase, which can synthesize compound 25.

25

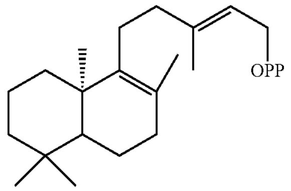

The combination of PcTPS1 and SsSS, both in-vitro, and in *N. benthamiana* expression produced (10R)-labda-8,14-en-13-ol [26], shown below.

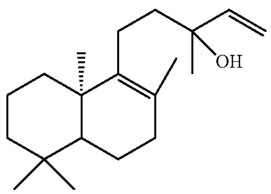

26

This *Pogostemon cablin* (10R)-labda-8,13E-dienyl diphosphate synthase (PcTPS1) can have the amino acid sequence shown below (SEQ ID NO:37).

MSFASQSHVA FVLRRPSAVA PPPPTRIPTT AALSPLKPGD

FSHGRSSFMP TSIKCNAIST SRVEEYKYTD DHNQSGLLEH

DGLISDKINE LVTKIQLMLQ NMDDGEISIS PYDTAWVSLV

EDVGGNDRPQ FPTSLEWISN NQLPDGSWGD PNAFLVHDRI

LNTLACVVAL KSWKMHPHKC NRGVSFVREN IYRMDDEKEE

HMPNGFEVVF PALLQKAKTL NIDIPYEFPG IQKFYAKRDL

KFARIPMDIL HSVPTTLLFS LEGVRCGLDL DWGKLLELQA

ADGSFLYSPS STAFALEQTK DQNCLKYLSK LVRKFDGGVP

NVYPVDLFEH NWAVDRLQRL GISRYFTPEI NQCLDYSYRY

WSNSKGMYSA SNSQIQDVDD TAMGFRLLRL NGYDVSTQGF

RQFEAGGDFF CFAGQSSQAV TGMYNLYRAS QVMFPGEKLL

EDAKKFSTNF LQQKRANNQL TDKWVIAKDV PAEVGYALDI

PWYASLPRLE ARFFIQQYGG DDDVWIGKTL YRMGYVNNNT

YLELAKLDYN TCQRLHQHEW ITIQRWYEIN LKITSVGLSK

RGVLLSYYLA AANLFEPQNS THRIAWAKTS ILVSAIQLSP

LQKRDFINQF HRSTANNGYE TSNVLVKSVI KGVHELSMDA

MLTHNKDIHR QLFNAWRKWM SVWEEGGDGE AELLLSTLNT

CDGVDESTFS DPKYEHLLEI TVRVTHQLHL IQNAETKRVG

DREEIDLSMQ QLVKLVFTKS SSDLDSCIKQ RFFAIARSFY

YVAHCDPEMV DSHIAKVLFE RVM

A nucleic acid encoding the *Pogostemon cablin* (10R)-labda-8,13E-dienyl diphosphate synthase (PcTPS1) enzyme with SEQ ID NO:35 is shown below as SEQ ID NO:38.

ATGTCATTTG CTTCTCAATC ACATGTCGCC TTTGTACTCC

GACGGCCATC TGCCGTTGCT CCGCCACCAC CGACTAGAAT

TCCGACAACA GCCGCTCTTT CTCCTCTCAA ACCAGGTGAT

TTTTCCCATG GCAGATCATC ATTTATGCCC ACTTCCATTA

AATGTAATGC AATTTCCACA TCTCGCGTCG AAGAATACAA

GTACACGGAT GATCATAATC AGAGTGGTTT ATTGGAGCAT

-continued

GATGGTTTGA TATCAGACAA GATAAATGAA TTGGTGACCA

AGATACAATT GATGCTACAA AACATGGATG ACGGAGAGAT

AAGCATCTCC CCATATGACA CCGCATGGGT GTCGTTGGTG

GAGGATGTGG GCGGCAACGA CCGCCCACAG TTTCCTACGA

GCCTGGAGTG GATATCGAAT AACCAGCTCC CCGACGGCTC

GTGGGGCGAC CCGAATGCCT TTTTGGTGCA CGACCGTATC

CTCAACACAT TGGCATGCGT CGTTGCACTC AAATCCTGGA

AAATGGACCC CCACAAATGC AATAGAGGAG TTAGTTTCGT

GAGAGAAAAT ATATACAGAA TGGATGATGA AAAAGAGGAA

CACATGCCAA ATGGATTCGA AGTGGTATTT CCAGCACTCC

TTCAAAAAGC GAAAACCCTA AACATTGATA TCCCGTACGA

GTTTCCAGGA ATACAAAAAT TTTATGCCAA AAGAGATTTA

AAATTCGCCA GGATTCCAAT GGATATATTG CATAGCGTTC

CGACAACATT ACTGTTCAGC TTAGAAGGTG TAAGATGTGG

TCTTGATCTG GATTGGGGGA AGCTTCTAGA ATTGCAAGCT

GCTGATGGCT CATTTCTCTA CTCTCCATCC TCTACTGCCT

TTGCACTAGA ACAAACCAAG GATCAAAACT GCCTCAAATA

TCTATCTAAA CTTGTTCGAA AATTCGATGG CGGAGTACCC

AACGTGTACC CGGTGGACTT GTTCGAACAT AATTGGGCAG

TTGATCGTCT CCAAAGGCTC GGAATTTCTC GTTATTTTAC

GCCTGAAATC AACCAATGTC TTGATTATTC TTACAGATAT

TGGTCAAATA GTAAAGGGAT GTACTCGGCA AGCAATTCCC

AGATTCAGCA CGTTGATGAC ACCGCCATGG GATTCAGGCT

TTTGAGACTC AACGGCTACG ATGTCTCTAC ACAAGGGTTT

AGGCAATTCG AGGCAGGGGG GGACTTCTTC TGCTTCGCGG

GGCAGTCGAG CCAAGGTGTA ACCGGAATGT ACAACCTCTA

CAGAGCTTCC CAAGTGATGT TCCCTGGAGA GAAGCTACTG

GAAGATGCCA AGAAATTCTC CACCAACTTC TTGCAACAAA

AACGAGCCAA TAACCAGCTC ACTGACAAGT GGGTTATTGC

CAAAGATGTT CCAGCTGAGG TGGGATATGC CTTGGATATT

CCCTGGTATG CCAGTCTGCC CCGACTGGAA GCAAGATTTT

TCATACAACA ATACGGTGGA GACGACGACG TTTGGATCGG

CAAAACCTTG TATAGAATGG GATATGTGAA CAACAACACT

TATCTGGAAC TCGCAAAGCT AGACTACAAC ACCTGCCAAA

GGTTGCATCA GCATGAGTGG ATAACCATTC AACGATGGTA

CGAAATTAAT TTAAAAATTA CTAGTGTTGG GTTGAGCAAA

AGAGGGGTCC TGTTGAGTTA TTACTTAGCC GCAGCCAATC

TGTTTGAGCC TCAAAACTCA ACACACCGCA TCGCTTGGGC

CAAAACTTCG ATTTTAGTAA GCGCTATTCA ACTTTCTCCC

CTCCAAAAGC GCGACTTTAT TAACCAATTC CACCGCTCCA

CCGCAAATAA TGGGTATGAA ACAAGTAATG TGTTGGTGAA

-continued

```
GAGTGTAATC AAGGGTGTGC ATGAGCTCTC CATGGACGCT

ATGTTGACGC ACAATAAAGA CATACATCGC CAACTTTTTA

ATGCTTGGCG AAAGTGGATG TCAGTGTGGG AAGAGGGAGG

TGATGGAGAA GCGGAGCTGT TATTGTCGAC GCTTAAGACG

TGCGACGGAG TAGATGAATC CACATTCAGC GATCCCAAAT

ACGAGCACCT CTTAGAGATC ACCGTCAGAG TCACCCACCA

GCTTCATCTC ATTCAGAATG CAGAGACGAA GCGTGTGGGT

GACCGTGAGG AAATAGATTT GAGCATGCAA CAACTTGTTA

AGTTGGTGTT CACTAAATCA TCATCGGATC TGGATTCTTG

TATCAAGCAA AGATTTTTTG CGATTGCCAG AAGTTTCTAT

TACGTGGCTC ATTGTGATCC GGAGATGGTG GACTCCCACA

TAGCCAAAGT ATTGTTTGAG AGGGTGATGT AG
```

*Prunella vulgaris* 11-hydroxy vulgarisane synthase (PvHVS) was identified and isolated as described herein. The *Prunella vulgaris* 11-hydroxy vulgarisane synthase (PvHVS) enzyme catalyzes the first Committed step and forms the scaffold found in all Vulgarisins, a class of diterpenes with pharmaceutical applications (e.g., gout, cancer). For example, PvH-VS can synthesize 11-hydroxy vulgarisane (shown below).

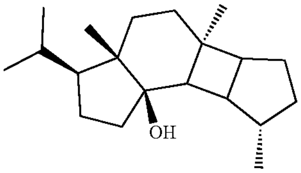

11-hydroxy vulgarisane

An example of a formula for several Vulgarisin diterpenes is shown below.

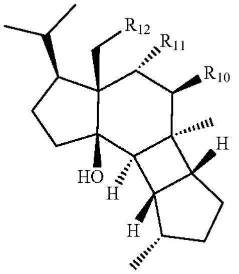

Vulgarisin B (1)

$R_{10}$ = 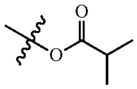 $R_{11}$ = OH $R_{12}$ = 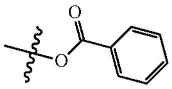

Vulgarisin C (2)

$R_{10}$ = OH $R_{11}$ = 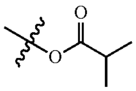 $R_{12}$ = 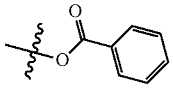

-continued

Vulgarisin D (3)

$R_{10}$ = OH $R_{11}$ = 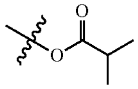 $R_{12}$ = 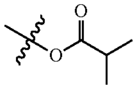

Vulgarisins B (1) and C (2) exhibit modest cytotoxicity activity against human lung carcinoma A549 cell line (Lou et al. Tetrahedron Letters 58: 401-404 (2017)).

The *Prunella vulgaris* 11-hydroxy vulgarisane synthase (PvHVS) can have the amino acid sequence shown below (SEQ ID NO:39).

```
MSSLSIPFSS AICTSSIPKI STGHHRRTAR MPAHDTSRLV

FRPSAVMVEG SPMTTSSNGK EVQRLITTFK PSMWKDIFST

FSFDNQVQEK YLKEIEELKK EVRSTLMSAT HRKLFDLIDN

LERMGIAYHF ETEIEDKLKQ AHASLEEEDD YDLFTTALRF

RLLRQHRYHV SCDPFAKFVD QDNKLKESLS SDVEGLLSLF

EASHLRIHNE DVLDEAIVFT THHLNRMKPQ LESPLKEEVK

HALRYPLHKC LGILSLRFHI DRYENDKSRD EVVLRLGQVN

FNYMQNIYMN ELYEITTWWN KLQMTSKVPY FRDRLVECYM

WGLAYHFEPE YAPVRVLITK YYMTATTVDD TYDNYATLEE

IELFTQAIDR WSEDEIDQLP DEYLKIVYKG LMNFTEEFRR

DAEERGKGYV IPYFIEETKR ATQGYANEQR WIMKREMPSF

EEYMVNSRVT SLMYVTYVAV VAVIESATKE TVDWALSDSD

IFVYTNDIGR LIDDLATHRR ERKDGTMLTS MDYYMKEYGG

TMEEGEAAFR KLMEEKWKLL NAAWVDTING KESKEIVVQV

LDLARICGTL YGDEEDGFTY PEKNFAPLVA ALLMNPIHI
```

A nucleic acid encoding the *Prunella vulgaris* 11-hydroxy vulgarisane synthase (PvHVS) enzyme with SEQ ID NO:39 is shown below as SEQ ID NO:40.

```
ATGAGCTCTC TCTCAATTCC CTTTTCTTCC GCCATTTGCA

CTTCATCAAT CCCAAAGATC AGTACTGGGC ATCATCGCCG

CACCGCGAGG ATGCCCGCGC ACGACACATC GCGTCTCGTC

TTTCGCCCTT CAGCTGTGAT GGTGGAAGGA AGTCCGATGA

CTACTTCAAG CAACGGGAAG GAAGTCCAAC GACTTATAAC

CACTTTCAAG CCTAGCATGT GGAAAGATAT TTTTTCTACC

TTCTCTTTCG ATAATCAGGT GCAAGAAAAG TATTTGAAAG

AAATTGAGGA ATTGAAGAAA GAAGTAAGAA GCACACTAAT

GAGTGCTACG CATAGGAAAT TGTTTGACTT GATCGACAAT

CTCGAGCGTA TGGGAATCGC CTATCATTTC GAGACAGAAA

TCGAAGACAA GCTCAAACAA GCTCATGCTT CTCTAGAGGA

GGAAGATGAC TACGACTTGT TCACTACTGC ACTTCGCTTT

CGTCTGCTCA GACAACATCG CTATCATGTT TCTTGCGATC

CCTTTGCGAA ATTTGTTGAC CAAGACAACA AATTGAAAGA
```

-continued

```
GAGTCTTAGT AGCGACGTCG AGGGGCTATT AAGCTTGTTC
GAGGCATCCC ATCTTCGGAT CCACAACGAG GATGTTCTAG
ATGAAGCTAT AGTGTTCACA ACCCATCACT TGAATCGAAT
GATGCCACAA TTGGAATCGC CCCTTAAAGA AGAAGTGAAG
CATGCTCTTC GATACCCCCT TCACAAGTGT CTTGGAATCC
TTAGCCTTCG TTTTCATATC GACAGATATG AGAATGATAA
GTCGAGGGAT GAAGTTGTTC TCAGACTAGG CCAAGTTAAT
TTCAATTACA TGCAGAACAT TTACATGAAC GAGCTCTATG
AAATCACCAC GTGGTGGAAC AAGTTGCAGA TGACTTCAAA
AGTACCTTAC TTTAGAGATA GATTGGTAGA GTGCTATATG
TGGGGTTTGG CATATCATTT CGAACCAGAA TACGCTCCCG
TTCGAGTCCT CATTACCAAG TACTATATGA CCGCCACAAC
TGTCGACGAT ACCTATGATA ATTATGCTAC ACTCGAAGAA
ATCGAACTCT TCACTCAGGC CATTGACAGG TGGAGCGAGG
ATGAGATTGA TCAGCTACCT GATGAATACC TAAAAATAGT
GTACAAAGGT CTAATGAACT TCACTGAAGA GTTTAGACGT
GACGCAGAAG AGCGAGCGAA AGGCTATGTG ATTCCTTACT
TTATTGAAGA AACGAAGAGA GCAACACAGG GTTATGCAAA
CGAGCAGAGG TGGATAATGA AGAGAGAAAT GCCGAGTTTT
GAAGAGTATA TGGTGAACTC AAGGGTAACA TCACTTATGT
ATGTGACCTA CGTTGCTGTT GTGGCAGTCA TAGAATCAGC
TACCAAAGAA ACCGTAGATT GGGCGCTAAG TGACTCCGAT
ATCTTTGTCT ACACTAACGA TATCGGCCGA CTTATCGACG
ACCTTGCCAC TCATCGACGC GAGAGGAAAG ACGGGACAAT
GCTTACATCG ATGGATTATT ACATGAAGGA ATATGGCGGT
ACGATGGAAG AGGGGGAAGC TGCATTTAGG AAATTGATGG
AGGAGAAATG GAAACTTTTG AATGCAGCAT GGGTAGATAC
TATTAATGGA AAAGAGTCGA AGGAAATAGT TGTGCAAGTT
CTCGACCTCG CCAGGATATG CGGAACGCTC TATCGGGACG
AAGAAGATGG CTTCACCTAC CCAGAGAAGA ATTTTGCACC
ACTCGTTGCT GCTCTATTGA TGAATCCTAT ACATATTTGA
```

A *Chiococca alba* ent-CPP synthase (CaTPS1) was identified and isolated. This CaTPS1 enzyme was identified that converts GGPP to ent-CPP [16].

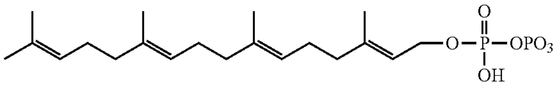

Geranylgeranyl diphosphate (GGPP)

-continued

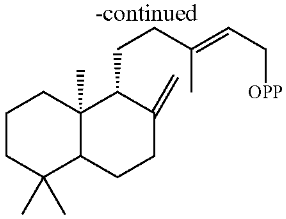

16

The *Chiococca alba* ent-CPP synthase (CaTPS1) has the amino acid sequence shown below (SEQ ID NO:41).

```
  1 MSSSTSAAAT LLGLSPASRR FVSFPPANGP IETITGIWSP
 41 GKALHHFNFR LRCSTVSSPR TQELGQVSQN GMSGIKWHDI
 81 VEEGVTEKGT LEANTSSWIK ESIEAIRWML RTMDDGDISI
121 SAYDTAWVAL VEDINGSGGP QFPSSLEWIA NNQLPDGSWG
161 DSDIFSAHDR ILNTLGCVVA LKSWNMHPEK SEKGLLYLRD
201 NIHKLEDENV EHMPIGFEVA FPSLIEIAKK LSIDIPDDSA
241 ILQEIYARRN LKLTRIPKDI MHTVPTTLLH SLEGMPELDW
281 KRLISLKCED GSFLFSPSST AFALTQTKDA DCLRYLIKTV
321 QKFNGGVPNV YPVDLFEHIW AVDRLQRLGI SRYFQSEIRE
361 CIDYVHRYWT DKGICWARNT HVYDIDDTAM GFRLLRLHGY
401 DVSADVFRYY EKDGEFVCFA GQSNQAVTGM YNLYRASQVM
441 FPGENILSDA RKFSSEFLHD KRANNELLDK WIITKDLPGE
481 VAYALDVPWY ASLPRLETRL YLEQYGGEDD VWIGKTLYRM
521 QKVNNNIYLE LGKLDYNNCQ ALHQLEWRSI QKWYNECGLG
561 EYGLSERSLL LSYYLAAASI FEPERSKERL AWAKTTMLIR
601 TIESYLSSEQ MVEDHNGAFV SEFQYYCSNL DYVNGGRHKP
641 TQRLVRTLLG TLNQISLDAV LVHGRDIHQY LRQAWEKWLI
681 ALQEGDDSDM GQEEAELLVR TLNLCAGRYA SEELLLSHPK
721 YQQLLHITTR VCNQIRHFQH KKVQDGENGR ANMGDGITSI
761 SSIESDMQEL TKLVVGNTQN DLDADTKQTF LTVAKSFYYT
801 AHCNPGTINC HIAKVLFERV L
```

A nucleic acid encoding the *Chiococca alba* ent-CPP synthase (CaTPS1) with SEQ ID NO:41 is shown below as SEQ ID NO:42.

```
  1 ATGTCTTCTT CTACCTCAGC AGCAGCAACC CTTCTCGGAT
 41 TATCGCCGGC AAGCCGCCGG TTTGTATCAT TTCCTCCGGC
 81 AAATGGACCT ATAGAAACTA TTACCGGTAT TTGGTCGCCC
121 GGCAAAGCTC TTCATCACTT TAATTTCCGT CTGCGTTGTA
161 GCACGGTGTC CAGTCCTCGC ACCCAAGAAT TGGGCCAGGT
201 GTCACAAAAT GGCATGTCTG GTATAAAGTG GCATGACATA
241 GTGGAAGAAG GAGTCACAGA AAAAGGAACT CTTGAGGCGA
281 ACACATCAAG CTGGATAAAA GAAAGCATAG AAGCCATTCG
```

-continued

```
 321 TTGGATGCTG CGTACCATGG ATGACGGGGA TATCAGCATA
 361 TCTGCTTATG ATACTGCATG GGTTGCCCTT GTGGAAGATA
 401 TCAACGGAAG TGGCGGTCCT CAATTTCCTT CAAGCCTCGA
 441 GTGGATTGCC AACAATCAGC TTCCTGATGG TTCATGGGGC
 481 GACAGCGACA TCTTTTCAGC TCACGATCCG ATTCTCAACA
 521 CTTTGGGATG CGTTGTTGCA TTAAAATCTT GGAACATGCA
 561 CCCTGAAAAG AGTGAAAAAG GATTATTATA TTTAAGGGAT
 601 AACATTCACA AGCTTGAGGA TGAAAATGTC GAGCACATGC
 641 CTATCGGTTT TGAAGTGGCA TTTCCTTCAC TAATTGAGAT
 681 AGCCAAAAAG TTGAGCATTG ATATTCCGGA TGATTCTGCA
 721 ATCTTGCAGG AGATATATGC CAGAAGAAAT CTAAAGCTAA
 761 CAAGGATACC GAAGGACATT ATGCACACAG TGCCCACAAC
 801 ATTGCTCCAC AGCTTGGAAG GCATGCCAGA ACTAGACTGG
 841 AAAAGGCTAA TATCTCTAAA GTGTCAGGAT GGTTCCTTTC
 881 TGTTTTCTCC ATCCTCCACT GCTTTTGCCC TCACGCAAAC
 921 TAAAGATGCT GATTGCCTCA GATATTTAAC TAAAACCGTA
 961 CAAAAATTCA ATGGAGGAGT TCCCAATGTT TACCCCGTGG
1001 ACTTATTCGA ACACATCTGG GCTGTTGATC GACTTCAAAG
1041 ACTAGGAATT TCTCGATACT TCCAGTCAGA AATCCGCGAG
1081 TGCATCGATT ATGTTCACCG ATATTGGACG GATAAAGGTA
1121 TCTGTTGGGC TAGAAATACC CACGTTTATG ACATTGATGA
1161 TACAGCTATG GGTTTTAGAC TTCTAAGGTT GCATGGCTAC
1201 GATGTTTCTG CAGATGTTTT CAGATACTAT GAGAAGGATG
1241 GCGAATTCGT TTGCTTTGCC GGACAGTCAA ACCAGGCGGT
1281 GACCGGAATG TATAACCTGT ATAGAGCTTC TCAAGTGATG
1321 TTTCCAGGGG AGAATATACT TTCGGATGCT AGGAAATTCT
1361 CGTCCGAATT CTTGCATGAT AAGCGAGCCA ACAATGAGCT
1401 CCTAGATAAA TGGATCATAA CCAAAGATTT GCCTGGGGAG
1441 GTAGCATATG CTTTAGATGT TCCATGGTAT GCCAGTTTAC
1481 CTCGTTTAGA AACCAGATTG TATTTGGAAC AATATGGCGG
1521 CGAAGATGAT GTCTGGATTG GCAAGACATT GTACAGGATG
1561 CAAAAAGTTA ACAACAACAT CTATCTTGAA CTTGGCAAAT
1601 TAGATTACAA CAACTGTCAG GCATTGCATC AGCTTGAGTG
1641 GAGAAGCATC CAAAAATGGT ACAATGAATG CGGTCTTGGA
1681 GAGTACGGAT TAAGCGAGAG AAGCCTCCTT CTTTCGTATT
1721 ATTTGGCCGC AGCCAGTATA TTTGAAGCGG AGAGGTCAAA
1761 GGAACGGCTT GCCTGGGCCA AAACTACTAT GCTAATCCGC
1801 ACAATTGAAT CTTATTTGAG TAGTGAACAA ATGGTTGAGG
1841 ATCACAATGG AGCCTTTGTT AGCGAGTTCC AATACTATTG
1881 CAGTAACCTT GACTACGTAA ATGGTGGAAG GCATAAGCCA
```

-continued

```
1921 ACACAAAGGC TAGTGAGGAC TCTACTCGGA ACTTTAAATC
1961 AGATTTCTTT GGACGCAGTG TTAGTCCACG GCAGAGATAT
2001 CCATCAATAT TTGCGTCAAG CCTGGGAAAA GTGGTTGATA
2041 GCTTTGCAAG AGGGAGATGA TAGTGACATG GGTCAAGAGG
2081 AAGCAGAACT TTTAGTGCGC ACACTAAACC TATGCGCCGG
2121 TCGCTACGCA TCGGAGGAGC TATTGTTGTC CCATCCCAAG
2161 TATCAACAAC TTTTGCACAT CACTACTAGA GTCTGTAACC
2201 AAATTCGTCA TTTCCAACAC AAAAAGGTGC AAGATGGGGA
2241 AAATGGAAGA GCAAACATGG GTGATGGCAT CACAAGCATC
2281 AGCTCAATAG AGTCGGACAT GCAAGAACTA ACGAAATTAG
2321 TTGTCGGCAA TACCCAAAAC GATCTAGATG CTGATACGAA
2361 GCAAACATTT CTCACGGTGG CAAAAAGCTT CTACTACACC
2401 GCCCACTGCA ATCCCGGAAC AATCAATTGC CATATTGCTA
2441 AAGTATTATT TGAGAGAGTA CTTTGA
```

A *Chiococca alba* (5R,8S,9S,10S)-labda-13-en-8-ol diphosphate (ent-8-LPP) synthase (CaTPS2) was identified and isolated as described herein. This CaTPS2 enzyme was identified as an 5R,8S,9S,10S)-labda-13-en-8-ol diphosphate (ent-8-LPP) synthase, which converts GGPP to 5R,8S,9S,10S)-labda-13-en-8-ol diphosphate (ent-8-LPP, [7]).

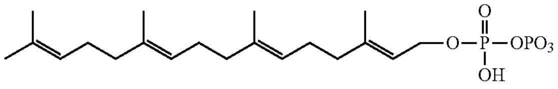

Geranylgeranyl diphosphate (GGPP)

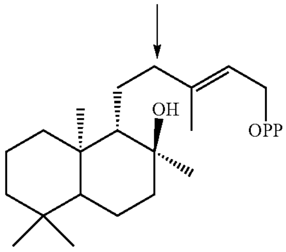

7

The *Chiococca alba* (5R,8S,9S,10S)-labda-13-en-8-ol diphosphate (ent-8-LPP) synthase (CaTPS2) has the amino acid sequence shown below (SEQ ID NO:43).

```
  1 MPVIKSHEFI EEVGPEKGTL KLSRSSRINE LVESIQTMLQ
 41 SMDDGEISMS AYDTAWVALV EDINGSSYPQ FPMSLEWIAN
 81 NQLPDGSWGD GSIFSVHDRI ISTLGCVLAL KSWNMHPDKS
121 EKGLLFIRDN IHKVGDESAE HMPIGFEVVF PSLIERAKNL
161 DIDIPDISAI LQEIYARRNL KLARIPKDIL YTVPTTLLHS
201 LEGMPELDWQ KLLPLKCEDG SFLFSPSCTA FALMQTKDGD
241 CLRYLTNTIE KFNGGVPGVY PVDLFEHIWA VDRLQRLGIS
```

-continued

281 RYFQTEIEEC MSYVYRYWTD KGICWARNSK VEDIDDTAMG

321 FRLLRLHGYM VSADVFAQFE KGGEFVCFAG QSNQALTGMF

361 NLYRASQVMF PGEKILADAK KFSSNFLHEK RANNELLDKW

401 IITKDLPGEV TYALDVPWYA SLPRVETRLY LEQYGGEDDV

441 WIAKTLYRMR KVNNKIYLEL GILDYNNCQA LHQLEWRSIQ

481 KWYKDSGLEE YGLSERNLLL AYYLATACIF EPERLVERLS

521 WAKTTALIYT TKSYFRTECN SGEQRKAFLH EFQQYCNDLD

561 YVSGARHKPT IRLIEALLGT LEQVSLDAIL DHGRYIHQDL

601 RNAWEKWLIA LQEGVDMDQE EAELTVLTLH LCAGSYTSEE

641 LLLSHPKYQQ LLNITSRVCH QIRQFQREKA QDTDNGRENL

681 VAITSIKAIE SDMQELAKLV LTKSTGDLAA KIKQTFLIVA

721 KSFYYTAHCL PGIISTHIAK VLFEKVF

A nucleic acid encoding the *Chiococca alba* (5R,8S,9S,10S)-labda-13-en-8-ol diphosphate (ent-8-LPP) synthase (CaTPS2) with SEQ ID NO:43 is shown below as SEQ ID NO:44.

1 ATGCCAGTAA TAAAGTCGCA TGAGTTTATT GAAGAGGTCG

41 GCCCGGAAAA AGGAACTCTG AAGCTGAGCA GATCAAGTAG

81 GATAAACGAA CTTGTAGAAT CAATTCAAAC GATGCTTCAA

121 TCGATGGATG ATGGGGAAAT AAGCATGTCT GCTTATGACA

161 CCGCGTGGGT TGCCCTTGTG GAAGATATTA ATGGAAGCAG

201 CTACCCTCAA TTCCCTATGA GCCTCGAGTG GATTGCCAAC

241 AATCAGCTTC CTGATGGTTC ATGGGGTGAC GGCAGTATCT

281 TTTCGGTTCA TGATCGGATA ATCAGCACAT TAGGATGTGT

321 TCTTGCATTA AAATCATGGA ACATGCACCC GGACAAAAGC

361 GAAAAAGGAC TGTTATTTAT AAGGGACAAT ATTCACAAGG

401 TTGGAGATGA CAGCGCTGAG CACATGCCTA TTGGTTTTGA

441 GGTGGTATTT CCTTCGCTTA TTGAGAGAGC CAAAAACTTG

481 GACATTGATA TTCCAGATAT TTCTGCTATC TTGCAAGAGA

521 TTTATGCACG AAGAAATCTA AAGCTCGCAA GGATTCCAAA

561 GGATATACTG TATACCGTGC CCACGACATT ACTTCATAGC

601 TTAGAAGGAA TGCCAGAACT GGACTGGCAA AAGCTACTGC

641 CATTAAAATG TGAGGATGGT TCATTTCTAT TTTCTCCATC

681 GTGCACTGCT TTTGCCCTCA TGCAGACTAA GGATGGTGAT

721 TGCCTCAGAT ATCTAACTAA TACCATAGAA AAATTCAATG

761 GGGGAGTTCC CGGTGTATAC CCTGTGGACT TGTTCGAACA

801 CATTTGGGCT GTTGATCGCT TGCAAAGACT AGGAATTTCC

841 CGGTATTTTC AGACAGAAAT TGAAGAATGT ATGAGTTATG

881 TTTACCGATA TTGGACGGAT AAAGGTATCT GTTGGGCTAG

921 AAACTCCAAA GTTGAAGACA TCGATGACAC AGCCATGGGT

961 TTTAGACTTC TAAGGTTGCA TGGTTACATG GTTTCTGCAG

-continued

1001 ATGTGTTTGC ACAGTTTGAG AAAGGGGGTG AATTCGTTTG

1041 CTTTGCTGGA CAGTCGAACC AGGCGCTGAC TGGAATGTTT

1081 AACCTGTATA GAGCTTCTCA AGTAATGTTT CCAGGGGAGA

1121 AGATACTTGC TGATGCCAAG AAATTCTCAT CGAACTTCTT

1161 ACATGAAAAG CGTGCAAACA ACGAGCTTCT AGATAAATGG

1201 ATCATAACTA AAGATTTGCC TGGAGAGGTG ACGTATGCGC

1241 TAGATGTTCC ATGGTACGCC AGTTTACCTC GTGTAGAAAC

1281 GAGATTATAT CTGGAACAAT ATGGAGGAGA GGATGATGTC

1321 TGGATTGCCA AGACATTGTA CAGGATGAGA AAAGTTAACA

1361 ACAAAATTTA CCTTGAACTT GGCATATTAG ATTACAATAA

1401 CTGTCAAGCA TTGCATCAGC TGGAGTGGAG AAGCATCCAA

1441 AAATGGTATA AGGATTCTGG CCTTGAAGAG TACGGGTTGA

1481 GCGAGAGGAA CCTTCTCCTG GCATATTATC TGGCCACAGC

1521 TTGTATATTT GAACCCGAAA GGTTGGTGGA GCGCCTTTCC

1561 TGGGCGAAAA CAACCGCCTT AATCTACACA ACAAAATCTT

1601 ATTTCAGAAC TGAATGCAAC TCTGGGGAAC AGAGAAAAGC

1641 TTTTCTTCAT GAGTTCCAAC AGTACTGCAA TGACCTGGAC

1681 TACGTTAGTG GCGCAAGGCA CAAGCCAACA ATAAGATTGA

1721 TCGAAGCTCT ACTTGGAACC CTAGAGCAGG TCTCTTTGGA

1761 TGCAATATTA GATCATGGCC GATATATCCA TCAAGATTTG

1801 CGTAATGCTT GGGAGAAATG GTTGATAGCT TTGCAAGAGG

1841 GAGTTGACAT GGACCAAGAA GAAGCAGAAC TTACAGTGCT

1881 CACACTACAC CTGTGTGCCG GCAGCTACAC ATCGGAGGAG

1921 TTACTGTTAT CTCATCCCAA GTATCAACAA CTTTTAAATA

1961 TCACTAGTAG AGTCTGCCAC CAAATTCGTC AATTCCAGCG

2001 CGAAAAGGCA CAGGATACGG ATAATGGAAG AGAAAACTTG

2041 CTTGCCATCA CAAGCATCAA GGCGATAGAA TCAGACATGC

2081 AAGAACTTGC GAAATTAGTT CTGACCAAAT CCACTGGCGA

2121 TTTAGCTGCT AAAATCAAGC AAACATTTCT TATAGTGGCA

2161 AAGAGCTTCT ACTACACCGC ACATTGCCTT CCTGGAATTA

2201 TCAGTACCCA CATTGCCAAA GTACTATTTG AGAAAGTTTT

2241 CTGA

A *Chiococca alba* CaTPS3 and CaTPS4 were identified and isolated. CaTPS3 and CaTPS4 were identified as an ent-kaurene synthase, converting ent-CPP [16] into ent-kaurene [19].

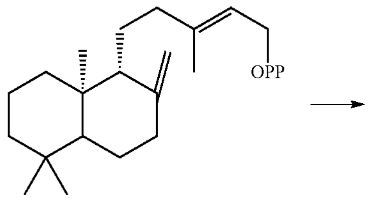

16

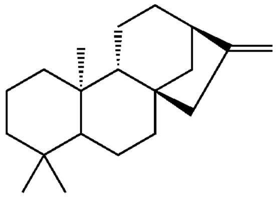

19

The *Chiococca alba* ent-kaurene synthase (CaTPS3) has the amino acid sequence shown below (SEQ ID NO:45).

```
  1 MMMMMVVMNT APAHSYHPFP FAGPKSSATL FSNYYCSSRK
 41 KSSPPRISAS VSLLTGVEST TAINSSDPEI KERIRKLFHD
 81 VDISLSSYDT AWVAMVPAPH SSQSPLFPQC INWLLDNQLP
121 DGSWSLPPPH HHPLLLKDAL SSTLACVLAL RRWGIGQEQV
161 DKGIRFVELN FASASDQNQH LPVGFDIIFP GMLEYARDLN
201 LNLQLESATV NALLLKRDQE LTRFFKSYSD ESKAYLAYVS
241 EGIVKLQNWD TVMKFQRKNG SLFNSPSATA AAVMHVHNPG
281 CLDYLHSVLE KHGNAVPTVY PLDIYPRLCL VDNLERLGIC
321 GHFRKEILSV LDDTYRCWMQ GDEEIFAEKS TCAIAFTLLR
361 KHGYNISADP LTPFLKEECF SNSLGGCLKD TSAVLELYRA
401 LEMIISQNES ALVKKSLWSR SFLKEHISGG CDLKGFSNQI
441 SILVDDILNF PSHATLQRVA NRRSIEQYNL DSTKILKTSY
481 CSSNFSNKDL LILAVKDFNH CQLIHREELK ELERWVTDNR
521 LDKLKFARQK SAYCYFSAAA TIFSPELSDA RMSWAKNGVL
561 ATLVDDFFDV GGSLEELKKL IELVEKWDIN VSDGCCSEPV
601 QILFSALHST IQEIGDkAFK WQARSVTNHI FKIWLDLLNS
641 MLREAEWARN ATVPTVEEYM TNGYVSFALG PIILPALYLV
681 GPKLSEEVVK DSEFHSLFKL VSTCGRLLND VHSFERESKS
721 GQLNALSLRL IHGGVGITEA AAVAEMKSSI ENLRRELLRL
761 VLRKEGSVVP RACKDLFWNM SKVLHQFYNK DDGFTSEEMI
801 QLVKSIIYEP IAVNEFLNSC HT
```

A nucleic acid encoding the *Chiococca alba* ent-kaurene synthase (CaTPS3) with SEQ ID NO:45 is shown below as SEQ ID NO:46.

```
   1 ATGATGATCA TGATGGTGGT GATGAACACA GCTCCCGCCC
  41 ACTCTTACCA TCCTTTCCCC TTTGCCGGCC CAAAATCCTC
```

-continued

```
  81 AGCCACACTT TTTTCCAATT ATTATTGTTC CAGTAGGAAG
 121 AAATCATCGC CACCTCGCAT CTCTGCCTCA GTTTCTTTGC
 241 TAACTGGAGT TGAAAGCACA ACTGCAATTA ATTCTTCAGA
 281 CCCGGAGATC AAAGAAAGAA TAAGGAAACT ATTTCATGAT
 321 GTTGATATCT CGCTTTCTTC ATATGACACT GCATGGGTGG
 361 CAATGGTCCC TGCTCCACAT TCTTCCCAGT CTCCCCTTTT
 401 TCCCCAGTGC ATTAATTGGT TATTGGACAA TCAGCTTCCT
 441 GATGGCTCAT GGAGTCTTCC TCCTCCTCAT CATCATCCTC
 481 TATTACTTAA AGATGCATTA TCCTCTACCC TTGCATGTGT
 521 TCTTGCGCTC AGGAGATGGG GAATTGGTCA AGAACAAGTT
 561 GACAAGGGTA TTCGTTTTGT TGAGTTAAAT TTTGCTTCAG
 601 CATCTGACCA GAACCAGCAT TTGCCACTTG GATTTGACAT
 641 TATATTCCCT GGCATGCTCG AATATGCTAG AGATTTAAAT
 681 TTAAATCTTC AACTAGAATC TGCAACAGTA AATGCCTTAC
 721 TTCTTAAAAG AGATCAGGAG CTTACAAGAT TCTTTAAAAG
 761 CTACTCAGAC GAGAGTAAAG CATACCTTGC ATATGTATCA
 801 GAAGGTATAG TAAAGTTACA GAACTGGGAT ACAGTTATGA
 841 AGTTCCAAAG AAAGAACGGG TCACTATTCA ATTCACCTTC
 881 AGCTACAGCA GCTGCTGTTA TGCATGTCCA CAATCCTGGT
 921 TGCCTCGATT ACCTTCACTC AGTGTTGGAG AAGCATGGAA
 961 ATGCTGTTCC AACAGTTTAC CCTTTGGATA TATATCCACG
1001 CCTCTGCTTG GTTGACAACC TTGAGAGACT GGGTATTTGT
1041 GGTCATTTTA GGAAGGAAAT TCTGAGTGTA TTGGATGATA
1081 CATACAGATG CTGGATGCAG GGGGATGAAG AGATATTTGC
1121 AGAAAAATCA ACTTGTGCCA TAGCATTTAC ATTATTGCGA
1161 AAGCATGGGT ACAACATCTC TGCAGATCCA TTGACCCCAT
1201 TCTTAAAGGA AGAGTGTTTT TCCAATTCTT TGGGTGGATG
1241 TTTGAAAGAT ACTAGTGCTG TACTTGAATT ATACCGGGCA
1281 TTAGAGATGA TTATTAGCCA GAATGAATCA GCTCTGGTGA
1321 AAAAAAGCTT GTGGTCCAGA AGCTTCCTGA AAGAGCATAT
1361 TTCTGGTGGT TGTGATTTAA AGGGATTCAG CAATCAAATT
1401 TCCATACTGG TGGATGATAT CCTCAACTTT CCATCGCATG
1481 CTACTTTGCA ACGGGTTGCT AACAGGAGAA GCATAGAGCA
1521 ATACAACTTA GACAGTACAA AAATTTTAAA AACTTCATAT
1561 TGCTCGTCGA ATTTTAGCAA CAAAGATTTA TTGATCCTGG
1601 CAGTCAAAGA TTTTAATCAT TGCCAACTCA TACACCGTGA
1641 AGAACTGAAA GAACTAGAAA GGTGGGTCAC AGACAATAGA
1681 TTGGACAAGT TAAAGTTTGC TAGGCAGAAG TCTGCATACT
1721 GTTACTTTTC TGCTGCAGCA ACCATATTCT CACCTGAACT
1761 TTCTGATGCC CGCATGTCAT GGGCCAAGAA TGGTGTACTT
```

-continued

```
1801 GCTACTTTGG TTGATGACTT CTTTGACGTG GGAGGTTCTC
1841 TAGAGGAATT AAAGAAACTG ATTGAGTTGG TTGAAAAGTG
1881 GGATATAAAT GTCAGTGATG GTTGTTGCTC TGAACCAGTG
1921 CAAATCCTCT TCTCAGCACT ACATAGTACA ATCCAGGAGA
1961 TTGGAGATAA AGCATTCAAA TGGCAAGCAC GCAGTGTAAC
2001 AAACCACATA TTTAAGATAT GGTTAGATTT GCTTAATTCT
2041 ATGTTGAGGG AAGCTGAGTG GGCTAGAAAT GCAACAGTGC
2081 CTACAGTTGA AGAATATATG ACAAATGGTT ATGTATCATT
2121 TGCTTTGGGG CCAATTATCC TCCCTGCTCT TTATCTTGTT
2161 GGACCTAAGC TGTCAGAGGA AGTAGTTAAG GATTCTGAAT
2201 TCCACTCCCT TTTTAAGCTA GTGAGTACCT GTGGGCGGCT
2241 TCTGAATGAT GTCCACAGCT TCGAGAGGGA ATCAAAGTCC
2281 GGCCAACTAA ATGCTCTGTC TCTGCGCCTG ATTCATGGTG
2321 GTGTTGGCAT TACTGAAGCA GCTGCTGTTG CAGAGATGAA
2361 GAGTTCAATT GAGAATCTAA GGAGAGAACT GCTGAGACTA
2401 GTCTTGCGCA AAGAGGGTAG TGTAGTTCCA AGAGCTTGCA
2441 AGGATTTGTT TTGGAATATG AGTAAAGTGC TACATCAATT
2481 TTACAACAAA GATGATGGAT TTACTTCAGA GGAGATGATT
2521 CAGCTTGTGA AGTCGATCAT TTATGAGCCA ATTGCGGTCA
2561 ATGAATTTTT GAATAGTTGC CATACATGA
```

The *Chiococca alba* ent-kaurene synthase (CaTPS4) has the amino acid sequence shown below (SEQ ID NO:47).

```
  1 MMIMVMNTAP VHAYHALPIP TQKSSTTLFP NYNCSSRKKS
 41 SPPRISAASV SLQTGVERTT AIHSSDLEIK ERIRKLFHDV
 81 DISLSSYDTA WVAMVPAPHS SQSPLFPQCI NWLLDNQLPD
121 GSWSLPPHHH HHHPLLLKDA LSSTLACVLA LRRWGIGQEQ
161 VDKGIRFVEL NFASASDQNQ HLPVGFDIIF PGMLEYARDL
201 NLNLQLESAT VDALLLKRDQ ELIRFFKSYS DESKAYLAYV
241 SEGIIKLQNW DTVMKFQRKN GSLFNSPSAT AAAVMHVHNP
281 GCLDYLHSVL EKHGNAVPTV YPLDIYPRLC LVDNLERLGI
321 CGHFRKEILS VLDDTYRCWM QGDEEIFAEK STCAIAFTLL
361 RKHGYNISAD PLTPFLKEEC FSNSLGGCLK DTSAVLELYR
401 ALEMIISQNE SALVKKSLWS RSFLKEHISG GCDLKGFSNQ
441 ISKQVDDILN FPSHATLQRV ANRRSIEQYN LDSTKILKTS
481 YCSSNFSNKD LLILAVKDFN HCQLIHREEL KELERWVADN
521 RLDKLKFARQ KSAYCYFSAA ATIFSPELSD ARISWAKNGV
561 LTTLVDDFFD VGGSLEELKK LIELVEKWDI NVSDGCCSEP
601 VQILFSALHS TIQEIGDKAF KWQARSVTNH IIKIWLDLLN
641 SMLREAEWAR NATVPTVEEY MTNGYVSFAL GPIILPALYL
681 VGPKLSEELV KDSEFHSLFK LVSTCGRLLN DVHSFERESK
```

-continued

```
721 AGQLNALSLR LIHGGVGITE AAAVAEMKSS IEKQRRELLR
761 LVLRKEGSVV PRACKDLFWN MSRVLHQFYV KDDGFTSEEM
801 IELVKSIIYE PIAVNEF
```

A nucleic acid encoding the *Chiococca alba* ent-kaurene synthase (CaTPS4) with SEQ ID NO:47 is shown below as SEQ ID NO:48.

```
   1 ATGATGATAA TGGTGATGAA CACAGCTCCC GTCCACGCTT
  41 ACCACGCTTT ACCCATTCCC ACCCAAAAAT CCTCAACCAC
  81 ACTTTTTCCC AATTATAACT GTTCCAGTAG GAAGAAATCA
 121 TCGCCACCTC GCATCTCTGC CGCCTCAGTT TCTTTGCAAA
 161 CTGGAGTTGA AAGAACGACG GCAATTCATT CTTCAGACCT
 201 AGAGATCAAA GAAAGAATAA GGAAACTATT TCATGATGTT
 241 GATATCTCGC TTTCTTCATA TGACACTGCA TGGGTGGCAA
 281 TGGTCCCTGC TCCACATTCT TCCCAGTCTC CCCTTTTTCC
 321 CCAGTGCATT AATTGGTTAT TGGACAATCA GCTTCCTGAT
 361 GGCTCATGGA GTCTTCCTCC TCATCATCAT CATCATCATC
 401 CCCTATTACT TAAAGATGCA TTATCCTCTA CGCTTGCATG
 441 TGTTCTTGCG CTCAGGAGAT GGGGAATTGG TCAAGAACAA
 481 GTTGACAAGG GTATTCGTTT TGTTGAGTTA AATTTTGCTT
 521 CTGCATCTGA CCAGAACCAG CATTTGCCAG TTGGATTTGA
 561 CATTATATTC CCTGGCATGC TCGAATATGC TAGAGATTTA
 601 AATTTAAATC TTCAACTAGA ATCCGCAACT GTAGATGCCT
 641 TACTTCTCAA AAGAGATCAG GAGCTTATAA GATTCTTTAA
 681 AAGCTACTCA GACGAGAGTA AAGCATACCT TGCATATGTA
 721 TCAGAAGGTA TCATAAAGTT ACAGAACTGG GATACAGTTA
 761 TGAAGTTCCA AAGAAAGAAC GGGTCACTGT TCAATTCACC
 801 TTCAGCTACA GCAGCTGCTG TTATGCATGT CCACAATCCT
 841 GGCTGCCTCG ATTACCTTCA CTCAGTGTTG GAGAAGCATG
 881 GCAATGCTGT TCCAACAGTT TACCCTTTGG ATATATATCC
 921 ACGCCTCTGC TTGGTTGACA ACCTTGAGAG ACTGGGTATT
 961 TGTGGTCATT TTAGGAAGGA AATTCTGAGT GTATTGGATG
1001 ATACATACAG ATGCTGGATG CAGGGGGATG AAGAGATATT
1041 TGCAGAAAAA TCAACTTGTG CCATAGCATT TACATTATTG
1081 CGAAAGCATG GGTACAACAT CTCTGCAGAT CCATTGACCC
1121 CATTCTTAAA GGAAGAGTGT TTTTCCAATT CTTTGGGTGG
1161 ATGTTTGAAA GATACTAGTG CTGTACTTGA ATTATACCGG
1201 GCATTAGAGA TGATTATTAG CCAGAATGAA TCAGCTCTGG
1241 TGAAAAAAAG CTTGTGGTCC AGAAGCTTCC TGAAAGAGCA
1281 TATTTCTGGT GGTTGTGATT TAAAGGGATT CAGCAATCAA
1321 ATTTCCAAAC AGGTGGATGA TATCCTCAAC TTTCCATCGC
1361 ATGCTACTTT GCAACGGGTT GCTAACAGGA GAAGCATAGA
```

-continued

```
1401 GCAATACAAC TTAGACAGTA CAAAAATTTT AAAAACTTCA

1441 TATTGCTCGT CGAATTTTAG TAACAAAGAT TTATTGATCC

1481 TGGCAGTCAA AGATTTTAAT CATTGCCAAC TCATACACCG

1521 TGAAGAACTG AAAGAACTAG AAAGGTGGGT CGCAGACAAT

1561 AGATTGGACA AGTTAAAGTT TGCTAGGCAG AAGTCTGCAT

1601 ACTGTTACTT TTCTGCTGCA GCAACCATAT TCTCACCTGA

1641 ACTTTCTGAT GCCCGCATCT CATGGGCCAA AAATGGTGTA

1681 CTTACTACTT TGGTTGATGA CTTCTTTGAC GTGGGAGGTT

1721 CTCTAGAGGA ATTAAAGAAA CTGATTGAGT TGGTTGAAAA

1761 GTGGGATATA AATGTCAGTG ATGGTTGTTG CTCTGAACCA

1801 GTGCAAATCC TCTTCTCAGC ACTACATAGT ACAATCCAGG

1841 AGATTGGAGA TAAAGCATTC AAATGGCAAG CACGCAGTGT

1881 AACAAACCAC ATAATTAAGA TATGGTTAGA TTTGCTTAAT

1921 TCTATGTTGA GGGAAGCTGA GTGGGCTAGA AATGCAACAG

1961 TGCCTACAGT TGAAGAATAT ATGACAAATG GTTATGTATC

2001 ATTTGCCTTG GGGCCAATTA TCCTCCCTGC TCTTTATCTT

2041 GTTGGACCTA AGCTCTCAGA GGAATTAGTT AAGGATTCTG

2081 AATTCCACTC CCTTTTTAAG CTAGTGAGTA CCTGTGGGCG

2121 GCTTCTGAAT GATGTCCACA GCTTCGAGAG GGAATCAAAG

2161 GCCGGCCAAC TAAATGCTCT TTCTCTGCGC CTGATTCATG

2201 GTGGAGTTGG CATTACTGAA GCAGCTGCTG TTGCAGAGAT

2241 GAAGAGTTCA ATTGAGAAGC AAAGGAGAGA ACTGCTGAGA

2281 CTAGTCTTGC GCAAAGAGGG TAGTGTAGTT CCAAGAGCTT

2321 GCAAGGATTT GTTTTGGAAT ATGAGTAGGG TGCTACATCA

2361 ATTTTACGTC AAAGATGATG GATTTACTTC AGAGGAGATG

2401 ATTGAGCTTG TGAACTCGAT CATTTATGAG CCAATTGCGG

2441 TCAATGAATT TTGA
```

A *Chiococca alba* 13(R)-epi-dolabradiene synthase (CaTPS5) was identified and isolated. This CaTPS5 enzyme was identified as an 13(R)-epi-dolabradiene synthase, which converts ent-CPP [16] to 13(R)-epi-dolabradiene.

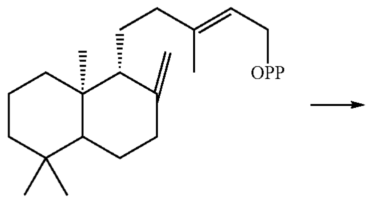

16

-continued

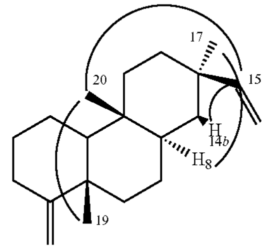

The *Chiococca alba* 13(R)-epi-dolabradiene synthase (CaTPS5) has the amino acid sequence shown below (SEQ ID NO:49).

```
  1 MIHTLPHGGQ AHFISHKTQP YYSSRPRFSS AASLDTRVRR

 41 TSPSNSSVLD FNETKERITK LFHNVDYSIS SYDTAWVAMV

 81 PDPHSSQAPL FPECINWLLD NQFHDGSWSL PHHNSLLLKD

121 VLSSTLACVL ALKRWGIGGR QIDKGVRFIE MNFGSASDNC

161 QHTPIGFDII FPGMLENARD LDLNLRLEPR IVTDMQRKRD

201 MQLTRLHESD LKGDQAYLAY VSEGMQKLQN WDLAMKFQRK

241 NGSLFNSPSA TAAAVMHVQN PASLNYLHSV VDKFGHAVPA

281 VYPLDLYARL CLVDNLERLG ICRHFTNEIE IVMEDTYRCW

321 LQDDEDIFAE ISTCALAFRL LRKHGYVVSP DPLTKIIEEE

401 DVSNSSGNGY WNDIHAVMEV HRASEVVIHE NESDLKNQNT

441 ISKHLLRHHL FNGSDVKPFP NPIYKQVDYA LKFPTPLILQ

481 RVENKTLIQN YDVDSTRLLK TSYRSSNFCN EDLLRLAVKD

521 FNDCQLLHRK ELKELERWSA DNRLHELKFA RQKAIYCSFS

561 AAATIFIPEW YEARMSLAKN SVLATVVDDF FDVGGSMEEL

601 KKLIEFVEKW DIDITKESCS EPLKIIFSAL HSTISEIGEQ

641 AVKWQGRNVT SHIIEIWLDL LNSMLRESEW TTDVHMPTLD

681 EYMEAAYVSF AMGPIIIPAL YFVGPKLSDE IVRDPEIRSL

721 HKLVSICGRL LNDMQGFERE KKAGKPNAVS IRISQNGDGI

761 TESAAFEEVK MELEDARREL LRLVVQKDGS VVPRACKDAF

801 WSVSRMLHHF YFNNDGYTSE VEMVELVNSI IHEPLK
```

A nucleic acid encoding the *Chiococca alba* 13(R)-epi-dolabradiene synthase (CaTPS5) with SEQ ID NO:49 is shown below as SEQ ID NO:50.

```
  1 ATGATTCATA CTCTCCCTCA TGGCGGCCAG GCTCACTTCA

 41 TTTCCCACAA AACACAGCCT TATTATTCCA GTAGACCTCG

 81 CTTTTCTTCA GCAGCTTCTT TGGACACACG AGTCCGGAGA

121 ACATCGCCCT CTAATTCCTC TGTCCTAGAC TTCAACGAGA

161 CCAAAGAAAG AATCACAAAA TTATTTCATA ATGTTGATTA

201 TTCAATTTCT TCATATGATA CAGCATGGGT TGCTATGGTC

241 CCGGACCCAC ATTCTTCTCA GGCTCCCCTT TTCCCAGAGT

281 GCATAAATTG GTTGCTAGAT AATCAATTTC ATGATGGCTC
```

-continued

```
 321 CTGGAGTCTT CCTCATCACA ATTCTCTATT GCTTAAGGAT
 361 GTTTTATCCT CTACGCTTGC GTGTGTTCTT GCTCTTAAGA
 401 GATGGGGAAT AGGAGGAAGG CAGATTGACA AAGGTGTTCG
 441 CTTTATTGAG ATGAATTTTG GCTCAGCATC TGACAATTGC
 481 CAGCATACTC CAATAGGATT TGACATAATA TTTCCAGGAA
 521 TGCTTGAAAA TGCCAGAGAT TTGGATCTAA ATCTTAGACT
 561 ACAACCCAGA ATTGTAACTG ACATGCAACG TAAAAGAGAC
 601 ATGCAGCTTA CAAGACTCCA TGAAAGCGAT CTAAAGGGGG
 641 ACCAAGCATA CTTGGCATAT GTATCCGAAG GGATGCAAAA
 681 GTTACAGAAT TGGGATTTGG CGATGAAGTT TCAAAGGAAG
 721 AATGGATCGC TCTTCAACTC ACCATCAGCT ACAGCAGCCG
 801 CTGTTATGCA TGTCCAAAAT CCTGCTTCCC TCAATTATCT
 841 TCATTCAGTC GTCGACAAAT TCGGCCATGC AGTTCCGGCT
 881 GTTTACCCTT TGGATCTCTA TGCGCGCCTT TGCTTGGTTG
 921 ACAATCTTGA GAGGCTGGGT ATCTGTCGAC ATTTTACTAA
 961 TGAAATTGAA ATTGTAATGG AGGACACGTA CAGGTGCTGG
1001 CTGCAGGATG ATGAAGATAT ATTTGCCGAA ATATCAACTT
1041 GTGCCTTAGC TTTTCGGTTA TTGAGAAAAC ATGGCTATGT
1081 TGTCTCCCCA GATCCACTGA CAAAAATCAT AGAAGAAGAA
1121 GATGTTTCCA ATTCTTCTGG TAATGGATAT TGGAATGATA
1161 TACATGCTGT AATGGAAGTG CATCGGGCAT CAGAGGTGGT
1201 TATACATGAA AATGAATCAG ATTTAAAGAA TCAAAATACC
1241 ATATCAAAAC ACCTTCTCAG ACACCATCTT TTCAATGGTT
1281 CTGATGTGAA GCCCTTTCCT AATCCAATAT ACAAGCAGGT
1321 GGACTATGCT CTCAAGTTTC CAACCCCCTT AATTCTACAA
1361 CGTGTTGAAA ACAAGACCCT CATACAGAAC TACGACGTAG
1401 ACAGTACAAG ACTTCTTAAA ACTTCATATC GATCATCAAA
1441 TTTCTGCAAT GAAGATTTAC TGAGGTTAGC AGTGAAAGAT
1481 TTTAATGACT GTCAACTCCT GCACCGGAAA GAACTAAAAG
1521 AACTAGAAAG ATGGTCCGCA GATAACAGAC TGCACGAACT
1601 AAAATTTGCT CGGCAGAAAG CTATATACTG CTCCTTTTCT
1641 GCTGCAGCAA CGATTTTCAT ACCTGAATGG TACGAAGCCC
1681 GCATGTCATT GGCCAAAAAT AGTGTACTTG CTACTGTGGT
1721 TGATGACTTC TTTGATGTGG GTGGTTCGAT GGAGGAATTA
1761 AAGAAGCTAA TTGAATTTGT TGAAAAGTGG GATATTGACA
1801 TCACCAAGGA ATCCTGCTCT GAGCCACTCA AAATCATATT
1841 TTCAGCACTG CACAGTACAA TCTCTGAGAT TGGAGAGCAA
1881 GCAGTTAAAT GGCAAGGACG CAATGTAACA AGCCACATAA
1921 TTGAGATCTG GTTGGATTTG CTCAATTCGA TGTTGAGGGA
1961 GTCTGAATGG ACTACAGATG TGCACATGCC AACATTGGAT
```

-continued

```
2001 GAATATATGG AAGCTGCTTA TGTATCATTC GCCATGGGGC
2041 CAATTATCAT CCCTGCTCTG TATTTTGTTG GGCCTAAGCT
2081 ATCTGATGAA ATTGTTCGGG ATCCTGAAAT ACGATCCCTC
2121 CATAAGCTTG TGAGCATTTG TGGGCGGCTT CTAAATGATA
2161 TGCAAGGGTT CGAGAGGGAA AAGAAGGCTG GTAAACCAAA
2201 TGCCGTGTCT ATACGCATTA GTCAAAATGG TGATGGCATT
2241 ACCGAATCAG CAGCTTTCGA AGAAGTGAAG ATGGAATTAG
2281 AGGATGCAAG GAGAGAATTG CTAAGATTAG TTGTGCAAAA
2321 AGATGGTAGT GTAGTTCCAA GAGCTTGCAA GGATGCGTTT
2361 TGGAGCGTAA GCAGAATGTT GCATCATTTC TACTTCAATA
2401 ATGATGGATA CACGTCAGAG GTGGAGATGG TTGAGCTCGT
2441 GAATTCAATT ATTCATGAAC CACTAAAATA A
```

A *Salvia hispanica* (−)-kolavenyl diphosphate synthase (ShTPS1) was identified and isolated. This ShTPS1 enzyme was identified as an (−)-kolavenyl diphosphate synthase, which converts GGPP to (−)-kolavenyl diphosphate [36].

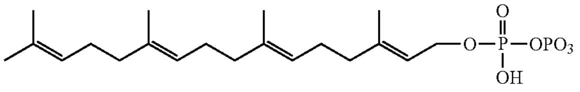

Geranylgeranyl diphosphate (GGPP)

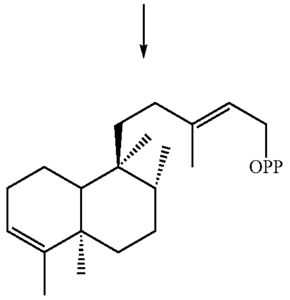

36

The *Salvia hispanica* (−)-kolavenyl diphosphate synthase (ShTPS1) has, for example, an amino acid sequence shown below (SEQ ID NO:51).

```
  1 MSIQANMSFA TSLHRSTTPG VGLPLKPCIS PSPSLSFSPN
 41 FGTFNNTSLR LKPEAGSKSY EGIRRSHQLA ASTILEGQTP
 81 ITPEVESEKT RLIERIRSML QDMDNDGQIS VSPYDTAWVA
121 LVEDIGGSGG PQFPTSLEWI SNHQYDDGSW GDRKFVLYDR
161 ILNTLACVVA LTNWKMHPNK CEKGLRFIHE NIKKLADEDE
201 ELMPVGFEIA LPSVIDLAKR LGIEIPENSA SIKRIYELRD
241 SKLKKIPMDL VHKRPTSLLF SLEGMEGLNW DKLMNFLAEG
281 SFLSSPSSTA YALQHTKNEL CLEYLLKAVK RFNGGVPNAY
321 PVDMFEHLWS VDRLQRLGIS RYFQAEIEEN MAYAYRYWTN
```

-continued

361 KGITWARNMV VQDSDDSAQG FRLLRLYGYD IPIDVFKHFE

401 QGGQFCSIPG QMTHAITGMY NLYRASELLF PGEHILSDAR

441 KYTGNFLHQR RITNTVVDKW IITKDLHGEV AYALDVPFYA

481 SLPRLEARFF IEQYGGDEDV WIGKTLYRMF KVNSDTYLEM

521 AKLDYKQCQS VHQLEWNSMQ RLYRDCNLGE FGLSERSLLL

561 AYYIAASTTF EPEKSSERLA WAITTILVEI IASQKLSDEQ

601 KREFVDEFVK GSIVNNQNGG RHKPGNRLVE VLINNITLMA

641 EGRGTYQQLS NAWKKWLKTW EEGGDLGEAE ARLLLHTIHL

681 SSGLDDSSFS HPKYQQLLEA TSKVCHQLRV FQSVKVYDDQ

721 ESTSQLVTRT TFQIEAGMQE LVKLVFTKTL EDLPSTTKQS

761 FFSVARSFYY TACIHADTID SHINKVLFEK IV

A nucleic acid encoding the *Salvia hispanica* (−)-kolavenyl diphosphate synthase (ShTPS1) with SEQ ID NO:51 is shown below as SEQ ID NO:52.

1 ATGAGTATTC AAGCAAACAT GTCATTTGCC ACCTCCCTCC

41 ACCGATCAAC CACCCCCGGA GTTGGCCTTC CGCTAAAACC

81 ATGTATCTCT CCCTCTCCCT CTCTTTCCTT TTCCCCAAAC

121 TTTGGCACTT TTAACAACAC AAGTTTGAGA CTCAAACCAG

161 AGGCTGGGAG CAAAAGTTAT GAGGGGATTC GAAGAAGTCA

201 TCAATTAGCA GCATCAACAA TTTTGGAGGG TCAAACTCCG

241 ATTACTCCGG AGGTTGAATC GGAGAAAACA CGCCTGATTG

281 AAAGGATTCG TTCGATGTTA CAAGACATGG ACAACGATGG

321 CCAGATAAGT GTGTCACCAT ACGACACAGC ATGGGTGGCG

361 CTCGTGGAAG ATATTGGTGG CAGCGGAGGG CCACAGTTTC

401 CAACGAGCCT AGAGTGGATT TCTAACCACC AGTACGACGA

441 TGGATCGTGG GGGGATCGCA AATTTGTTCT CTATGACCGG

481 ATACTCAATA CATTAGCATG TGTTGTCGCA CTCACGAATT

521 GGAAAATGCA TCCTAACAAA TGCGAAAAAG GGTTGAGGTT

561 TATTCATGAG AATATTAAGA AACTCGCGGA TGAAGATGAA

601 GAGCTCATGC CCGTAGGATT CGAAATCGCA CTGCCATCAG

641 TCATTGATTT AGCTAAAAGA CTGGGTATAG AAATCCCAGA

681 AAATTCTGCA AGCATAAAAA GAATTTATGA ATTGAGAGAT

721 TCAAAACTTA AAAAAATACC AATGGATTTA GTGCACAAAA

761 GGCCCACATC ACTACTCTTC AGCTTGGAAG GCATGGAAGG

301 CCTTAACTGG GACAAACTAA TGAATTTTCT AGCCGAGGGT

841 TCGTTTCTTT CATCGCCATC GTCCACTGCC TACGCTCTCC

881 AACACACCAA GAATGAGTTA TGCCTAGAGT ATTTACTCAA

921 GGCAGTCAAG AGATTCAATG GTGGAGTTCC AAATGCATAC

961 CCTGTCGACA TGTTTGAGCA TCTGTGGTCC GTGGATCGCT

1001 TACAGAGATT AGGAATTTCT CGGTATTTTC AAGCTGAAAT

1041 TGAAGAAAAC ATGGCCTATG CTTACAGATA CTGGACAAAT

-continued

1081 AAAGGAATCA CCTGGGCAAG AAATATGGTT GTCCAAGACA

1121 GTGACGACAG CGCACAGGGA TTCAGGCTCT TAAGGTTGTA

1161 CGGATACGAT ATTCCTATAG ATGTTTTCAA ACATTTCGAG

1201 CAAGGTGGAC AATTCTGCAG CATACCAGGA CAGATGACAC

1241 ACGCTATTAC AGGAATGTAC AACTTGTATA GAGCTTCTGA

1281 ACTTCTGTTC CCTGGAGAAC ACATACTTTC TGATGCTAGA

1321 AAATACACAG GTAACTTCTT GCATCAAAGA AGAATTACTA

1361 ACACGGTAGT AGACAAGTGG ATCATTACCA AAGACCTTCA

1401 CGGCGAGGTG GCTTATGCAT TGGATGTGCC ATTCTACGCC

1441 AGTCTGCCAC GACTGGAAGC ACGATTCTTC ATAGAACAAT

1481 ATGGGGGTGA TGAAGATGTT TGGATTGGGA AAACATTGTA

1521 CAGGATGTTT AAAGTAAACT CCGACACATA CCTTGAGATG

1561 GCAAAATTAG ATTACAAACA ATGCCAGTCT GTGCATCAGT

1601 TAGAGTGGAA TAGCATGCAA AGATTGTATA GAGATTGCAA

1641 TCTAGGAGAG TTTGGGTTGA GCGAAAGAAG CCTTCTCCTA

1681 GCTTACTACA TAGCAGCCTC AACTACATTT GAGCCGGAAA

1721 AATCAAGTGA AAGACTGGCT TGGGCTATAA CAACAATTTT

1761 AGTCGAAATA ATCGCATCCC AAAAACTCTC TGATGAGCAA

1801 AAGAGAGAGT TTGTTGATGA ATTTGTAAAA GGAAGCATCG

1841 TCAATAACCA AAATGGAGGA AGACATAAAC CGGGAAACAG

1881 ATTGGTTGAA GTTTTGATCA ACAATATAAC ACTGATGGCA

1921 GAAGGCAGAG GCACATATCA GCAGTTGTCT AATGCGTGGA

1961 AAAAATGGCT AAAGACATGG GAAGAGGGAG GTGACCTGGG

2001 GGAAGCACAA GCACGGCTTC TCCTGCACAC GATACATTTG

2041 AGCTCCGGAT TGGATGATTC ATCATTTTCC CATCCAAAAT

2081 ATCAGCAGCT CTTGGAGGCA ACCAGCAAAG TCTGCCACCA

2121 ACTTCGCGTA TTCCAGAGTG TAAAGGTGTA TGATGACCAA

2161 GAGTCTACAA GCCAACTGGT AACTAGGACA ACTTTCCAAA

2201 TAGAAGCAGG CATGCAAGAA CTAGTGAAAT TAGTTTTCAC

2241 AAAAACCTTG GAAGATTTGC CTTCTACTAC CAAGCAAAGC

2281 TTTTTTAGTG TTGCTAGAAG TTTCTATTAC ACTGCCTGTA

2321 TTCATGCAGA CACTATAGAC TCCCACATAA ACAAAGTATT

2361 GTTTGAAAAA ATTGTCTAG

A *Teucrium canadense* cleroda-4(18),13E-dienyl diphosphate synthase (TcTPS1) was identified and isolated as described herein. This TcTPS1 enzyme was identified as a cleroda-4(18),13E-dienyl diphosphate synthase, which converts GGPP to cleroda-4(18),13E-dienyl diphosphate [38]. In addition, the combination of TcTPS1 and SsSS enzymes generated neo-cleroda-4(18),14-dien-13-ol [37]. These compounds are shown below.

37

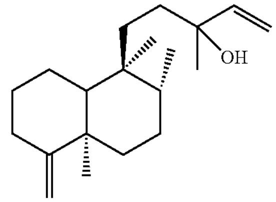

38

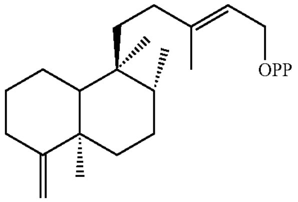

The *Teucrium canadense* cleroda-4(18),13E-dienyl diphosphate synthase (TcTPS1) amino acid sequence is shown below as SEQ ID NO:53.

```
  1 MSFASQATSL LLSSHNATAL PPLSAARLPP LTAGAAPFGR
 41 ISFTTTSLRQ YKLVSRAQSQ EVDEIEKVTQ VVLEAEKDID
 81 QEAKVRELVE NVRVKLQNIG EGGISISPYD TAWVALVEDV
121 GGSGRPQFPE SLDWISNHQF PDGSWGSHKF LYYDRVLCTL
161 ACIVALKTWN LHPHKFDKGL KFVRENIGKL ADEEDVHMPI
201 GFEVAFPSLI ETAKRKGIDI PEDFPGKKEI YAKRDLKLKK
241 IPMDILHKIP TPLLFSIEGI EGLDWQKLFK FRDHGSFLTS
281 PSSTAHALQQ TKDELCLKYL TNLVKKNNGG VPNAFPVDLF
321 DRNYTVDRLR RLGILRYFQP EIEECMKYVY RFWDKRGISW
361 ARNTHVQDLD DTVQGFRNLR MHGYDVTLDV FKQFERCGEF
401 FSFHGQSSDA VLCMFNLYRA SQVLFPGEDM LADARKYAAN
441 YLHKRRVSNR VVDKWIINKD LPGEVAYGLD VPFYASLPRL
481 EARFYVEQYG GNDDVWIGKA LYRMLNVSCD TYLELAKLDY
521 NICQAVHQKE WKSFQKWHRD GEFGLDEKSL LLAYYIAAST
561 VFEPEKSLER LAWAKTAVLM EAILSQQLPS TKKHELVDEF
601 KHASILNNQN GGSYKTRTPL VETLVNAISE LSTTILLEQD
641 RDIHLQLSNA WLKWLSRWEA RGNLVEAEAE LLLQTLHLSN
681 GLEESSFSHP KYQQLLQVTS KVCHLLRLFQ KRKVHDPEGC
721 TTDIATGTTF QIEACMQQVV KLVFTKSSHD LDSVVKQRFL
761 DVARSFYYTA HCDPQVIQSH INKVLFEKVV
```

A nucleic acid encoding the *Teucrium canadense* Cleroda-4(18),13E-dienyl diphosphate synthase (TcTPS1) has with SEQ ID NO:53 is shown below as SEQ ID NO:54.

```
   1 ATGTCATTTG CTTCCCAAGC CACCTCCCTC CTCCTTTCTT
  41 CCCACAACGC CACCGCTCTT CCGCCTCTCT CTGCCGCCCG
  81 CCTTCCGCCT CTCACTGCCG GTGCTGCTCC ATTCGGAAGA
```

-continued

```
 121 ATATCATTTA CTACTACCTC TCTTCGGCAG TATAAACTGG
 161 TGTCAAGAGC TCAAAGCCAA GAGGTGGATG AGATTGAAAA
 201 AGTGACACAA GTGGTATTGG AGGCAGAAAA AGACATCGAT
 241 CAAGAGGCGA AGGTAAGGGA GCTGGTGGAA AATGTCCGAG
 281 TGAAGCTGCA AAATATCGGG GAAGGAGGGA TAAGCATATC
 321 GCCGTACGAC ACCGCATGGG TGGCGCTGGT GGAGGATGTC
 361 GGCGGCAGCG GCAGACCGCA GTTCCCGGAG AGCCTGGATT
 401 GGATATCAAA CCACCAGTTC CCGGACGGGT CGTGGGGCAG
 441 CCACAAATTC TTGTACTATG ACCGGGTTTT GTGCACGTTA
 481 GCATGTATAG TTGCATTGAA AACTTGGAAT CTGCATCCTC
 521 ACAAATTCGA CAAAGGGTTG AAATTCGTCA GAGAGAACAT
 561 TGGAAAGCTC GCGGATGAAG AAGACGTGCA CATGCCGATT
 601 GGGTTCGAAG TGGCATTCCC ATCACTTATA GAGACTGCAA
 641 AGAGAAAAGG AATTGACATC CCGGAAGATT TCCCTGGCAA
 681 GAAAGAAATC TATGCAAAAA GAGACCTAAA GCTGAAAAAG
 721 ATACCTATGG ATATACTGCA CAAAATCCCC ACACCATTAC
 761 TGTTCAGCAT AGAAGGGATA GAAGGCCTTG ATTGGCAGAA
 801 GCTATTCAAA TTCCGCGATC ACGGCTCCTT CCTCACGTCC
 841 CCGTCCTCAA CGGCCCACGC TCTCCAGCAA ACAAAGGACG
 881 AGTTATGCCT CAAATATCTG ACCAATCTTG TCAAAAAGAA
 921 CAATGGGGGA GTTCCAAATG CATTTCCGGT GGACCTATTT
 961 GATCGTAACT ATACAGTAGA TCGCCTGAGG AGGCTGGGAA
1001 TTTTGCGCTA TTTTCAACCT GAAATCGAGG AATGCATGAA
1041 ATATGTATAC AGATTCTGGG ATAAAAGAGG AATCAGCTGG
1081 GCAAGAAATA CCCATGTTCA GGACCTTGAT GATACCGTAC
1121 AGGGATTCAG GAACTTAAGG ATGCATGGTT ATGATGTCAC
1161 CTTAGATGTT TTCAAACAGT TCGAGAGATG TGGAGAATTC
1201 TTTAGCTTCC ACGGGCAATC AAGTGATGCT GTCTTAGGAA
1241 TGTTCAACTT GTACCGAGCT TCTCAGGTTC TGTTTCCAGG
1281 AGAAGACATG CTTGCAGATG CAAGGAAGTA CGCGGCCAAC
1321 TATTTGCATA AAAGAAGAGT TAGTAATAGG GTCGTGGACA
1401 AATGGATTAT TAACAAAGAT CTTCCAGGCG AGGTGGCGTA
1441 TGGGCTAGAT GTTCCGTTCT ACGCCAGTCT ACCTCGACTG
1481 GAAGCAAGAT TCTACGTCGA ACAATATGGG GGTAACGATG
1521 ATGTCTGGAT TGGAAAAGCT TTATATAGAA TGTTGAATGT
1601 GAGCTGTGAT ACTTACCTTG AGCTAGCAAA ATTAGACTAC
1641 AATATTTGCC AGGCTGTGCA TCAGAAAGAG TGGAAAAGCT
1681 TTCAAAAATG GCACAGGGAT GGGGAGTTTG GATTGGATGA
1721 AAAAAGCTTA CTTTTAGCTT ACTACATAGC AGCCTCGACT
1761 GTTTTCGAGC CTGAAAAATC TCTAGAGCGA CTGGCTTGGG
1801 CTAAAACCGC AGTTCTAATG GAGGCAATTT TGTCCCAACA
```

-continued

```
1841 ACTTCCTAGC ACAAAAAAAC ATGAGCTTGT TGACGAATTT
1881 AAACATGCAA GCATCCTCAA CAACCAAAAT GGAGGAAGCT
1921 ATAAAACAAG AACTCCTTTG GTAGAGACTC TAGTAAACGC
1961 CATAAGTGAG CTCTCAACTA CCATACTATT GGAGCAAGAC
2001 AGAGACATTC ATCTGCAATT ATCTAATGCG TGGCTGAAGT
2041 GGCTAAGTAG ATGGGAGGCA AGAGGCAACC TAGTGGAAGC
2081 AGAAGCAGAG CTTCTTCTGC AAACCTTACA TCTGAGCAAT
2121 GGATTAGAAG AATCATCATT TTCTCATCCA AAATATCAAC
2161 AACTCTTACA GGTTACCAGC AAAGTCTGTC ACCTACTTCG
2201 GCTATTCCAG AAACGAAAGG TGCATGATCC GGAAGGGTGT
2241 ACAACAGACA TTGCAACAGG GACAACTTTC CAAATAGAAG
2281 CATGCATGCA ACAAGTAGTG AAATTAGTGT TCACCAAATC
2321 CTCACATGAT TTAGATTCTG TTGTTAAGCA GAGATTTTTG
2361 GATGTTGCCA GAAGTTTCTA TTACACAGCC CACTGTGATC
2401 CACAAGTGAT CCAGTCCCAC ATTAATAAAG TGTTGTTTGA
2441 AAAAGTAGTC TAG
```

*Salvia officinalis* (SoTPS2), *Scutellaria baicalensis* SbTPS1, and SbTPS2 enzymes were identified and isolated. These SoTPS2, SbTPS1, SbTPS2, CfTPS18a and CfTPS18b enzymes were all identified as ent-CPP synthases, which convert GGPP to ent-CPP.

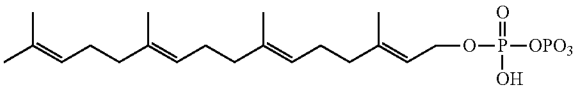

Geranylgeranyl diphosphate (GGPP)

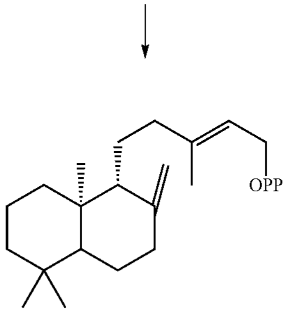

16

The *Salvia officinalis* (SoTPS2) enzyme can have the amino acid sequence shown below (SEQ ID NO:55).

```
  1 MSFASTTSLL RPSVTGFGVS PRVTSTSILS RSYGQILKGK
 41 TKYITDNRRN RQLAVKFEGQ IALDLEDGVA KQTNQEAESE
 81 KIRQLKGKIR WILQNMEDGE MSVSPYDTAW VALVEDISGG
121 GGPQFPTSLE WISKNQLADG SWGDPNYFLL YDRILNTLAC
161 VVALTTWNMH PHKCDQGLRF IRDNIEKLED EDEELILVGF
```

-continued

```
201 EIALPSLIDY AQNLGIQIQY DSPFIKKICA KRDLKLRKIP
241 MDLMHRKPTS LLYSLEGMEG LEWEKLMNLR SEGSFLSSPS
281 STAYALQHTK DELCLDYLVK AVNKFNGGVP NVYPVDMYEH
321 LWCVDRLQRL GISRYFQLEI QQCLDYVYRY WTNEGISWAR
361 YTNIRDSDDT AMGFRLLRLY GYDVSIDAFK PFEESGEFYS
401 MAGQMNHAVT GMYNLYRASQ LMFPQEHILS DARNFSAKFL
441 HQKRRTNALV DKWIITKDLP GEVGYALDVP FYASLPRLEA
481 RFFLEQYGGD DDVWIGYTLY RMPYVNSNTY LELAKVDYKN
521 CQSVHQLEWK SMQKWYRECN IGEFGLSERS LLLAYYIAAS
561 TTFEPEKSGE RLAWATTAIL IETIASQQLS DEQKREFVDE
601 FENSIIIKNQ NGGRYKARNR LVKVLINTVT LVAEGRGINQ
641 QLFNAWQKWL KTWEEGGDMG EAEAQLLLRT LHLSSGFDQS
681 SFSHPKYEQL LEATSKVCHQ LRLFQNRKVD DGQGCISRLV
721 IGTTSQIEAG MQEVVKLVFT KTSQDLTSAT KQSFFNIARS
761 FYYTAYFHAD TIDSHIYKVL FQTIV
```

A nucleic acid encoding the *Salvia officinalis* (SoTPS2) has with SEQ ID NO:55 is shown below as SEQ ID NO:56.

```
  1 ATGTCATTTG CTTCCACCAC CTCCCTCCTC CGACCAAGCG
 41 TCACTGGGTT CGGTGTTTCT CCAAGGGTTA CTTCCACCTC
 81 CATTCTTAGC CGAAGTTATG GTCAAATATT AAAAGGAAAA
121 ACAAAATACA TAACTGATAA CCGTAGAAAT CGACAATTGG
161 CGGTAAAATT TGAGGGCCAA ATTGCTTTGG ATTTGGAGGA
201 TGGCGTAGCA AAGCAGACGA ATCAAGAGGC GGAATCTGAG
241 AAGATAAGGC AACTGAAGGG AAAGATCCGA TGGATTCTGC
281 AAAACATGGA GGACGGCGAG ATGAGCGTGT CGCCGTACGA
321 CACCGCATGG GTGGCGCTGG TGGAAGATAT CAGCGGCGGC
361 GGCGGGCCGC AGTTCCCGAC GAGCCTCGAG TGGATTTCCA
401 AGAATCAGTT GGCGGATGGG TCATGGGGGG ATCCTAATTA
441 TTTCCTTCTC TACGACAGAA TACTCAATAC TTTAGCATGT
481 GTAGTCGCAC TCACGACTTG GAATATGCAT CCTCACAAAT
521 GCGATCAAGG GTTGAGGTTT ATAAGAGACA ACATTGAGAA
561 ACTTGAGGAT GAAGATGAGG AGCTAATTCT CGTAGGATTC
601 GAGATCGCAC TGCCTTCACT CATTGATTAT GCTCAAAACC
641 TTGGGATACA AATCCAATAT GATTCTCCAT TCATTAAAAA
681 AATTTGTGCA AAGAGAGATC TAAAACTCAG AAAAATACCA
721 ATGGATTTAA TGCACAGAAA GCCAACATCA TTGCTCTACA
761 GCTTGGAAGG CATGGAAGGC CTTGAGTGGG AAAAGCTAAT
801 GAATTTGCGA TCGGAGGGTT CGTTTCTGTC ATCGCCGTCG
841 TCCACGGCCT ACGCTCTCCA ACACACCAAG GATGAGTTAT
881 GCCTTGACTA TCTGGTCAAG GCGGTCAACA AATTCAATGG
```

-continued

```
 921 TGGAGTTCCC AACGTGTACC CTGTCGACAT GTATGAGCAT
 961 CTATGGTGCG TAGACCGCTT GCAGAGGTTG GGAATTTCTC
1001 GCTATTTTCA ACTTGAAATT CAACAATGCC TCGACTATGT
1041 TTACAGATAC TGGACAAATG AAGGAATTTC GTGGGCAAGA
1081 TATACTAATA TCCGGGATAG TGACGACACC GCAATGGGAT
1121 TCAGGCTTCT AAGGTTGTAC GGCTATGATG TCTCTATAGA
1161 TGCTTTTAAA CCATTCGAGG AAAGCGGAGA ATTCTATAGC
1201 ATGGCAGGGC AGATGAACCA CGCTGTTACA GGAATGTACA
1241 ACTTGTACAG AGCTTCTCAA CTTATGTTCC CTCAAGAACA
1281 CATACTTTCC GATGCCAGAA ACTTCTCTGC CAAATTCTTG
1321 CATCAAAAGA GGCGTACTAA TGCACTAGTA GACAAGTGGA
1361 TCATTACCAA AGACCTTCCC GGCGAGGTTG GATATGCATT
1401 GGATGTGCCG TTCTACGCCA GTCTGCCTCG ACTGGAAGCA
1441 CGATTCTTCT TAGAACAATA TGGGGGTGAT GATGATGTTT
1481 GGATTGGAAA AACTTTGTAC AGGATGCCAT ATGTGAACTC
1521 CAACACATAC CTTGAGCTTG CAAAAGTAGA CTACAAAAAC
1561 TGCCAGTCCG TGCATCAGTT GGAGTGGAAG AGCATGCAAA
1601 AATGGTACAG AGAATGCAAT ATAGGTGAGT TTGGGTTGAG
1641 CGAAAGAAGC CTTCTCCTAG CTTACTACAT AGCAGCCTCA
1681 ACTACATTCG AGCCAGAAAA ATCAGGTGAG CGGCTCGCTT
1721 GGGCTACAAC AGCAATTTTA ATCGAGACAA TCGCGTCCCA
1761 ACAACTCTCC GATGAACAAA AGAGAGAGTT CGTTGATGAA
1801 TTTGAAAACA GCATCATTAT CAAGAATCAA AATGGAGGGA
1841 GATATAAAGC AAGAAACAGA TTGGTCAAGG TTTTGATCAA
1381 CACTGTAACA CTGGTAGCAG AAGGCAGAGG CATAAATCAG
1921 CAGTTGTTTA ATGCGTGGCA AAAATGGCTA AAGACATGGG
1961 AAGAAGGAGG TGACATGGGG GAAGCAGAAG CCCAGCTTCT
2001 TCTGCGCACG CTACATTTGA GCTCCGGATT CGATCAATCA
2041 TCATTTTCCC ATCCAAAATA TGAGCAGCTC TTGGAGGCGA
2081 CCAGCAAAGT TTGCCACCAA CTTCGCCTAT TCCAGAATCG
2121 AAAGGTGGAT GATGGCCAAG GGTGTATAAG TCGATTGGTA
2161 ATTGGGACAA CTTCCCAAAT AGAAGCAGGC ATGCAAGAAG
2201 TAGTGAAATT AGTTTTCACC AAAACCTCAC AAGACTTGAC
2241 TTCTGCTACC AAGCAAAGCT TTTTCAATAT TGCTAGAAGT
2281 TTCTATTATA CTGCCTACTT TCATGCAGAC ACTATAGACT
2321 CCCACATATA CAAAGTATTG TTTCAAACAA TAGTATAG
```

A *Scutellaria baicalensis* SbTPS1 amino acid sequence shown below (SEQ ID NO:57).

```
  1 MPFLLPSSAT SSPAFYTPAA PLAGHHVFPS FKPLIISRSS
 41 LQCNAISRPR TQEYIDVIQN GLPVIKWHEA VEEDETDKDS
```

-continued

```
 81 LNKEATSDKI RELVNLIRSM LQSMGDGEIS SSPYDAAWVA
121 LVPDVGGSGG PQFPSSLEWI SKNQLPDGSW GDTCTFSIYD
161 RIINTLACVV ALKSWNIHPH KTYQGISFIK ANMDKLEDEN
201 EEHMPIGFEV ALPSLIEIAK RLDIDISSDS RGLQEIYTRR
241 EVKLKRIPKE IMHQVPTTLL HSLEGMAELT WHKLLKLQCQ
281 DGSFLFSPSS TAFALHQTKD HNCLHYLTKY VHKFHGGVPN
321 VYPVDLFEHL WAVDRIQRLG ISRHFKPQVD ECIAYVYRYW
361 TDKGICWARN SVVQDLDDTA MGFRLLRLHG YDVSADVFKH
401 FENGGEFFCF KGQSTQAVTG MYNLYRASQL MFPGESILED
441 AKTESSKFLQ RKRANNELLD KWIITKDLPG EVGYALDVPW
481 YASLPRVETR FYLEQYGGED DVWIGKTLYR MPYVNNNKYL
521 ELAKLDYSNC QSLHQQEWKN IQKWYESCNL GEFGLSERRV
561 LLAYYVAAAC IYEPEKSNQR LAWAKTVILM ETITSYFEHQ
601 QLSAEQRRAF VNEFEHGSIL KYANGGRYKR RSVLGTLLKT
641 LNQLSLDILL THGRNVHQPF KNAWHKWLKT WEEGGDIEEG
681 EAEVLVRTLN LSGEGRHDSY VLEQSLLSQP IYEQLLKATM
721 SVCKKLRLFQ HRKDENGCMT KMRGITTLEI ESEMQELVKL
761 VFTKSSDDLD CEIKQNFFTI ARSFYYVAYC NQGTINYHIA
801 KVLFERVL
```

A nucleic acid encoding the *Scutellaria baicalensis* SbTPS1 with SEQ ID NO:57 is shown below as SEQ ID NO:58.

```
  1 ATGCCTTTCC TCCTCCCTTC CTCCGCCACC AGCTCCCCCG
 41 CGTTCTATAC TCCGGCCGCG CCTCTCGCCG GTCATCATGT
 31 TTTTCCATCT TTCAAGCCAC TCATTATTTC CCGTTCTTCA
121 CTCCAATGCA ATGCAATCTC TCGACCTCGT ACCCAAGAAT
161 ACATAGATGT GATTCAGAAT GGATTGCCAG TAATAAAGTG
201 GCACGAAGCT GTGGAAGAAG ATGAGACAGA TAAAGATTCT
241 CTTAATAAGG AGGCCACGTC AGACAAGATA AGAGAGTTGG
281 TAAATCTGAT CCGTTCGATG CTCCAATCAA TGGGCGACGC
521 AGAGATAAGC TCGTCGCCGT ACGACGCCGC ATGGGTGGCG
561 CTGGTGCCGG ACGTCGGCGG CTCCGGCGGG CCCCAGTTCC
601 CCTCCAGCCT CGAATGGATA TCCAAAAACC AACTCCCCGA
641 CGGCTCCTGG GGCGACACGT GTACCTTTTC CATTTATGAT
681 CGAATCATCA ACACACTGGC TTGCGTTGTT GCTTTGAAAT
721 CTTGGAACAT ACATCCCCAC AAAACTTATC AAGGGATTTC
761 ATTCATAAAG GCAAATATGG ACAAACTTGA AGACGAGAAC
801 GAGGAGCACA TGCCGATCGG ATTTGAAGTG GCACTCCCGT
841 CGCTAATCGA GATAGCGAAA AGGCTCGATA TCGATATTTC
881 CAGCGATTCG AGAGGGCTGC AAGAGATATA CACGAGGAGG
921 GAGGTAAAGC TGAAAAGGAT ACCGAAAGAG ATAATGCACC
```

-continued

```
 961 AAGTGCCCAC AACACTGCTT CATAGCTTGG AGGGTATGGC
1041 CGAGCTGACG TGGCACAAGC TTTTGAAATT ACAGTGCCAA
1081 GATGGCTCCT TTCTTTTCTC TCCATCTTCA ACTGCCTTTG
1121 CTCTTCACCA AACTAAGGAC CATAATTGTC TCCATTATTT
1161 GACCAAATAT GTTCACAAAT TTCATGGTGG AGTGCCAAAT
1201 GTGTATCCGG TGGACTTGTT CGAGCATCTA TGGGCAGTTG
1241 ATCGGATCCA ACGGCTGGGG ATTTCCCGGC ATTTCAAGCC
1281 CCAAGTTGAT GAATGTATTG CCTATGTTTA TAGATATTGG
1321 ACAGATAAAG GAATATGCTG GGCAAGAAAT TCAGTAGTTC
1361 AAGATCTTGA TGACACAGCC ATGGGATTCA GGCTTCTTAG
1401 GTTGCATGGC TACGATGTTT CAGCAGATGT TTTCAAACAT
1441 TTTGAAAATG GTGGAGAGTT CTTCTGCTTC AAAGGGCAAA
1481 GCACGCAGGC AGTGACTGGA ATGTACAATC TGTACAGAGC
1521 TTCTCAGTTG ATGTTTCCTG GAGAAAGCAT ACTGGAAGAT
1601 GCTAAGACCT TCTCATCTAA GTTTTTGCAA CGAAAACGAG
1641 CCAATAACGA GTTGTTAGAT AAGTGGATTA TTACCAAGGA
1681 TCTTCCTGGA GAGGTGGGAT ATGCTCTAGA TGTACCATGG
1721 TATGCTAGCT TACCTAGAGT TGAAACTAGA TTCTACTTGG
1801 AACAATATGG TGGTGAAGAT GATGTTTGGA TTGGCAAAAC
1841 TTTATACAGG ATGCCATATG TTAACAATAA TAAATATCTA
1881 GAACTGGCAA AATTAGACTA TAGTAACTGC CAGTCATTAC
1921 ATCAACAAGA GTGGAAAAAC ATTCAAAAAT GGTATGAGAG
1961 TTGCAATCTG GGAGAATTTG GTTTGAGTGA AAGAAGGGTT
2001 CTACTAGCCT ACTACGTAGC TGCTGCCTGT ATATATGAGC
2041 CCGAAAAGTC AAACCAGCGC TTGGCTTGGG CCAAAACCGT
2081 AATTTTAATG GAGACTATTA CTTCCTATTT TGAGCACCAA
2121 CAACTCTCCG CAGAACAGAG ACGCGCCTTT GTTAATGAAT
2161 TTGAACATGG GAGTATCCTC AAATATGCAA ATGGAGGAAG
2201 ATACAAAAGG AGGAGTGTTT TGGGGACTTT GCTCAAAACA
2241 CTAAATCAGC TTTCATTGGA TATATTATTG ACACACGGTC
2281 GAAACGTCCA TCAGCCTTTC AAAAATGCGT GGCACAAGTG
2321 GCTAAAAACG TGGGAAGAAG GAGGTGACAT TGAAGAAGGC
2361 GAAGCAGAGG TATTGGTCCG AACCCTAAAC CTAAGCGGCG
2401 AAGGGAGGCA CGACTCCTAT GTATTGGAGC AATCATTATT
2441 GTCAGAACCT ATATATGAAC AACTTTTGAA AGCCACCATG
2481 AGTGTTTGCA AGAAGCTTCG ATTGTTCCAA CATCGAAAGG
2521 ATGAGAATGG ATGTATGACG AAGATGAGAG GCATTACAAC
2561 GTTAGAGATA GAATCGGAGA TGCAAGAATT AGTGAAATTA
2601 GTATTTACTA AATCCTCAGA TGATTTAGAT TGTGAAATTA
2641 AACAAAACTT TTTTACAATT CGTAGGAGTT TCTATTATGT
2681 GGCTTATTGT AACCAAGGAA CTATCAACTT TCACATTGCT
2721 AAGGTGCTCT TTGAAAGAGT TCTTTAG
```

A *Scutellaria baicalensis* SbTPS2 amino acid sequence is shown below (SEQ ID NO:59).

```
  1 MASLSTLSLN FSPAIHRKIQ QSSAKLQFQG HCFTISSCMN
 41 NSKRLSLNHQ SNHKRTSNVS ELQVATLDAP QIREKEDYST
 81 AQGYEKVDEV EDPIEYIRML LNTTGDGRIS VSPYDTAWIA
121 LIKDVEGRDA PQFPSSLEWI ANNQLSDGSW GDEKFFCVYD
161 RLVNTLACVV ALRSWNIDAE KSEKGIRYIK ENVDKLKDGN
201 PEHMTCGFEV VFPSLLQRAQ SMGIHDLPYD APVIQDIYNT
241 RESKLKRIPM EVMHKVPTSL LFSLEGLENL EWDKLLKLQS
281 SDGSFLTSPS STAYAFMHTK DPKCFEFIKN TVETFNGGAP
321 HTYPVDVFGR LWAIDRLQRL GISRFFESEI ADCLDHIYKY
361 WTDKGVFSGR ESDFVDVDDT SMGVRLLRMH GYQVDPNVLR
401 NFKQGDKFSC YGGQMIESSS PIYNLYRASQ LRFPGEDILE
441 DANKFAYEFL QEQLSNNQLL DKWVISKHLP DEIKLGLQMP
481 WYATLPRVEA KYYLQYYAGA DDVWIGKTLY RMPEISNDTY
521 LELARMDFKR CQAQHQFEWI SMQEWYESCN IEEFGISRKE
561 LLQAYFLACS SVFELERTTE RIGWAKSQII SRMIASFFNN
601 ETTTADEKDA LLTRFRNING PNRTKSGQRE SEAVNMLVAT
641 LQQYLAGFDR YTRHQLKDAW SVWFRKVQEE EAIYGAEAEL
681 LTTTLNICAG HIAFDENIMA NKDYTTLSSL TSKICQKLSE
721 IRNEKVEEME SGIKAKSSIK DKEVEHDMQS LVKLVLERCE
761 GINNRKLKQT FLSVAKTYYY RAYNADETMD IHMFKVLFEP
801 VM
```

A nucleic acid encoding the *Scutellaria baicalensis* SbTPS2 with SEQ ID NO:59 is shown below as SEQ ID NO:60.

```
  1 ATGGCCTCTC TATCAACTCT GAGCCTCAAC TTTTCCCCAG
 41 CAATTCACCG CAAAATACAG CAATCATCTG CAAAACTTCA
 81 GTTCCAGGGA CATTGTTTCA CCATAAGTTC ATGCATGAAC
121 AACAGTAAAA GACTGTCTTT GAACCACCAA TCTAATCACA
161 AAAGAACGTC AAACGTATCT GAGCTGCAAG TTGCCACTTT
201 GGATGCGCCC CAAATACGTG AAAAAGAAGA CTACTCCACT
241 GCTCAAGGCT ATGAGAAGGT GGATGAAGTA GAGGATCCTA
281 TCGAATATAT TAGAATGCTG TTGAACACAA CAGGTGATGG
321 GCGAATAAGT GTGTCGCCAT ACGACACAGC CTGGATCGCT
361 CTTATTAAAG ACGTGGAAGG ACGTGATGCT CCCCAGTTCC
401 CATCTAGTCT CGAATGGATT GCCAATAATC AACTGAGTGA
441 TGGGTCGTGG GGCGATGAGA AGTTTTTCTG TGTGTATGAT
481 CGCCTTGTTA ATACACTTGC ATGTGTCGTG GCATTGAGAT
```

-continued

```
 521 CATGGAATAT TGATGCTGAA AAGAGCGAGA AAGGAATAAG
 561 ATACATAAAA GAAAACGTGG ATAAACTGAA AGATGGGAAT
 601 CCAGAGCACA TGACCTGTGG TTTTGAGGTG GTGTTTCCTT
 641 CCCTTCTTCA GAGAGCCCAA AGTATGGGAA TTCATGATCT
 681 TCCCTATGAT GCTCCTGTCA TCCAAGACAT TTACAATACC
 721 AGGGAGAGTA AATTGAAAAG CATTCCAATG GAGGTTATCC
 761 ACAAGGTGCC AACATCTCTA TTGTTCAGCT TGGAAGGATT
 801 GGAGAATTTG GAGTGGGATA AGCTCCTCAA ACTTCAGTCT
 841 TCTGATGGTT CATTCCTCAC TTCTCCATCC TCAACTGCCT
 881 ATGCTTTCAT GCACACTAAG GACCCTAAAT GCTTCGAATT
 921 CATCAAAAAC ACCGTCGAAA CATTTAATGG AGGAGCACCT
 961 CATACTTATC CGGTGGATGT TTTTGGAAGA CTGTGGGCCA
1001 TTGACAGGCT GCAGCGCCTC GGAATCTCTC GCTTCTTTGA
1041 GTCCGAGATT GCTGATTGCT TAGATCACAT CTATAAATAT
1081 TGGACAGACA AAGGAGTGTT CAGTGGAAGA GAATCAGATT
1121 TTGTGGATGT GGATGACACA TCCATGGGTG TTAGGCTTCT
1161 AAGGATGCAC GGATATCAAG TTGATCCAAA TGTATTGAGG
1201 AACTTCAAGC AGGGTGACAA ATTTTCATGC TATGGTGGTC
1241 AAATGATAGA GTCATCATCT CCGATATACA ATCTCTATAG
1281 GGCTTCTCAA CTCCGATTTC CAGGAGAAGA CATTCTTGAA
1321 GATGCCAACA AATTCGCATA CGAGTTCTTG CAAGAACAGC
1361 TATCCAACAA TCAACTTTTG GACAAATGGG TTATATCCAA
1401 GCACTTGCCT GATGAGATAA AGCTTGGATT GCAGATGCCA
1441 TGGTATGCCA CCCTACCCCG AGTGGAGGCT AAATACTACC
1481 TACAGTATTA TGCTGGTGCT GATGATGTCT GGATCGGCAA
1521 GACTCTCTAC AGAATGCCAG AAATCAGTAA TGATACATAT
1561 CTGGAGTTAG CAAGAATGGA TTTCAAGAGA TGCCAAGCAC
1601 AGCATCAATT TGAGTGGATT TCCATGCAAG AATGGTATGA
1641 AAGTTGCAAC ATTGAAGAAT TTGGGATAAG CAGAAAAGAG
1681 CTTCTTCAGG CTTACTTTTT GGCCTGCTCA AGTGTATTTG
1721 AACTCGAGAG GACAACAGAG AGAATAGGAT GGGCCAAATC
1761 CCAAATTATT TCAAGGATGA TAGCTTCTTT CTTCAACAAT
1801 GAAACTACAA CAGCCGATGA AAAAGATGCA CTTTTAACCA
1841 GATTCAGAAA CATCAATGGC CCAAACAAAA CAAAAAGTGG
1881 TCAGAGAGAG AGTGAAGCTG TGAACATGTT GGTAGCAACG
1921 CTCCAACAAT ACCTGGCAGG ATTTGATAGA TATACCAGAC
1961 ATCAATTGAA AGATGCTTGG AGTGTGTGGT TCAGAAAAGT
2001 GCAAGAAGAA GAGGCCATCT ACGGGGCAGA AGCGGAGCTT
2041 CTAACAACCA CCTTAAACAT CTGTGCTGGT CATATTGCTT
2081 TCGACGAAAA CATAATGGCC AACAAAGATT ACACCACTCT
```

-continued

```
2121 TTCCAGCCTT ACAAGCAAAA TTTGCCAGAA GCTTTCTGAA
2161 ATTCGAAATG AAAAGGTTGA GGAAATGGAG AGTGGAATTA
2201 AAGCAAAATC AAGCATCAAA GACAAGGAAG TGGAACATGA
2241 TATGCAGTCA CTGGTGAAAT TAGTCCTGGA GAGATGTGAA
2281 GGCATAAACA ACAGAAAACT GAAGCAAACA TTTCTATCGG
2321 TTGCAAAAAC ATATTACTAC AGAGCCTATA ATGCTGATGA
2361 AACCATGGAC ATCCATATGT TCAAAGTACT TTTCGAACCA
2401 GTCATGTGA
```

An example of a *Salvia sclarea* sclareol synthase amino acid sequence is shown below (SEQ ID NO:176, NCBI accession no. AET21246.1).

```
  1 MSLAFNVGVT PFSGQRVGSR KEKFPVQGFP VTTPNRSRLI
 41 VNCSLTTIDF MAKMKENFKR EDDKFPTTTT LRSEDIPSNL
 81 CIIDTLQRLG VDQFFQYEIN TILDNTFRLW QEKHKVIYGN
121 VTTHAMAFRL LRVKGYEVSS EELAPYGNQE AVSQQTNDLP
161 MIIELYRAAN ERIYEEERSL EKILAWTTIF LNKQVQDNSI
201 PDKKLHKLVE FYLRNYKGIT IRLGARRNLE LYDMTYYQAL
241 KSTNRFSNLC NEDFLVFAKQ DFDIHEAQNQ KGLQQLQRWY
281 ADCRLDTLNF GRDVVIIANY LASLIIGDHA FDYVRLAFAK
321 TSVLVTIMDD FFDCHGSSQE CDKIIELVKE WKENPDAEYG
361 SEELEILFMA LYNTVNELAE RARVEQGRSV KEFLVKLWVE
401 ILSAFKIELD TWSNGTQQSF DEYISSSWLS NGSRLTGLLT
441 MQFVGVKLSD EMLMSEECTD LARHVCMVGR LLNDVCSSER
481 EREENIAGKS YSILLATEKD GRKVSEDEAI AEINEMVEYH
521 WRKVLQIVYK KESILPRRCK DVFLEMAKGT FYAYGINDEL
561 TSPQQSKEDM KSFVF
```

A nucleic acid encoding the *Salvia sclarea* sclareol synthase with SEQ ID NO:176 is shown below as SEQ ID NO:177.

```
  1 ATGTCGCTCG CCTTCAACGT CGGAGTTACG CCTTTCTCCG
 41 GCCAAAGAGT TGGGAGCAGG AAAGAAAAAT TTCCAGTCCA
 81 AGGATTTCCT GTGACCACCC CCAATAGGTC ACGTCTCATC
121 GTTAACTGCA GCCTTACTAC AATAGATTTC ATGGCGAAAA
161 TGAAAGAGAA TTTCAAGAGG GAAGACGATA AATTTCCAAC
201 GACAACGACT CTTCGATCCG AAGATATACC CTCTAATTTG
241 TGTATAATCG ACACCCTTCA AAGGTTGGGG GTCGATCAAT
231 TCTTCCAATA TGAAATCAAC ACTATTCTAG ATAACACATT
321 CAGGTTGTGG CAAGAAAAAC ACAAAGTTAT ATATGGCAAT
361 GTTACTACTC ATGCAATGGC ATTTAGGCTT TTGCGAGTGA
401 AAGGATACGA AGTTTCATCA GAGGAGTTGG CTCCATATGG
441 TAACCAAGAG GCTGTTAGGC AGCAAACAAA TGACCTGCCG
```

-continued

```
481 ATGATTATTG AGCTTTATAG AGCAGCAAAT GAGAGAATAT
521 ATGAAGAAGA GAGGAGTCTT GAAAAAATTC TTGCTTGGAC
561 TACCATCTTT CTCAATAAGC AAGTGCAAGA TAACTCAATT
601 CCCGACAAAA AACTGCACAA ACTGGTGGAA TTCTACTTGA
641 GGAATTACAA AGGCATAACC ATAAGATTGG GAGCTAGACG
681 AAACCTCGAG CTATATGACA TGACCTACTA TCAAGCTCTG
721 AAATCTACAA ACAGGTTCTC TAATTTATGC AACGAAGATT
761 TTCTAGTTTT CGCAAAGGAA GATTTCGATA TACATGAAGC
801 CCAGAACCAG AAAGGACTTC AACAACTGCA AAGGTGGTAT
841 GCAGATTGTA GGTTGGACAC CTTAAACTTT GGAAGAGATG
831 TAGTTATTAT TGCTAATTAT TTGGCTTCAT TAATTATTGG
921 TGATCATGCG TTTGACTATG TTCGTCTCGC ATTTGCCAAA
961 ACATCTGTGC TTGTAACAAT TATGGATGAT TTTTTCGACT
1001 GTCATGGCTC TAGTCAAGAG TGTGAGAAGA TCATTGAATT
1041 AGTAAAAGAA TGGAAGGAGA ATCCGGATGC AGAGTACGGA
1081 TCTGAGGAGC TTGAGATCCT TTTTATGGCG TTGTACAATA
1121 CAGTAAATGA GTTGGCGGAG AGGGCTCGTG TTGAACAGGG
1161 GCGTAGTGTC AAAGAGTTTC TAGTCAAACT GTGGGTTGAA
1201 ATACTCTCAG CTTTCAAGAT AGAATTAGAT ACATGGAGCA
1241 ATGGCACGCA GCAAAGCTTC GATGAATACA TTTCTTCGTC
1281 GTGGTTGTCG AACGGTTCCC GGCTGACAGG TCTCCTGACG
1321 ATGCAATTCG TCGGAGTAAA ATTGTCCGAT GAAATGCTTA
1361 TGAGTGAAGA GTGCACTGAT TTGGCTAGGC ATGTCTGTAT
1401 GGTCGGCCGG CTGCTCAACG ACGTGTGCAG TTCTGAGAGG
1441 GAGCGCGAGG AAAATATTGC AGGAAAAAGT TATAGCATTC
1431 TACTAGCAAC TGAGAAAGAT GGAAGAAAAG TTAGTGAAGA
1521 TGAAGCCATT GCAGAGATCA ATGAAATGGT TGAATATCAC
1561 TGGAGAAAAG TGTTGCAGAT TGTGTATAAA AAAGAAAGCA
1601 TTTTGCCAAG AAGATGCAAA GATGTATTTT TGGAGATGGC
1641 TAAGGGTACG TTTTATGCTT ATGGGATCAA CGATGAATTG
1681 ACTTCTCCTC AGCAATCCAA GGAAGATATG AAATCCTTTG
1721 TCTTTTGA
```

Enzymes described herein can have one or more deletions, insertions, replacements, or substitutions in a part of the enzyme. The enzyme(s) described herein can have, for example, at least 60%, or at least 70%, or at least 80%, or at least 90%, or at least 93%, or at least 95%, or at least 96%, or at least 97%, or at least 98%, or at least 99% sequence identity to a sequence described herein.

In some cases, enzymes can have conservative changes such as one or more deletions, insertions, replacements, or substitutions that have no significant effect on the activities of the enzymes. Examples of conservative substitutions are provided below in Table 1A.

TABLE 1A

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulfhydryl | Cys |
| Aliphatic | Val, Ile, Leu, Met |
| Basic | Lys, Arg, His |
| Aromatic | Phe, Tyr, Trp |

Figure 2A:
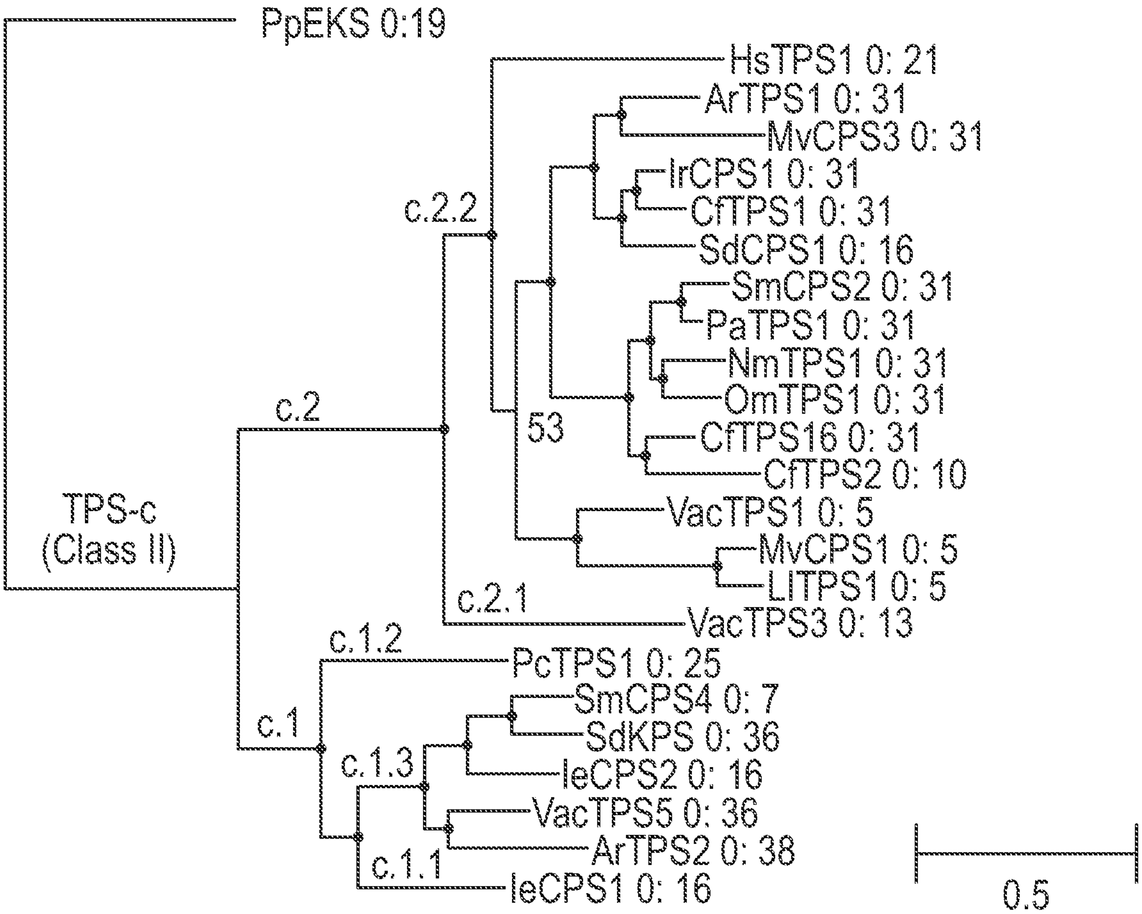
FIG. 2A-2B illustrate maximum likelihood trees of diterpene synthase (diTPS) enzymes.

Due to an increase in resolution at the taxonomic level and consistent clustering of enzymes with identical, or related function, the inventors propose a hierarchical scheme for classifying TPS genes in Lamiaceae from the TPS-e and TPS-c subfamilies. TPS-c genes (class II diTPSs) from Lamiaceae fall broadly into two clades (FIG. 2A), which are referred to herein as c.1 and c.2. These c.1 and c.2 clades are further divided into three, and two subclades, respectively. The characterized genes from c.1.1 are all ent-CPP [16] synthases, presumably involved in primary metabolism. The taxonomic organization among c.1.1 sequences closely resembles the consensus phylogeny generated from 520 genes from each species (19), together with the short branch lengths compared to other TPS-c clades suggests that diTPSs in c.1.1 are more conserved and evolve more slowly.

The remaining TPS-c clades contain genes involved in specialized metabolism. The only characterized gene from clade c.1.2 is PcTPS1 which makes an ent-labda-8-ene diphosphate product [25]. Enzymes from clade c.1.3 catalyze the production of a variety of products, including ent-CPP [16], ent-8-LPP [7], kolavenyl-PP [36], and 38. 36 and 38 are the only products without the labdane (Sk4) skeleton produced by Lamiaceae class II diTPSs. Compounds apparently derived from 36 are widespread among Lamiaceae (Table 6), so the inventors hypothesize that the progenitor of c.1.3 was a kolavenyl-PP synthase present in an early common ancestor. The labdane compounds produced by enzymes in c.1 are all in the ent-configuration. With two exceptions, the known enzymes from clade c.2 all make products with the labdane skeleton in the normal configuration, suggesting that the founder of that clade may have been a normal configuration labdadiene diphosphate synthase. The exceptions are VacTPS3, the only characterized member of c.2.1, which produces syn-CPP [13], and the curious case of SdCPS1, which produces ent-CPP.

Among TPS-e (class I) genes, all but one of the characterized enzymes from e.1 are ent-kaurene [19] synthases, presumably involved in gibberellin biosynthesis. As with the c.1.1 clade, e.1 reflects the taxonomic distribution among the species. Notable in this clade are IrKSL4, which is an ent-atiserene synthase, and SmKSL2, which, in addition to ent-kaurene synthase activity, can convert ent-8-LPP 7 into ent-13-epi-manoyl oxide [6]. Andersen-Ranberg et al. (Angew Chem Int Ed 55(6):2142-2146 (2016)) have tested four of four ent-kaurene synthases and have data indicating that one was from Lamiaceae, which had the ability to convert 7 to 6, so it is likely that this is a general characteristic of enzymes in the e.1 group.

Most of the specialized class I diTPSs in Lamiaceae fall into clade e.2. Enzymes in e.2 have lost the γ domain, present in many diTPSs, and located on the opposite end of the peptide from the class I active site. Characteristic of enzymes in e.2 is their ability to act on multiple substrates. The extreme example is SsSS (Caniard et al. M C Plant Biology 12:119 (2012)) which so far has been able to catalyze the dephosphorylation and minor rearrangement of all class II enzyme products that it has been tested. The range of substrates accepted by other enzymes in this group has not been tested systematically, but among the e.2 enzymes characterized in this study, only one (OmTPS4) accepted ent-CPP, and all accepted (+)-CPP [31], (+)-8-LPP [10], and PgPP [5]. There is great diversity the products of e.2 enzymes, with over 20 distinct compounds represented. Most of the enzymes in e.2 convert (+)-CPP to miltiradiene [32], and (+)-8-LPP to 13R-(+)-manoyl oxide [8], with other activities arising sporadically across the clade. Both characterized enzymes in the Nepetoideae specific e.2.2 have unusual activities: IrKSL6 converts (+)-CPP to isopimara-7,15-diene [28], and OmTPS5 converts (+)-CPP to palustradiene [29]. Most of the enzymes in e.2 fall into the e.2.1 clade which also accounts for most of the known products. Enzymes that we characterized from e.2.1 lent support to emerging functionally consistent subclades. OmTPS4 activity, for three out of four substrates tested, mimics that of its nearest homolog (SsSS), notably accepting ent-CPP as a substrate to produce ent-manool [20]. LITPS4 likewise has activities most similar to its closest homolog, MvELS, converting PgPP into 9,13(S)-epoxy-labd-14-ene [2] with greater specificity than other enzymes tested, although the products from (+)-CPP are different. From the remaining clade, e.2.3, the three characterized enzymes all come from Nepetoideae, and convert (+)-CPP into different products: IrKSL3 produces miltiradiene, IrTPS2 produces nezukol [30], and MsTPS1 produces sandaracopimaradiene [27].

The existence of two strongly supported subclades of specialized diTPSs within c.1, together with the presence of an ent-atiserene synthase in e.1, indicate that the emergence of specialized diTPSs from ent-CPP and ent-kaurene synthases is an ongoing process that has occurred multiple times in the Lamiaceae lineage. While it is evident that candidates selected from anywhere in the phylogenetic tree may have novel activities, clades that seem particularly promising and underexplored are c.2.1, c.1.2, and e.2.3. So far, including this work and previous work, diTPSs have been characterized from only four of the twelve major Lamiaceae clades: Ajugoideae, Lamioideae, Nepetoideae, and Viticoideae. Further expanding to the remaining eight Lamiaceae clades may also be a promising strategy for finding new enzyme activities.

Expression of Enzymes

Also described herein are expression systems that include at least one expression cassette (e.g., expression vectors or transgenes) that encode one or more of the enzyme(s) described herein. The expression systems can also include one or more expression cassettes encoding an enzyme that can synthesize terpene building blocks. For example, the expression systems can include one or more expression cassettes encoding terpene synthases that facilitate production of terpene precursors or building blocks such as those involved in the synthesis of isopentenyl diphosphate (IPP) or dimethylallyl diphosphate (DMAPP).

Cells containing such expression systems are further described herein. The cells containing such expression systems can be used to manufacture the enzymes (e.g., for in vitro use) and/or one or more terpenes, diterpenes, or terpenoids produced by the enzymes. Methods of using the enzymes or cells containing expression cassettes encoding such enzymes to make products such as terpenes, diterpenes, terpenoids, and combinations thereof are also described herein.

Nucleic acids encoding the enzymes can have sequence modifications. For example, nucleic acid sequences described herein can be modified to express enzymes that have modifications. Most amino acids can be encoded by more than one codon. When an amino acid is encoded by more than one codon, the codons are referred to as degenerate codons. A listing of degenerate codons is provided in Table 1B below.

TABLE 1B

| Degenerate Amino Acid Codons | |
|---|---|
| Amino Acid | Three Nucleotide Codon |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |
| START | ATG |
| STOP | TAG, TGA, TAA |

Different organisms may translate different codons more or less efficiently (e.g., because they have different ratios of tRNAs) than other organisms. Hence, when some amino acids can be encoded by several codons, a nucleic acid segment can be designed to optimize the efficiency of expression of an enzyme by using codons that are preferred by an organism of interest. For example, the nucleotide coding regions of the enzymes described herein can be codon optimized for expression in various plant species. For example, many of the enzymes described herein were originally isolated from the mint family (Lamiaceae), however such enzymes can be expressed in a variety of host cells, including for example, as *Nicotiana benthamiana, Nicotiana tabacum, Nicotiana rustica, Nicotiana excelsior*, and *Nicotiana excelsiana.*

An optimized nucleic acid can have less than 98%, less than 97%, less than 95%, or less than 94%, or less than 93%, or less than 92%, or less than 91%, or less than 90%, or less than 89%, or less than 88%, or less than 85%, or less than 83%, or less than 80%, or less than 75% nucleic acid sequence identity to a corresponding non-optimized (e.g., a non-optimized parental or wild type enzyme nucleic acid) sequence.

The enzymes described herein can be expressed from an expression cassette and/or an expression vector. Such an expression cassette can include a nucleic acid segment that encodes an enzyme operably linked to a promoter to drive expression of the enzyme. Convenient vectors, or expression systems can be used to express such enzymes. In some instances, the nucleic acid segment encoding an enzyme is operably linked to a promoter and/or a transcription termination sequence. The promoter and/or the termination sequence can be heterologous to the nucleic acid segment that encodes an enzyme. Expression cassettes can have a promoter operably linked to a heterologous open reading frame encoding an enzyme. The invention therefore provides expression cassettes or vectors useful for expressing one or more enzyme(s).

Constructs, e.g., expression cassettes, and vectors comprising the isolated nucleic acid molecule, e.g., with optimized nucleic acid sequence, as well as kits comprising the isolated nucleic acid molecule, construct or vector are also provided.

The nucleic acids described herein can also be modified to improve or alter the functional properties of the encoded enzymes. Deletions, insertions, or substitutions can be generated by a variety of methods such as, but not limited to, random mutagenesis and/or site-specific recombination-mediated methods. The mutations can range in size from one or two nucleotides to hundreds of nucleotides (or any value there between). Deletions, insertions, and/or substitutions are created at a desired location in a nucleic acid encoding the enzyme(s).

Nucleic acids encoding one or more enzyme(s) can have one or more nucleotide deletions, insertions, replacements, or substitutions. For example, the nucleic acids encoding one or more enzyme(s) can, for example, have less than 95%, or less than 94.8%, or less than 94.5%, or less than 94%, or less than 93.8%, or less than 94.50% nucleic acid sequence identity to a corresponding parental or wild-type sequence. In some cases, the nucleic acids encoding one or more enzyme(s) can have, for example, at least 50%, or at least 55%, or at least 60%, or at least 65%, or at least 70%, or at least 75%, or at least 80%, or at least 85%, or at 90% sequence identity to a corresponding parental or wild-type sequence. Examples of parental or wild type nucleic acid sequences for unmodified enzyme(s) with amino acid sequences SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176 include nucleic acid sequences SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, or 177 respectively. Any of these nuclei acid or amino acid sequences can, for example, encode or have enzyme sequences with less than 99%, less than 98%, less than 97%, less than 96%, less than 95%, less than 94.8%, less than 94.5%, less than 94%, less than 93.8%, less than 93.5%, less than 93%, less than 92%, less than 91%, or less than 90% sequence identity to a corresponding parental or wild-type sequence.

Also provided are nucleic acid molecules (polynucleotide molecules) that can include a nucleic acid segment encoding an enzyme with a sequence that is optimized for expression in at least one selected host organism or host cell. Optimized sequences include sequences which are codon optimized, i.e., codons which are employed more frequently in one organism relative to another organism. In some cases, the balance of codon usage is such that the most frequently used codon is not used to exhaustion. Other modifications can include addition or modification of Kozak sequences and/or introns, and/or to remove undesirable sequences, for instance, potential transcription factor binding sites.

An enzyme useful for synthesis of terpenes, diterpenes, and terpenoids may be expressed on the surface of, or within, a prokaryotic or eukaryotic cell. In some cases, expressed enzyme(s) can be secreted by that cell.

Techniques of molecular biology, microbiology, and recombinant DNA technology which are within the skill of the art can be employed to make and use the enzymes, expression systems, and terpene products described herein. Such techniques available in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series *Methods In Enzymology* (S. Colowick and N. Kaplan eds., Academic Press, Inc.); *Current Protocols In Molecular Biology* (John Wiley & Sons, Inc), *Current Protocols In Protein Science* (John Wiley & Sons, Inc), *Current Protocols In Microbiology* (John Wiley & Sons, Inc), *Current Protocols In Nucleic Acid Chemistry* (John Wiley & Sons, Inc), and *Handbook of Experimental Immunology*, Vols. I-IV (D. M. Weir and C. C. Blackwell eds., 1986, Blackwell Scientific Publications).

Modified plants that contain nucleic acids encoding enzymes within their somatic and/or germ cells are described herein. Such genetic modification can be accomplished by available procedures. For example, one of skill in the art can prepare an expression cassette or expression vector that can express one or more encoded enzymes. Plant cells can be transformed by the expression cassette or expression vector, and whole plants (and their seeds) can be generated from the plant cells that were successfully transformed with the enzyme nucleic acids. Some procedures for making such genetically modified plants and their seeds are described below.

Promoters: The nucleic acids encoding enzymes can be operably linked to a promoter, which provides for expression of mRNA from the nucleic acids encoding the enzymes. The promoter is typically a promoter functional in plants and can be a promoter functional during plant growth and development. A nucleic acid segment encoding an enzyme is operably linked to the promoter when it is located downstream from the promoter. The combination of a coding region for an enzyme operably linked to a promoter forms an expression cassette, which can optionally include other elements as well.

Promoter regions are typically found in the flanking DNA upstream from the coding sequence in both the prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning gene expression on and off in response to an exogenously added agent, or to an environmental or developmental stimulus. For example, a bacterial promoter such as the $P_{tac}$ promoter can be induced to varying levels of gene expression depending on the level of isopropyl-beta-D-thiogalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, examples of plant promoters such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al. *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al, *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al, *The Plant Cell.* 1:1175-1183 (1989)). Further suitable promoters include a CYP71D16 trichome-specific promoter and the CBTS (cembratrienol synthase) promotor, cauliflower mosaic virus promoter, the Z10 promoter from a gene encoding a 10 kD zein protein, a Z27 promoter from a gene encoding a 27 kD zein protein, the plastid rRNA-operon (rrn) promoter, inducible promoters, such as the light inducible promoter derived from the pea rbcS gene (Coruzzi et al., *EMBO J.* 3:1671 (1971)), RUBISCO-SSU light inducible promoter (SSU) from tobacco and the actin promoter from rice (McElroy et al., *The Plant Cell.* 2:163-171 (1990)). Other promoters that are useful can also be employed.

Alternatively, novel tissue specific promoter sequences may be employed. cDNA clones from a particular tissue can be isolated and those clones which are expressed specifically in that tissue can be identified, for example, using Northern blotting. Preferably, the gene isolated is not present in a high copy number but is relatively abundant in specific tissues. The promoter and control elements of corresponding genomic clones can then be localized using techniques well known to those of skill in the art.

A nucleic acid encoding an enzyme can be combined with the promoter by standard methods to yield an expression cassette, for example, as described in Sambrook et al. (Molecular Cloning: A Laboratory Manual. Second Edition (Cold Spring Harbor, NY: Cold Spring Harbor Press (1989); Molecular Cloning: A Laboratory Manual. Third Edition (Cold Spring Harbor, NY: Cold Spring Harbor Press (2000)). Briefly, a plasmid containing a promoter such as the 35S CaMV promoter or the CYP71D16 trichome-specific promoter can be constructed as described in Jefferson (*Plant Molecular Biology Reporter* 5:387-405 (1987)) or obtained from Clontech Lab in Palo Alto. California (e.g., pBI121 or pBI221). Typically, these plasmids are constructed to have multiple cloning sites having specificity for different restriction enzymes downstream from the promoter.

The nucleic acid sequence encoding for the enzyme(s) can be subcloned downstream from the promoter using restriction enzymes and positioned to ensure that the DNA is inserted in proper orientation with respect to the promoter so that the DNA can be expressed as sense RNA. Once the nucleic acid segment encoding the enzyme is operably linked to a promoter, the expression cassette so formed can be subcloned into a plasmid or other vector (e.g., an expression vector).

In some embodiments, a cDNA clone encoding an enzyme is isolated from a mint species, for example, from leaf, trichome, or root tissue. In other embodiments, cDNA clones from other species (that encode an enzyme) are isolated from selected plant tissues, or a nucleic acid encoding a wild type, mutant or modified enzyme is prepared by available methods or as described herein. For example, the nucleic acid encoding the enzyme can be any nucleic acid with a coding region that hybridizes to SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, or 177, and that has enzyme activity. Using restriction endonucleases, the entire coding sequence for the enzyme is subcloned downstream of the promoter in a 5' to 3' sense orientation.

Targeting Sequences: Additionally, expression cassettes can be constructed and employed to target the nucleic acids encoding an enzyme to an intracellular compartment within plant cells or to direct an encoded protein to the extracellular environment. This can generally be achieved by joining a DNA sequence encoding a transit or signal peptide sequence to the coding sequence of the nucleic acid encoding the enzyme. The resultant transit, or signal, peptide can transport the protein to a particular intracellular, or extracellular, destination and can then be co-translationally or post-translationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product within a particular location. For example, see U.S. Pat. No. 5,258,300.

For example, in some cases it may be desirable to localize the enzymes to the plastidic compartment and/or within plant cell trichomes. The best compliment of transit peptides/secretion peptide/signal peptides can be empirically ascertained. The choices can range from using the native secretion signals akin to the enzyme candidates to be transgenically expressed, to transit peptides from proteins known to be localized into plant organelles such as trichome plastids in general. For example, transit peptides can be selected from proteins that have a relative high titer in the trichomes. Examples include, but not limited to, transit peptides form a terpenoid cyclase (e.g. cembratrieneol cyclase), the LTP1 protein, the Chlorophyll a-b binding protein 40, Phylloplanin, Glycine-rich Protein (GRP), Cytochrome P450 (CYP71D16); all from *Nicotiana* sp. alongside RUBISCO (Ribulose bisphosphate carboxylase) small unit protein from both *Arabidopsis* and *Nicotiana* sp.

3' Sequences: When the expression cassette is to be introduced into a plant cell, the expression cassette can also optionally include 3' untranslated plant regulatory DNA sequences that act as a signal to terminate transcription and allow for the polyadenylation of the resultant mRNA. The 3' untranslated regulatory DNA sequence can include from about 300 to 1,000 nucleotide base pairs and can contain plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium*

*tumefaciens*, and/or the 3' end of the protease inhibitor I or 11 genes from potato or tomato. Other 3' elements known to those of skill in the art can also be employed. These 3' untranslated regulatory sequences can be obtained as described in An (*Methods in Enzymology.* 153:292 (1987)). Many such 3' untranslated regulatory sequences are already present in plasmids available from commercial sources such as Clontech, Palo Alto, California. The 3' untranslated regulatory sequences can be operably linked to the 3' terminus of the nucleic acids encoding the enzyme.

Selectable and Screenable Marker Sequences: To improve identification of transformants, a selectable or screenable marker gene can be employed with the expressible nucleic acids encoding the enzyme(s). "Marker genes" are genes that impart a distinct phenotype to cells expressing the marker gene and thus allow such transformed cells to be distinguished from cells that do not have the marker. Such genes may encode either a selectable or a screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are available can be employed in the practice of the invention.

Included within the terms 'selectable or screenable marker genes' are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of an expression system that encodes a polypeptide that becomes sequestered in the cell wall, where the polypeptide includes a unique epitope may be advantageous. Such a cell wall antigen can employ an epitope sequence that would provide low background in plant tissue, a promoter-leader sequence that imparts efficient expression and targeting across the plasma membrane, and that can produce protein that is bound in the cell wall and yet is accessible to antibodies. A normally secreted cell wall protein modified to include a unique epitope would satisfy such requirements.

Example of protein markers suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich cell wall proteins (Keller et al., *EMBO J.* 8:1309-1314 (1989)) could be modified by the addition of an antigenic site to create a screenable marker.

Selectable markers for use in connection with the present invention can include, but are not limited to, a neo gene (Potrykus et al., *Mol. Gen. Genet.* 199:183-188 (1985)) which codes for kanamycin resistance and can be selected for using kanamycin, G418; a bar gene which codes for bialaphos resistance; a gene which encodes an altered EPSP synthase protein (Hinchee et al., *Bio/Technology* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al, *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide. CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al. *Mol. Gen. Genet.* 205:42-50 (1986); Twell et al., *Plant Physiol.* 91:1270-1274 (1989)) causing rapid accumulation of ammonia and cell death. Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* $18^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA* 80:1101 (1983)) which encodes a catechol dioxygenase that can convert chromogenic catechols; an α-amylase gene (Ikuta et al, *Bio/technology* 8:241-242 (1990)); a tyrosinase gene (Katz et al., *J Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

Another screenable marker contemplated for use is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also include plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences can include origins of replication to provide for autonomous replication of the vector, additional selectable marker genes, for example, encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods In Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors can include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells but is usually used to transform dicot plant cells.

DNA Delivery of the DNA Molecules into Host Cells: Methods described herein can include introducing nucleic acids encoding enzymes, such as a preselected cDNA encoding the selected enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some recipient cells may show only initial and transient gene expression. However, certain cells from virtually any dicot or monocot species may be stably transformed, and these cells regenerated into transgenic plants, through the application of the techniques disclosed herein.

Another aspect of the invention is a plant that can produce terpenes, diterpenes and terpenoids, wherein the plant has introduced nucleic acid sequence(s) encoding one or more enzymes. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. In some embodiments, the plant or cell is a monocotyledon plant or cell. In some embodiments, the plant or cell is a dicotyledon plant or cell. For example, the plant or cell can be a tobacco plant or cell. The cell(s) may be in a suspension cell culture or may be in an intact plant part, such as an immature embryo, or in a specialized plant tissue, such as callus, such as Type I or Type II callus.

Transformation of plant cells can be conducted by any one of a number of methods available in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack the functions for disease induction.

One method for dicot transformation, for example, involves infection of plant cells with *Agrobacterium tumefaciens* using the leaf-disk protocol (Horsch et al., *Science* 227:1229-1231 (1985). Methods for transformation of monocotyledonous plants utilizing *Agrobacterium tumefaciens* have been described by Hiei et al. (European Patent 0 604 662, 1994) and Saito et al. (European Patent 0 672 752, 1995).

Monocot cells such as various grasses or dicot cells such as tobacco can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128.

The choice of plant tissue source for transformation may depend on the nature of the host plant and the transformation protocol. Useful tissue sources include callus, suspensions culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells.

The transformation is carried out under conditions directed to the plant tissue of choice. The plant cells or tissue are exposed to the DNA or RNA encoding enzymes for an effective period of time. This may range from a less than one second pulse of electricity for electroporation to a 2-day to 3-day co-cultivation in the presence of plasmid-bearing *Agrobacterium* cells. Buffers and media used will also vary with the plant tissue source and transformation protocol. Many transformation protocols employ a feeder layer of suspended culture cells (tobacco, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in selected plant cells. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, microprojectile bombardment does not require the isolation of protoplasts (Christou et al., *PNAS* 84:3962-3966 (1987)), the formation of partially degraded cells, and no susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing the damage inflicted on recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein, one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with the bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore, influence transformation and integration efficiencies. For example, the osmotic state, tissue hydration and the subculture stage or cell cycle of the recipient cells may be adjusted for optimum transformation. Execution of such routine adjustments will be known to those of skill in the art.

Selection: An exemplary embodiment of methods for identifying transformed cells involves exposing the bombarded cultures to a selective agent, such as a metabolic inhibitor, an antibiotic, or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations that provide 100% inhibition followed by screening of growing tissue for expression of a screenable marker gene such as luciferase would allow one to recover transformants from cell or tissue types that are not amenable to selection alone.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants to introgress the nucleic acids encoding an enzyme into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced nucleic acids, the plant is self-pollinated at least once in order to produce a homozygous backcross converted inbred containing the nucleic acids encoding the enzyme(s). Progeny of these plants are true breeding.

Alternatively, seed from transformed plants regenerated from transformed tissue cultures is grown in the field and self-pollinated to generate true breeding plants.

Seed from the fertile transgenic plants can then be evaluated for the presence and/or expression of the enzyme(s). Transgenic plant and/or seed tissue can be analyzed for enzyme expression using methods such as SDS polyacrylamide gel electrophoresis, Western blot, liquid chromatography (e.g., HPLC) or other means of detecting an enzyme product (e.g., a terpene, diterpene, terpenoid, or a combination thereof).

Once a transgenic seed expressing the enzyme(s) and producing one or more terpenes, diterpenes, and/or terpenoids in the plant is identified, the seed can be used to develop true breeding plants. The true breeding plants are used to develop a line of plants expressing terpenes, diterpenes, and/or terpenoids in various plant tissues (e.g., in leaves, bracts, and/or trichomes) while still maintaining other desirable functional agronomic traits. Adding the trait of terpene, diterpene, and/or terpenoid production can be accomplished by back-crossing with selected desirable functional agronomic trait(s) and with plants that do not exhibit such traits and studying the pattern of inheritance in segregating generations. Those plants expressing the target trait(s) in a dominant fashion are preferably selected. Back-crossing is carried out by crossing the original fertile transgenic plants with a plant from an inbred line exhibiting desirable functional agronomic characteristics while not necessarily expressing the trait of terpene, diterpene, and/or terpenoid production in the plant. The resulting progeny can then be crossed back to the parent that expresses the terpenes, diterpenes, and/or terpenoids. The progeny from this cross will also segregate so that some of the progeny carry the trait and some do not. This back-crossing is repeated until the goal of acquiring an inbred line with the desirable functional agronomic traits, and with production of terpenes, diterpenes, and/or terpenoids within various tissues of the plant is achieved. The enzymes can be expressed in a dominant fashion.

Subsequent to back-crossing, the new transgenic plants can be evaluated for synthesis of terpenes, diterpenes, and/or terpenoids in selected plant lines. This can be done, for example, by gas chromatography, mass spectroscopy, or NMR analysis of whole plant cell walls (Kim, H., and Ralph, J. Solution-state 2D NMR of ball-milled plant cell wall gels in DMSO-$d_6$/pyridine-$d_5$. (2010) *Org. Biomol. Chem.* 8(3), 576-591; Yelle, D. J., Ralph, J., and Frihart, C. R. Characterization of non-derivatized plant cell walls using high-resolution solution-state NMR spectroscopy. (2008) *Magn. Reson. Chem.* 46(6), 508-517; Kim, H., Ralph, J., and Akiyama, T. Solution-state 2D NMR of Ball-milled Plant Cell Wall Gels in DMSO-$d_6$. (2008) *BioEnergy Research* 1(1), 56-66; Lu, F., and Ralph, J. Non-degradative dissolution and acetylation of ball-milled plant cell walls; high-resolution solution-state NMR. (2003) *Plant J.* 35(4), 535-544). The new transgenic plants can also be evaluated for a battery of functional agronomic characteristics such as lodging, yield, resistance to disease, resistance to insect pests, drought resistance, and/or herbicide resistance.

Determination of Stably Transformed Plant Tissues: To confirm the presence of the nucleic acids encoding terpene synthesizing enzymes in the regenerating plants, or seeds or progeny derived from the regenerated plant, a variety of assays may be performed. Such assays include, for example, molecular biological assays, such as Southern and Northern blotting and PCR; biochemical assays, such as detecting the presence of enzyme products, for example, by enzyme assays, by immunological assays (ELISAs and Western blots). Various plant parts can be assayed, such as trichomes, leaves, bracts, seeds or roots. In some cases, the phenotype of the whole regenerated plant can be analyzed.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced nucleic acids. PCR can also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting may be used to detect the nucleic acid encoding the enzyme(s) in question, it may not provide information as to whether the preselected DNA segment is being expressed. Expression may be evaluated by specifically identifying the protein products of the introduced nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as, native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the enzyme such as evaluation by amino acid sequencing following purification. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Hosts

Terpenes, including diterpenes and terpenoids, can be made in a variety of host organisms either in vitro or in vivo. In some cases, the enzymes described herein can be made in host cells, and those enzymes can be extracted from the host cells for use in vitro. As used herein, a "host" means a cell, tissue or organism capable of replication. The host can have an expression cassette or expression vector that can include a nucleic acid segment encoding an enzyme that is involved in the biosynthesis of terpenes.

The term "host cell", as used herein, refers to any prokaryotic or eukaryotic cell that can be transformed with an expression cassettes or vector carrying the nucleic acid segment encoding an enzyme that is involved in the biosynthesis of one or more terpenes. The host cells can, for example, be a plant, bacterial, insect, or yeast cell. Expression cassettes encoding biosynthetic enzymes can be incorporated or transferred into a host cell to facilitate manufacture of the enzymes described herein or the terpene, diterpene, or terpenoid products of those enzymes. The host cells can be present in an organism. For example, the host cells can be present in a host such as a plant.

For example, the enzymes, terpenes, diterpenes, and terpenoids can be made in a variety of plants or plant cells. Although some of the enzymes described herein are from species of the mint family, the enzymes, terpenes, diterpenes, and terpenoids can be made in species other than in mint plants or mint plant cells. The terpenes, diterpenes, and terpenoids can, for example, be made and extracted from whole plants, plant parts, plant cells, or a combination thereof. Enzymes can conveniently, for example, be produced in bacterial, insect, plant, or fungal (e.g., yeast) cells.

Examples of host cells, host tissues, host seeds and plants that may be used for producing terpenes and terpenoids (e.g., by incorporation of nucleic acids and expression systems described herein) include but are not limited to those useful for production of oils such as oilseeds, camelina, canola, castor bean, corn, flax, lupins, peanut, potatoes, safflower, soybean, sunflower, cottonseed, oil firewood trees, rapeseed, rutabaga, sorghum, walnut, and various nut species. Other types host cells, host tissues, host seeds and plants that can be used include fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., poplar, pine, and eucalyptus), oil (oilseeds, camelina, canola, castor bean, lupins, potatoes, soybean, sunflower, cottonseed, oil firewood trees, rapeseed, rutabaga, sorghum), starch plants (wheat, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, pine, oak, maple, walnut, rubber tree, willow, and the like. Plants useful for generating forage include legumes such as alfalfa, as well as forage grasses such as bromegrass, and bluestem. In some cases, the plant is a Brassicaceae or other Solanaceae species. In some embodiments, the plant is not a species of *Arabidopsis*, for example, in some embodiments, the plant is not *Arabidopsis thaliana*.

Additional examples of hosts cells and host organisms include, without limitation, tobacco cells such as *Nicotiana benthamiana, Nicotiana tabacum, Nicotiana rustica, Nicotiana excelsior*, and *Nicotiana excelsiana* cells; cells of the genus *Escherichia* such as the species *Escherichia coli*, cells of the genus *Clostridium* such as the species *Clostridium ljungdahlii, Clostridium autoethanogenum* or *Clostridium kluyveri*, cells of the genus *Corynebacterium* such as the species *Corynebacterium glutamicum*, cells of the genus *Cupriavidus* such as the species *Cupriavidus necator* or *Cupriavidus metallidurans*; cells of the genus *Pseudomonas* such as the species *Pseudomonas fluorescens Pseudomonas putida* or *Pseudomonas oleovorans*; cells of the genus *Delftia* such as the species *Delftia acidovorans*; cells of the genus *Bacillus* such as the species *Bacillus subtilis*, cells of the genus *Lactobacillus* such as the species *Lactobacillus delbrueckii*, or cells of the genus *Lactococcus* such as the species *Lactococcus lactis*.

"Host cells" can further include, without limitation, those from yeast and other fungi, as well as, for example, insect cells. Examples of suitable eukaryotic host cells include yeasts and fungi from the genus *Aspergillus* such as *Aspergillus niger*, from the genus *Saccharomyces* such as *Saccharomyces cerevisae*, from the genus *Candida* such as *C. tropicalis, C. albicans, C. cloacae, C. guilliermondii, C. intermedia, C. maltosa, C. parapsilosis*, and *C. zeylenoides*; from the genus *Pichia* (or *Komagataella*) such as *Pichia pastoris*; from the genus *Yarrowia* such as *Yarrowia lipolytica*; from the genus *Issatchenkia* such as *Issatchenkia orientalis*, from the genus *Debaryomyces* such as *Debaryomyces hansenii*, from the genus *Arxula* such as *Arxula adeninivorans*, or from the genus *Kluyveromyces* such as *Kluyveromyces lactis* or from the genera *Exophiala, Mucor, Trichoderma, Cladosporium, Phanerochaete, Cladophialophora, Paecilomyces, Scedosporium*, and *Ophiostoma*.

In some cases, the host cells can have organelles that facilitate manufacture or storage of the terpenes, diterpenes, and terpenoids. Such organelles can include lipid droplets, smooth endoplasmic reticulum, plastids, trichomes, vacuoles, vesicles, plastids, and cellular membranes. During and after production of the terpenes, diterpenes, and terpenoids these organelles can be isolated as a semi-pure source of the of the terpenes, diterpenes, and terpenoids.

The Diterpene Skeletons of Lamiaceae and how to Make them

Enzymes responsible for all new skeletons were not specifically located, but considering the known skeletons and diTPS activities, the inventors have deduced how diverse skeletons arise and what strategies may be used for finding the enzymes responsible. All of the six diterpene skeletons with a known biosynthetic route in Lamiaceae contain a decalin core: Sk2, and Sk4 (FIG. 1B-1C) are skeletons of the direct products of TPS-c enzymes, while Sk1, Sk3, Sk6, and Sk14 are skeletons of the products a TPS-e enzyme acting on a labdadiene diphosphate (Sk4) precursor.

Many diterpene skeletons with an intact decalin core can be made by as-yet undiscovered diTPSs from the TPS-c and TPS-e subfamilies, for example through methyl shifts during cyclization. Examples of diTPSs that catalyze methyl shifts are the TPS-c enzymes SdKPS and ArTPS2 which produce the clerodane skeleton (Sk2), and the TPS-e enzyme OmTPS5 which has a product with the abietane skeleton (Sk3). The same mechanisms may form skeletons such as Sk8 and Sk12. Other decalin-containing skeletons, for example the nor-diterpenes (missing one or more methyl side chains, e.g. Sk7) are can be made by oxidative decarboxylation occurring after the TPS steps. Ring rearrangements catalyzed by TPS-e enzymes also have precedent, for example the generation of ent-kaurene (with skeleton Sk1) or ent-atiserene (with skeleton Sk14) from ent-CPP (with skeleton Sk4), but always preserve the decaline core structure.

Figures 1B, 1C:
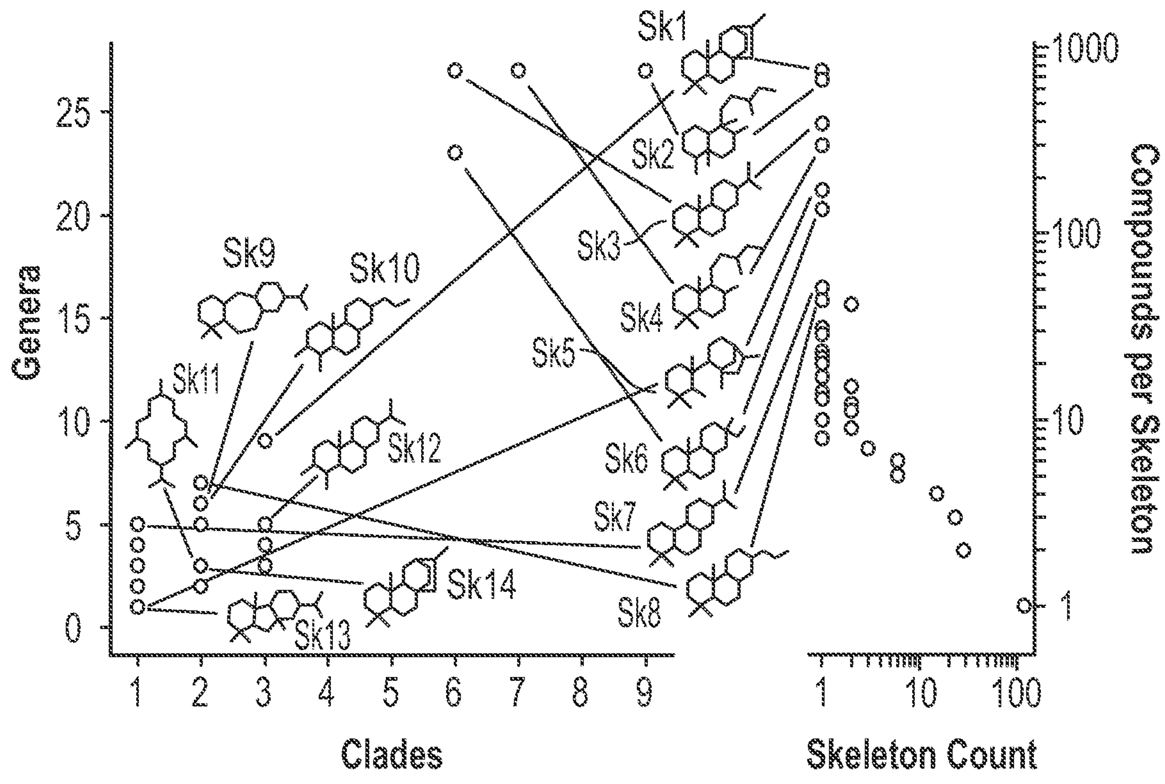

Diterpenoids lacking a decalin core are taxonomically restricted within Lamiaceae, with no single skeleton being reported in more than two clades (FIG. 1B). Many can be explained as modifications occurring after the TPS steps to decalin-containing skeletons. Cytochrome P450 driven ring contraction, akin to that in the gibberellin pathway, can play a role in the formation of skeletons such as Sk13. Ring opening and ring expansion may also occur, for example in pathways to compounds with the 6,7-seco-kaurane (Sk5), and icetaxane (Sk9) skeletons, respectively. Skeletons such as cembrane (Sk11), lacking any apparent biosynthetic connection to a decalin core can arise from diTPSs outside the TPS-c and TPS-e subfamilies. In Euphorbiaceae and Solanaceae, where cembranoid compounds are common, the relevant TPSs come from the TPS-a subfamily. Elucidation of pathways to the remaining diterpene skeletons in Lamiaceae will depend on broadening the search to new genera and species and new TPS subfamilies, eventually moving beyond TPSs to look at cytochromes P450 and other enzyme families.

Implications for Biotechnology

Arrays of compounds can be produced by combining class II diTPSs with different class I diTPSs. Particularly prolific enzymes for combinatorial biosynthesis have been Cyc2 from the bacterium *Streptomyces griseolosporeus* (Hamano et al. J Biol Chem 277(40):37098-37104 (2002); Dairi et 1. J Bacteriol 183(20):6085-4094 (2001)), which generates alkene moieties on prenyl-diphosphate substrates, and SsSS, which installs an alcohol at the 13 position and a double bond at the 14 position; both of these enzymes have demonstrated activity on 12 different class II enzyme products. The inventors have found that SsSS is also active on the products of PcTPS1 and ArTPS2. In addition, the inventors have found class I enzymes that provide routes to products that previously were biosynthetically inaccessible or poorly accessible. OmTPS3 is active on class II products with a labdane skeleton and normal absolute configuration, typically generating a trans-methyl-pentadiene moiety, as in 11, 34, and 24. An enzyme with similar activity, producing 24 and 34, was recently reported from the bacterium *Streptomyces cyslabdanicus* (Yamada et al. The Journal of Antibiotics 69(7):515-523 (2016); Ikeda et al. J Ind Microbiol Biotechnol 43(2-3):325-342 (2016)) but was not tested against additional substrates. LlTPS4 produces sandaracopimaradiene [27] from 31, with greater specificity than the earlier enzyme, *Euphorbia peplus* TPS8 (Andersen-Ranberg et al. Angew Chem Int Ed 55(6):2142-2146 (2016)). Finally, OmTPS5 enables efficient and specific production of palustradiene 1291 from 31. The other known biosynthetic route to 29 is as a minor spontaneous degradation product of 13-hydroxy-8(14)-abietane from *Picea abies* levopimaradiene/abietadiene synthase and related enzymes.

ArTPS2 is of particular interest for applications in agricultural biotechnology. Neo-clerodane diterpenoids, particularly those with an epoxide moiety at the 4(18)-position, have garnered significant attention for their ability to deter insect herbivores. The 4(18)-desaturated product of ArTPS2 could be used in biosynthetic or semisynthetic routes to potent insect antifeedants.

Definitions

As used herein, the singular forms "a," "an," and "the" are intended to include the plural forms as well, unless the context clearly indicates otherwise. Also, as used herein, "and/or" refers to, and encompasses, any and all possible combinations of one or more of the associated listed items. Unless otherwise defined, all terms, including technical and scientific terms used in the description, have the same meaning as commonly understood by one of ordinary skill in the art to which this invention pertains.

The term "about", as used herein, can allow for a degree of variability in a value or range, for example, within 10%, within 5%, or within 1% of a stated value or of a stated limit of a range.

The term "enzyme" or "enzymes", as used herein, refers to a protein catalyst capable of catalyzing a reaction. Herein, the term does not mean only an isolated enzyme, but also includes a host cell expressing that enzyme. Accordingly, the conversion of A to B by enzyme C should also be construed to encompass the conversion of A to B by a host cell expressing enzyme C.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location or are associated with portions of the chromosome not found in nature (e.g., the heterologous nucleic acids are expressed in tissues where the gene is not normally expressed).

The terms "identical" or percent "identity", as used herein, in the context of two or more nucleic acids or polypeptide sequences, refer to two or more sequences or subsequences that are the same or have a specified percentage of amino acid residues or nucleotides that are the same (e.g., 75% identity, 80% identity, 85% identity, 90% identity, 95% identity, 97% identity, 98% identity, 99% identity, or 100% identity in pairwise comparison). Sequence identity can be determined by comparison and/or alignment of sequences for maximum correspondence over a comparison window, or over a designated region as measured using a sequence comparison algorithm, or by manual alignment and visual inspection. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. A "reference sequence" is a defined sequence used as a basis for a sequence comparison; a reference sequence may be a subset of a larger sequence.

As used herein, a "native" nucleic acid or polypeptide means a DNA, RNA or amino acid sequence or segment that has not been manipulated in vitro, i.e., has not been isolated, purified, amplified and/or modified.

As used herein, the term "plant" is used in its broadest sense. It includes, but is not limited to, any species of grass (fodder, ornamental or decorative), crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances, the plant part can include vegetative tissues of the plant.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

As used herein the term "terpene" includes any type of terpene or terpenoid, including for example any monoterpene, diterpene, sesquiterpene, sesterterpene, triterpene, tetraterpene, polyterpene, and any mixture thereof.

The term "transgenic" when used in reference to a plant or leaf or vegetative tissue or seed for example a "transgenic plant," transgenic leaf," "transgenic vegetative tissue," "transgenic seed," or a "transgenic host cell" refers to a plant or leaf or tissue or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples describe some procedures that can be performed to facilitate making and using the invention.

Example 1: Materials and Methods

This Example illustrates some of the materials and methods used in the development of the invention.

Data Mining

A subset of the NAPRALERT database including all the occurrences of diterpenoids in mint species was obtained. NAPRALERT reports chemical names, but not structures. For Lamiaceae, the species reported in NAPRALERT largely overlap with those from the Dictionary of Natural Products (DNP), which does include structures. A simplifying assumption was therefore made that each unique name represents a unique compound, and structures for the 3080 Lamiaceae diterpenes in NAPRALERT were not all located due to the deficiencies of the NAPRALERT database.

For SISTEMAT, structure files were obtained by redrawing the structures from the publication by Alvarenga et al. (2001) into MarvinSketch (ChemAxon, Budapest. Hungary). The occurrence counts were obtained by transcribing the association table into a spreadsheet. A publicly available digital version of SISTEMAT, called SISTAMATX exists (see website at sistematx.ufpb.br/), but there is no option for bulk downloads, limiting assessment of its completeness or the ability to cross-reference it with other data. For the present work, the proprietary DNP therefore appeared to be one of the only viable option for many analyses.

Lamiaceae diterpene structures were obtained from the DNP by searching for them through the DNP web interface. Additional compounds were found by searching for individual species names for which transcriptome data was available. This additional search step was used because some species have been reclassified between families, or their family is not correctly annotated in the DNP. Records for all the Lamiaceae diterpenes were downloaded and converted into a spreadsheet using a Python script. Species names were extracted from the Biological Source field in a semi-automated method. The DNP contains structural information in the form of IUPAC International Chemical Identifier (InChI) strings (Heller et al. J Cheminform 7 (2015)). In most cases, the DNP InChIs do not include stereochemical information, so for consistency, all stereochemical information was ignored. Skeletons were extracted from the structures using the RDKit (see website at rdkit.org) Python interface. Briefly, all bonds were converted into single bonds, bonds involving at least one non-carbon atom were broken, and the fragment with a carbon-count closest to 35 was retained as the skeleton. The resulting skeletons were then manually examined to correct those where the algorithm chose the wrong fragment, for example, a small number of diterpenoids are attached to acyl chains of more than 20 carbons, in which case the algorithm would incorrectly select the acyl chain as the skeleton; the diterpenoid was therefore selected instead. There are a few cases where sesquiterpenes or other terpenes seemed to have been misannotated in DNP as diterpenes, and those sesquiterpenes or other terpenes were left in the dataset, but their presence or absence does not significantly change any of the analyses.

For all three databases, genus and species names were cross-referenced to TaxIDs from the NCBI Taxonomy database (Federhen Nucleic Acids Res 40(D1): D136-D143 (2012)), first by automated text comparisons, then by manual inspection of un-matched names. Genus level TaxID assignments were possible for every entry in NAPRALERT and the DNP, but in some cases, species-level TaxID assignments were not possible, so species-level analyses were avoided.

Phylogenetic Trees

Peptide sequences were aligned using Clustal Omega (v. 1.2.1) (Sievers et al., Molecular Systems Biology 7:539 (2011)) and maximum likelihood trees were generated using RAxML (v. 8.2.11) (Stamatakis Bioinformatics 30(9):1312-1313 (2014)) using automatic model selection and 1000 bootstrap iterations. Tree visualizations were generated using ETE3 (Huerta-Cepas Mol Biol Evol 33(6):1635-1638 (2016)).

Plant Material, RNA Isolation and cDNA Synthesis

The following types of plants were obtained from different commercial nurseries or botanical gardens: *Ajuga reptans* L., *Hyptis suaveolens* (L.) Poit., *Leonotis leonurus* (L.) R.Br., *Mentha spicata* L., *Nepeta mussinii* Spreng. ex Henckel, *Origanum majorana* L., *Perovskia atriplicifolia* Benth., *Plectranthus barbatus, Pogostemon cablin* (Blanco) Benth., *Prunella vulgaris* L., and *Salvia officinalis* L. The plants were grown in a greenhouse under ambient photoperiod and 24° C. day/17° C. night temperatures. *Nicotiana benthamiana* were grown in a greenhouse under 16 h light (24° C.) and 8 h dark (17° C.) regime.

Total RNA from leaf tissues of *A. reptans, N. mussinii, L. leonurus, P. atriplicifolia*, and *S. officinalis* was extracted using methods described by Hamberger et al. (*Plant Physiology* 157(4):1677-1695 (2011)). Total RNA from leaves of *P. vulgaris, M. spicata, P. cablin, H. Suaveolens, O. majorana* was extracted using the Spectrum Plant Total RNA Kit (Sigma-Aldrich, St. Louis, MO, USA). RNA extraction was followed by DNase I digestion using DNA-Free™ DNA Removal Kit (Thermo Fisher Scientific, Waltham, MA, USA). First-strand cDNAs were synthesized from 5 μg of total RNA, with oligo(dT) primer, using the RevertAid First Strand cDNA Synthesis Kit (Thermo Fisher Scientific, Waltham, MA, USA). cDNA was diluted 5-fold and used as template for cloning of full length cDNAs. See Table 2 for primers and other oligonucleotides.

Characterization of diTPS Genes by Transient Expression in *N. benthamiana*

Full length coding sequences of diTPSs were cloned into pEAQ-HT vector (Sainsbury et al., 2009: kindly provided by Prof. G. Lomonossoff, John Innes Centre, UK) using In-Fusion® HD Cloning Plus (Takara Bio, California, USA). pEAQ-HT vector contains a copy of anti-post transcriptional gene silencing protein p19 that suppresses the silencing of transgenes (Voinnet et al. *The Plant Journal* 33(5):949-956). Expression vectors carrying full length coding sequence of candidate diTPS genes were transformed into the LBA4404 *A. tumefaciens* strain by electroporation. DXS and GGPPS are known to be the rate limiting enzymes in GGPP biosynthesis and have been shown to substantially increase the production of diterpenes in *N. benthamiana* system. Therefore, the *Plectranthus barbatus* 1-deoxy-D-xylulose 5-phosphate synthase (CfDXS) (genbank accession: KP889115) and geranylgeranyl diphosphate synthase (CfGGPPS) (genbank accession: KP889114) coding regions were cloned, and a chimeric polyprotein was created with a LP4-2A hybrid linker peptide between CfDXS and CfGGPPS. LP4/2A contains the first nine amino acids of LP4 (a linker peptide originating from a natural polyprotein occurring in seeds of *Impatiens balsamina*) and 20 amino acids of the self-processing FMDV 2A (2A is a peptide from the foot-and-mouth disease virus).

The transformed *A. tumefaciens* were subsequently transferred to 1 mL SOC media and grown for 1 hour at 28° C. 100 μL cultures were transferred to LB-agar solid media containing 50.0 μg/mL rifampicin and 50.0 μg/mL kanamycin and grown for 2 days. A single colony PCR positive clone was transferred to 10 mL LB media in a falcon tube containing 50.0 μg/mL rifampicin and 50.0 μg/mL kanamycin and grown at 28° C. over-night (at 225 rpm). About 1% of the primary culture was transferred to 25 mL of fresh LB media and grown overnight. Cells were pelleted by centrifugation at 4000×g for 15 min and resuspended in 10 mL water containing 200 μM acetosyringone. Cells were diluted with water-acetosyringone solution to a final $OD_{600}$ of 1.0 and incubated at 28° C. for 2-3 hours to increase the infectivity. Equal volumes of culture containing the plasmids with cDNA encoding different diTPS genes were mixed. Each combination of *A. tumefaciens* culture mixture was infiltrated into independent 4-5 weeks old *N. benthamiana* plants. Plants were grown for 5-7 days in the greenhouse before metabolite extraction. Leaf discs of 2 cm diameter (approximately 0.1 g fresh weight) were cut from the infiltrated leaves. Diterpenes were extracted in 1 mL n-hexane with 1 mg/L 1-eicosene as internal standard (IS) at room temperature overnight in an orbital shaker at 200 rpm. Plant material was collected by centrifugation and the organic phase transferred to GC vials for analysis.

In-Vitro Enzyme Activity Assays

To confirm the biosynthetic products obtained in *N. benthamiana*, diTPS combinations were tested in in vitro assays as described by Pateraki et al. (*Plant Physiol* 164(3): 1222-1236 (2014)). TargetP (Emanuelsson et al. *Journal of Molecular Biology* 300(4):1005-1016 (2000)) was used for prediction of the plastidial target sequence. Pseudo mature variants versions of HsTPS1, ArTPS2, PcTPS1, OmTPS3, OmTPS5, SsSS, CfTPS1, CfTPS2 and codon optimized CfTPS3 (IDT, USA), lacking the predicted plastidial targeting sequences were cloned in pET-28b(+) (EMD Millipore, Burlington, MA), then expressed and purified from *E. coli.* The pET_diTPS constructs were transformed into chemically competent OverExpress™ C41(DE3) cells (Lucigen, Middleton, WI, USA), the cells were inoculated in a starter culture with terrific broth medium and 50 μg $mL^{-1}$ kanamycin, then grown overnight. About 1% of the starter culture was used to inoculate 50 mL terrific broth medium having 50 μg $mL^{-1}$ kanamycin, and the culture was grown at 37° C. with mixing at 200 rpm until the $OD_{600}$ reached 0.4. Cultures were grown at 16° C. until an $OD_{600}$ of approximately 0.6-0.8 was achieved at which point cultures were induced by 0.2 mM IPTG. Expression was allowed to proceed overnight, and cells were harvested by centrifugation at 5000 g/4° C. for 15 minutes. Cell pellets were resuspended in lysis buffer containing 20 mM HEPES, pH 7.5, 0.5 M NaCl, 25 mM Imidazole, 5% [v/v] glycerol, using one protease inhibitor cocktail tablet per 100 mL (Sigma Aldrich, St. Louis, MO, USA). Lysozyme (0.1 mg per liter) was added to the cell pellet, and the mixture was gently shaken for 30 min, then lysed by sonication. Cell lysate was centrifuged for 25 min at 14000 g, and the supernatant was subsequently used for purification of the recombinant proteins. Proteins were purified on 1-mL His SpinTrap columns (GE Healthcare Life Sciences, Piscataway, NJ, USA) using elution buffer (HEPES, pH 7.5, 0.5 M NaCl, 5% [v/v] glycerol, 350 mM Imidazole and 5 mM dithiothreitol [DTT]) and desalted on PD MiniTrap 0-25 columns (GE Healthcare, Life Sciences, Piscataway, NJ, USA) with a desalting buffer (20 mM HEPES, pH 7.2, 350 mM NaCl, 5 mM DTT, 1 mM $MgCl_2$, 5% [v/v] glycerol). In-vitro diTPS assays were performed by adding 15 μM GGPP and 50-100 μg purified enzymes in 400 μL enzyme assay buffer (50 mM HEPES, pH 7.2, 7.5 mM $MgCl_2$, 5% [v/v] glycerol, 5 mM DTT). 500 mL n-hexane (Fluka GC-MS grade) containing 1 ng/ml 1-eicosene as internal standard was gently added as an overlay onto the reaction mix. Assays were incubated for 60-120 min at 30° C. with mixing at approximately 75 rpm, and the hexane overlay was subsequently removed by centrifugation at 1500×g for 15 min before proceeding for GC-MS analysis.

Metabolite Analysis of *O. majorana*

Fresh leaf, stem, root, and flowers (20 to 50 mg) of *O. majorana* were harvested. Flowers were further separated with forceps into two parts, the green part ("calyx"), and the rest of the flower ("corolla"). Tissues were extracted overnight in 500 μL of methyl tert-butyl ether. Extracts were concentrated to 100 μL and subjected to GC-MS analysis.

Compound Purification

For bulk production of diterpenes for structural determination, 15-30 *N. benthamiana* plants were vacuum infiltrated with diTPS combinations as well as CfGGPPS and CfDXS (46). After 5 days, 100-200 g (fresh weight) of leaves were subjected to two rounds of overnight extractions in 500 mL hexane, which was then concentrated using a rotary evaporator. Compounds were purified on silica gel columns using a mobile phase of hexane with 0-20% ethyl-acetate. In some cases, additional rounds of column purification, or preparative TLC using a hexane/ethyl-acetate or chloroform/methanol mobile phase, were necessary to obtain compounds of sufficient purity for structural determination by NMR.

GC-MS

All GC-MS analyses were performed on an Agilent 7890A GC with an Agilent VF-5 ms column (30 m×250 μm×0.25 μm, with 10m EZ-Guard) and an Agilent 5975C detector. For *N. benthamiana* and in-vitro assays, the inlet was set to 250° C. splitless injection, using helium carrier gas with column flow of 1 mL/min. The oven program was 45° C. hold 1 min, 40° C./min to 230° C., 7° C./min to 320° C. hold 3 min. The detector was activated after a four-minute solvent delay. For analysis of *O. majorana* extracts, conditions were the same, except that the solvent cutoff was set to six minutes to allow monoterpenes to pass, and the oven program was a 45° C. hold for 1 min., 40° C./min to 200° C. 5° C./min to 260° C., 40° C./min to 320° C. with a hold for 3 min.

NMR and Optical Rotation

The NMR spectra for trans-biformene (Yamada et al. The Journal of Antibiotics 69(7):515-523 (2016)) were measured on a Bruker AVANCE 900 MHz spectrometer. All other spectra were measured on an Agilent DirectDrive2 500 MHz spectrometer. All NMR was done in $CDCl_3$ solvent. The $CDCl_3$ peaks were referenced to 7.24 ppm and 77.23 ppm for $^1H$ and $^{13}C$ spectra, respectively. To aid in the interpretation of NMR spectra, the NAPROC-13 (Lopez-Perez et al. Bioinformatics 23(23):3256-3257 (2007)), and Spektraris (Fischedick et al., Phytochemistry 113:87-95 (2015)) databases were used. Reconstruction of $^{13}C$ spectra from the literature was performed with MestReNova (Mestrelab Research, Santiago de Compostela, Spain). Optical rotation was measured in chloroform at ambient temperature using a Perkin Elmer Polarimeter 341 instrument.

TABLE 2

List of synthetic oligonucleotides

| Primer Name (gene) | Sequence |
|---|---|
| Amplification of full length genes from cDNA synthesized from plant tissues total RNA | |
| ZmAN2-F (ZmAN2) | ATGGTTCTTTCATCGTCTTGCACA (SEQ ID NO: 61) |
| ZmAN2-R (ZmAN2) | TTATTTTGCGGCGGAAACAGGTTCA (SEQ ID NO: 62) |
| CfTPS2-F (CfTPS2) | AGATTGAGGATTCCATTGAGTACGTGAAGG (SEQ ID NO: 63) |

TABLE 2-continued

List of synthetic oligonucleotides

| Primer Name (gene) | Sequence |
|---|---|
| CfTPS2-R (CfTPS2) | GAAGTTTAATATCCTTCATTCTTTATTACA (SEQ ID NO: 64) |
| CfTPS3-F (CfTPS3) | AGCTCCATTCAACTAGAGTCATGTCGT (SEQ ID NO: 65) |
| CfTPS3-R (CfTPS3) | TTCATCTGGCTTAACTAGTTGCTGACAC (SEQ ID NO: 66) |
| CfTPS16-F (CfTPS16) | TTAAAGTACTCTCTCAAAGAGTACTTTGG (SEQ ID NO: 67) |
| CfTPS16-R (CfTPS16) | GCGACCAACCATCATACGACT (SEQ ID NO: 68) |
| LlTPS1-F (LlTPS1) | AATGGCCTCCACTGCATCCACTCTA (SEQ ID NO: 69) |
| LlTPS1-R (LlTPS1) | CCATACTCATTCAACTGGTTCGAACA (SEQ ID NO: 70) |
| LlTPS4-F (LlTPS4) | AGCCTGTGTACTCGAAATGTC (SEQ ID NO: 71) |
| LlTPS4-R (LlTPS4) | CAAGAGGATGATTCATGTACCAAC (SEQ ID NO: 72) |
| SoTPS1-F (SoTPS1) | TCTCTTTCAAGAATATCCCCTCTC (SEQ ID NO: 73) |
| SoTPS1-R (SoTPS1) | GGCATTCAATGATTTTGAGTCG (SEQ ID NO: 74) |
| ArTPS1-F (ArTPS1) | AAATGGCCTCTTTGTCCACTCTC (SEQ ID NO: 75) |
| ArTPS1-R (ArTPS1) | TTACGCAACTGGTTCGAAAAGCA (SEQ ID NO: 76) |
| ArTPS2-F (ArTPS2) | TAATGTCATTTGCTTCCCAAGCCA (SEQ ID NO: 77) |
| ArTPS2-R (ArTPS2) | GGCCTAGACTATACCTTCTCAAACAA (SEQ ID NO: 78) |
| ArTPS3-F (ArTPS3) | AATGTCACTCTCGTTCACCATCAA (SEQ ID NO: 79) |
| ArTPS3-R (ArTPS3) | ACTTCAAGAGGATGAAGTGTTTAGG (SEQ ID NO: 80) |
| PaTPS1-F (PaTPS1) | CTCCAAAACTCGGGCCGGTAAAT (SEQ ID NO: 81) |
| PaTPS1-R (PaTPS1) | TACGTATTTCCTCACAATCGAGCA (SEQ ID NO: 82) |
| PaTPS3-F (PaTPS3) | CTAGAAATGTTACTTGCGTTCAAC (SEQ ID NO: 83) |
| PaTPS3-R (PaTPS3) | GGGTAAGAGTTGAATTTAGATGTCT (SEQ ID NO: 84) |
| NmTPS1-F (NmTPS1) | ATGACTTCAATATCCTCTCTAAATTTGAGC (SEQ ID NO: 85) |
| NmTPS1-R (NmTPS1) | GAATATAGTAATCAGACGACCGGTCCA (SEQ ID NO: 86) |
| NmTPS2-F (NmTPS2) | GCCATATCATGTCTCTTCCGCTCT (SEQ ID NO: 87) |
| NmTPS2-R (NmTPS2) | TTATTCATGCACCTTAAAATCCTTGAGAG (SEQ ID NO: 88) |

TABLE 2-continued

| Primer Name (gene) | Sequence |
|---|---|
| List of synthetic oligonucleotides | |
| OmTPS1-F (OmTPS1) | ATGACCGATGTATCCTCTCTTCGT (SEQ ID NO: 89) |
| OmTPS1-R (OmTPS1) | AAACACTCACATAACCGGCCCAA (SEQ ID NO: 90) |
| OmTPS3-F (OmTPS3) | GTCCTTGCTTTCGGAATACT (SEQ ID NO: 91) |
| OmTPS3-R (OmTPS3) | GAAGTGATCTACAAGGATTCATAAA (SEQ ID NO: 92) |
| OmTPS4-F (OmTPS4) | TCATTGATTTGCCCTGCATCCAC (SEQ ID NO: 93) |
| OmTPS4-R (OmTPS4) | CAAAGCTAGTGCTGCTTCTGATT (SEQ ID NO: 94) |
| OmTPS5-F (OmTPS5) | ATGGTATCTGCATGTCTAAAACTCAA (SEQ ID NO: 95) |
| OmTPS5-R (OmTPS5) | CTTTCTCTCTCTTGTGCATCTTAGT (SEQ ID NO: 96) |
| MsTPS1-F (MsTPS1) | ACGTTCATCTTCAATGAGTTCCA (SEQ ID NO: 97) |
| MsTPS1-R (MsTPS1) | TACGTGTATGTCGATCTGTTCCAAT (SEQ ID NO: 98) |
| PcTPS1-F (PcTPS1) | CATGTCATTTGCTTCTCAATCAC (SEQ ID NO: 99) |
| PcTPS1-R (PcTPS1) | CCCATTATCTAAAAGTCTACATCACC (SEQ ID NO: 100) |
| HsTPS1-F (HsTPS1) | TCCTCATAAAGCAATGGCGTATA (SEQ ID NO: 101) |
| HsTPS1-R (HsTPS1) | CTAAGATTCAGACAATGGGCTCA (SEQ ID NO: 102) |
| EpTPS8-F (EpTPS8) | GCAGACGCCAATCTTTCTTGGT (SEQ ID NO: 103) |
| EpTPS8-R (EpTPS8) | TTATGAAGTTAAAAGGAGTGGTTCGTTGAC (SEQ ID NO: 104) |
| PVTPS1-F (PVTPS1) | GGAACGAGAAATGTCACTCAC (SEQ ID NO: 105) |
| PVTPS1-R (PVTPS1) | TTCTAGTTTCTCACAGAAGTCAA (SEQ ID NO: 106) |
| LP4-2A Ver.1 sequence | TCAAATGCAGCAGACGAAGTTGCTACT CAACTTTTGAATTTTGACTTGCTGAAGTT GGCTGGTGATGTTGAGTCAAACCCTGGACCT (SEQ ID NO: 107) |
| Cloning of full length diTPS genes into pEAQ-HT for transient expression in N. benthamiana | |
| pEAQ_Infusion_CfTPS1-F (CfTPS1) | TTCTGCCCAAATTCGATGGGGTCTCTATC CACTATGA (SEQ ID NO: 108) |
| pEAQ_Infustion_CfTPS1-R (CfTPS1) | AGTTAAAGGCCTCGATCAGGCGACTGGTTCG AA AAGTA (SEQ ID NO: 109) |
| pEAQ_Infusion_SsSCS-F (SsSS) | TTCTGCCCAAATTCGATGTCGCTCGCCTT CAAC (SEQ ID NO: 110) |

TABLE 2-continued

| List of synthetic oligonucleotides | |
|---|---|
| Primer Name (gene) | Sequence |
| pEAQ_Infusion_SsSCS-R (SsSS) | AGTTAAAGGCCTCGATCAAAAGACAAAGGAT T TCATA (SEQ ID NO: 111) |
| pEAQ_Infusion_ZmAN2-F (ZmAN2) | TTCTGCCCAAATTCGATGGTTCTTTCATCG TCTT GCAC (SEQ ID No: 112) |
| pEAQ_Infusion_ZmAN2-R (ZmAN2) | AGTTAAAGGCCTCGATTATTTTGCGGCGGAA AC AGGT (SEQ ID NO: 113) |
| pEAQ_Infusion_CfTPS2-F (CfTPS2) | TTCTGCCCAAATTCGATGAAAATGTTGATG ATCA AAAGT (SEQ ID NO: 114) |
| pEAQ_Infusion_CfTPS2-R (CfTPS2) | AGTTAAAGGCCTCGATCAGACCACTGGTT CAAA TAGTA (SEQ ID NO: 115) |
| pEAQ_Infusion_CfTPS3-F (CfTPS3) | TTCTGCCCAAATTCGATGTCGTCCCTCGCC GGC AACCT (SEQ ID NO: 116) |
| pEAQ_Infusion_CfTPS3-R (CfTPS3) | AGTTAAAGGCCTCGACTAGTTGCTGACACAA CT CATT (SEQ ID NO: 117) |
| pEAQ_Infusion_CfTPS16-F (CfTPS16) | TTCTGCCCAAATTCGATGCAGGCTTCTATGTC ATCT (SEQ ID NO: 118) |
| pEAQ_Infusion_CfTPS16-R (CfTPS16) | AGTTAAAGGCCTCGATCATACGACTGGTTCA AA CATT (SEQ ID NO: 119) |
| pEAQ_Infusion_LlTPS1-F (LlTPS1) | TTCTGCCCAAATTCGATGGCCTCCACTGCATC C (SEQ ID NO: 120) |
| pEAQ_Infusion_LlTPS1-R (LlTPS1) | AGTTAAAGGCCTCGATCATTCAACTGGTTCGA ACAA (SEQ ID NO: 121) |
| pEAQ_Infusion_LlTPS2-F (LlTPS2) | TTCTGCCCAAATTCGATGATTCCTAATCCCGA AA (SEQ ID NO: 122) |
| pEAQ_Infusion_LlTPS2-R (LlTPS2) | AGTTAAAGGCCTCGATTACATTGGCAATCCG ATGAA (SEQ ID NO: 123) |
| pEAQ_Infusion_LlTPS4-F (LlTPS4) | TTCTGCCCAAATTCGATGTCGGTGGCGTTCAA CCT (SEQ ID NO: 124) |
| pEAQ_Infusion_LlTPS4-R (LlTPS4) | AGTTAAAGGCCTCGATCAAGAGGATGATTCA TG TACC (SEQ ID NO: 125) |
| pEAQ_Infusion_SoTPS1-F (SoTPS1) | TTCTGCCCAAATTCGATGTCCCTCGCCTTCAA CG (SEQ ID NO: 126) |
| pEAQ_Infusion_SoTPS1-R (SoTPS1) | AGTTAAAGGCCTCGATCATTTGCCACTCACAT TT (SEQ ID NO: 127) |
| pEAQ_Infusion_ArTPS1-F (ArTPS1) | TTCTGCCCAAATTCGATGGCCTCTTTGTCCAC TTTCC (SEQ ID NO: 128) |
| pEAQ_Infusion_ArTPS1-R (ArTPS1) | AGTTAAAGGCCTCGATCACGCAACTGGTTCG AAA AGA (SEQ ID NO: 129) |

TABLE 2-continued

List of synthetic oligonucleotides

| Primer Name (gene) | Sequence |
|---|---|
| pEAQ_Infusion_ArTPS2-F (ArTPS2) | TTCTGCCCAAATTCGATGTCATTTGCTTCCCA AG CCAC (SEQ ID NO: 130) |
| pEAQ_Infusion_ArTPS2-R (ArTPS2) | AGTTAAAGGCCTCGACTAGACTACCTTCTCAA ACA ATAC (SEQ ID NO: 131) |
| pEAQ_Infusion_ArTPS3-F (ArTPS3) | TTCTGCCCAAATTCGATGTCACTCTCGTTCAC CATCA (SEQ ID NO: 132) |
| pEAQ_Infusion_ArTPS3-R (ArTPS3) | AGTTAAAGGCCTCGATCAAGAGGATGAAGTG TTTAG (SEQ ID NO: 133) |
| pEAQ_Infusion_PaTPS1-F (PaTPS1) | TTCTGCCCAAATTCGATGACCTCTATGTCCTC TCTAA (SEQ ID NO: 134) |
| pEAQ_Infusion_PaTPS1-R (PaTPS1) | AGTTAAAGGCCTCGATCATACGACCGGTCCA AAC AGT (SEQ ID NO: 135) |
| pEAQ_Infusion_PaTPS3-F (PaTPS3) | TTCTGCCCAAATTCGATGTTACTTGCGTTCAA CATA AGC (SEQ ID NO: 136) |
| pEAQ_Infusion_PaTPS3-R (PaTPS3) | AGTTAAAGGCCTCGATTAATTAGGTAGGTAG AGGG GTT (SEQ ID NO: 137) |
| pEAQ_Infusion_NmTPS1-F (NmTPS1) | ATATTCTGCCCAAATTCGATGACTTCAATATC CTCT CTAAATTTGAGCAATG (SEQ ID NO: 138) |
| pEAQ_Infusion_NmTPS1-R (NmTPS1) | CAGAGTTAAAGGCCTCGATCAGACGACCGGT CCAA (SEQ ID NO: 139) |
| pEAQ_Infusion_NmTPS2-F (NmTPS2) | TTCTGCCCAAATTCGATGTCTCTTCCGCTCTC CTCT (SEQ ID NO: 140) |
| pEAQ_Infusion_NmTPS2-R (NmTPS2) | GATAAGTTAAAGGCCTCGATTATTCATGCACC TTA AAATCCTTGAGAGC (SEQ ID NO: 141) |
| pEAQ_Infusion_OmTPS1-F (OmTPS1) | TTCTGCCCAAATTCGATGACCGATGTATCCTC TCTTC (SEQ ID NO: 142) |
| pEAQ_Infusion_OmTPS1-R (OmTPS1) | AGTTAAAGGCCTCGATCACATAACCGGCCCA AACA (SEQ ID NO: 143) |
| pEAQ_Infusion_OmTPS3-F (OmTPS3) | TTCTGCCCAAATTCGATGGCGTCGCTCGCGTT CAC (SEQ ID NO: 144) |
| pEAQ_Infusion_OmTPS3-R (OmTPS3) | AGTTAAAGGCCTCGACTACAAGGATTCATAA ATT AAGGA (SEQ ID NO: 145) |
| pEAQ_Infusion_OmTPS4-F (OmTPS4) | TTCTGCCCAAATTCGCGAATGTCACTCGCCTT CAGC (SEQ ID NO: 146) |
| pEAQ_Infusion_OmTPS4-R (OmTPS4) | AGTTAAAGGCCTCGAGCTAGGAGCTTAGGGT TT TCAT (SEQ ID NO: 147) |
| pEAQ_Infusion_OmTPS5-F (OmTPS5) | TTCTGCCCAAATTCGATGGTATCTGCATGTCT AAA (SEQ ID NO: 148) |

TABLE 2-continued

| List of synthetic oligonucleotides | |
|---|---|
| Primer Name (gene) | Sequence |
| pEAQ_Infusion_OmTPS5-R (OmTPS5) | AGTTAAAGGCCTCGATCATGAAGGAATTGAA GGAA (SEQ ID NO: 149) |
| pEAQ_Infusion_MsTPS1-F (MsTPS1) | TTCTGCCCAAATTCGATGAGTTCCATTCGAAA TTT AAGT (SEQ ID NO: 150) |
| pEAQ_Infusion_MsTPS1-R (MsTPS1) | AGTTAAAGGCCTCGATCACTTGAGAGGCTCA AAC ATCAT (SEQ ID NO: 151) |
| pEAQ_Infusion_PcTPS1-F (PCTPS1) | TTCTGCCCAAATTCGATGTCATTTGCTTCTCA AT CAC (SEQ ID NO: 152) |
| pEAQ_Infusion_PcTPS1-R (PcTPS1) | AGTTAAAGGCCTCGACTACATCACCCTCTCAA ACA ATAC (SEQ ID NO: 153) |
| pEAQ_Infusion_HsTPS1-F (HsTPS1) | TTCTGCCCAAATTCGATGGCGTATATGATATC TAT TTCAAATCTC (SEQ ID NO: 154) |
| pEAQ_Infusion_HsTPS1-R (HsTPS1) | AGTTAAAGGCCTCGATCAGACAATGGGCTCA AAT AGAAC (SEQ ID NO: 155) |
| pEAQ_Infusion_EpTPS8-F (EpTPS8) | TTCTGCCCAAATTCGATGCAAGTCTCTCTCTC C CTCA (SEQ ID NO: 156) |
| pEAQ_Infusion_EpTPS8-R (EpTPS8) | AGTTAAAGGCCTCGATTATGAAGTTAAAAGG AG TGGTT (SEQ ID NO: 157) |
| pEAQ_Infusion_PVTPS1-F (PVTPS1) | TTCTGCCCAAATTCGCGAATGTCACTCACTTT CA ACG (SEQ ID NO: 158) |
| pEAQ_Infusion_PVTPS1-R (PVTPS1) | AGTTAAAGGCCTCGAGCTAGTTTCTCACAGA AG TCAA (SEQ ID NO: 159) |
| Cloning of diTPS genes into pET-28 b (+) for *E. coli* expression | |
| pET28_CfTPS1-F (CfTPS1) | AGGAGATATACCATGGCCGAGATTCGAGTG CCAC (SEQ ID NO: 160) |
| pET28_CfTPS1-R (CfTPS1) | GGTGGTGGTGCTCGAAGGCGACTGGTTCGAA AAG TAC (SEQ ID NO: 161) |
| pET28_SsSS-F (SsSS) | AGGAGATATACCATGGATTTCATGGCGAAAA TGAA AGAGA (SEQ ID NO: 162) |
| pET28_SsSS-R (SsSS) | GGTGGTGGTGCTCGAAAAAGACAAAGGATTT CATAT (SEQ ID NO: 163) |
| pET28_CfTPS2-F (cfTPS2) | AGGAGATATACCATGCAAATTCGTGGAAAGC AAAG ATCAC (SEQ ID NO: 164) |
| pET28_CfTPS2-R (CfTPS2) | GGTGGTGGTGCTCGAAGACCACTGGTTCAAA TAG AACT (SEQ ID NO: 165) |
| pET28_CfTPS3-F (CfTPS3) | AGGAGATATACCATGTCTAAATCATCTGCAG CTGT (SEQ ID NO: 166) |

TABLE 2-continued

| List of synthetic oligonucleotides | |
|---|---|
| Primer Name (gene) | Sequence |
| pET28_CfTPS3-R (CfTPS3) | GGTGGTGGTGCTCGAAGTTGCTGACACAACT CATT (SEQ ID NO: 167) |
| pET28_OmTPS3-F (OmTPS3) | AGGAGATATACCATGACCGTCAAATGCTAC (SEQ ID NO: 168) |
| pET28_OmTPS3-R (OmTPS3) | GGTGGTGGTGCTCGAACAAGGATTCATAAAT TAAG (SEQ ID NO: 169) |
| pET28_OmTPS5-F (OmTPS5) | AGGAGATATACCATGACTGTCAAGTGCAGC (SEQ ID NO: 170) |
| pET28_OmTPS5-R (OmTPS5) | GGTGGTGGTGCTCGAATGAAGGAATTGAAG (SEQ ID NO: 171) |
| pET28_PcTPS1-F (PcTPS1) | AGGAGATATACCATGTTTATGCCCACTTCCAT TAA ATGTA (SEQ ID NO: 172) |
| pET28_PcTPS1-R (PcTPS1) | GGTGGTGGTGCTCGAACATCACCCTCTCAAA CAA TACTTTGG (SEQ ID NO: 173) |
| pET28_HsTPS1-F (HsTPS1) | AGGAGATATACCATGGTAGCAAAAGTGATCG AGAG CCGAGTTA (SEQ ID NO: 174) |
| pET28_HsTPS1-R (HsTPS1) | GGTGGTGGTGCTCGAAGACAATGGGCTCAAA TAGA ACTTTAAAT (SEQ ID NO: 175) |

Example 2: Diversity of Diterpenoids in Lamiaceae

To help determine the most promising species in which to find previously unknown but useful diterpene synthase (diTPS) activities, a dataset of diterpene occurrences in Lamiaceae species and a dataset of functionally characterized diTPS genes from Lamiaceae were generated. Information about diterpene occurrence was collected from three sources, SISTEMAT, DNP, and NAPRALERT.SISTEMAT (Vestri et al. Phytochemistry 56(6):583-595 (2001)) contains Lamiaceae diterpenes reported up to 1997, including 91 unique carbon skeletons (the core alkanes, disregarding all desaturation, acyl-side chains, heteroatoms, and stereochemistry) from 295 species and 51 genera. An electronic copy of SISTEMAT was not available, so it was reconstructed based on the figures and tables in the paper.

The Dictionary of Natural Products (DNP; see website at dnp.chemnetbase.com, accessed Jan. 11, 2018) includes a wealth of information on diterpenes from Lamiaceae, including full structures and the species where those structures have been reported. NAPRALERT (Loub et al., J Chem Inf Comput Sci 25(2):99-103 (1985)) identifies compounds by their common name rather than their structure or skeleton, but it does associate the compounds to genus and species names, and gives various other information, such as the tissue where the compound was found.

To enable comparison among the databases, and cross-referencing with transcriptome and enzyme data, all genus and species names were converted into TaxIDs from the NCBI Taxonomy database (Federhen Nucleic Acids Res 40(D1): D136-D143 (2012)). To put structure occurrences into clearer evolutionary context, each genus was annotated as a member of one of the 12 monophyletic clades that form the backbone of Lamiaceae, as delineated by Li and colleagues (Li et al. Scientific Reports 6:34343 (2016)).

In the context of diTPSs, examination of skeletons can be helpful because the skeleton often resembles the diterpene synthase product more obviously than a highly decorated downstream product would. Therefore, the skeletons were extracted from the DNP structures. An example of such skeleton extraction is shown below, where Table 3A provides an example of which class I diTPS generate which products when using a *N. benthamiana* transient expression. Bold numbers refer to assigned compound numbers; "np" indicates that the combination was tested but no product was detected: "-" indicates that the combination was not tested. The following are newly identified enzymes: LITPS1, HsPS1, PcTPS1, ArTPS2, OmTPS1, ArTPS3, LITPS4, MsTPS1, NmTPS2, OmTPS3, OmTPS4, OmTPS5, PaTPS3, PvTPS1, and SoTPS1.

TABLE 3A

Index of Enzyme Types and Products Observed in Transient Expression Assays

| Enzyme | CfTPS1 [31] | CfTPS2 [10] | LlTPS1 [5] | ZmAN2 [16] | HsPS1 [21] | PcTPS1 [25] | ArTPS2 [38] | OmTPS1 [31] |
|---|---|---|---|---|---|---|---|---|
| ArTPS3 | 32 | 8 | 1, 2, 3 | np | — | — | np | — |
| LlTPS4 | 27 | 8 | 1, 2, 3 | np | — | — | — | — |
| MsTPS1 | 27 | 8 | 3 | np | — | — | np | — |
| NmTPS2 | np | np | np | 19 | — | — | np | — |
| OmTPS3 | 34 | 11 | 1, 2 | np | 24 | — | np | 34 |
| OmTPS4 | 33 | 8 | 1, 2, 3, 4 | 20 | — | — | — | 33 |
| OmTPS5 | 29 | 8 | 1, 2, 3 | np | — | — | np | 29 |
| PaTPS3 | 32 | 8 | 1, 2, 3 | np | — | — | — | — |
| PvTPS1 | 32 | 8 | 1, 2, 3 | np | — | — | — | — |
| SoTPS1 | 32 | 8 | 1, 2, 3 | np | — | — | — | — |
| CfTPS3 | 32 | 8 | 1, 2, 3 | np | 22 | np | np | 32 |
| SsSS | 33 | — | 4 | 20 | 23 | 26 | 37 | — |

Table 3B provides an example of an index of new class 11 diTPS enzymes and the products identified by functional assays of these enzymes using the *N. benthamiana* transient expression assay. The products were identified by GC-MS chromatography of hexane extracts from *N. benthamiana* transient expression assays that expressed new (+)-CPP synthases or new class II diTPSs along with reference combinations.

TABLE 3B

Products Identified for New Class II diTPS Enzymes

| Enzyme | Product |
|---|---|
| ArTPS1 | Copalyl-PP [31] |
| CfTPS16 | Copalyl-PP [31] |
| NmTPS1 | Copalyl-PP [31] |
| OmTPS1 | Copalyl-PP [31] |
| PaTPS1 | Copalyl-PP [31] |
| ArTPS2 | Neo-cleroda-4(18), 13E-dienyl-PP [38] |
| HsTPS1 | Labda-7,13E-dienyl-PP [21] |
| LlTPS1 | Peregrinol-PP [7] |
| PcTPS1 | Ent-labda-8,13E-dienyl-PP [25] |

Using data like that obtained in Tables 3A and 3B, a labdane skeleton was extracted from the forskolin structure shown below by deleting all heteroatoms, desaturations, and stereochemistry.

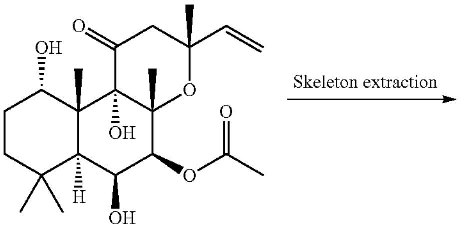

Forskolin

-continued

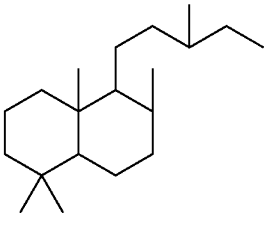

Labdane

A tabulation of the skeletons from SISTEMAT and DNP was therefore generated.

Figure 1D:
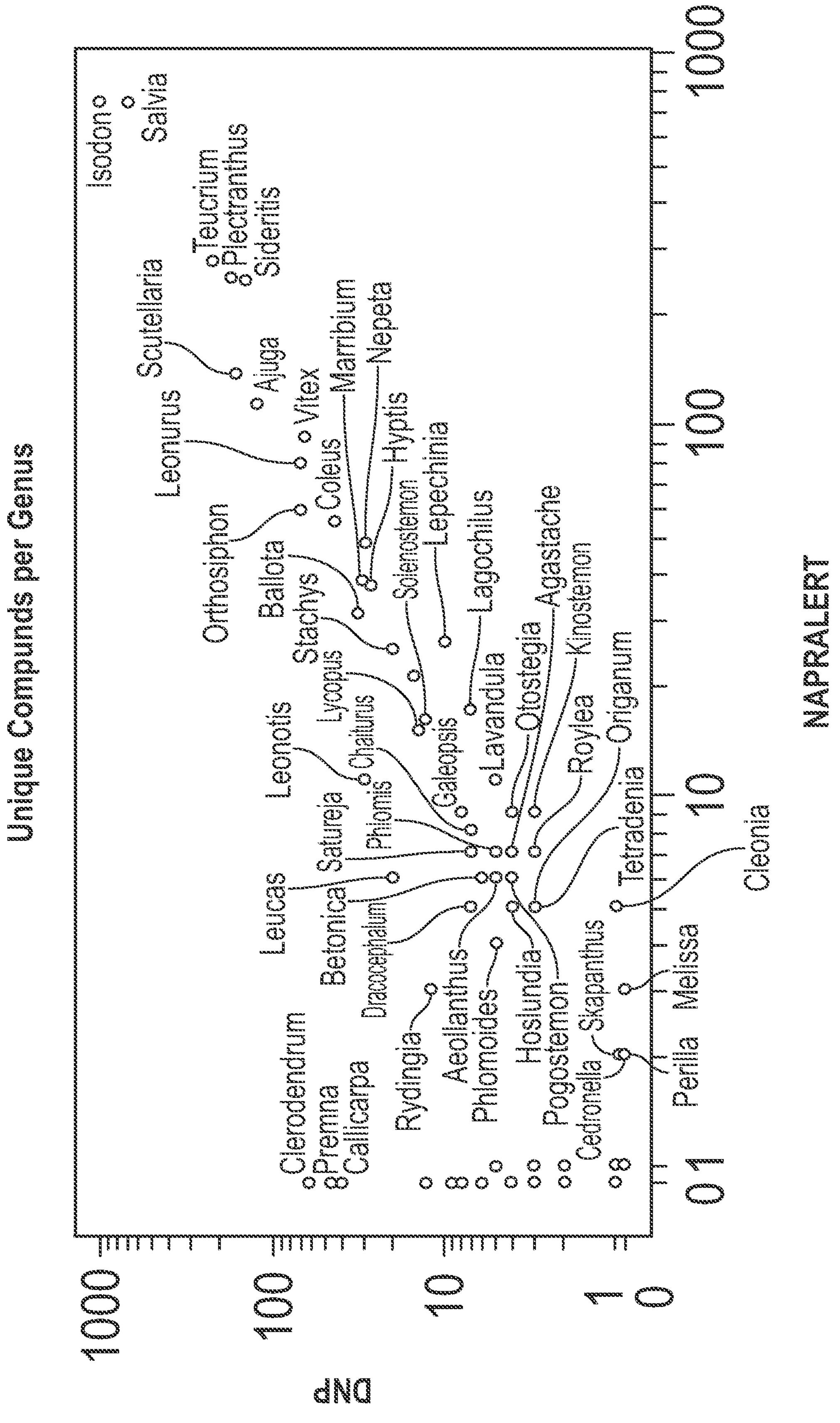

The three databases were relatively consistent in their estimations of the diversity and distribution of diterpenes and diterpene skeletons, as illustrated in Table 4 and FIG. 1B, 1D.

TABLE 4

Comparison of different sources for data about Lamiaceae diterpene chemotaxonomy

| | DNP | NAPRALERT | SISTEMAT |
|---|---|---|---|
| Genera | 67 | 60 | 44 |
| Species | 342 | 378 | — |
| Diterpene names | 3336 | 3080 | — |
| Diterpene structures | 3268 | — | — |
| Diterpene skeletons | 229 | — | 91 |

A total of 239 skeletons are represented, with five, the kaurane (Sk1), clerodane (Sk2), abietane (Sk3), labdane (Sk4), and pimarane (Sk6) being, by far, the most widely distributed and accounting for most of the total structures (Table 4, FIG. 1B-1C). The clerodane skeleton, for example, has the widest distribution, having been reported in 27 genera representing 9 of the 12 backbone clades, absent only in Tectona and two clades from which no diterpenes have yet been reported. The large number of less common, taxonomically restricted skeletons, including over 100 skeletons with only one associated compound (FIG. 1C), indicted to the inventors that searching across many species and genera would be a good strategy for finding diterpene synthases with new activities.

Example 3: Identifying Candidate Diterpene Synthase Genes

Through a comprehensive literature search, a reference set was built of known Lamiaceae diTPSs and their activities. Fifty-four functional diTPSs have been reported in this family, which correspond to thirty class II and 24 class I enzymes. Combinations of these diterpene synthases account for twenty-seven distinct products represented by six different skeletons, the five widely distributed skeletons, Sk1-4 and Sk6, as well as the less common atisane (Sk14) skeleton. This leaves 233 skeletons for which the biosynthetic route remains unknown. Further, a single skeleton can correspond to multiple distinct diTPS products, so there is also a possibility of finding new diTPS activities for skeletons already accounted for by known enzymes.

BLAST homology searches (Camacho et al. BMC Bioinformatics 10: 421 (2009)) were performed to the list of Lamiaceae diTPSs to mine 48 leaf transcriptomes made available by the Mint Genome Project (Boachon et al. Molecular Plant. (2018)) for candidate diTPSs. The number of diTPS candidates was cross-referenced to the number of diterpenes and diterpene skeletons reported from each species and genus (Table 5). Table 5 shows species from which diTPSs were selected for cloning, the total number of diTPS candidate sequences, and the number of unique diterpene structures and skeletons for those species, based on DNP.

TABLE 5

Species from which diTPSs were Isolated

| Full name | Code | diTPS hits | Diterpenes | Skeletons |
|---|---|---|---|---|
| *Ajuga reptans* | Ar | 5 | 13 | 2 |
| *Hyptis suaveolens* | Hs | 7 | 4 | 1 |
| *Leonotis leonurus* | Ll | 5 | 14 | 2 |
| *Mentha spicata* | Ms | 5 | 0 | 0 |
| *Nepeta mussinii* | Nm | 3 | 0 | 0 |
| *Origanum majorana* | Om | 5 | 0 | 0 |
| *Perovskia atriplicifolia* | Pa | 5 | 2 | 2 |
| *Plectranthus barbatus* | Cf | 5 | 50 | 10 |
| *Pogostemon cablin* | Pc | 2 | 0 | 0 |
| *Pruneila vulgaris* | Pv | 1 | 1 | 1 |
| *Salvia officinalis* | So | 5 | 13 | 5 |

A phylogenetic tree was generated from the peptide sequences from the reference set, alongside those from the new transcriptome data, including established substrates and products for each enzyme (FIG. 3A, 3B-1 to 3B-4). Candidate genes were selected from species such as *Mentha x spicata* and *Origanum majorana*, where the transcriptome data showed multiple candidate diTPSs likely existed but where few or no diterpene product structures have been reported. Genes were also selected that had relatively low homology to known enzymes. In this way, the inventors attempted to evenly cover of the sequence homology space. A few candidates from *Plectranthus* and *Salvia* were also selected based on the great diversity of diterpenes that have been reported from these genera.

Example 4: Characterization of Class H diTPSs

Figure 3A:
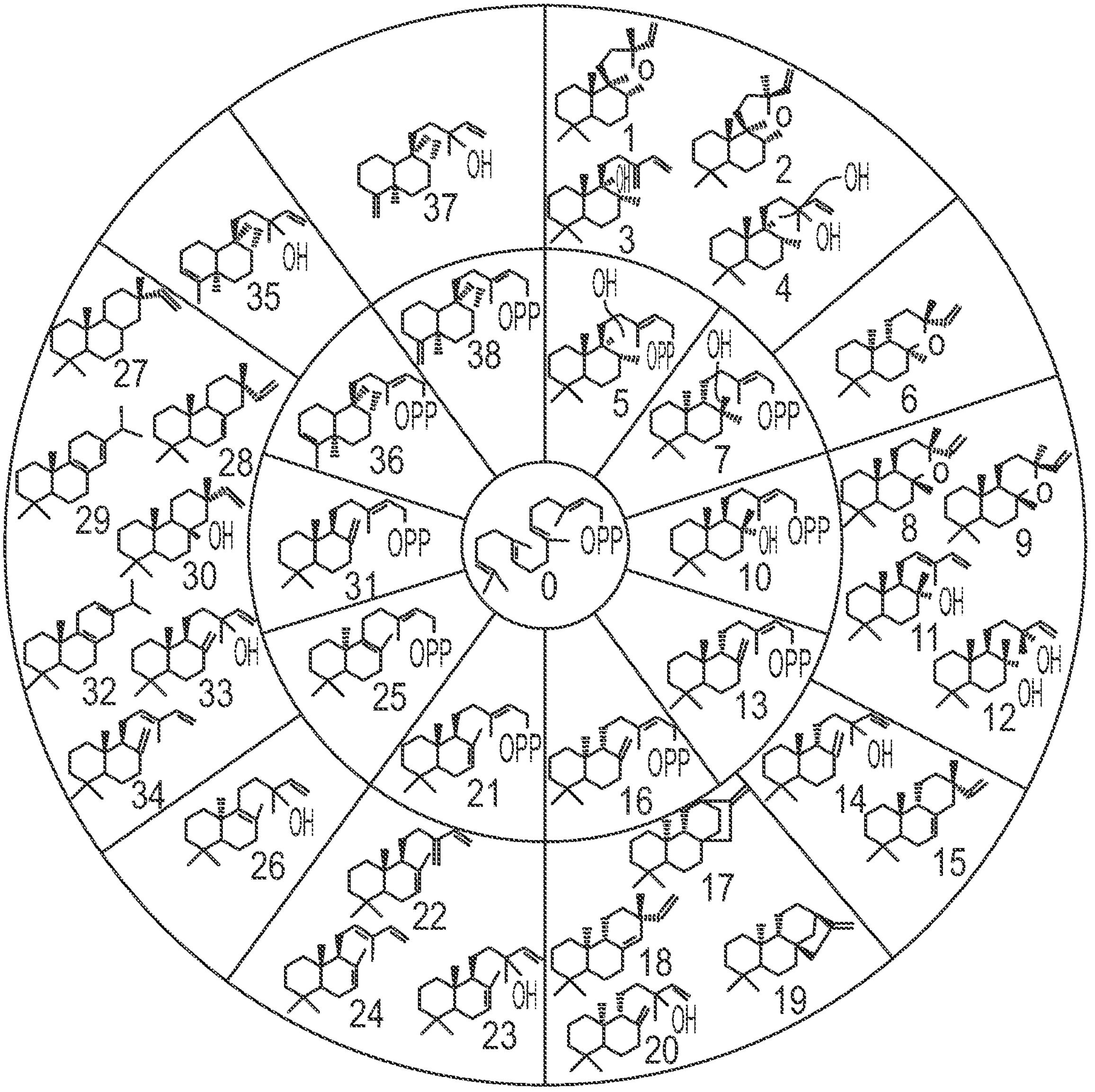
FIG. 3A-3B show structures of products of diterpene synthases from Lamiaceae and a phylogenetic tree was generated from the peptide sequences.
Figure 3B:
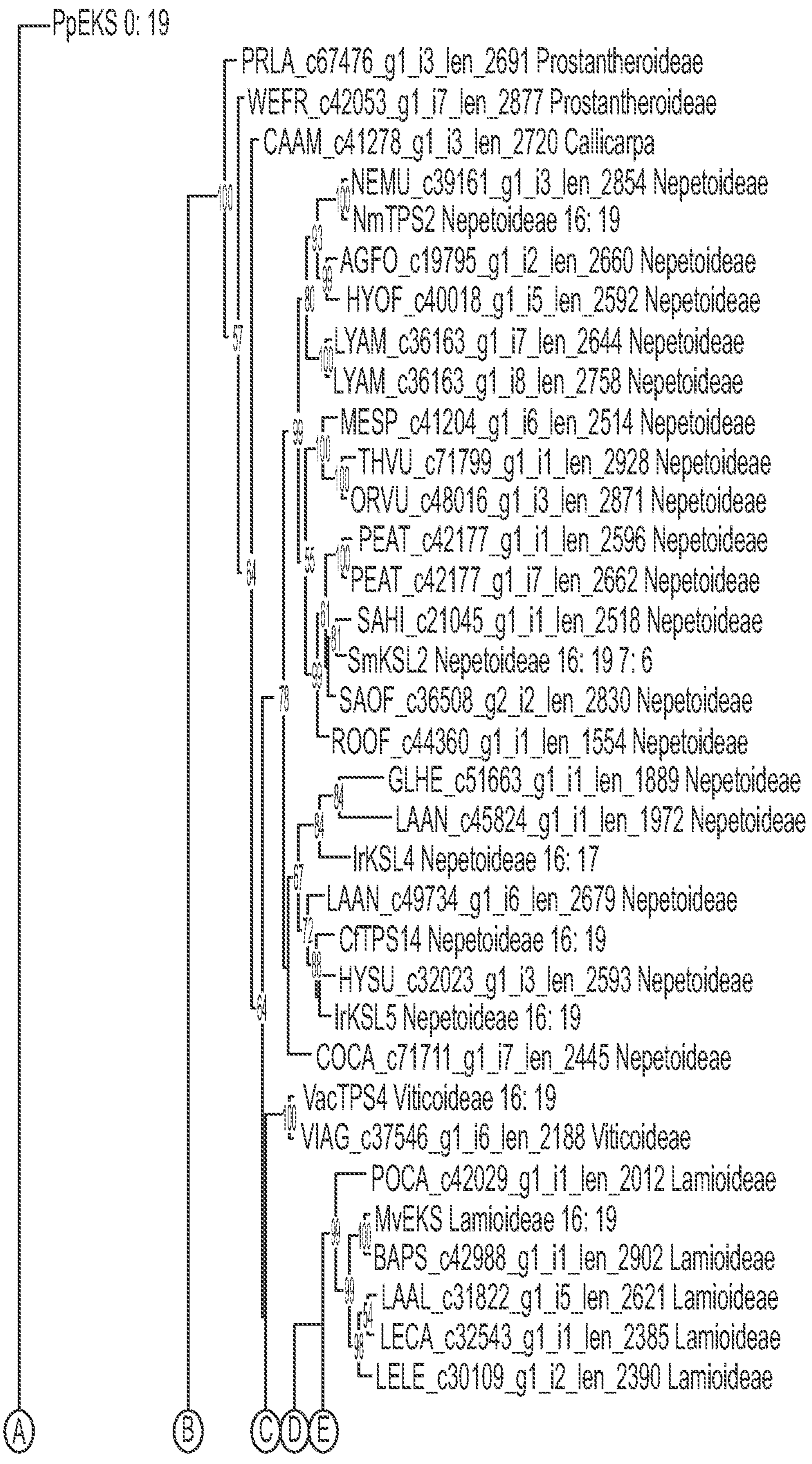
Figure 3B:
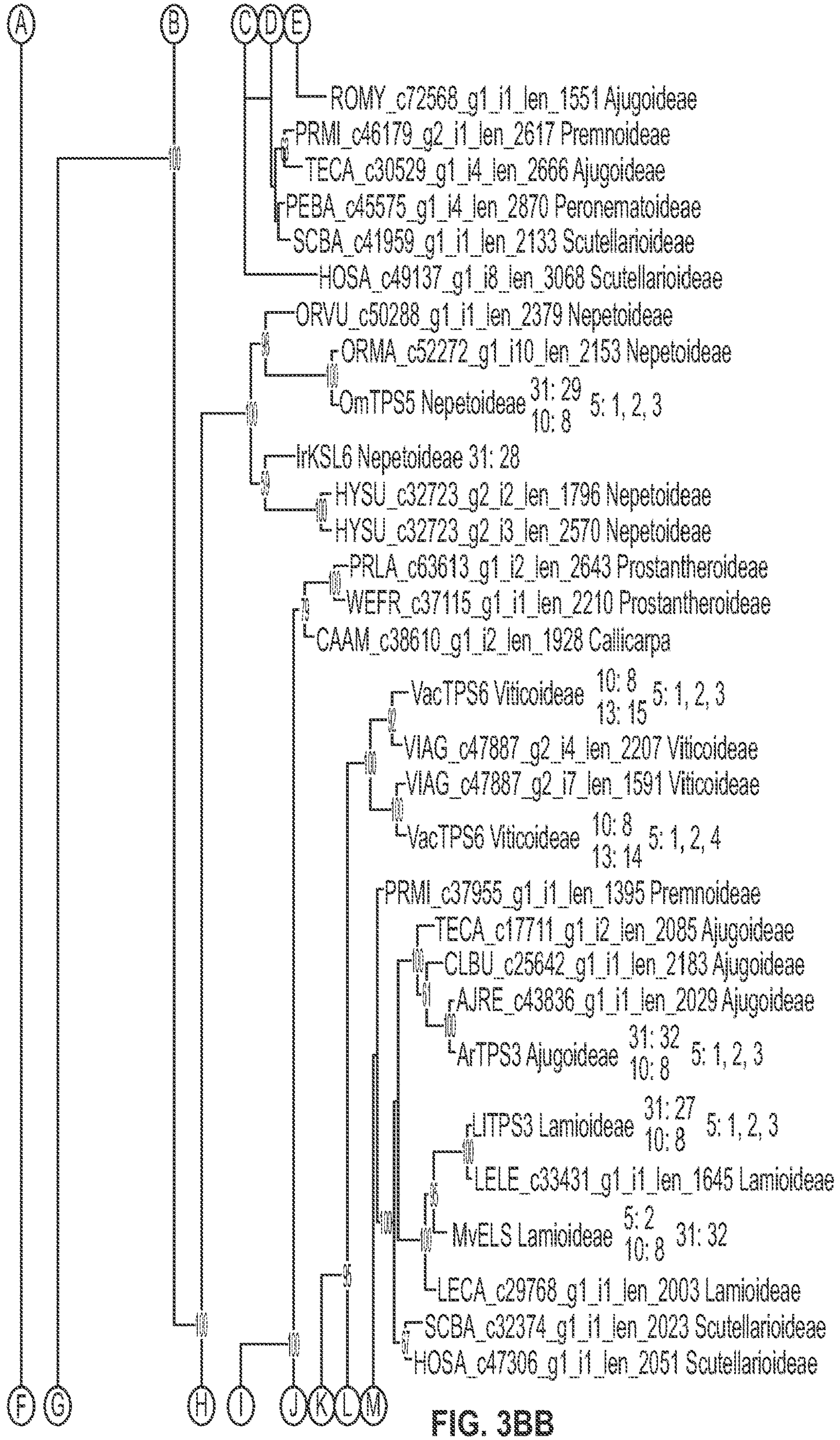
Figure 3B:
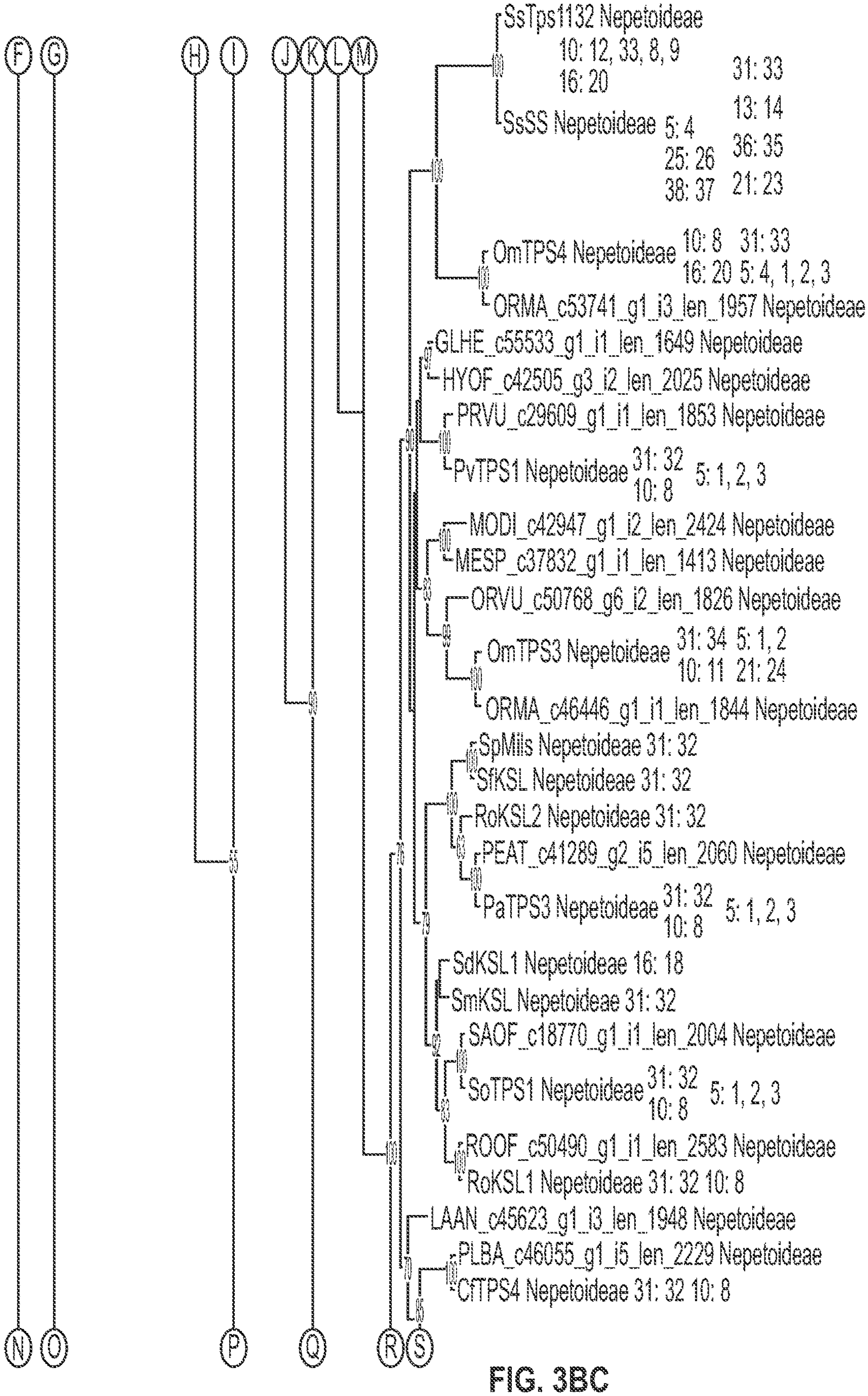
Figure 3B:
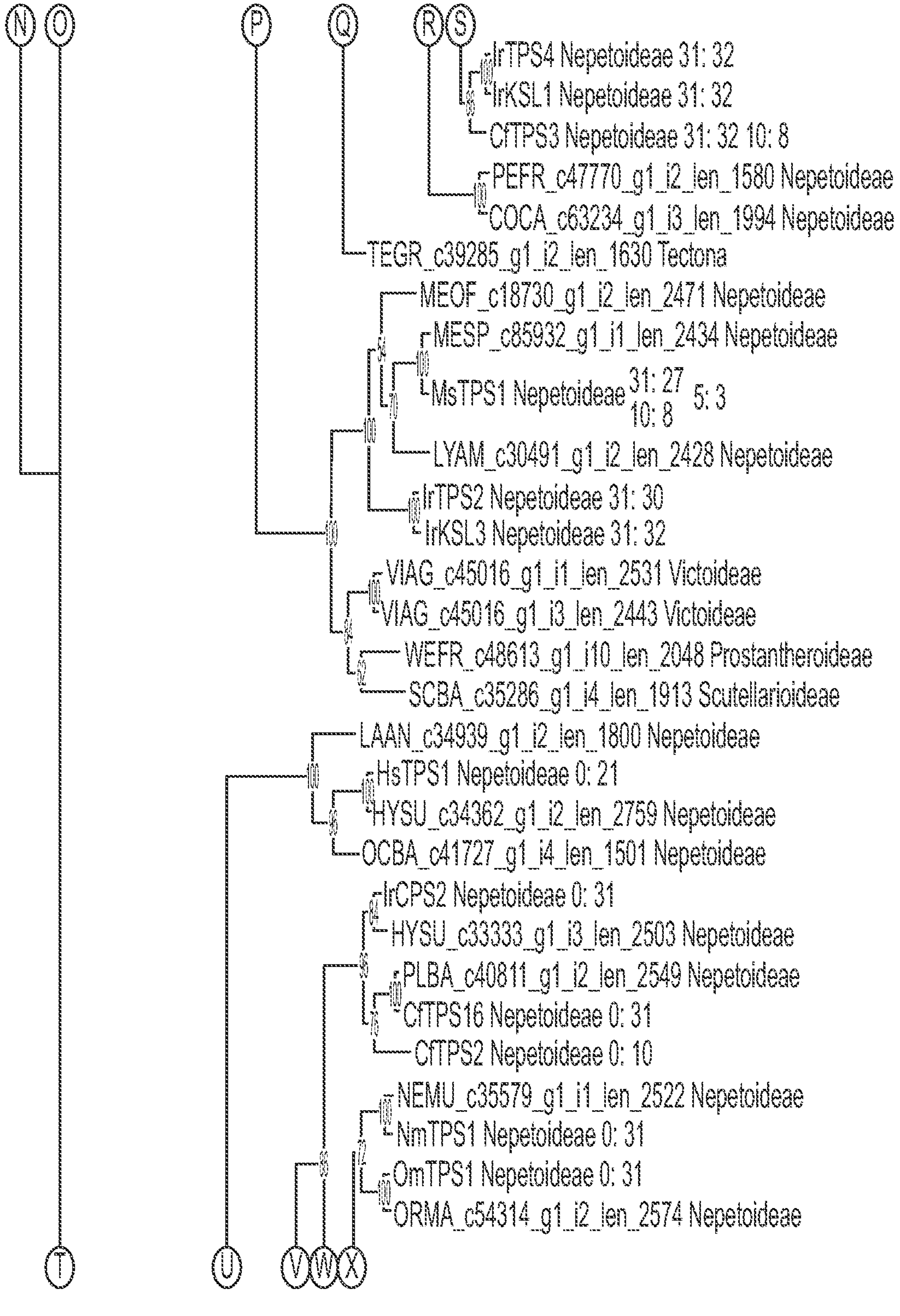
Figure 3B:
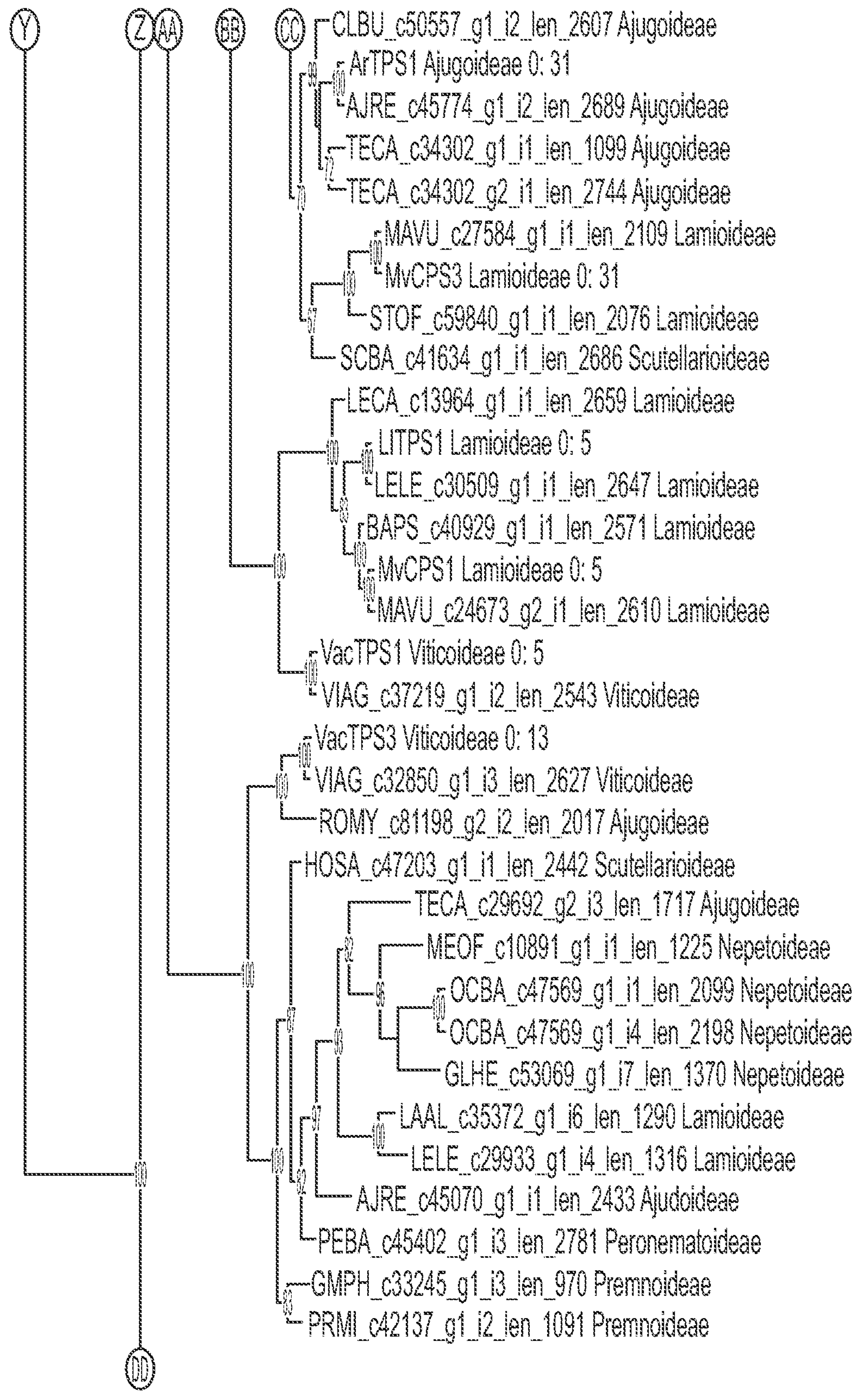
Figure 3B:
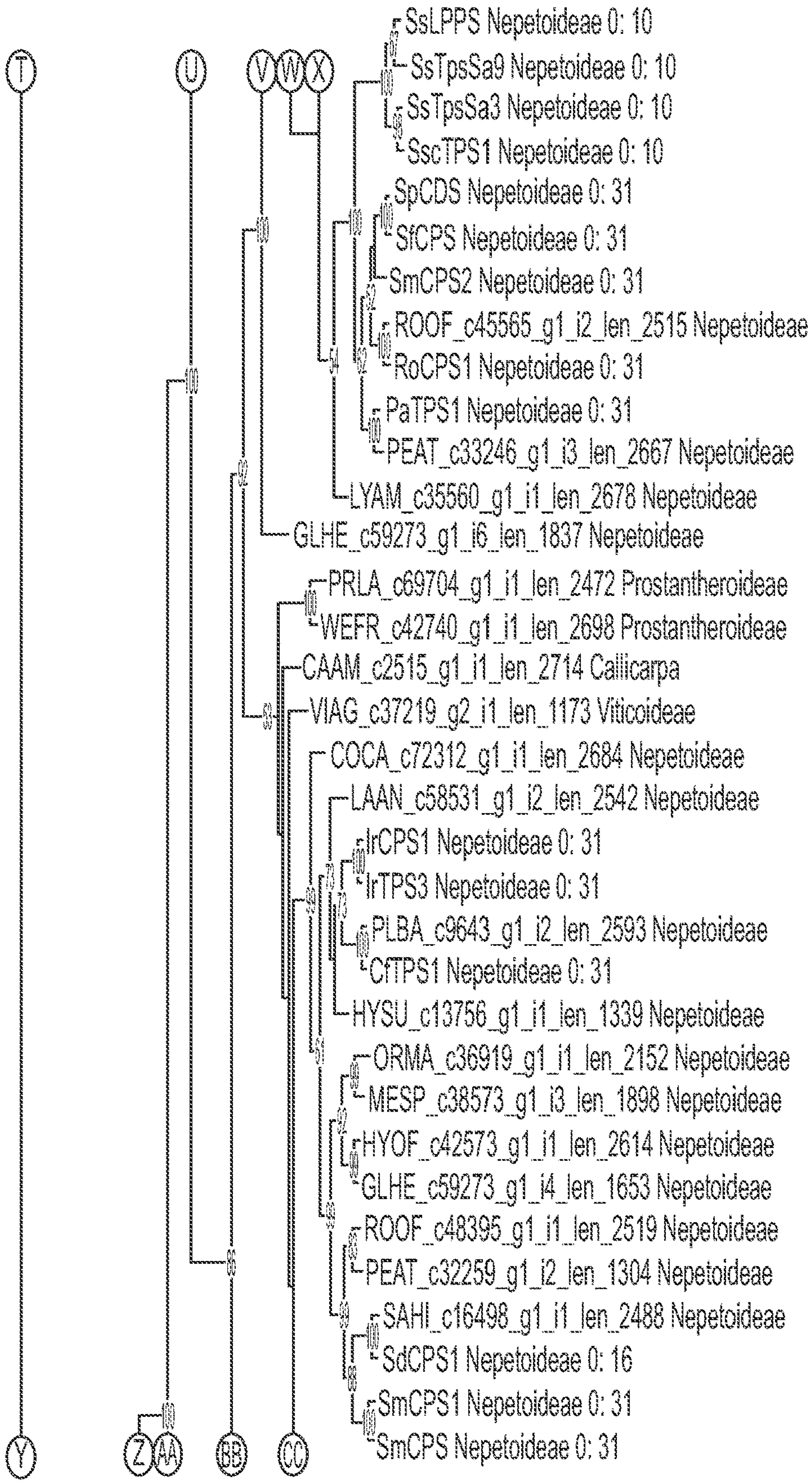
Figure 3B:
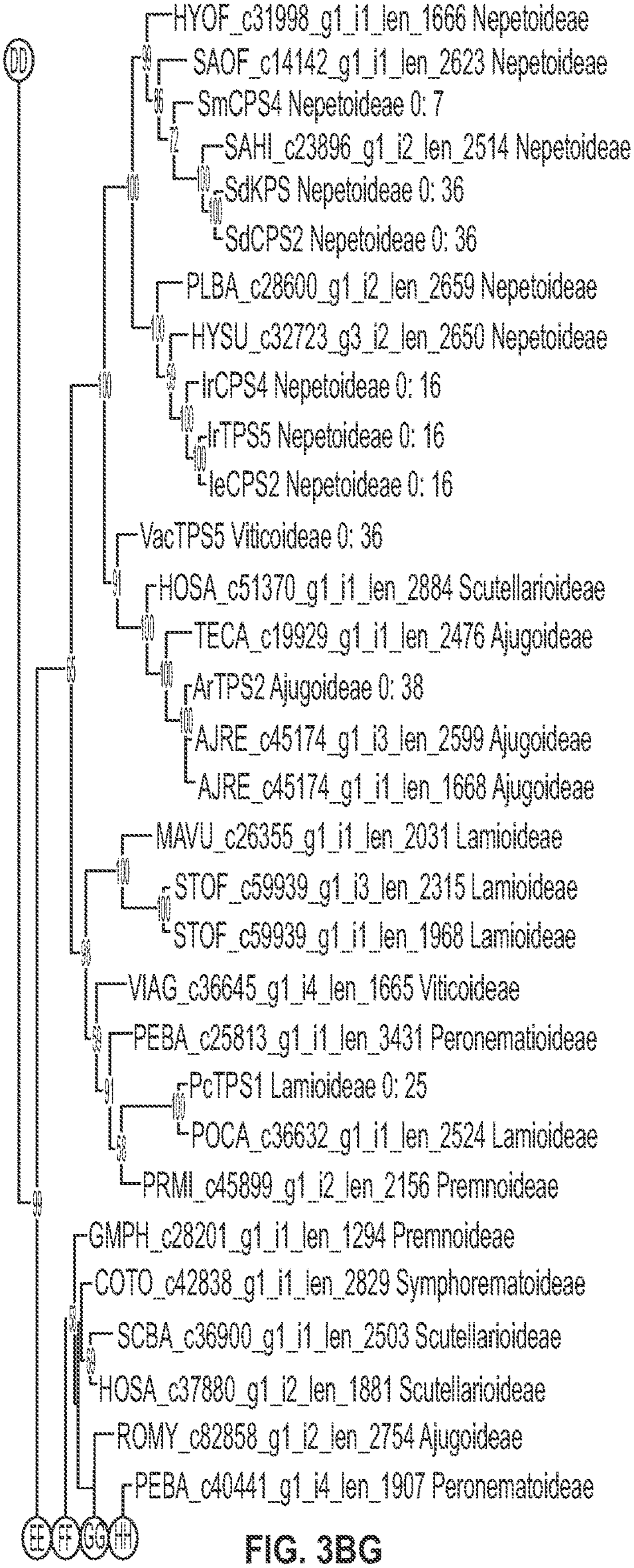
Figure 3B:
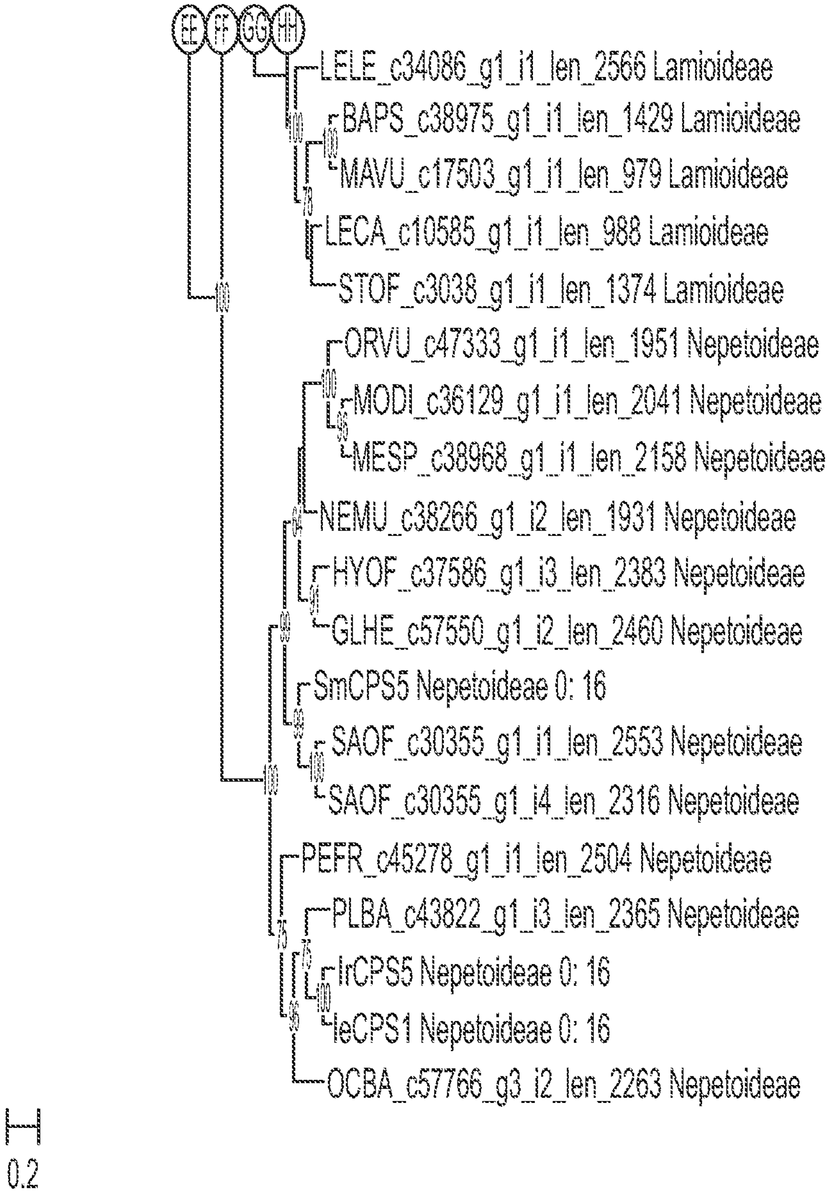

FIG. 3A presents a summary of Lamiaceae diTPS structures and activities reported from previous work, together with the newly characterized diTPS activities identified as described herein. Class II activities were established based on the activities of extracts from *Nicotiana benthamiana* that transiently expressed the new genes, compared with the activities of known diTPS (or combinations) that were similarly expressed.

Class II diTPS products retained the diphosphate group from the GGPP substrate. When expressed in-vivo, whether in *E. coli* or *N. benthamiana*, without a compatible class I diTPS, a diphosphate product degrades to the corresponding alcohol, presumably by the action of non-specific endogenous phosphatases. Due to difficulties in purifying and structurally characterizing diphosphate class II products it is customary in the field to instead characterize the alcohol derivatives (Heskes et al. Plant J 93(5):943-958 (2018): Pelot et al. Plant J 89(5):885-897 (2017)), which is the approach taken in this study. For clarity, the alcohol has been indicated by appending an "a" to the compound number, for example, 16a refers to ent-copalol.

ArTPS1, PaTPS1, NmTPS1, OmTPS1, and CfTPS1 were identified as (+)-copalyl diphosphate ((+)-CPP) [31] synthases by comparison to products of *Plectranthus barbatus* (synonym *Coleus forskohli*) CfTPS1, and the reference combination of CfTPS1 combined with CfTPS3, yielding miltiradiene (Pateraki et al. Plant Physiol 164(3):1222-1236 (2014)). LlTPS1 was identified as a peregrinol diphosphate (PgPP) [5] synthase based on a comparison of products with *Marrubium vulgare* MvCPS1 (Zerbe et al. Plant J 79(6): 914-927 (2014)), and MvCPS1 combined with *M. vulgare* 9,13-epoxylabdene synthase (MvELS), and *Salvia sclarea* sclareol synthase (SsSS) (Jia et al. Metabolic Engineering 37:24-34 (2016)).

Table 6 illustrates the distribution among selected Lamiaceae clades of diterpenes with various structural patterns. Blue enzyme names are placed according to the pattern they install and the clade of the species they were cloned from. A solid line indicates that only compounds with the bond-type shown at that position are counted. A dashed line indicates that all types of bonds and substituents are counted at that position. Based on data from the DNP.

TABLE 6A

Lamiaceae clades of diterpenes with various structural patterns.

| | Clerodane | Cleroda-4(18)-ene | 4(18)-epoxy-Clerodane |
|---|---|---|---|
| | 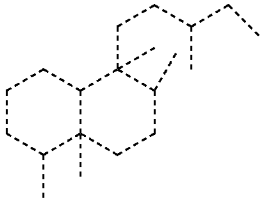 | 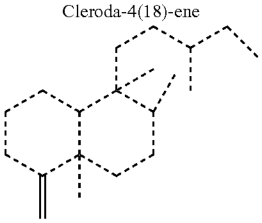 | 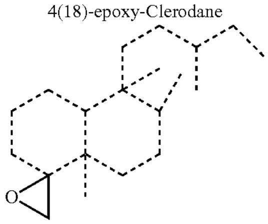 |
| Ajugoideae | 317 | (ArTPS2) 6 | 206 |
| Lamioideae | 32 | 3 | 1 |
| Nepetoideae | 132 | 1 | 1 |
| Scutellarioideae | 160 | 19 | 78 |
| Viticoideae | 1 | 0 | 0 |
| All clades | 668 | 31 | 289 |

TABLE 6B

Lamiaceae clades of diterpenes with various structural patterns.

| | Clerodane-3-ene | Labdane |
|---|---|---|
| | 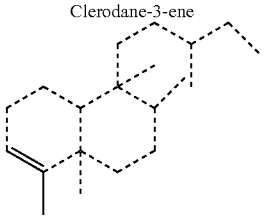 | 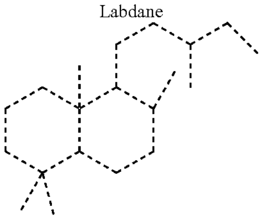 |
| Ajugoideae | 23 | 3 |
| Lamioideae | 25 | 201 |
| Nepetoideae | 84 | 60 |
| Scutellarioideae | 44 | 0 |
| Viticoideae | 0 | 37 |
| All clades | 189 | 300 |

TABLE 6C

Lamiaceae clades of diterpenes with various structural patterns.

| | Labda-8-ene | Labda-7-ene |
|---|---|---|
| | 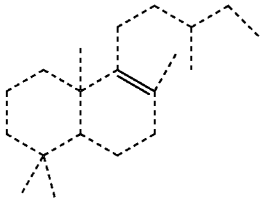 | 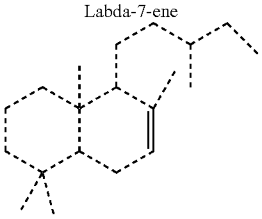 |
| Ajugoideae | 2 | 0 |
| Lamioideae | (PcTPS1) 27 | 5 |
| Nepetoideae | 1 | (HsTPS1) 1 |
| Scutellarioideae | 0 | 0 |
| Viticoideae | 2 | 2 |
| All clades | 33 | 9 |

HsTPS1 was identified as a (5S,9S,10S) labda-7,13E-dienyl diphosphate [21] synthase based on comparison to the product of an enzyme from *Grindelia robusta*, GrTPS2 (Zerbe et al. The Plant Journal 83(5):783-793 (2015)), and by NMR of the alcohol derivative [21a]. Normal absolute stereochemistry was assigned to the HsTPS1 product based on the optical rotation of 21a, $[\alpha]_D$ +8.3° (c. 0.0007, $CHCl_3$) (c.f. lit. $[\alpha]_D$+5°, c. 1.0, $CHCl_3$ (Urones et al. Phytochemistry 35(3):713-719 (1994)); $[\alpha]_D^{25}$+12°, c. 0.69, $CHCl_3$ (Suzuki et al. Phytochemistry 22(5):1294-1295 (1983)).

When HsTPS1 was expressed in *N. benthamiana*, labda-7, 13(16),14-triene [22] was formed, which seemed to be enhanced by co-expression with CfTPS3. The combination of HsTPS1 with OmTPS3 produced labda-7,12E,14-triene [24] (Roengsumran et al. Phytochemistry 50(3):449-453 (1999)), which has previously been accessible only by combinations of bacterial enzymes (Yamada et al. The Journal of Antibiotics 69(7):515-523 (2016)). Labdanes with a double bond at the 7-position have not been reported in *H. suaveolens*, and such labdanes do not seem to be common in Lamiaceae. Of nine compounds with the labdane skeleton and a double bond at position-7 (Table 6) only one was from the same clade as *H. suaveolens*. (13E)-ent-labda-7,13-dien-15-oic acid, from *Isodon scoparius* (Xiang et al. *Helvetica Chimica Acta* 87(11):2860-2865 (2004)), has the opposite absolute stereochemistry to the HsTPS1 product, likely not deriving from a paralog of HsTPS1 because absolute stereochemistry of a skeleton is not known to change after the diTPS steps.

Figure 4A:
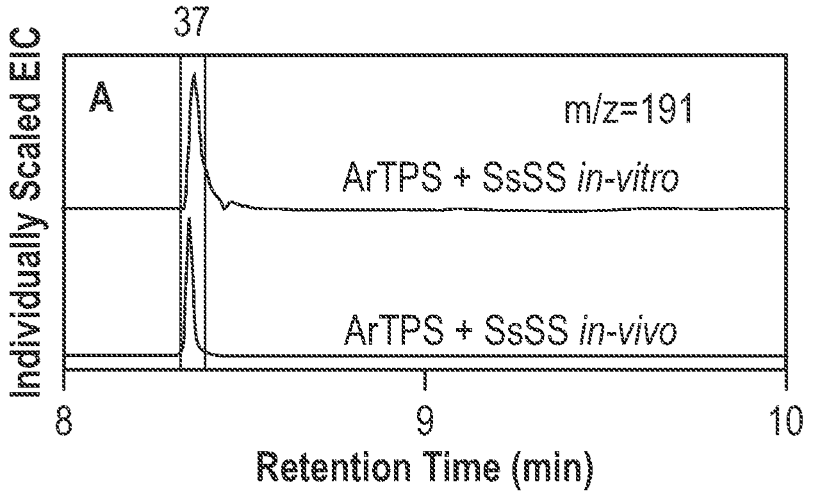
FIG. 4A-4C illustrate results of activity assays for several enzymes.
Figure 4B:
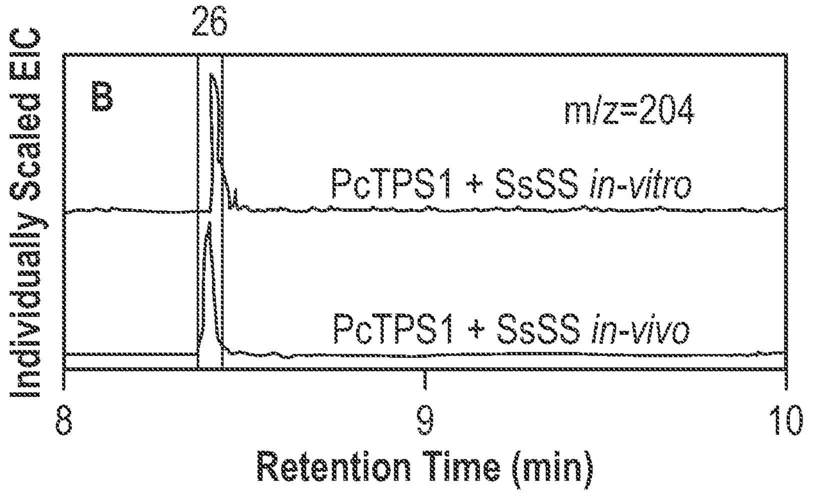
Figure 4C:
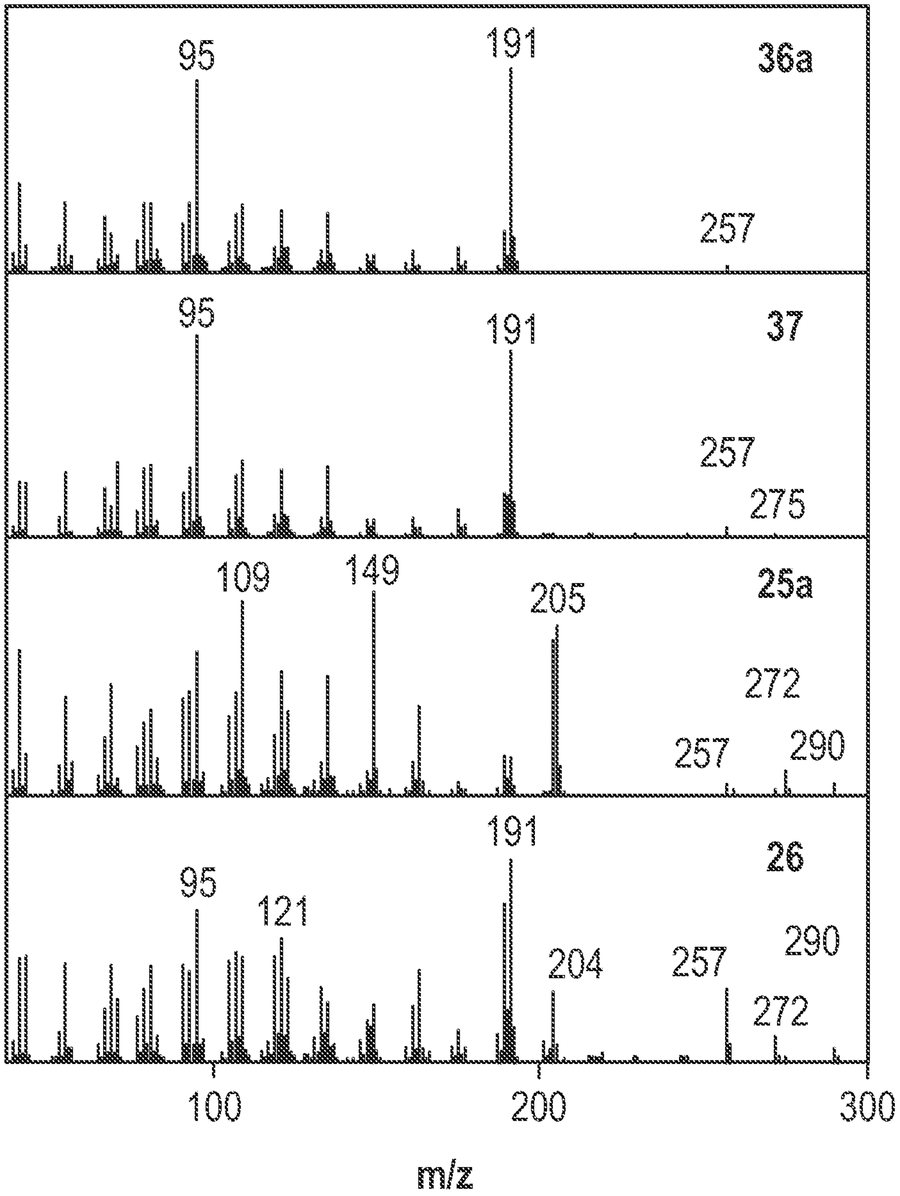

ArTPS2 was identified as a (5R,8R,9S,10R) neo-cleroda-4(18),13E-dienyl diphosphate [38] synthase. The combination of ArTPS2 and SsSS generated neo-cleroda-4(18),14-dien-13-ol [37] (FIG. 4A). The structures of compounds 37 and 38a were determined by NMR. The analysis included a comparison of compound 37 to chelodane (Rudi et al. J Nat Prod 55(10):1408-1414 (1992)), which based on small differences in $^{13}C$ shifts, may be a stereoisomer of compound 37 at the 13 position, and a comparison of the NMR results for compound 38a with the NMR of its enantiomer (Ohaski et al. Bioorganic & Medicinal Chemistry Letters 4(24): 2889-2892 (1994)). There were 20 to 19, and 20 to 17 NOE interactions in the NMR spectra of 37 and 38a, which closely resembled those reported for (−)-kolavelol [36a] (Pelot et al. Plant J 89(5):885-897 (2017)), indicating that the stereochemistry may be 5R,8R,9S,10R. The "neo" absolute configuration was established through optical rotation of 38a, $[\alpha]_D$+30° (c. 0.0025, $CHCl_3$) (c.f. lit. $[\alpha]_D$ +20.9°, c. 0.7, $CHCl_3$) (Monaco et al. Rendiconto della Academia delle scienze fisiche e matematiche 48:465-470 (1982)).

Previously reported clerodane diTPSs from Lamiaceae produce kolavenyl diphosphate [36] (Heskes et al. Plant J 93(5):943-958 (2018); Chen et al. J Exp Bot 68(5):1109-1122 (2017): Pelot et al. Plant J 89(5):885-897 (2017)), and kolavenyl diphosphate [36] has a double bond at the 3-position. Clerodanes with desaturation at position-3 are spread throughout multiple clades but are most common in Nepetoideae (Table 6A-6C), which includes *Salvia divinorum*. Clerodanes with a double bond at the 4(18)-position are rare by comparison, but those with a 4(18)-epoxy moiety, make up nearly half of the clerodanes reported in Lamiaceae, including two-thirds of those reported from the Ajugoideae clade (Table 6A-6C), one of which is clerodin (Barton et al. *J Chem Soc:* 5061-5073 (1961)) and from which the clerodane skeleton gets its name. Neo-cleroda-4(18),13E-dienyl diphosphate is a logical biosynthetic precursor for the 4(18)-epoxy clerodanes. It is unclear if any of the previously described diTPSs directly produce an epoxide moiety.

PcTPS1 was identified as a (10R)-labda-8,13E-dienyl diphosphate [25] synthase. The structure was established by comparison of $^{13}C$ NMR of compound 25a to previously reported spectra (Suzuki et al. Phytochemistry 22(5):1294-1295 (1983)). The 10R (ent-) absolute stereochemistry was established by optical rotation of compound 25a $[\alpha]_D$ −64° (c. 0.0008, $CHCl_3$), (c.f. lit. $[\alpha]_D^{25}$ −71.2°, c. 1.11, $CHCl_3$) (Arima et al. Tetrahedron: Asymmetry 18(14):1701-1711 (2007)). The combination of PcTPS1 and SsSS, both in-vitro, and in *N. benthamiana* expression produced (10R)-labda-8,14-en-13-ol [26] (FIG. 4B), the structure of which was determined by comparison of $^{13}C$ NMR to a published spectrum (Wu & Lin Phytochemistry 44(1):101-105 (1997)). The double bond between positions 8 and 9 is present in 33 distinct compounds isolated from Lamiaceae (Table 6A-6C), most of which occur in the Lamioideae clade, which includes *Pogostemon cablin*, the source of PcTPS1. Absolute stereochemistries of the reported compounds are mixed, with some in the normal configuration (Boalino et al. J Nat Prod 67(4):714-717 (2004)), and others in the ent-configuration (Gray et al. Phytochemistry 63(4): 409-413 (2003)). As normal configuration 9-hydroxy labdanes are also abundant in Lamioideae, it is possible that the normal configuration 8(9) desaturated labdanes arise from dehydratase activities downstream of a PgPP synthase (MvCPS1 and its paralogs), while those in the ent-configuration arise from paralogs of PcTPS1. Another possibility is that some of the 8(9) desaturated labdanes reported as having normal absolute stereochemistry are actually ent-labdanes that were mis-assigned, as has occurred in at least one documented case (Gray et al. Phytochemistry 63(4): 409-413 (2003)).

Example 5: Characterization of Class I dITPSs

Class I diTPS candidates were characterized by transient expression in *N. benthamiana* in combination with four class II enzymes:

CfTPS1, a (+)-CPP [31] synthase;

CfTPS2, a labda-13-en-8-ol diphosphate ((+)-8-LPP) [10] synthase (Pateraki et al. Plant Physiol 164(3):1222-1236 (2014);

LITPS1, a PgPP 151 synthase; or

*Zea mays* ZmAN2, an ent-copalyl diphosphate (ent-CPP) [16] synthase (Harris et al. Plant Mol Biol 59(6):881-894 (2005)).

Figure 2B:
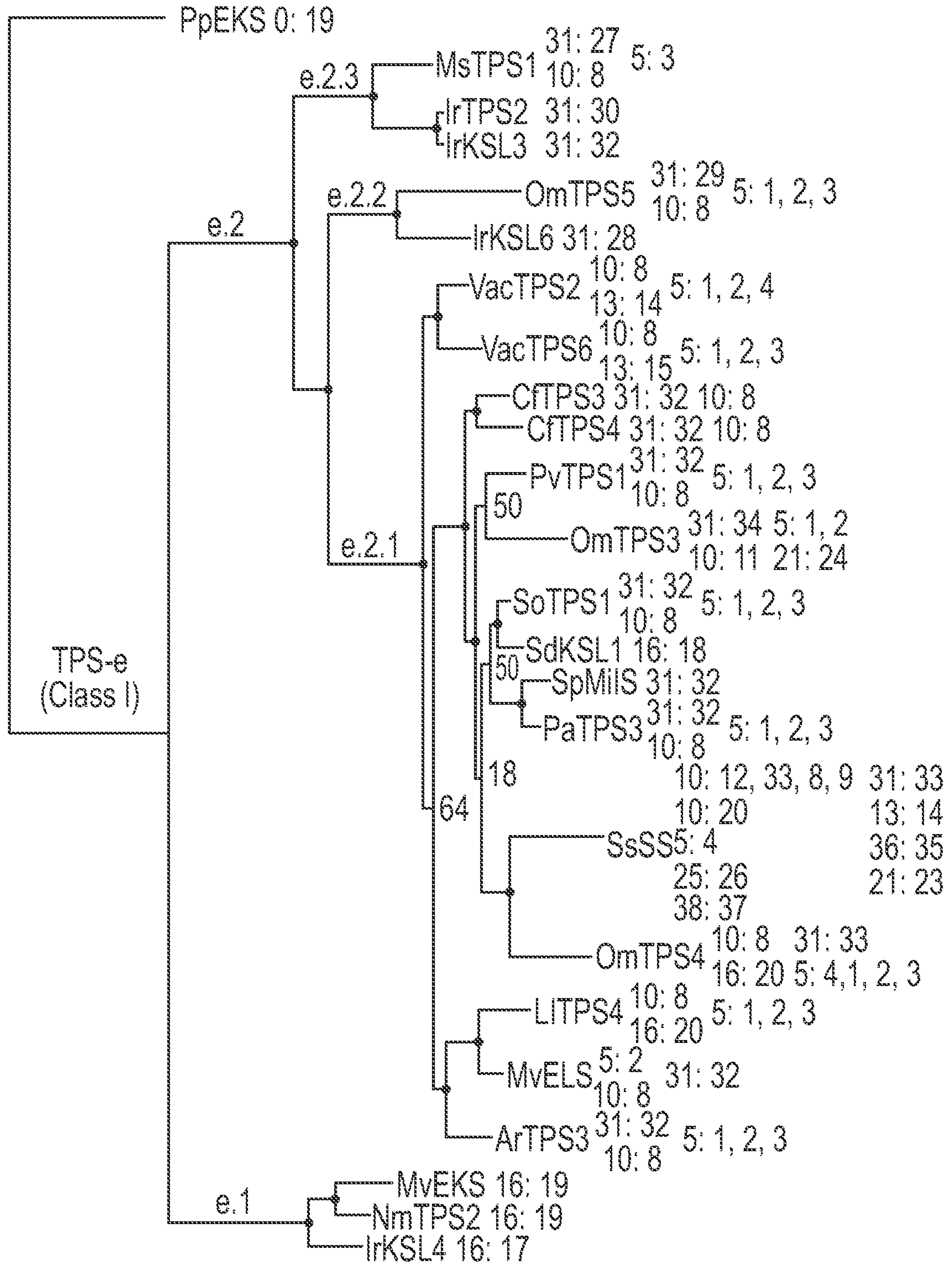
Figure 5A:
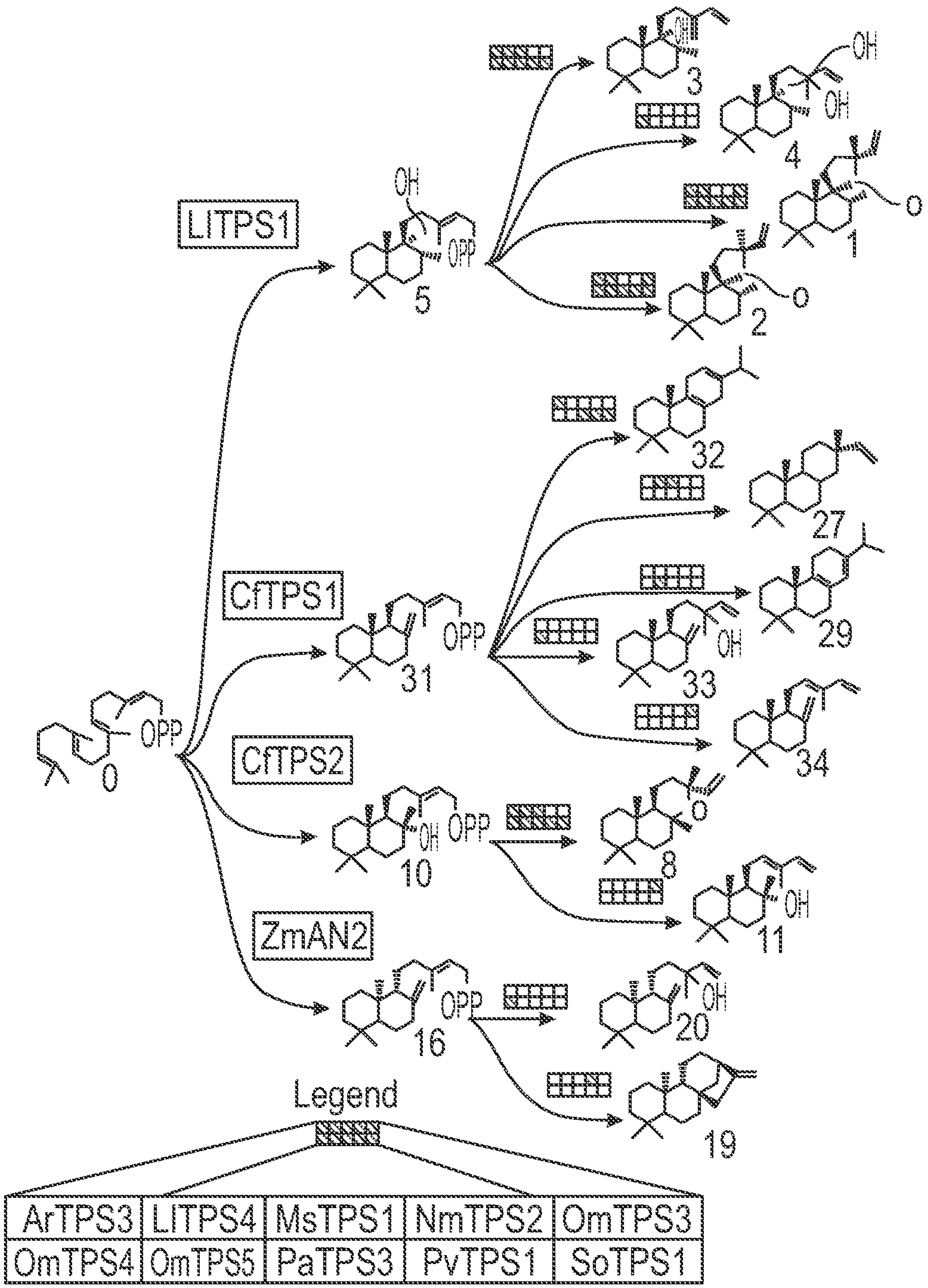
FIG. 5A-5B illustrates the structures that can be produced by the activities of new class I diTPSs.
Figure 5B:
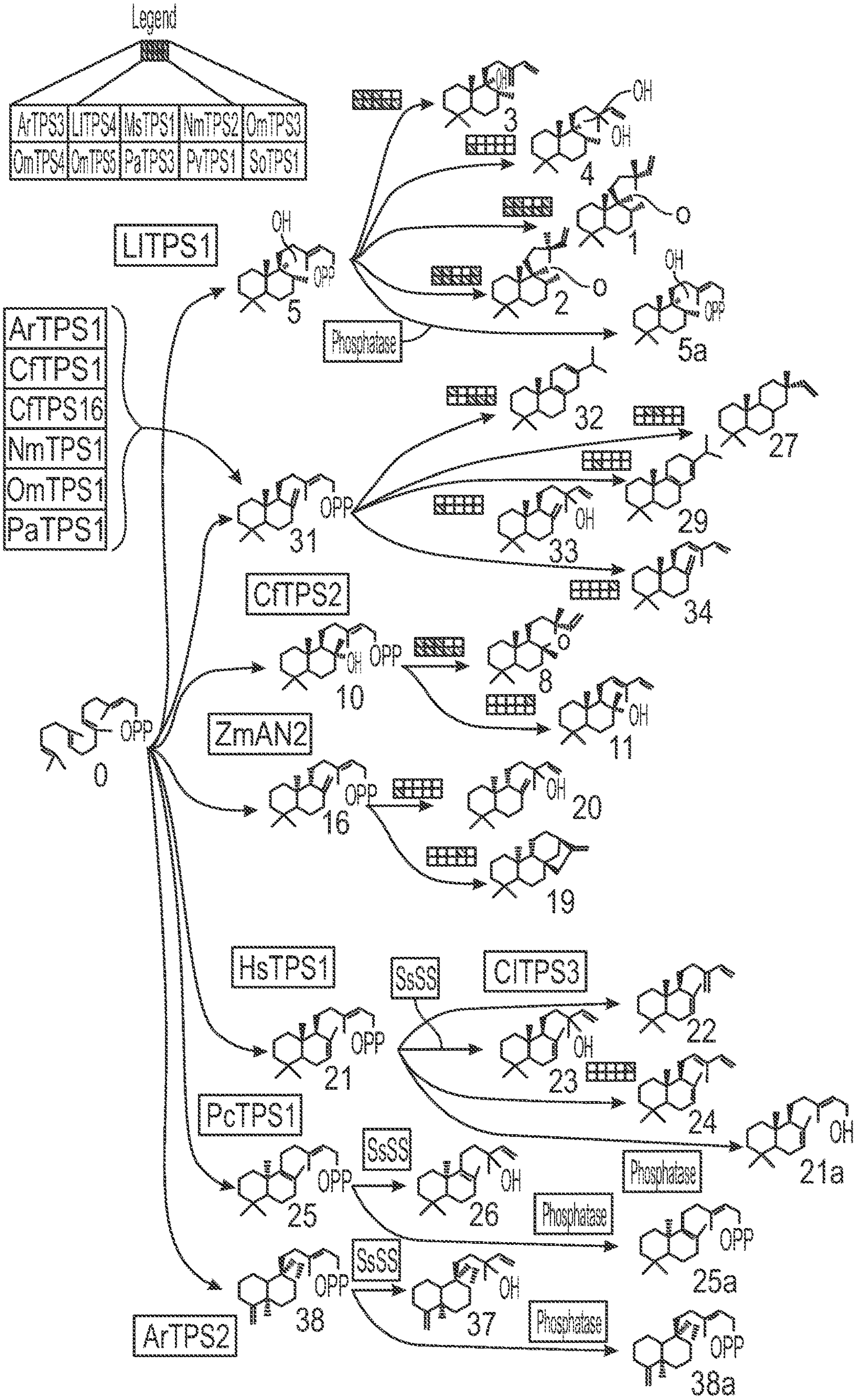

Substrates accepted by each enzyme and the products are indicated in FIG. 2B and FIG. 5. NmTPS2 was identified as an ent-kaurene [19] synthase, converting ent-CPP into ent-kaurene (identified using *Physcomitrella patens* extract as a standard (Zhan et al. Plant Physiology and Biochemistry 96:110-114 (2015))), but not showing activity with any other substrate. The only other enzyme to show activity with ent-CPP was OmTPS4, which produced ent-manool [20], just as SsSS produces from ent-CPP.

PaTPS3, PvTPS1, SoTPS1, ArTPS3, OmTPS4, LITPS4, OmTPS5, and MsTPS1 converted (+)-8-LPP to 13R-(+)-manoyl oxide [8], verified by comparison to the product of CfTPS2 and CfTPS3 (Pateraki et al. Plant Physiol 164(3): 1222-1236 (2014)). OmTPS3 produced trans-abienol [11]. The trans-abienol structure was determined by NMR, with the stereochemistry of the 12(13)-double bond supported by comparison of the NOESY spectrum to that of a commercial standard for cis-abienol (Toronto Research Chemicals. Toronto Canada). The trans-abienol showed clear NOE correlation between positions 16 and 11, while the cis-abienol standard showed correlations between 14 and 11.

PaTPS3, PvTPS1, SoTPS1, and ArTPS3, LITPS4, and OmTPS5 converted PgPP to a combination of 1, 2, and 3, with some variation in the ratios between the products. Because perigrinol [5a] spontaneously degrades into 1, 2, and 3 under GC conditions (Zerbe et al. Plant J 79(6):914-927 (2014)), it was difficult to distinguish whether these enzymes have low activity, but specific products, or moderate activity with a mix of products. Nevertheless, differences in relative amounts of the products observed between LITPS1 alone and in combination with these class 1 enzymes suggest that they do have some activity on PgPP. OmTPS4 produced 1, 2, 3, and 4. MsTPS1 produced only 3, and OmTPS3 produced only 1, and 2. PgPP products were established by comparison to MvCPS1, MvCPS1 with MvELS (Zerbe et al. Plant J 79(6):914-927 (2014)), and MvCPS1 with SsSS (Jia et al. Metabolic Engineering 37:24-34 (2016)).

PaTPS3, PvTPS1, SoTPS1, and ArTPS3 converted (+)-CPP to miltiradiene [32], similarly to CfTPS3. OmTPS4 produced manool [33], as compared to SsSS. LITPS4 and MsTPS1 produced sadaracopimaradiene [27], by comparison to a product from *Euphorbia peplus* EpTPS8 (Andersen-Ranberg et al. Angew Chem Int Ed 55(6):2142-2146 (2016)). OmTPS5 produced palustradiene [29], as compared to a minor product from *Abies grandis* abietadiene synthase (Vogel et al. J Biol Chem 271(38):23262-23268 (1996)). OmTPS3 produced trans-biformene [34], as established by comparison of $^{3}$C-NMR of compounds described by Bohlmann & Czerson, Phytochemistry 18(1):115-118 (1979)), with a trans configuration further supported by clear NOE correlations between 16 and 11, and the absence of NOE correlations between 14 and 11.

Example 6: *Origanum majorana* Enzymes can Make Palustradiene and Other Diterpenoids The class I enzymes from *Origanum majorana*, OmTPS3, OmTPS4, and OmTPS5 all produced different products from (+)-CPP, which itself is the product of OmTPS1 from the same species. Despite the apparent richness of activities of enzymes from *O. majorana*, no reports of diterpenes were located from that species either in database searches, or in a subsequent literature search.

Figure 6A:
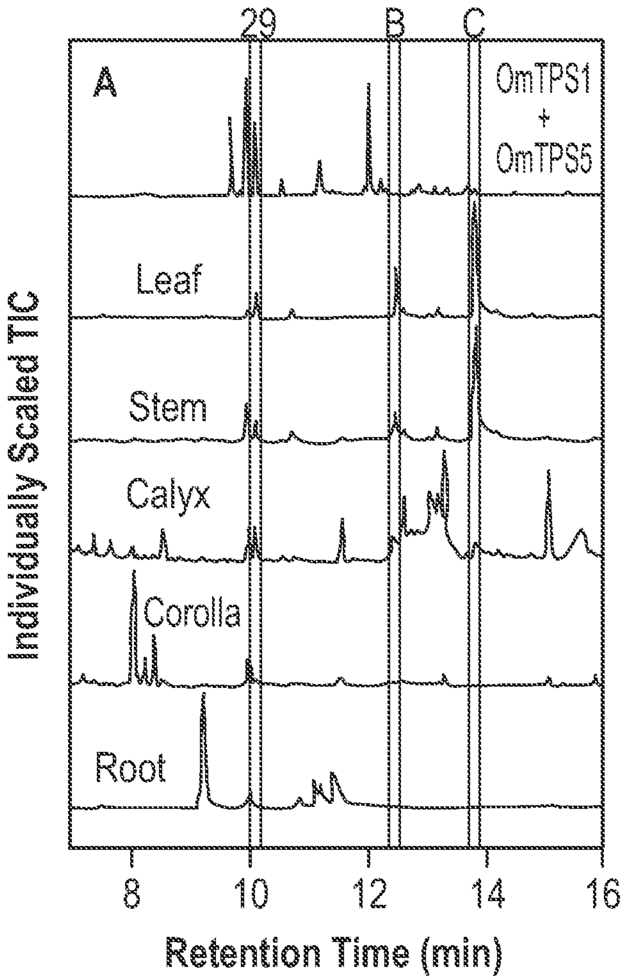
FIG. 6A-6C illustrate analysis of compounds from *O. majorana*.
Figure 6B:
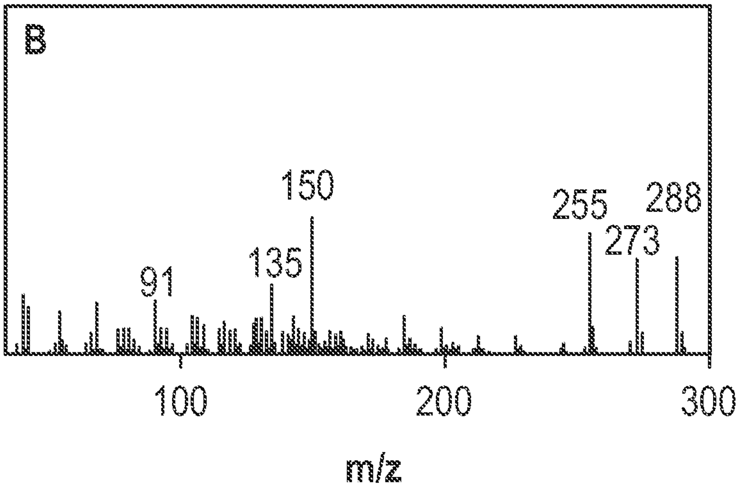
Figure 6C:
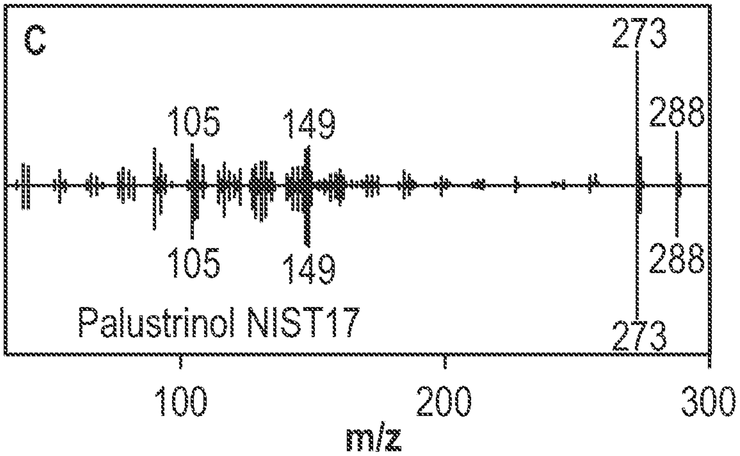

To determine whether diterpene synthases are active in *O. majorana*, the products of enzyme combinations with extracts from *O. majorana* leaf, stem, calyx, corolla, and root were evaluated. Palustradiene [29], the product of OmTPS1 and OmTPS5, was detected in all tissues except roots (FIG. 6). In addition, two diterpene alcohols were detected in the stem, leaf, and calyx. One diterpene alcohol, could not be identified, but the other was a close match to palustrinol, the 19-hydroxy derivative of palustradiene, in the NIST17 spectral library. The structures of the palustrinol, and the 19-hydroxy derivative of palustradiene are shown below.

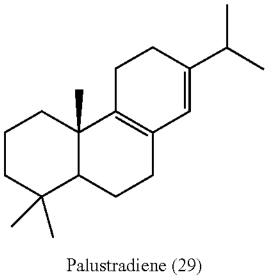

Palustradiene (29)

-continued

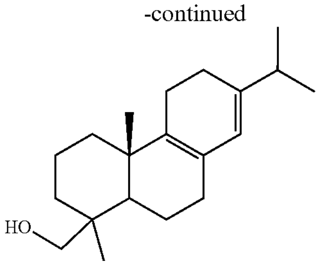

Palustrinol

Example 7: *Chiococca alba* Enzymes can Make 13(R)-Epi-Dolabradiene and Other Compounds This Example illustrates that enzymes from *Chiococca alba* can produce products such as ent-kaurene, ent-dolabradiene (13-epi-dolabradiene), and (13R)-ent-manoyl oxide.

Enzyme assays were prepared as described herein that separately or in combination contained the following enzymes and substrates:

- class I terpene synthase enzyme from *Chiococca alba* (CaTPS1) with SoTPS2, SbTPS1, and SbTPS2 and the substrate ent-copalyl diphosphate.
- class II terpene synthase enzyme from *Chiococca alba* (CaTPS2) with substrate ent-labda-13-en-8-ol diphosphate
- class III and class IV terpene synthase enzymes from *Chiococca alba* (CaTPS3 and CaTPS4) with substrate ent-kaurene
- class V terpene synthase enzyme from *Chiococca alba* (CaTPS5) with substrate ent-dolabradiene
- class I (−)-kolavenyl diphosphate synthase enzyme from *Salvia hispanica* (ShTPS1) with substrate (−)-kolavenyl diphosphate
- class I cleroda-4(18),13E-dienyl diphosphate synthase enzyme from *Teucrium canadense* (TcTPS1) with substrate clerodadienyl diphosphate
- class I sclareol synthase enzyme from *Salvia sclarea* (SsSCS) with substrate neo-clerodadienol.

Figure 7A:
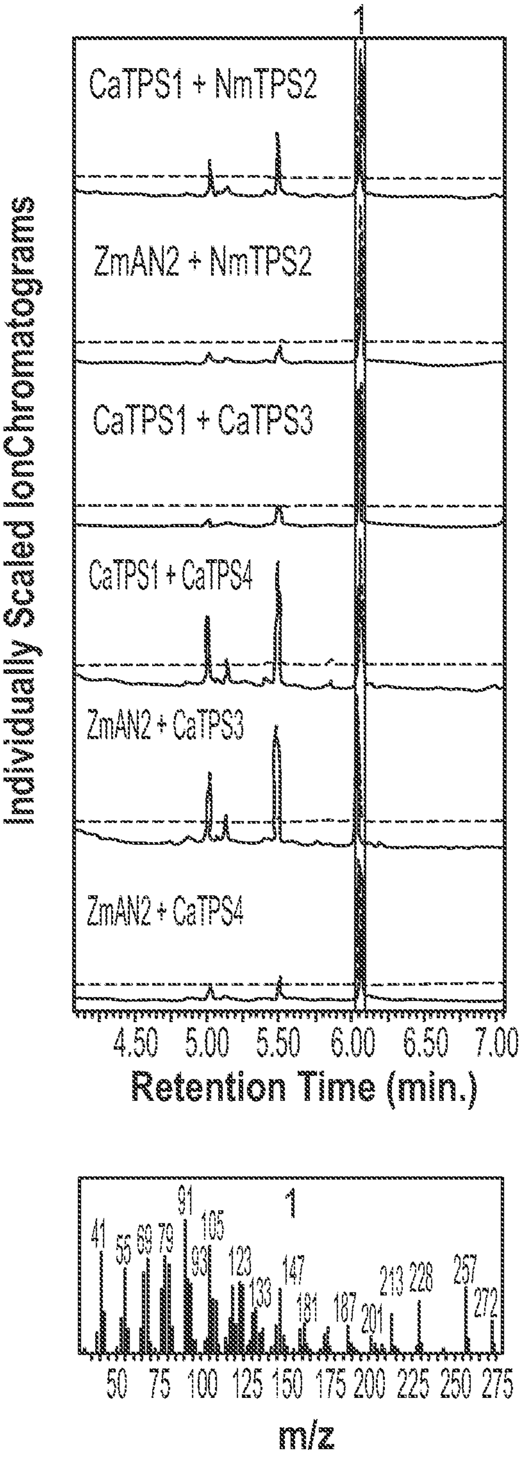
FIG. 7A-7C illustrate the activities of novel *Chiococca alba* terpene synthases CaTPS1-5.
Figure 7B:
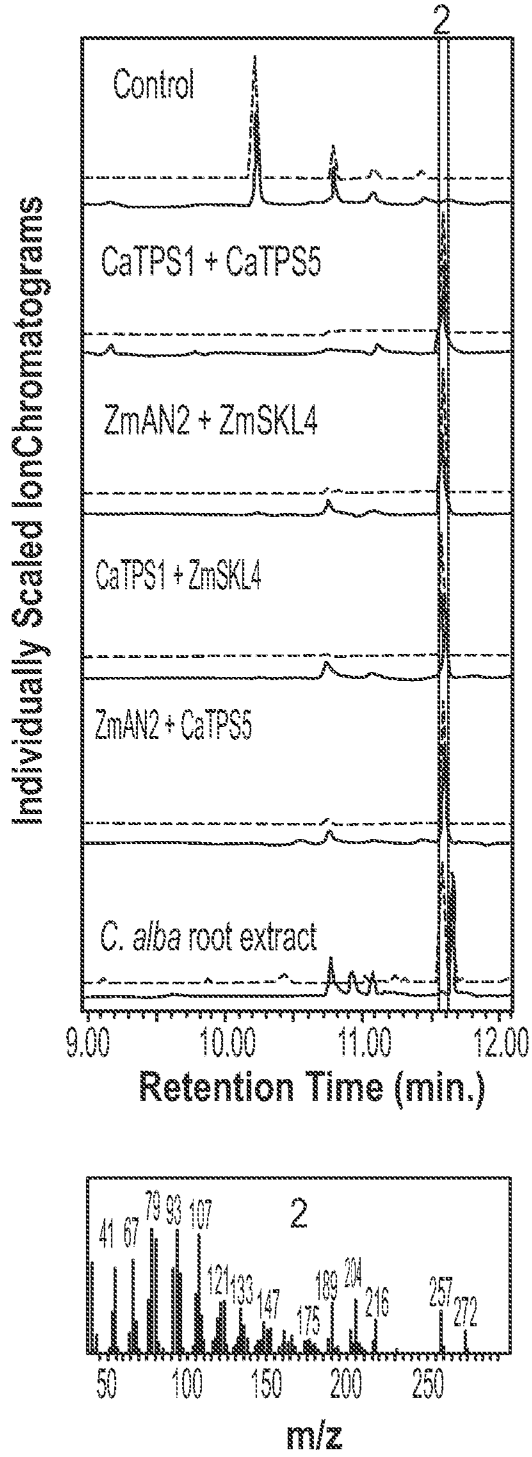
Figure 7C:
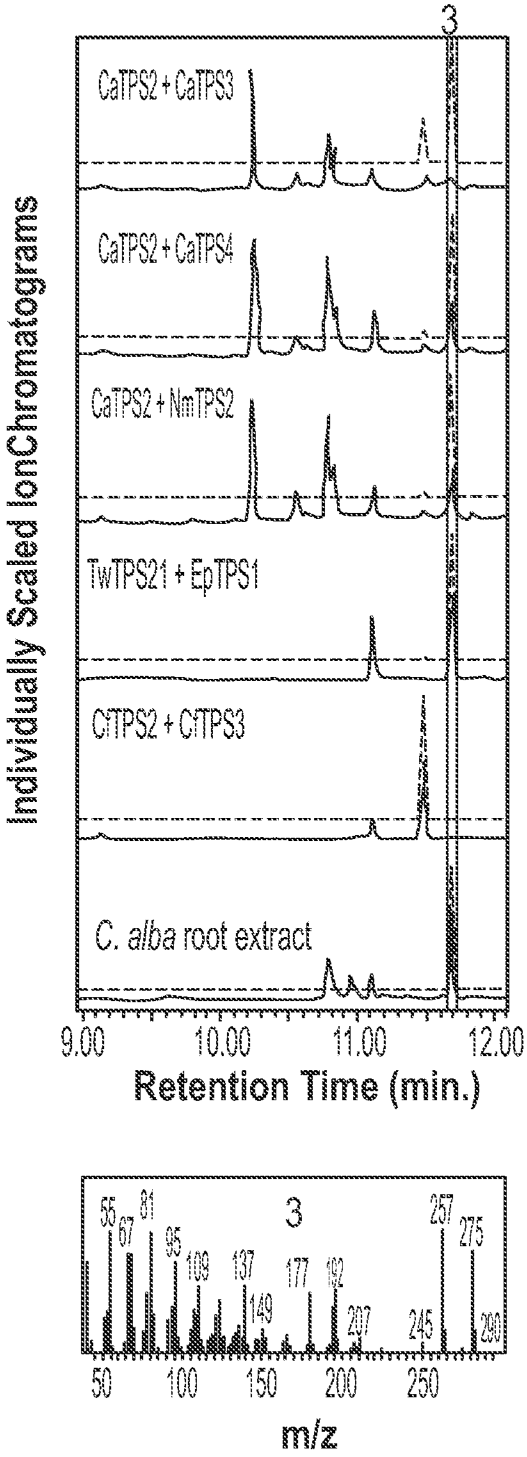

FIG. 7 illustrates the activities of the newly obtained *Chiococca alba* terpene synthases CaTPS1-5. FIGS. 7A-7C show GC-MS-total ion and extracted ion chromatograms from in vivo assays within *N. benthamiana* that transiently expressed various combinations of enzymes. Mass spectra are shown below the chromatograms of FIG. 7A-7C for peaks (1) to (3) containing the following products of the enzymatic conversion: (1) ent-kaurene; (2) ent-dolabradiene (13-epi-dolabradiene); (3) (13R)-ent-manoyl oxide. The ent-dolabradiene was identified through extensive structural studies with NMR and the stereochemistry at C-13 was unequivocally corroborated by optical rotation. The ent-kaurene and (13R)-ent-manoyl oxide were identified through direct comparison with biosynthesized authentic standards with reference enzymes.

Compounds ent-dolabradiene (13-epi-dolabradiene) and (13R)-ent-manoyl oxide are plausible intermediates in the biosynthetic routes to the structurally unusual merilactone and ribenone, that have demonstrated activity against Leishmania and potential anti-cancer activity (Piozzi, F., Bruno, M. Diterpenoids from Roots and Aerial Parts of the Genus Stachys Rec. Nat. Prod. 5, 1-11, (2011)).

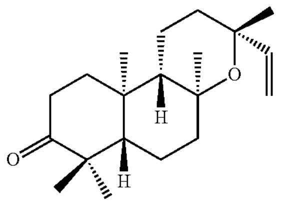

Ribenone

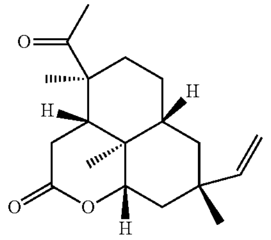

Merilactone

Both merilactone and ribenone are detected in the root extract of *C. alba*.

REFERENCES

1. Dictionary of Natural Products 26.2 Available at: http://dnp.chemnetbase.com [Accessed Jan. 11, 2018].
2. Peters R J (2010) Two rings in them all: The labdane-related diterpenoids. *Natural product reports* 27(11): 1521.
3. Chen F, Tholl D, Bohlmann J, Pichersky E (2011) The family of terpene synthases in plants: a mid-size family of genes for specialized metabolism that is highly diversified throughout the kingdom. *The Plant Journal* 66(1):212-229.
4. Zerbe P, Bohlmann J (2015) Plant diterpene synthases: exploring modularity and metabolic diversity for bioengineering. *Trends In Biotechnology* 33(7):419-428.
5. Hamberger B, Bak S (2013) Plant P450s as versatile drivers for evolution of species-specific chemical diversity. *Philosophical Transactions of the Royal Society of London B: Biological Sciences* 368(1612):20120426.
6. Banerjee A, Hamberger B (2018) P450s controlling metabolic bifurcations in plant terpene specialized metabolism. *Phytochem Rev* 17(1):81-111.
7. Pateraki I, et al. (2017) Total biosynthesis of the cyclic AMP booster forskolin from *Coleus forskohlii. elife* 6:e23001.
8. Ondari M E, Walker K D (2008) The Taxol Pathway 10-O-Acetyltransferase Shows Regioselective Promiscuity with the Oxetane Hydroxyl of 4-Deacetyltaxanes. *J Am Chem Soc* 130(50):17187-17194.
9. Chau M, Walker K, Long R, Croteau R (2004) Regioselectivity of taxoid-O-acetyltransferases: heterologous expression and characterization of a new taxadien-5α-ol-O-acetyltransferase. *Archives of Biochemistry and Biophysics* 430(2):237-246.
10. Cui G, et al. (2015) Functional divergence of diterpene syntheses in the medicinal plant *Salvia miltiorrhiza* Bunge. *Plant Physiol* 169(3):1607-1618.
11. Gao W, et al. (2009) A Functional Genomics Approach to Tanshinone Biosynthesis Provides Stereochemical Insights. *Org Lett* 11(22):5170-5173.
12. Guo J, et al. (2013) CYP76AH1 catalyzes turnover of miltiradiene in tanshinones biosynthesis and enables heterologous production of ferruginol in yeasts. *PNAS* 110 (29):12108-12113.

13. Heskes A M, et al. (2018) Biosynthesis of bioactive diterpenoids in the medicinal plant *Vitex agnus-castus. Plant J* 93(5):943-958.
14. Zerbe P, et al. (2014) Diterpene synthases of the biosynthetic system of medicinally active diterpenoids in *Marrubium vulgare*. Plant J 79(6):914-927.
15. Chen X, Berim A, Dayan F E, Gang D R (2017) A (−)-kolavenyl diphosphate synthase catalyzes the first step of salvinorin A biosynthesis in *Salvia divinorum. J Exp Bot* 68(5):1109-1122.
16. Pelot K A, et al. (2017) Biosynthesis of the psychotropic plant diterpene salvinorin A: Discovery and characterization of the *Salvia divinorum* clerodienyl diphosphate synthase. *Plant J* 89(5):885-897.
17. Caniard A, et al. (2012) Discovery and functional characterization of two diterpene synthases for sclareol biosynthesis in *Salvia sclarea* (L.) and their relevance for perfume manufacture. *BMC Plant Biology* 12:119.
18. Günnewich N, et al. (2013) A diterpene synthase from the clary sage *Salvia sclarea* catalyzes the cyclization of geranylgeranyl diphosphate to (8R)-hydroxy-copalyl diphosphate. *Phytochemistry* 91:93-99.
19. Boachon B, et al. (2018) Phylogenomic Mining of the Mints Reveals Multiple Mechanisms Contributing to the Evolution of Chemical Diversity in Lamiaceae. *Molecular Plant*. doi:10.1016/j.molp.2018.06.002.
20. Coll J, Tandrón Y A (2008) neo-Clerodane diterpenoids from *Ajuga*: structural elucidation and biological activity. *Phytochem Rev* 7(1):25.
21. Klein Gebbinck E A, Jansen B J M, de Groot A (2002) Insect antifeedant activity of clerodane diterpenes and related model compounds. *Phytochemistry* 61(7):737-770.
22. Li R, Morris-Natschke S L, Lee K-H (2016) Clerodane diterpenes: sources, structures, and biological activities. *Nat Prod Rep* 33(10):1166-1226.
23. Vestri Alvarenga S A, Pierre Gastmans J, do Vale Rodrigues G, Roberto H. Moreno P, de Paulo Emerenciano V (2001) A computer-assisted approach for chemotaxonomic studies—diterpenes in Lamiaceae. *Phytochemistry* 56(6):583-595.
24. Loub W D, Farnsworth N R, Soejarto D D, Quinn M L (1985) NAPRALERT: computer handling of natural product research data. *J Chem Inf Comput Sci* 25(2):99-103.
25. Federhen S (2012) The NCBI Taxonomy database. *Nucleic Acids Res* 40(D1):D136-D143.
26. Li B. et al. (2016) A large-scale chloroplast phylogeny of the Lamiaceae sheds new light on its subfamilial classification. *Scientific Reports* 6:34343.
27. Camacho C, et al. (2009) BLAST+: architecture and applications. *BMC Bioinformatics* 10:421.
28. Pateraki I, et al. (2014) Manoyl Oxide (13R), the Biosynthetic Precursor of Forskolin, Is Synthesized in Specialized Root Cork Cells in *Coleus forskohlii. Plant Physiol* 164(3):1222-1236.
29. Jia M, Potter K C, Peters R J (2016) Extreme promiscuity of a bacterial and a plant diterpene synthase enables combinatorial biosynthesis. *Metabolic Engineering* 37:24-34.
30. Zerbe P, et al. (2015) Exploring diterpene metabolism in non-model species: transcriptome-enabled discovery and functional characterization of labda-7,13 E-dienyl diphosphate synthase from *Grindelia robusta. The Plant Journal* 83(5):783-793.
31. Urones J G, et al. (1994) Compounds with the labdane skeleton from *Halimium viscosum. Phytochemistry* 35(3): 713-719.

32. Suzuki H, Noma M, Kawashima N (1983) Two labdane diterpenoids from *Nicotiana setchellii*. *Phytochemistry* 22(5):1294-1295.
33. Roengsumran S, Petsom A, Sommit D, Vilaivan T (1999) Labdane diterpenoids from *Croton oblongifolius*. *Phytochemistry* 50(3):449-453.
34. Yamada Y, Komatsu M, Ikeda H (2016) Chemical diversity of labdane-type bicyclic diterpene biosynthesis in Actinomycetales microorganisms. *The Journal of Antibiotics* 69(7):515-523.
35. Xiang W, Li R-T, Song Q-S, Na Z, Sun H-D ent-Clerodanoids from *Isodon scoparius*. *Helvetica Chimica Acta* 87(11):2860-2865.
36. Rudi A, Kashman Y (1992) Chelodane, Barekoxide, and Zaatirin-Three New Diterpenoids from the Marine Sponge *Chelonaplysilla erecta*. *J Nat Prod* 55(10):1408-1414.
37. Ohsaki A, et al. (1994) The isolation and in vivo Potent Antitumor activity of clerodane diterpenoid from the oleoresin of the brazilian medicinal plant, copaifera langsdorfi desfon. *Bioorganic & Medicinal Chemistry Letters* 4(24):2889-2892.
38. Monaco P, Previtera L, Mangoni L (1982) Terpenes from the bled resin of *Araucaria hunsteinii*. *Rendiconto della Academia delle scienze fisiche e matematiche* 48:465-470.
39. Barton D H R, Cheung H T, Cross A D, Jackman L M, Martin-Smith M (1961) 1003. Diterpenoid bitter principles. Part III. The constitution of clerodin. *J Chem Soc*. 5061-5073.
40. Arima Y, Kinoshita M, Akita H (2007) Natural product synthesis from (8aR)- and (8aS)-bicyclofarnesols: synthesis of (+)-wiedendiol A, (+)-norsesterterpene diene ester and (−)-subersic acid. *Tetrahedron: Asymmetry* 18(14): 1701-1711.
41. Wu C-L, Hsiang-Ru Lin (1997) Labdanoids and bis (bibenzyls) from *Jungermannia* species. *Phytochemistry* 44(1):101-105.
42. Boalino D M, McLean S, Reynolds W F, Tinto W F (2004) Labdane Diterpenes of *Leonurus sibiricus*. *J Nat Prod* 67(4):714-717.
43. Gray C A, Rivett D E A, Davies-Coleman M T (2003) The absolute stereochemistry of a diterpene from *Ballota aucheri*. *Phytochemistry* 63(4):409-413.
44. Harris L J, et al. (2005) The Maize An2 Gene is Induced by *Fusarium* Attack and Encodes an ent-Copalyl Diphosphate Synthase. *Plant Mol Biol* 59(6):881-894.
45. Zhan X, Bach S S, Hansen N L, Lunde C, Simonsen H T (2015) Additional diterpenes from *Physcomitrella patens* synthesized by copalyl diphosphate/kaurene synthase (PpCPS/KS). *Plant Physiology and Biochemistry* 96:110-114.
46. Andersen-Ranberg J, et al. (2016) Expanding the Landscape of Diterpene Structural Diversity through Stereochemically Controlled Combinatorial Biosynthesis. *Angew Chem Int Ed* 55(6):2142-2146.
47. Vogel B S, Wildung M R, Vogel G, Croteau R (1996) Abietadiene synthase from grand fir (*Abies grandis*) cDNA isolation, characterization, and bacterial expression of a bifunctional diterpene cyclase involved in resin acid biosynthesis. *J Biol Chem* 271(38):23262-23268.
48. Bohlmann F, Czerson H (1979) Neue labdan-und pimaren-derivate aus *Palafoxia rosea*. *Phytochemistry* 18(1):115-118.
49. Li J-L, et al. (2012) IeCPS2 is potentially involved in the biosynthesis of pharmacologically active Isodon diterpenoids rather than gibberellin. *Phytochemistry* 76:32-39.
50. Jin B, et al. (2017) Functional diversification of kaurene synthase-like genes. *Plant Physiol* 174:973-955.
51. Hillwig M L, et al. (2011) Domain loss has independently occurred multiple times in plant terpene synthase evolution. *The Plant Journal* 68(6):1051-1060.
52. Pelot K A, Hagelthorn D M, Addison J B, Zerbe P (2017) Biosynthesis of the oxygenated diterpene nezukol in the medicinal plant *Isodon rubescens* is catalyzed by a pair of diterpene synthases. *PLOS ONE* 12(4):e0176507.
53. Helliwell C A, Chandler P M, Poole A, Dennis E S, Peacock W J (2001) The CYP88A cytochrome P450, ent-kaurenoic acid oxidase, catalyzes three steps of the gibberellin biosynthesis pathway. *PNAS* 98(4):2065-2070.
54. Han Q-B, et al. (2006) Maoecrystal Z, a Cytotoxic Diterpene from *Isodon eriocalyx* with a Unique Skeleton. *Org Lett* 8(21):4727-4730.
55. Li X-N, et al. (2010) Structure and Cytotoxicity of Diterpenoids from *Isodon eriocalyx*. *J Nat Prod* 73(11): 1803-1809.
56. González A G, Andrés L S, Luis J G, Brito I, Rodríguez M L (1991) Diterpenes from *Salvia mellifera*. *Phytochemistry* 30(12):4067-4070.
57. Chen Y-L, et al. (2008) Bioactive Cembrane Diterpenoids of Anisomeles indica. *J Nat Prod* 71(7):1207-1212.
58. Li L-M, et al. (2009) ent-Kaurane and Cembrane Diterpenoids from *Isodon sculponeatus* and Their Cytotoxicity. *J Nat Prod* 72(10):1851-1856.
59. Kirby J, et al. (2010) Cloning of casbene and neocembrene synthases from Euphorbiaceae plants and expression in *Saccharomyces cerevisiae*. *Phytochemistry* 71(13):1466-1473.
60. Ennajdaoui H, et al. (2010) Trichome specific expression of the tobacco (*Nicotiana sylvestris*) cembratrien-ol synthase genes is controlled by both activating and repressing cis-regions. *Plant Mol Bio* 73(6):673-685.
61. Hamano Y, et al. (2002) Functional Analysis of Eubacterial Diterpene Cyclases Responsible for Biosynthesis of a Diterpene Antibiotic, Terpentecin. *J Biol Chem* 277(40): 37098-37104.
62. Dairi T, et al. (2001) Eubacterial Diterpene Cyclase Genes Essential for Production of the Isoprenoid Antibiotic Terpentecin. *J Bacteriol* 183(20):6085-6094.
63. Schalk M, et al. (2012) Toward a Biosynthetic Route to Sclareol and Amber Odorants. *J Am Chem Soc* 134(46): 18900-18903.
64. Ikeda H, Shin-ya K, Nagamitsu T, Tomoda H (2016) Biosynthesis of mercapturic acid derivative of the labdane-type diterpene, cyslabdan that potentiates imipenem activity against methicillin-resistant *Staphylococcus aureus*: cyslabdan is generated by mycothiol-mediated xenobiotic detoxification. *J Ind Microbiol Biotechnol* 43(2-3):325-342.
65. Keeling C I, Madilao L L, Zerbe P, Dullat H K, Bohlmann J (2011) The Primary Diterpene Synthase Products of *Picea abies* Levopimaradiene/Abietadiene Synthase (PaLAS) Are Epimers of a Thermally Unstable Diterpenol. *J Biol Chem* 286(24):21145-21153.
66. Geuskens R B M, Luteijn J M, Schoonhoven L M (1983) Antifeedant activity of some ajugarin derivatives in three lepidopterous species. *Experientia* 39(4):403-404.
67. Belles X, Camps F, Coll J, Piulachs M D (1985) Insect antifeedant activity of clerodane diterpenoids against larvae of *Spodoptera Littoralis* (Boisd.) (Lepidoptera). *J Chem Ecol* 11(10):1439-1445.
68. Challis G L (2008) Genome Mining for Novel Natural Product Discovery. *J Med Chem* 51(9):2618-2628.

69. Xu H, et al. (2016) Analysis of the Genome Sequence of the Medicinal Plant *Salvia miltiorrhiza*. *Molecular Plant* 9(6):949-952.
70. King A J, Brown G D, Gilday A D, Larson T R, Graham I A (2014) Production of Bioactive Diterpenoids in the Euphorbiaceae Depends on Evolutionarily Conserved Gene Clusters. *The Plant Cell Online* 26(8):3286-3298.
71. Huang A C, et al. (2017) Unearthing a sesterterpene biosynthetic repertoire in the Brassicaceae through genome mining reveals convergent evolution. *PNAS* 114 (29):E6005-E6014.
72. Busta L, Jetter R (2017) Moving beyond the ubiquitous: the diversity and biosynthesis of specialty compounds in plant cuticular waxes. *Phytochem Rev:* 1-30.
73. Kodama Y, Shumway M, Leinonen R (2012) The sequence read archive: explosive growth of sequencing data. *Nucleic Acids Res* 40(D1):D54-D56.
74. Benson D A, et al. (2013) GenBank. *Nucleic Acids Res* 41(D1):D36-D42.
75. Kuhn S, Schlörer N E, Kolshorn H, Stoll R (2012) From chemical shift data through prediction to assignment and NMR LIMS—multiple functionalities of nmrshiftdb2. *Journal of Cheminformatics* 4(Suppl 1):P52.
76. Fischedick J T, Johnson S R, Ketchum R E B, Croteau R B, Lange B M (2015) NMR spectroscopic search module for Spektraris, an online resource for plant natural product identification—Taxane diterpenoids from *Taxus x media* cell suspension cultures as a case study. *Phytochemistry* 113:87-95.
77. Scotti M T, et al. (2018) SistematX, an Online Web-Based Cheminformatics Tool for Data Management of Secondary Metabolites. *Molecules* 23(1):103.
78. Heller S R, McNaught A, Pletnev I, Stein S, Tchekhovskoi D (2015) InChI, the IUPAC International Chemical Identifier. *J Cheminform* 7. doi:10.1186/s13321-015-0068-4.
79. Sievers F, et al. (2011) Fast, scalable generation of high-quality protein multiple sequence alignments using Clustal Omega. *Molecular Systems Biology* 7:539.
80. Stamatakis A (2014) RAxML version 8: a tool for phylogenetic analysis and post-analysis of large phylogenies. *Bioinformatics* 30(9):1312-1313.
81. Huerta-Cepas J, Serra F, Bork P (2016) ETE 3: Reconstruction, Analysis, and Visualization of Phylogenomic Data. *Mol Biol Evol* 33(6):1635-1638.
82. Lopez-Perez J L, Theron R, del Olmo E, Diaz D (2007) NAPROC-13: a database for the dereplication of natural product mixtures in bioassay-guided protocols. *Bioinformatics* 23(23):3256-3257.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various features of the invention according to the foregoing description provided in the specification and figures.

Statements:

1. An expression system comprising at least one expression cassette having a heterologous promoter operably linked to a nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176
2. The expression system of statement 1, wherein at least one expression cassette is within at least one expression vector.
3. The expression system of statement 1 or 2, wherein the expression system comprises two, or three, or four, or five expression cassettes or expression vectors, each expression cassette encoding a separate enzyme.
4. The expression system of statement 1, 2 or 3, wherein the expression system further comprises one or more expression cassettes having a promoter operably linked to a nucleic acid segment encoding an enzyme that can synthesize isopentenyl diphosphate (IPP), dimethylallyl diphosphate (DMAPP), or geranylgeranyl diphosphate (GGPP).
5. The expression system of statement 1-3 or 4, wherein the expression system has at least one expression cassette having a constitutive promoter.
6. The expression system of statement 1-3 or 4, wherein the expression system has at least one expression cassette having an inducible promoter.
7. The expression system of statement 1-5 or 6, wherein the expression system has at least one expression cassette having a CaMV 35S promoter, CaMV 19S promoter, nos promoter, Adh1 promoter, sucrose synthase promoter, α-tubulin promoter, ubiquitin promoter, actin promoter, cab promoter, PEPCase promoter, R gene complex promoter, CYP71D16 trichome-specific promoter, CBTS (cembratrienol synthase) promotor, Z10 promoter from a 10 kD zein protein gene, Z27 promoter from a 27 kD zein protein gene, plastid rRNA-operon (rrn) promoter, light inducible pea rbcS gene, RUBISCO-SSU light-inducible promoter (SSU) from tobacco, or rice actin promoter.
8. A host cell comprising the expression system of statement 1-6 or 7, which is heterologous to the host cell.
9. The host cell of statement 8, which is a plant cell, an algae cell, a fungal cell, a bacterial cell, or an insect cell.
10. The host cell of statement 8 or 9, which is a *Nicotiana benthamiana, Nicotiana tabacum, Nicotiana rustica, Nicotiana excelsior, Nicotiana excelsiana, Escherichia coli. Clostridium Ijungdahlii, Clostridium autoethanogenum, Clostridium kluyveri, Corynebacterium glutamicum, Cupriavidus necator, Cupriavidus metallidurans; Pseudomonas fluorescens. Pseudomonas putida, Pseudomonas oleovorans; Delftia acidovorans, Bacillus subtilis, Lactobacillus delbrueckii, Lactococcus lactis, Aspergillus niger, Saccharomyces cerevisae, Candida tropicalis, Candida albicans, Candida cloacae, Candida guilliermondii, Candida intermedia, Candida maltosa, Candida parapsilosis, Candida zeylenoides, Pichia pastoris, Yarrowia lipolytica, Issatchenkia orientalis, Debaryomyces hansenii, Arxula adeninivorans, Kluyveromyces lactis*, or *Exophiala, Mucor, Trichoderma, Cladosporium, Phanerochaete, Cladophialophora, Paecilomyces*. Scedosporium, or *Ophiostoma* cell.
11. The host cell of statement 8, 9 or 10, which is a *Nicotiana benthamiana.*
12. A method of synthesizing a terpene comprising incubating a host cell that has the expression system of any of statements 1-7.
13. A method for synthesizing a terpene comprising incubating a host cell comprising a heterologous expression system that includes at least one expression cassette having a heterologous promoter operably linked to a nucleic acid segment encoding an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176.

14. A method for synthesizing a terpene comprising incubating a terpene precursor with an enzyme with at least 90% sequence identity to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 57, 59, or 176.

15. The method of statement 12, 13 or 14, wherein the terpene is a compound of formula I, II, or III:

I

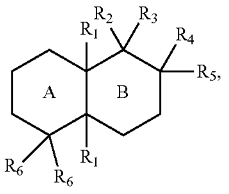

II

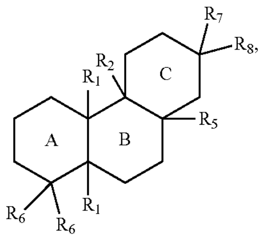

or

III

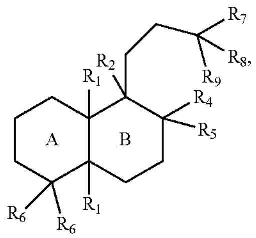

wherein each $R_1$ can separately be hydrogen or lower alkyl;

$R_2$ can be hydrogen, lower alkyl, hydroxy, a bond to an adjacent ring carbon, or form a $C_4$-$C_6$ cycloheteroalkyl with $R_3$;

$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;

$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;

$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;

each $R_6$ can separately be hydrogen, lower alkyl, lower alkene, or form a bond with an adjacent carbon;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; and $R_9$ can be hydrogen, lower alkyl, lower alkene, $=CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

16. The method of statement 12-14 or 15 wherein the terpene is a compound with a skeleton selected from Sk1-Sk14:

Sk1

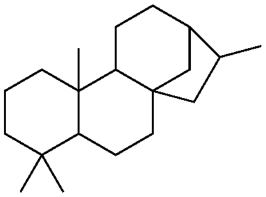

Sk2

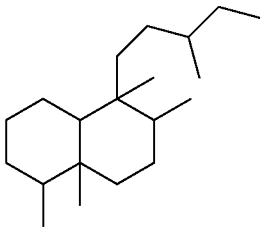

Sk3

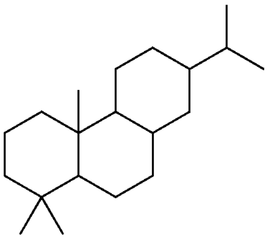

Sk4

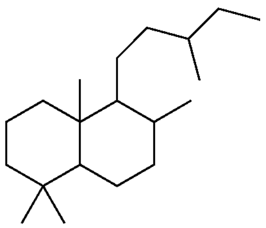

-continued
Sk5
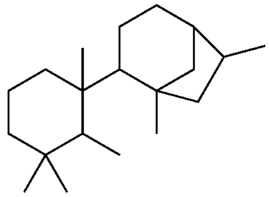
Sk6
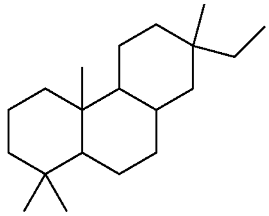
Sk7
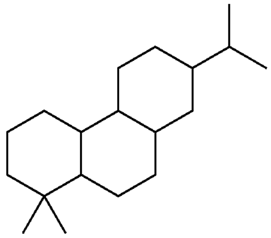
Sk8
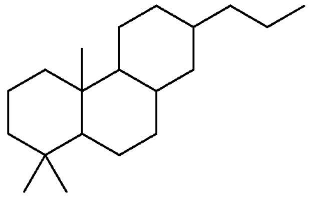
Sk9
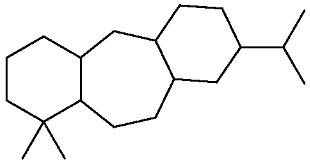
Sk10
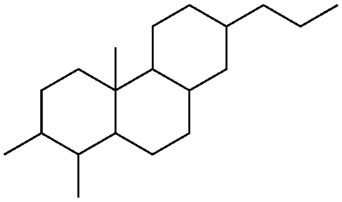
Sk11
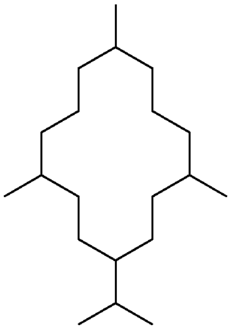
-continued
Sk12
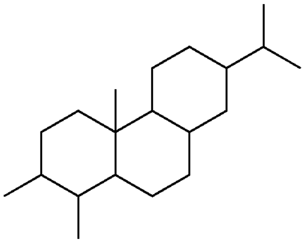
Sk13
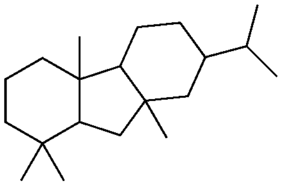
,
Sk14
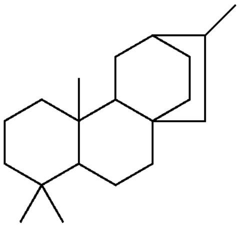
,
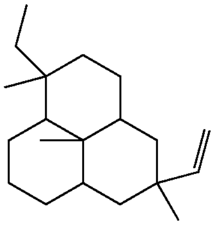
,
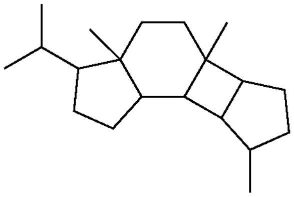
,
or a combination thereof.
17. The method of statement 12-15 or 16, wherein the terpene is any of the following compounds:
1
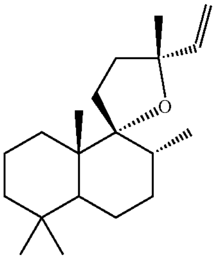

-continued
2
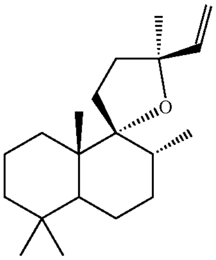
3
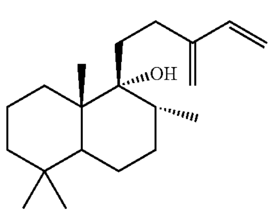
4
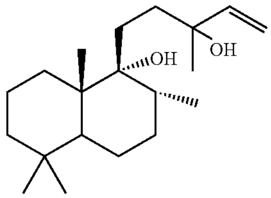
5
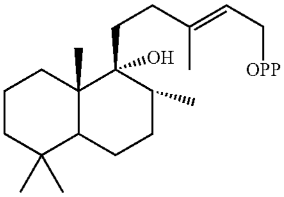
6
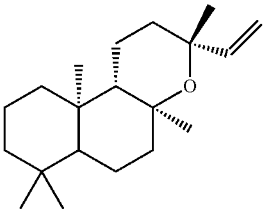
7
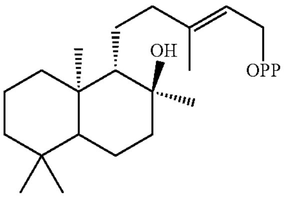
8
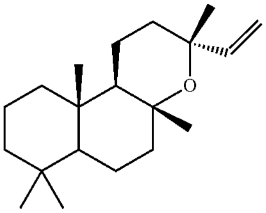
-continued
9
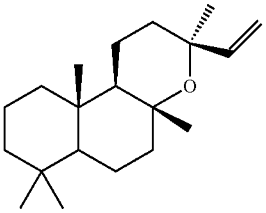
10
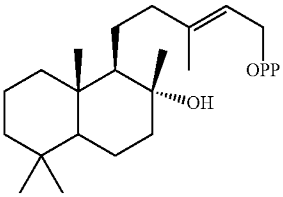
11
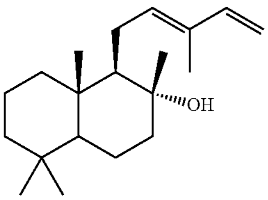
12
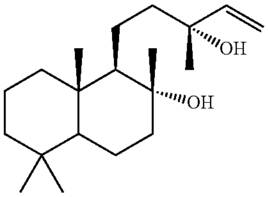
13
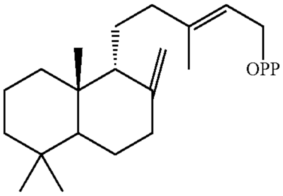
14
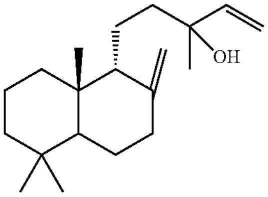
15
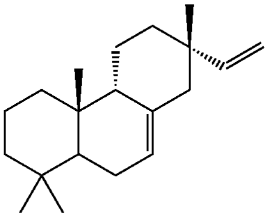

-continued
16
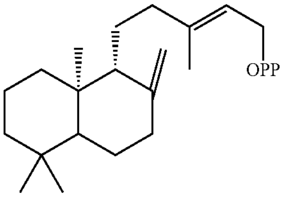
17
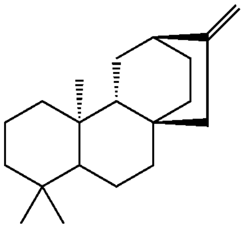
18
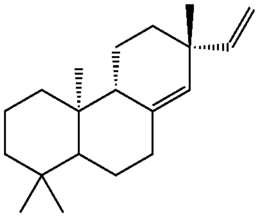
19
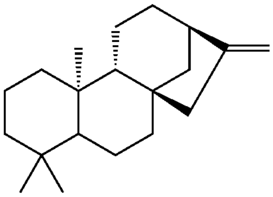
20
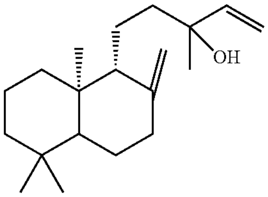
21
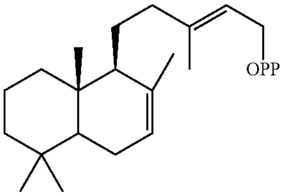
22
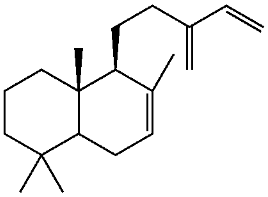
-continued
23
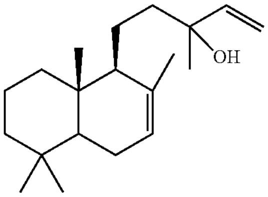
24
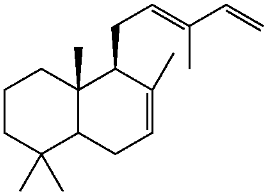
25
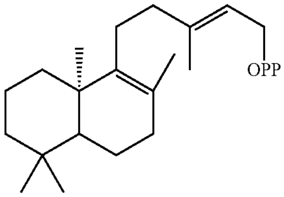
26
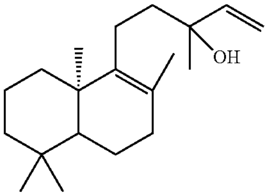
27
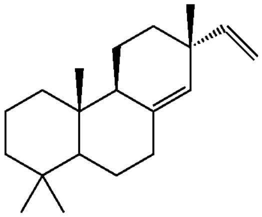
28
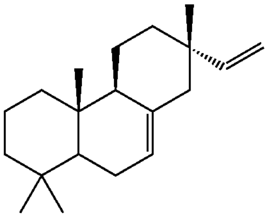
29
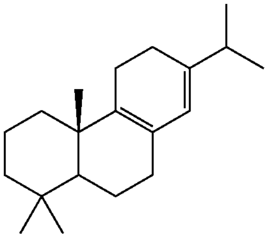

-continued
30
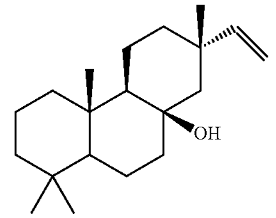
31
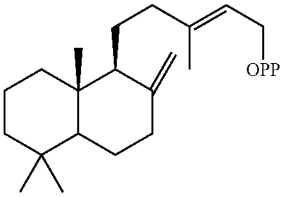
32
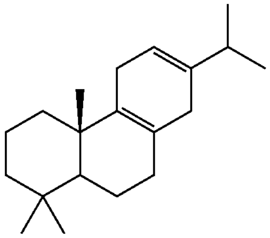
33
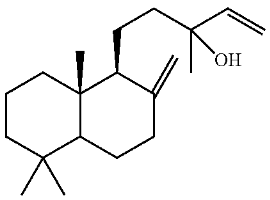
34
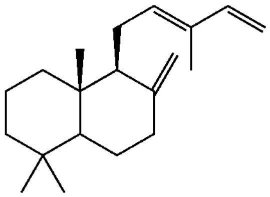
35
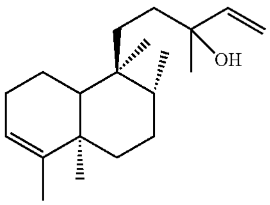
36
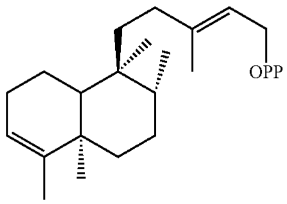
-continued
37
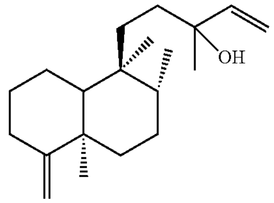
38
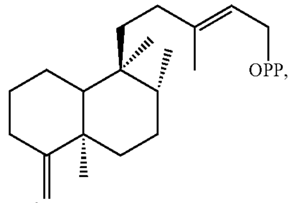
,
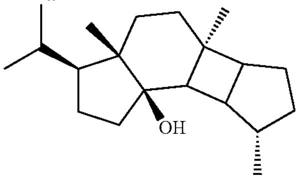
,
11-hydroxy vulgarisane
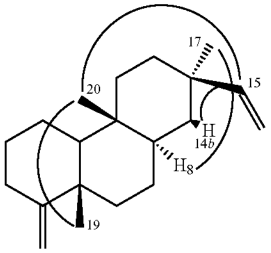
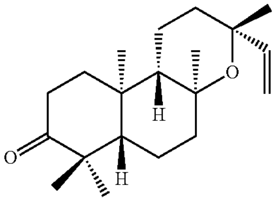
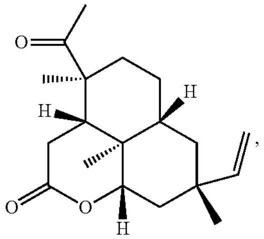
, Merilactone or
Ribenone
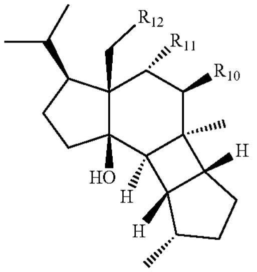

wherein:

Vulgarisin B (1)

$R_{10}$ = 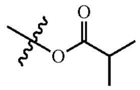 $R_{11}$ = OH $R_{12}$ = 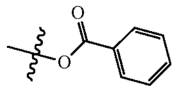

Vulgarisin C (2)

$R_{10}$ = OH $R_{11}$ = 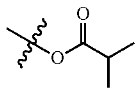 $R_{12}$ = 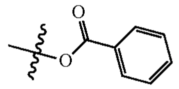

Vulgarisin D (3)

$R_{10}$ = OH $R_{11}$ = 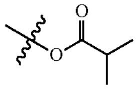 $R_{12}$ = 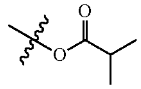

18. The method of statement 12-16 or 17, wherein the terpene is at least one of the following compounds:

37

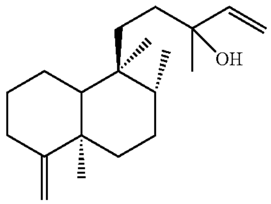

,

38

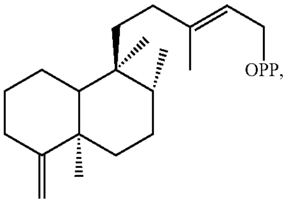

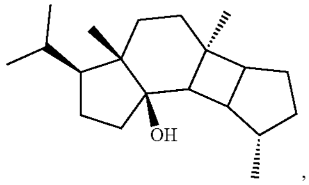

, 11-hydroxy vulgarisane

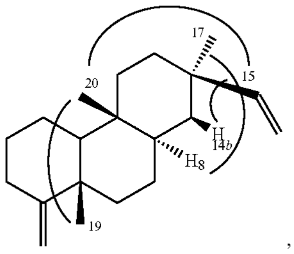

,

-continued

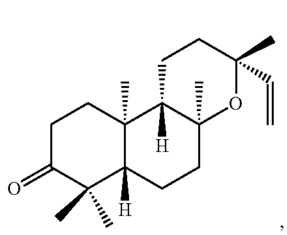

,

Ribenone

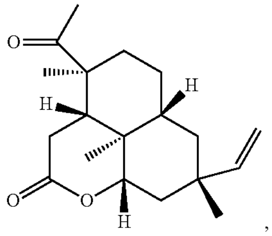

,

Merilactone

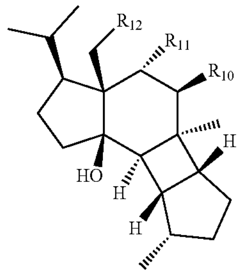

or wherein:

Vulgarisin B (1)

$R_{10}$ = 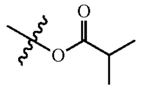 $R_{11}$ = OH $R_{12}$ = 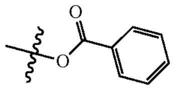

Vulgarisin C (2)

$R_{10}$ = OH $R_{11}$ = 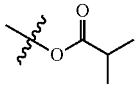 $R_{12}$ = 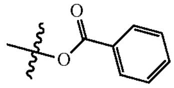

Vulgarisin D (3)

$R_{10}$ = OH $R_{11}$ = 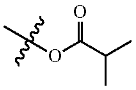 $R_{12}$ = 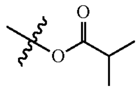

19. The method of statement 12-17 or 18 wherein the terpene precursor is geranylgeranyl diphosphate (GGPP).

20. A compound selected from:

1

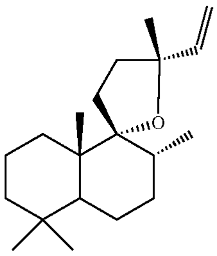

-continued
2
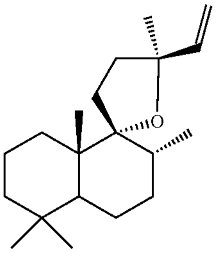
3
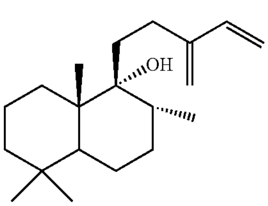
4
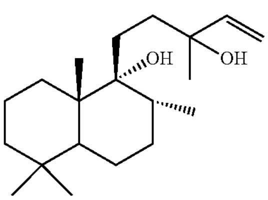
5
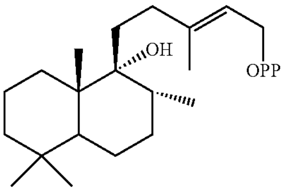
6
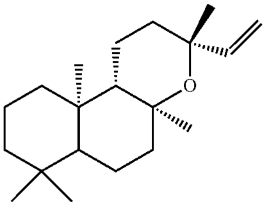
7
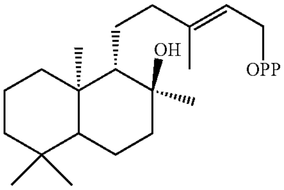
8
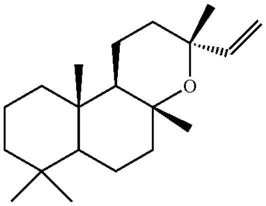
-continued
9
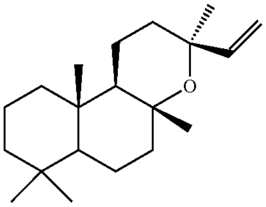
10
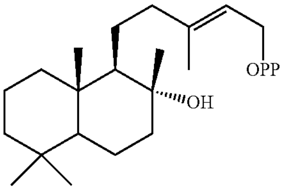
11
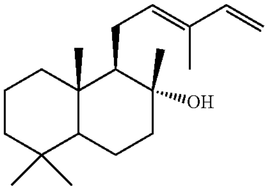
12
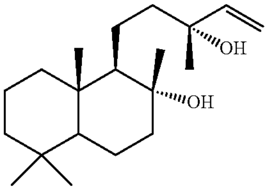
13
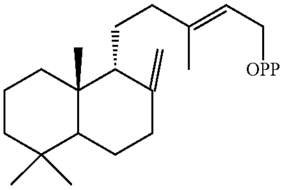
14
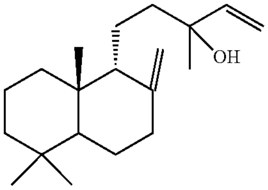
15
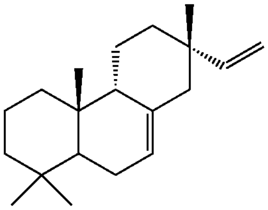
16
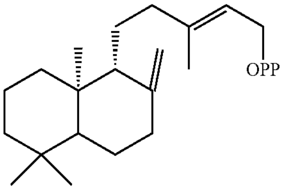

-continued
17
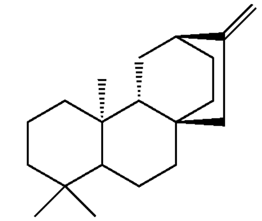
18
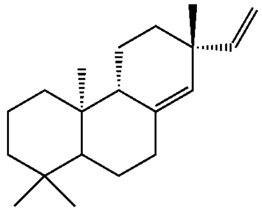
19
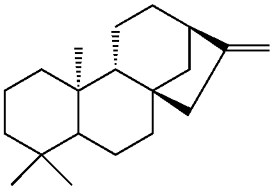
20
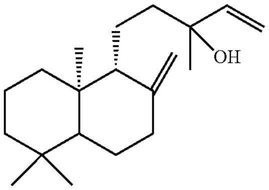
21
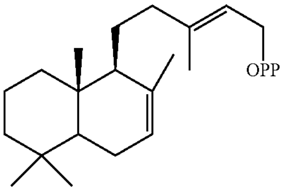
22
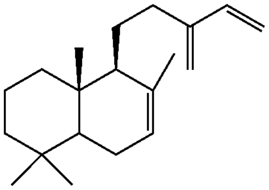
23
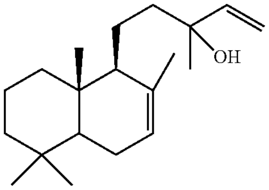
-continued
24
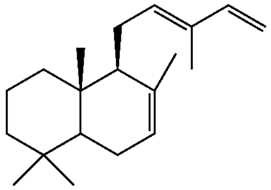
25
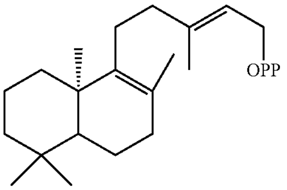
26
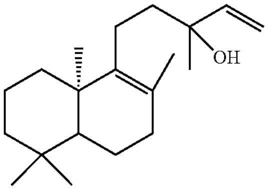
27
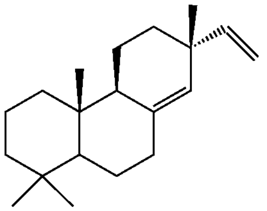
28
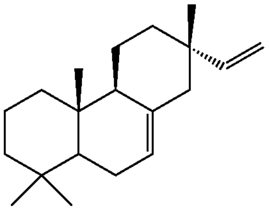
29
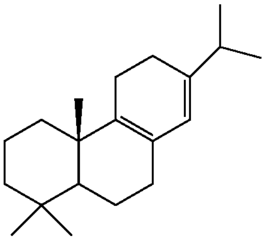
30
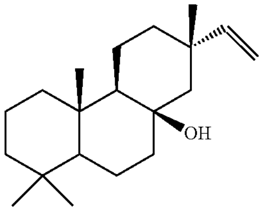

-continued
31
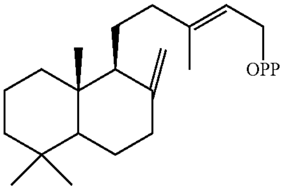
32
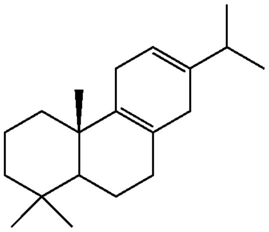
33
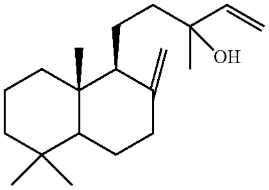
34
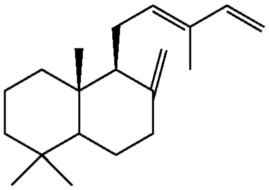
35
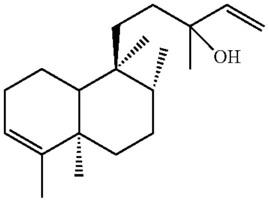
36
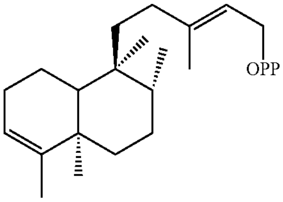
37
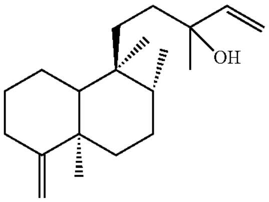
-continued
38
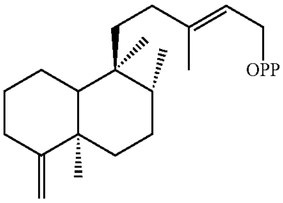
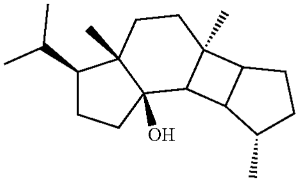
,
11-hydroxy vulgarisane
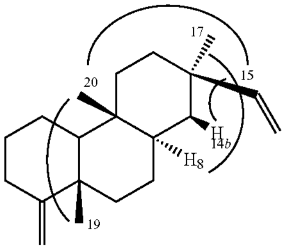
,
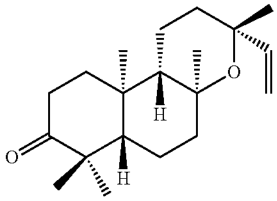
,
Ribenone
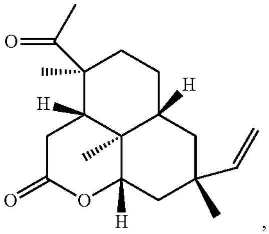
Merilactone
, or
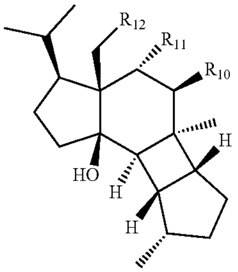
wherein:
Vulgarisin B (1)
$R_{10}$ = 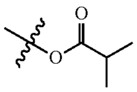 $R_{11}$ = OH $R_{12}$ = 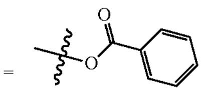
Vulgarisin C (2)
$R_{10}$ = OH $R_{11}$ = 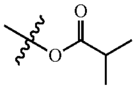 $R_{12}$ = 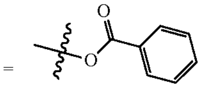

Vulgarisin D (3)
R10 = OH R11 = 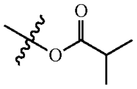 R12 = 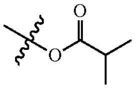
21. A reaction mixture comprising one or more of the following:
1
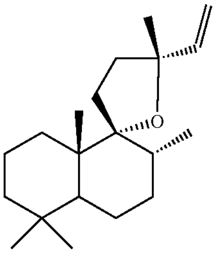
2
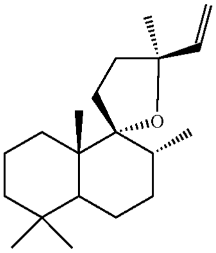
3
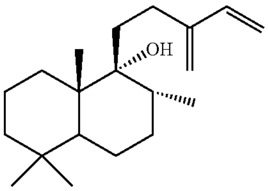
4
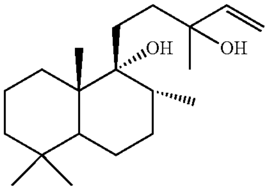
5
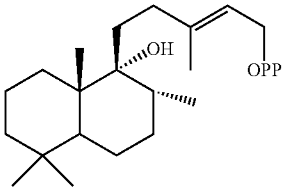
6
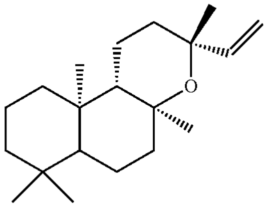
7
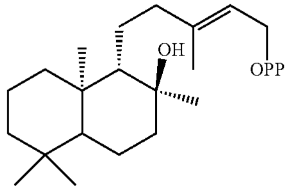
8
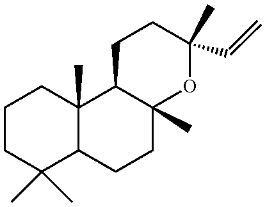
9
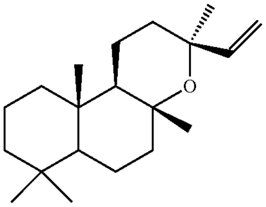
10
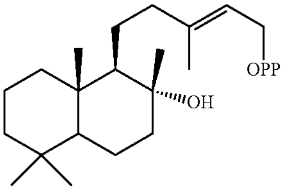
11
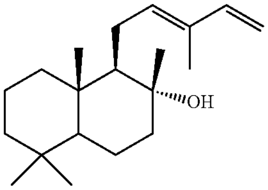
12
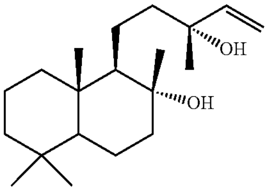
13
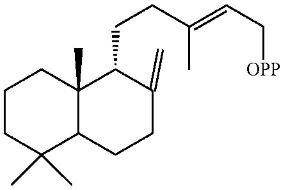
14
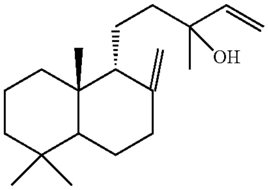

-continued
15
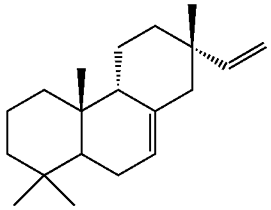
16
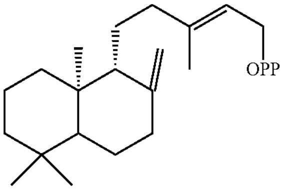
17
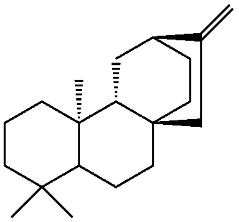
18
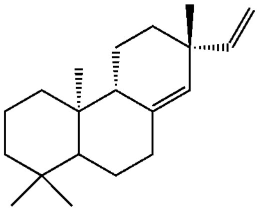
19
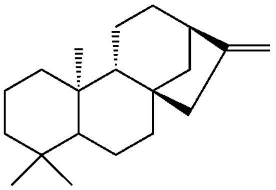
20
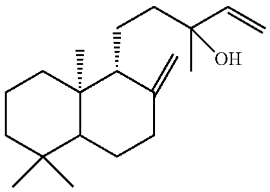
21
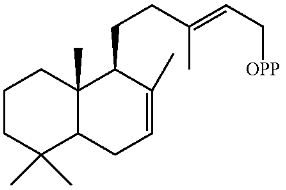
-continued
22
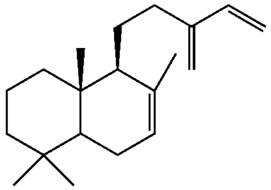
23
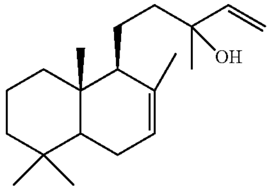
24
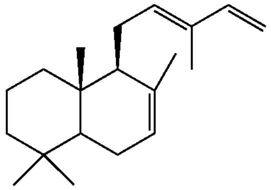
25
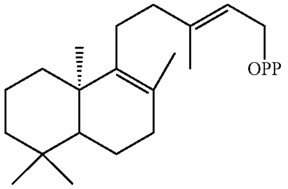
26
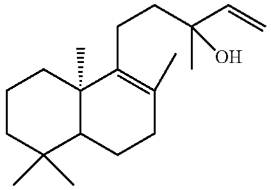
27
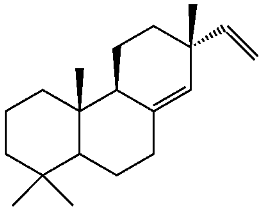
28
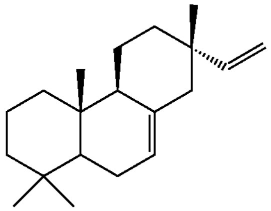

-continued
29
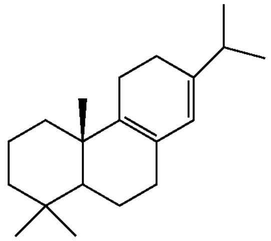
30
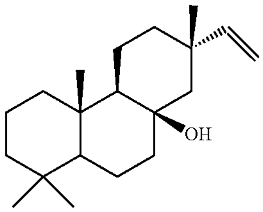
31
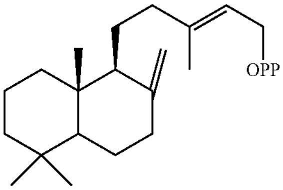
32
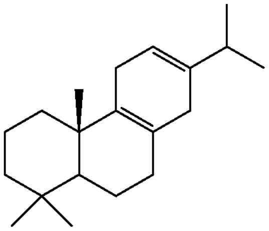
33
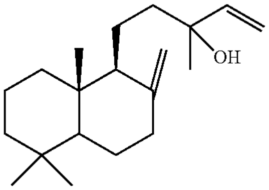
34
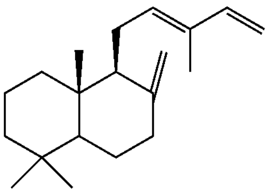
35
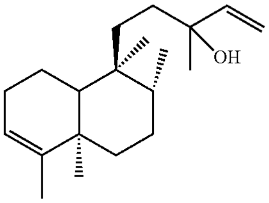
-continued
36
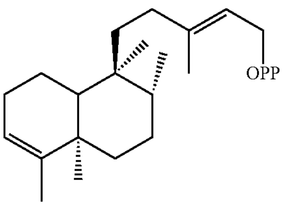
37
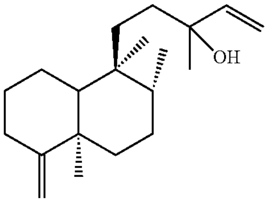
38
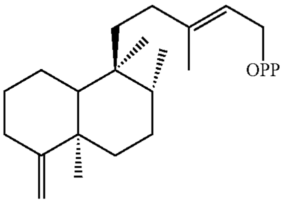
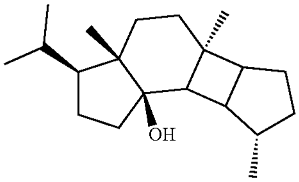
,
11-hydroxy vulgarisane
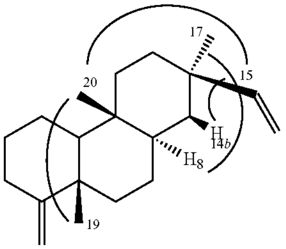
,
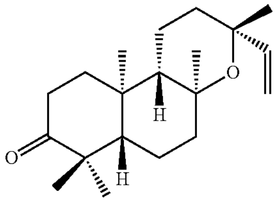
,
Ribenone
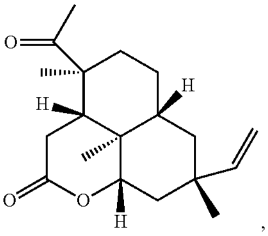
, or
Merilactone
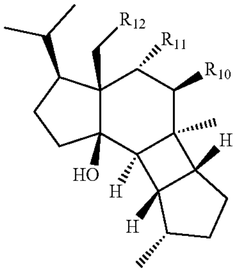

wherein:

Vulgarisin B (1)

$R_{10}$ = 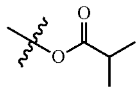 $R_{11}$ = OH $R_{12}$ = 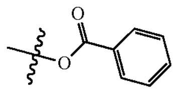

Vulgarisin C (2)

$R_{10}$ = OH $R_{11}$ = 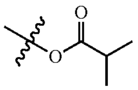 $R_{12}$ = 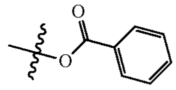

Vulgarisin D (3)

$R_{10}$ = OH $R_{11}$ = 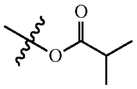 $R_{12}$ = 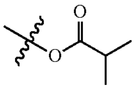

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method for synthesizing a terpene comprising incubating a terpene precursor with an enzyme with at least 95% sequence identity to the amino acid sequence of SEQ ID NO:9.

2. The method of claim 1, wherein the precursor comprises geranylgeranyl diphosphate (GGPP).

3. The method of claim 1, which comprises incubating a host cell that expresses a heterologous expression system comprising at least one expression cassette having a heterologous promoter operably linked to a nucleic acid segment encoding an enzyme with at least 95% sequence identity to the amino acid sequence of SEQ ID NO: 9.

4. The method of claim 1, wherein the terpene is a compound of formula I, II, or III:

I

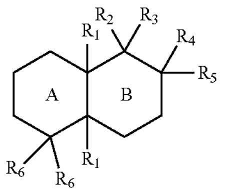

II

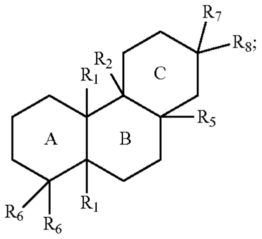

or

III

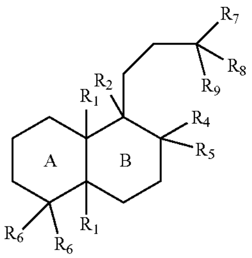

wherein each $R_1$ can separately be hydrogen;

$R_2$ can be hydrogen;

$R_3$ can be a branched $C_5$-$C_6$ alkyl with 0-2 double bonds, wherein the $C_5$-$C_6$ alkyl can optionally have one hydroxy, phosphate or diphosphate substituent;

$R_4$ can be lower alkyl;

$R_5$ can be hydroxy;

each $R_6$ can separately be lower alkyl;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; and $R_9$ can be hydrogen, lower alkyl, lower alkene, $=CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

5. The method of claim 1, wherein the terpene is a compound with a skeleton selected from:

Sk4

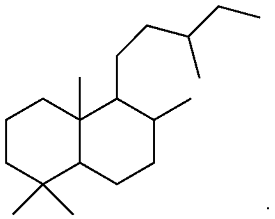

6. The method of claim 1, wherein the terpene is one or more of the following compounds:

11

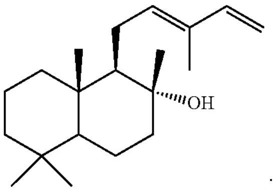

7. A method for synthesizing a terpene comprising incubating a terpene precursor of a terpene of formula I, II, or III, with an enzyme with at least 95% sequence identity to the amino acid sequence of SEQ ID NO:9, wherein the terpene of formula I, II, or III is:

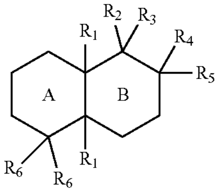

I

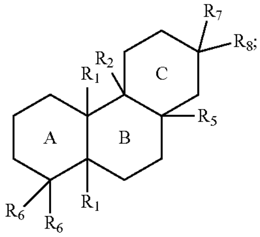

II or

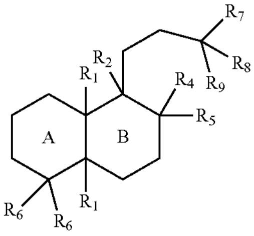

III wherein each $R_1$ can separately be hydrogen or lower alkyl;

$R_2$ can be hydrogen, lower alkyl, hydroxy, a bond to an adjacent ring carbon, or form a $C_4$-$C_6$ cycloheteroalkyl with $R_3$;

$R_3$ can be a branched $C_5$-$C_6$ alkyl with 0-2 double bonds, can form a $C_4$-$C_6$ cycloheteroalkyl with $R_2$; can form a cycloalkyl with $R_4$, or can form a cycloheteroalkyl ring with $R_4$, wherein the $C_5$-$C_6$ alkyl can optionally have one hydroxy, phosphate or diphosphate substituent, and wherein each cycloalkyl or cycloheteroalkyl ring can have 0-2 double bonds, and each cycloalkyl or cycloheteroalkyl ring can have 0-2 alkyl or 0-2 alkene substituents;

$R_4$ can be hydrogen, lower alkyl, lower alkene, hydroxy, a carbon bonded to $R_9$, an oxygen bonded to $R_9$, form a cycloalkyl ring with $R_3$, or form a cycloheteroalkyl ring with $R_3$, wherein each cycloalkyl ring or cycloheteroalkyl ring can have 0-2 double bonds, and each cycloalkyl ring or cycloheteroalkyl ring can have 0-2 alkyl or 0-2 alkene substituents;

$R_5$ can be hydrogen, hydroxy, lower alkyl, a lower alkene, a bond with an adjacent carbon, form a cycloalkyl ring with a ring atom of a ring formed by $R_3$ and $R_4$, wherein the cycloalkyl ring can have 0-2 double bonds, and the cycloalkyl ring can have 0-2 alkyl or 0-2 alkene substituents;

each $R_6$ can separately be hydrogen, lower alkyl, lower alkene, or form a bond with an adjacent carbon;

$R_7$ can be lower alkyl, lower alkene, or form a cycloalkyl ring with a $R_5$, $R_8$ can be lower alkyl, hydroxy, phosphate, diphosphate, or form a bond with an adjacent carbon; and $R_9$ can be hydrogen, lower alkyl, lower alkene, $=CH_2$, hydroxy, phosphate, diphosphate, form a bond with an adjacent carbon, form a cycloalkyl ring with $R_4$, or form a cycloheteroalkyl ring with $R_4$, wherein each cycloalkyl ring or cycloheteroalkyl ring can have 0-2 double bonds, and each cycloalkyl ring or cycloheteroalkyl ring can have 0-2 alkyl or 0-2 alkene substituents.

8. A method for synthesizing a terpene comprising incubating a terpene precursor with an enzyme with at least 95% sequence identity to the amino acid sequence of SEQ ID NO:9, wherein the terpene precursor comprises a diphosphate.

* * * * *